(12) United States Patent
Delouvrie et al.

(10) Patent No.: US 7,632,840 B2
(45) Date of Patent: Dec. 15, 2009

(54) QUINAZOLINE COMPOUNDS FOR THE TREATMENT OF HYPERPROLIFERATIVE DISORDERS

(75) Inventors: Benedicte Delouvrie, Reims (FR); Craig Steven Harris, Reims (FR); Laurent Francois Andre Hennequin, Reims (FR); Christopher Thomas Halsall, Macclesfield (GB); Janet Elizabeth Pease, Macclesfield (GB); Peter Mark Smith, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 42 days.

(21) Appl. No.: 10/586,965

(22) PCT Filed: Jan. 31, 2005

(86) PCT No.: PCT/GB2005/000237

§ 371 (c)(1),
(2), (4) Date: Aug. 3, 2007

(87) PCT Pub. No.: WO2005/075439

PCT Pub. Date: Aug. 18, 2005

(65) Prior Publication Data

US 2007/0293490 A1    Dec. 20, 2007

(30) Foreign Application Priority Data

Feb. 3, 2004    (EP)    ................... 04290274

(51) Int. Cl.
*A01N 43/54*    (2006.01)

(52) U.S. Cl. .................... 514/266.1; 544/283; 546/196; 548/579; 548/950

(58) Field of Classification Search ............. 514/266.1; 544/283; 546/196; 548/579, 950
See application file for complete search history.

(56) References Cited

U.S. PATENT DOCUMENTS

| | | | |
|---|---|---|---|
| 4,335,127 A | 6/1982 | Vandenberk et al. ... | 514/266.22 |
| 4,921,863 A | 5/1990 | Sugimoto et al. ........... | 514/319 |
| 5,457,105 A | 10/1995 | Barker .................... | 514/234.5 |
| 5,616,582 A | 4/1997 | Barker .................... | 514/234.5 |
| 5,747,498 A | 5/1998 | Schnur et al. ............ | 514/266.4 |
| 5,770,599 A | 6/1998 | Gibson .................... | 514/228.2 |
| 6,297,258 B1 | 10/2001 | Wissner et al. ............. | 514/313 |
| 6,562,319 B2 | 5/2003 | Mishani et al. ............ | 424/1.81 |
| 6,617,329 B2 | 9/2003 | Himmelsbach et al. | 514/252.14 |
| 6,972,288 B1 | 12/2005 | Himmelsbach et al. .. | 514/234.8 |
| 7,148,230 B2 | 12/2006 | Bradbury et al. | |
| 2002/0049197 A1 | 4/2002 | Himmelsbach et al. | 514/217.06 |
| 2002/0082270 A1 | 6/2002 | Himmelsbach et al. .. | 514/266.2 |
| 2002/0128553 A1 | 9/2002 | Mishani et al. ............ | 600/431 |
| 2002/0169180 A1 | 11/2002 | Himmelsbach et al. .. | 514/266.4 |
| 2002/0177601 A1 | 11/2002 | Himmelsbach et al. .. | 514/266.2 |
| 2004/0048880 A1 | 3/2004 | Himmelsbach et al. .. | 514/266.2 |
| 2004/0176361 A1 | 9/2004 | Fujio et al. ............... | 514/224.2 |
| 2005/0043336 A1 | 2/2005 | Hennequin et al. | |
| 2005/0054662 A1 | 3/2005 | Hennequin et al. | |
| 2005/0165035 A1 | 7/2005 | Bradbury et al. ....... | 514/266.22 |
| 2005/0215574 A1 | 9/2005 | Bradbury et al. | |
| 2006/0211714 A1 | 9/2006 | Hennequin et al. | |
| 2006/0287295 A1 | 12/2006 | Barlaam et al. | |
| 2007/0015743 A1 | 1/2007 | Bradbury et al. | |
| 2007/0032508 A1 | 2/2007 | Bradbury et al. | |
| 2007/0032513 A1 | 2/2007 | Hennequin et al. | |
| 2007/0037837 A1 | 2/2007 | Hennequin et al. | |
| 2007/0043009 A1 | 2/2007 | Hennequin et al. | |
| 2007/0043010 A1 | 2/2007 | Bradbury et al. | |
| 2007/0082921 A1 | 4/2007 | Hennequin et al. | |
| 2007/0088044 A1 | 4/2007 | Hennequin et al. | |
| 2007/0099943 A1 | 5/2007 | Bradbury et al. | |
| 2007/0149546 A1 | 6/2007 | Bradbury et al. | |
| 2007/0232607 A1 | 10/2007 | Bradbury et al. | |
| 2007/0244136 A1 | 10/2007 | Hennequin et al. | |

FOREIGN PATENT DOCUMENTS

| | | |
|---|---|---|
| DE | 10040527 | 2/2002 |
| EP | 0 288 563 | 5/1994 |
| EP | 0 566 226 | 11/1995 |
| EP | 0 837 063 | 4/1998 |
| EP | 1 230 919 | 8/2002 |
| EP | 1 369 418 | 12/2003 |
| WO | WO 88/02365 | 4/1988 |
| WO | WO 96/09294 | 3/1996 |

(Continued)

OTHER PUBLICATIONS

Jordan, V. C. Nature Reviews: Drug Discovery, 2, 2003, p. 205.*

(Continued)

*Primary Examiner*—James O Wilson
*Assistant Examiner*—Douglas M Willis
(74) *Attorney, Agent, or Firm*—Morgan, Lewis & Bockius LLP

(57) ABSTRACT

A quinazoline derivative of the formula I:

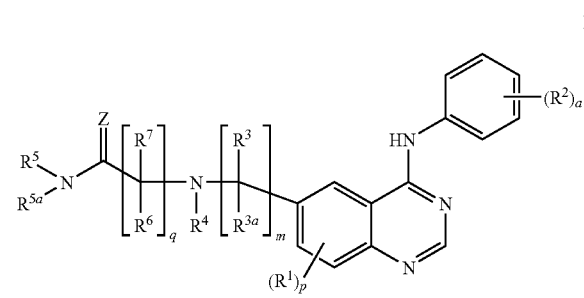

wherein: $R^1$, $R^2$, $R^3$, $R^{3a}$, $R^4$, $R^5$, $R^{5a}$ $R^6$, $R^7$, a, m and p are as defined in the description. Also claimed are pharmaceutical compositions containing the quinazoline derivative, the use of the quinazoline derivatives as medicaments and processes for the preparation of the quinazoline derivative. The quinazoline derivatives of formula I, are useful in the treatment of hyperproliferative disorders such as a cancer.

16 Claims, No Drawings

FOREIGN PATENT DOCUMENTS

| | | |
|---|---|---|
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/30034 | 8/1997 |
| WO | WO 97/30035 | 8/1997 |
| WO | WO 97/38983 | 10/1997 |
| WO | WO 97/38994 | 10/1997 |
| WO | WO 98/02434 | 1/1998 |
| WO | WO 98/13354 | 4/1998 |
| WO | WO 99/06378 | 2/1999 |
| WO | WO 99/35132 | 7/1999 |
| WO | WO 00/09481 | 2/2000 |
| WO | WO 00/18740 | 4/2000 |
| WO | WO 00/20402 | 4/2000 |
| WO | WO 00/20402 A | 4/2000 |
| WO | WO 00/24718 | 5/2000 |
| WO | WO 00/44728 | 8/2000 |
| WO | WO 00/51991 | 9/2000 |
| WO | WO 00/55141 | 9/2000 |
| WO | WO 00/56720 | 9/2000 |
| WO | WO 00/78735 | 12/2000 |
| WO | WO 01/04102 | 1/2001 |
| WO | WO 01/07432 | 2/2001 |
| WO | WO 01/21596 | 3/2001 |
| WO | WO 01/21597 | 3/2001 |
| WO | WO 01/32651 | 5/2001 |
| WO | WO 01/66099 | 9/2001 |
| WO | WO 01/94341 | 12/2001 |
| WO | WO 01/98277 | 12/2001 |
| WO | WO 02/02534 | 1/2002 |
| WO | WO 02/08224 | 1/2002 |
| WO | WO 02/16352 | 2/2002 |
| WO | WO 02/18372 | 3/2002 |
| WO | WO 02/24684 | 3/2002 |
| WO | WO 02/30924 | 4/2002 |
| WO | WO 02/34744 | 5/2002 |
| WO | WO 02/41882 | 5/2002 |
| WO | WO 02/44166 | 6/2002 |
| WO | WO 02/48117 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 | 11/2002 |
| WO | WO 02/097490 | 12/2002 |
| WO | WO 03/040108 | 5/2003 |
| WO | WO 03/040109 | 5/2003 |
| WO | WO 03/049740 | 6/2003 |
| WO | WO 03/082290 | 10/2003 |
| WO | WO 03/082831 | 10/2003 |
| WO | WO 2004/064718 | 8/2004 |
| WO | WO 2004/093880 | 11/2004 |
| WO | WO 2004/096226 | 11/2004 |
| WO | WO 2005/012290 | 2/2005 |
| WO | WO 2005/013998 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030757 | 4/2005 |
| WO | WO 2005/030765 | 4/2005 |
| WO | WO 2005/051923 | 6/2005 |
| WO | WO 2005/118572 | 12/2005 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |
| WO | WO 2006/117523 | 11/2006 |
| WO | WO 2007/034143 | 3/2007 |
| WO | WO 2007/034144 | 3/2007 |
| WO | WO 2007/063291 | 6/2007 |
| WO | WO 2007/063293 | 6/2007 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

Tsou, H-R, et al., "6-Substituted-4-(3-Bromophenylamino) Quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity", Journal of Medicinal Chemistry, American Chemical Society, US, vol. 44, No. 17, 2001, pp. 2719-2734.

A. Vema, et al., "Design of EGFR Kinase Inhibitors: A Ligand-Based Approach and Its Confirmation with Structure-Based Studies", Bioorg. Med. Chem., vol. 11, 2003, pp. 4643-4653.

Hennequin et al. "Novel 4-anilinoquinazolines with C-6 carbon-linked side chains: synthesis and structure-activity relationship of a series of potent, orally active, EGF receptor tyrosine kinase inhibitors" Bioorganic & Medicinal Chemistry Letters 16: 2672-2676 (2006).

Stamos et al. "Structure of the Epidermal Growth Factor Receptor Kinase Domain Alone and in Complex with a 4-Anilinoquinazoline Inhibitor" J. Biol. Chem. 277(48):46265-46272 (2002).

Traxler et al. "Protein tyrosine kinase inhibitors in cancer treatment" Exp. Opin. Ther. Patents 7(6):571-588 (1997).

Traxler et al. "Tyrosine kinase inhibitors in cancer treatment (Part II)" Exp. Opin. Ther. Patents 8(12):1599-1625 (1998).

Tsou et al. "6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity" J. Med. Chem. 44:2719-2734 (2001).

Vema et al. "Design of EGFR kinase inhibitors: a ligand-based approach and its confirmation with structure-based studies" Bioorg Med Chem. 11(21):4643-4653 (2003).

Ballard et al. "Inhibitors of epidermal growth factor receptor tyrosine kinase: Novel C-5 substituted anilinoquinazolines designed to target the ribose pocket" Bioorg Med Chem Lett. 16(6):1633-1637 (2006).

Ballard et al. "5-Substituted 4-anilinoquinazolines as potent, selective and orally active inhibitors of erbB2 receptor tyrosine kinase" Bioorg Med Chem Lett. 15(19):4226-4229 (2005).

Ballard et al. "Inhibitors of epidermal growth factor receptor tyrosine kinase: optimisation of potency and in vivo pharmacokinetics" Bioorg Med Chem Lett. 16(18):4908-4912 (2006).

Harris et al. "Facile synthesis of 7-amino anilinoquinazolines via direct amination of the quinazoline core" Tetrahedron letters 46(43): 7381-7384 (2005).

Harris et al. "Selective alkylation of a 6,7-dihydroxyquinazoline" Tetrahedron letters 46(45):7715-7719 (2005).

* cited by examiner

QUINAZOLINE COMPOUNDS FOR THE TREATMENT OF HYPERPROLIFERATIVE DISORDERS

CROSS-REFERENCE TO RELATED APPLICATIONS

This application is a U.S. National Phase Application of International Application No. PCT/GB2005/00237, filed Jan. 31, 2005, which claims the benefit of European Patent Application No. 04290274.2, filed Feb. 3, 2004.

STATEMENT REGARDING FEDERALLY SPONSORED RESEARCH OR DEVELOPMENT

Not Applicable

BACKGROUND OF THE INVENTION (1) Field of the Invention

The invention concerns certain novel quinazoline derivatives, or pharmaceutically-acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

(2) Description of the Related Art

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al., *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al., *Biochimica et Biophysica Acta*, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase subfamilies (Robinson et al, *Oncogene*, 2000, 19, 5548-5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.*, 2000, 19, 3159). One mechanism in which this can be accomplished is by overexpression of the receptor at the protein level, generally as a result of gene amplification. This has been observed in many common human cancers (reviewed in Klapper et al., *Adv. Cancer Res.*, 2000, 77, 25) such as breast cancer (Sainsbury et al., *Brit. J. Cancer*, 1988, 58, 458; Guerin et al., *Oncogene Res.*, 1988, 3, 21; Slamon et al., *Science*, 1989, 244, 707; Klijn et al., *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer*, 1986, 54, 265; Reubi et al., *Int. J. Cancer*, 1990, 45, 269; Rusch et al., *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol. Rep.*, 2000, 7, 603), bladder cancer (Neal et al., *Lancet*, 1985, 366; Chow et al., *Clin. Cancer Res.*, 2001, 7, 1957, Zhau et al., *Mol Carcinog.*, 3, 254), oesophageal cancer (Mukaida et al., *Cancer*, 1991, 68, 142), gastrointestinal cancer such as colon, rectal or stomach cancer (Bolen et al., *Oncogene Res.*, 1987, 1, 149; Kapitanovic et al., *Gastroenterology*, 2000, 112, 1103; Ross et al., *Cancer Invest.*, 2001, 19, 554), cancer of the prostate (Visakorpi et al., *Histochem. J.*, 1992, 24, 481; Kumar et al., 2000, 32, 73; Scher et al., *J. Natl. Cancer Inst.*, 2000, 92, 1866), leukaemia (Konaka et al., *Cell* 1984, 37, 1035, Martin-Subero et al., *Cancer Genet Cytogenet.*, 2001, 127, 174), ovarian (Hellstrom et al., *Cancer Res.*, 2001, 61, 2420), head and neck (Shiga et al., *Head Neck*, 2000, 22, 599) or pancreatic cancer (Ovotny et al., *Neoplasma*, 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors, it is widely believed that many tumours become clinically more aggressive and so correlate with a poorer prognosis for the patient (Brabender et al, *Clin. Cancer Res.*, 2001, 7, 1850; Ross et al, *Cancer Investigation*, 2001, 19, 554, Yu et al., *Bioessays*, 2000, 22.7, 673). In addition to these clinical findings, a wealth of pre-clinical information suggests that the erbB family of receptor tyrosine kinases are involved in cellular transformation. This includes the observations that many tumour cell lines overexpress one or more of the erbB receptors and that EGFR or erbB2 when transfected into non-tumour cells have the ability to transform these cells. This tumourigenic potential has been further verified as transgenic mice that overexpress erbB2 spontaneously develop tumours in the mammary gland. In addition to this, a number of pre-clinical studies have demonstrated that antiproliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al., Biochimica et Biophysica Acta, 1997, 133, F217-F248; Al-Obeidi et al., 2000, *Oncogene*, 19, 5690-5701; Mendelsohn et al, 2000, *Oncogene*, 19, 6550-6565).

Recently the small molecule EGFR tyrosine kinase inhibitor, Iressa (also known as gefitinib, and ZD1834) has been approved for use in the treatment of advanced non-small cell lung cancer. Furthermore, findings using inhibitory antibodies against EGFR and erbB2 (c-225 and trastuzumab respectively) have proven to be beneficial in the clinic for the treatment of selected solid tumours (reviewed in Mendelsohn et al., 2000, *Oncogene*, 19, 6550-6565).

Amplification and/or activity of members of the erbB receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., Science, 1989, 243, 811), benign prostatic hyperplasia (BPH) (Kumar et al., *Int. Urol. Nephrol.*, 2000, 32, 73), atherosclerosis and restenosis (Bokemeyer et al., *Kidney Int.*, 2000, 58, 549). It is therefore expected that inhibitors of erbB receptor tyrosine kinases will be useful in the treatment of these and other non-malignant disorders of excessive cellular proliferation.

Patent applications WO 94/27965, WO 95/03283, WO 96/09294, WO 96/30347, WO 96/33977, WO 96/33978, WO 96/33979, WO 96/33980, WO 96/33981, WO 97/03069, WO 97/30034, WO 97/30035, WO 97/30044, WO 97/38983, WO 97/38994, WO 98/02434, WO 98/13354, WO 99/06387, WO 99/35132, WO 00/51991, WO 00/55141, WO 00/56720, WO 01/21596, WO 01/98277, WO02/18351, WO 02/18372, WO 02/41882, WO 02/92577, WO 02/92578, WO 03/82290, WO 03/82831, EP 520 722, EP 566 226, EP 602 851, EP 635 507 and EP 837 063 disclose that certain quinazoline derivatives which bear a substituent at the 4-position and a substituent at the 5-, 6- and/or 7-position possess receptor tyrosine kinase inhibitory activity.

Patent application WO 00/20402 discloses certain quinazoline derivatives that carry a 3-carboxamidoanilino group at the 4-position on the quinazoline are cytokine inhibitors.

BRIEF SUMMARY OF THE INVENTION

We have now found that surprisingly certain quinazoline derivatives substituted at the 6-position with certain amide derivatives possess potent anti-tumour activity. The compounds of the present invention also possess high cellular potency. Many of the compounds according to the invention also possess favourable pharmacodynamic and physical properties, which may provide advantages in, for example, the formulation and delivery of the compound to patients. Furthermore, some of the compounds of the invention are inactive or only weakly active in the hERG assay described herein.

Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGFR receptor tyrosine kinase.

Generally the compounds of the present invention possess potent inhibitory activity against the erbB receptor tyrosine kinase family, for example by inhibition of EGFR and/or erbB2 and/or erbB4 receptor tyrosine kinases, whilst possessing less potent inhibitory activity against other kinases. Furthermore, generally the compounds of the present invention possess substantially better potency against the EGFR tyrosine kinase over that of the erbB2 tyrosine kinase. Accordingly, it may be possible to administer a compound according to the present invention at a dose that is sufficient to inhibit EGFR tyrosine kinase whilst having no significant effect upon erbB2 (or other) tyrosine kinases. The selective inhibition provided by the compounds according to the present invention may provide treatments for conditions mediated by EGFR tyrosine kinase, whilst reducing undesirable side effects that may be associated with the inhibition of other tyrosine kinases.

BRIEF DESCRIPTION OF DRAWINGS

Not Applicable

DETAILED DESCRIPTION OF THE INVENTION

According to a first aspect of the invention there is provided a quinazoline derivative of the formula I:

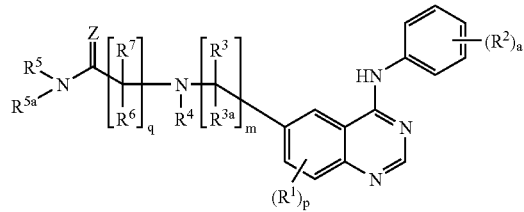

I wherein:
p is 1 or 2;
each $R^1$, which may be the same or different, is selected from hydrogen, hydroxy, (1-6C)alkoxy, (2-6C)alkenyloxy, (2-6C)alkynyloxy, or from a group of the formula:

$Q^1$—$X^1$— wherein $X^1$ is a direct bond or is O, and $Q^1$ is (3-7C) cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O, S, SO, $SO_2$, $N(R^8)$, CO, $CH(OR^8)$, $CON(R^8)$, $N(R^8)CO$, $SO_2N(R^8)$, $N(R^8)SO_2$, CH=CH and C≡C wherein $R^8$ is hydrogen or (1-6C)alkyl, and wherein any $CH_2$=CH— or HC≡C— group within a $R^1$ substituent optionally bears at the terminal $CH_2$= or HC= position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^2—X^2—$$

wherein $X^2$ is a direct bond or is selected from CO and $N(R^9)CO$, wherein $R^9$ is hydrogen or (1-6C)alkyl, and $Q^2$ is heterocyclyl or heterocyclyl-(1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, cyano, amino, carboxy, carbamoyl, sulfamoyl, oxo, thioxo, formyl, (1-6C)alkoxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$—X^3—Q^3$$

wherein $X^3$ is a direct bond or is selected from O, S, SO, $SO_2$, $N(R^{10})$, CO, $CH(OR^{10})$, $CON(R^{10})$, $N(R^{10})CO$, $SO_2N(R^{10})$, $N(R^{10})SO_2$, $C(R^{10})_2O$, $C(R^{10})_2S$ and $C(R^{10})_2N(R^{10})$, wherein $R^{10}$ is hydrogen or (1-6C)alkyl, and $Q^3$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein any heterocyclyl group within a substituent on $R^1$ optionally bears one or more (for example 1, 2 or 3) $R^{11}$ substituents, which may be the same or different, and wherein any heterocyclyl group within a substituent on $R^1$ optionally bears 1 or 2 oxo or thioxo substituents;

a is 1, 2, 3, 4 or 5;

each $R^2$, which may be the same or different, is selected from halogeno, cyano, nitro, hydroxy, amino, carboxy, carbamoyl, sulfamoyl, trifluoromethyl, trifluoromethoxy, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino and a group of the formula:

$$—X^4—R^{12}$$

wherein $X^4$ is a direct bond or is selected from O and $N(R^{13})$, wherein $R^{13}$ is hydrogen or (1-6C)alkyl, and $R^{12}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl;

m is 1 or 2;

each of $R^3$ and $R^{3a}$, which may be the same or different, is selected from hydrogen and (1-6C)alkyl, or $R^3$ and $R^{3a}$ together with the carbon atom to which they are attached form a (3-7C)cycloalkyl ring, and wherein any $R^3$ or $R^{3a}$ optionally bears on carbon one or more (for example 1, 2 or 3) $R^{14}$ substituents, which may be the same or different;

$R^4$ is selected from is selected from hydrogen, (1-6C)alkyl, (2-6C)alkenyl, (2-6C)alkynyl, carbamoyl, N-(1-6C)alkylcarbamoyl, N,N-di-[(1-6C)alkyl]carbamoyl, (2-6C)alkanoyl, (1-6C)alkoxycarbonyl and (1-6C)alkylsulfonyl, and wherein a $R^4$ substituent optionally bears on carbon one or more (for example 1, 2 or 3) $R^{15}$ substituents, which may be the same or different;

$R^5$ and $R^{5a}$, which may be the same or different, is selected from hydrogen, (1-4C)alkyl, (2-4C)alkenyl, (2-4C)alkynyl, (3-7C)cycloalkyl, (3-7C)cycloalkyl-(1-4C)alkyl, (3-7C)cycloalkenyl, (3-7C)cycloalkenyl-(1-4C)alkyl, heterocyclyl and heterocyclyl-(1-4C)alkyl, and wherein and wherein any $CH_2$ or $CH_3$, other than a $CH_2$ group within a heterocyclyl ring, within a $R^5$ or $R^{5a}$ substituent optionally bears on each said $CH_2$ or $CH_3$ one or more $R^{16}$ substituents, which may be the same or different, and wherein any heterocyclyl group within a substituent on $R^5$ or $R^{5a}$ optionally bears one or more (for example 1, 2 or 3) substituents, which may be the same or different, selected from halogeno, (1-4C)alkyl, (2-4C)alkanoyl, hydroxy-(2-4C)alkanoyl, (1-4C)alkoxy-(2-4C)alkanoyl and (1-4C)alkylsulfonyl, and wherein any heterocyclyl group within a $R^5$ or $R^{5a}$ substituent optionally bears 1 or 2 oxo or thioxo substituents, or $R^5$ and $R^{5a}$ together with the nitrogen atom to which they are attached form a heterocyclyl group, which group optionally bears one or more substituents (for example 1, 2 or 3), which may be the same or different, selected from halogeno, (1-4C)alkyl, (2-4C)alkanoyl, hydroxy-(2-4C)alkanoyl, (1-4C)alkoxy-(2-4C)alkanoyl and (1-4C)alkylsulfonyl, and wherein any heterocyclyl group formed by $R^5$ and $R^{5a}$ together with the nitrogen atom to which they are attached, optionally bears 1 or 2 oxo or thioxo substituents;

Z is O or S;

q is 1 or 2;

each $R^6$, which may be the same or different, is selected from hydrogen, (1-6C)alkyl, (2-6C)alkenyl, and (2-6C)alkynyl, and wherein $R^6$ optionally bears on carbon one or more (for example 1, 2 or 3) $R^{17}$ substituents, which may be the same or different;

each $R^7$, which may be the same or different, is selected from hydrogen, (1-6C)alkyl, (2-6C)alkenyl, (2-6C)alkynyl, aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl and heterocyclyl-(1-6C)alkyl, provided that when $R^7$ is heterocyclyl or heteroaryl and q is 1, $R^7$ is linked to the carbon carrying $R^6$ and the $R^{5a}R^5NC(Z)$ group by a ring carbon, and wherein adjacent carbon atoms in any (2-6C)alkylene chain within a $R^7$ substituent are optionally separated by the insertion into the chain of a group selected from O, S, SO, $SO_2$, $N(R^{18})$, CO, $CH(OR^{18})$, $CON(R^{18})$, $N(R^{18})CO$, $SO_2N(R^{18})$, $N(R^{18})SO_2$, CH=CH and C≡C wherein $R^{18}$ is hydrogen or (1-6C)alkyl, and wherein any $CH_2$=CH— or HC≡C— group within a $R^7$ substituent optionally bears at the terminal $CH_2$= or HC≡position a substituent selected from halogeno, carboxy, carbamoyl, (1-6C)alkoxycarbonyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^4—X^5—$$

wherein $X^5$ is a direct bond or is selected from CO and $N(R^{19})CO$, wherein $R^{19}$ is hydrogen or (1-6C)alkyl, and $Q^4$ is aryl, aryl-(1-6C)alkyl, heteroaryl, heteroaryl-(1-6C)alkyl, heterocyclyl or heterocyclyl-(1-6C)alkyl, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, carboxy, carbamoyl, sulfamoyl, oxo, thioxo, formyl, (1-6C)alkoxy, (1-6C)alkylthio, (1-6C)alkylsulfinyl, (1-6C)alkylsulfonyl, $NR^{32}R^{33}$, (1-6C)alkoxycarbonyl, $C(O)NR^{34}R^{35}$, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$—X^6—Q^5$$

wherein $X^6$ is a direct bond or is selected from O, S, SO, $SO_2$, $N(R^{20})$, CO, $CH(OR^{20})$, $CON(R^{10})$, $N(R^{20})CO$, $SO_2N(R^{20})$, $N(R^{20})SO_2$, $C(R^{20})_2O$, $C(R^{20})_2S$ and $N(R^{20})C(R^{20})_2$, wherein $R^{20}$ is hydrogen or (1-6C)alkyl, and $Q^5$ is aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl or heterocyclyl-(1-6C)alkyl, wherein each of $R^{32}$, $R^{33}$, $R^{34}$ and $R^{35}$, which may be the same or different, is selected from hydrogen (1-6C)alkyl, (2-6C)alkenyl and (2-6C)alkynyl, and wherein any of $R^{32}$, $R^{33}$, $R^{34}$ and $R^{35}$ optionally bears on carbon one or more (for example 1, 2 or 3) $R^{36}$ substituents, which may be the same or different, and wherein any aryl, heteroaryl or heterocyclyl group within a substituent on $R^7$ optionally bears one or more (for example 1, 2 or 3) $R^{21}$ substituents, which may be the same or different, and wherein any heterocyclyl group within a $R^7$ substituent optionally bears 1 or 2 oxo or thioxo substituents;

or $R^6$ and $R^7$ together with the carbon atom to which they are attached form a (3-7C)cycloalkyl, (3-7C)cycloalkenyl or heterocyclyl group, which group optionally bears one or more (for example 1, 2 or 3) $R^{22}$ substituents, which may be the same or different, and wherein any heterocyclyl group formed by $R^6$ and $R^7$ together with the carbon atom to which they are attached, optionally bears 1 or 2 oxo or thioxo substituents;

or $R^7$ and the group $R^{5a}R^5NC(Z)$ together with the carbon atom to which they are attached form a heterocyclyl group, which group optionally bears one or more (for example 1, 2 or 3) $R^{23}$ substituents, which may be the same or different, or $R^4$ and the group $R^{5a}R^5NC(Z)$ together with the atoms to which they are attached form a heterocyclyl group, which group optionally bears one or more (for example 1, 2 or 3) $R^{24}$ substituents, which may be the same or different;

each $R^{11}$, $R^{21}$, $R^{22}$, $R^{23}$ and $R^{24}$, which may be the same or different, is selected from halogeno, trifluoromethyl, cyano, nitro, hydroxy, amino, carboxy, carbamoyl, formyl, mercapto, sulfamoyl, (1-6C)alkyl, (2-8C)alkenyl, (2-8C)alkynyl, (1-6C)alkoxy, (2-6C)alkenyloxy, (2-6C)alkynyloxy, (1-6C) alkylthio, (1-6C)alkylsulfinyl, (1-6C)alkylsulfonyl, (1-6C) alkylamino, di-[(1-6C)alkyl]amino, (1-6C)alkoxycarbonyl, N-(1-6C)alkylcarbamoyl, N,N-di-[(1-6C)alkyl]carbamoyl, N-(1-6C)alkylsulfamoyl, N,N-di-[(1-6C)alkyl]sulfamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, a group of the formula:

$$—X^7—R^{25}$$

wherein $X^7$ is a direct bond or is selected from O, $N(R^{26})$ and C(O), wherein $R^{26}$ is hydrogen or (1-6C)alkyl, and $R^{25}$ is halogeno-(1-6C)alkyl, hydroxy-(1-6C)alkyl, carboxy-(1-6C) alkyl, (1-6C)alkoxy-(1-6C)alkyl, cyano-(1-6C)alkyl, amino-(1-6C)alkyl, (1-6C)alkylamino-(1-6C)alkyl, di-[(1-6C) alkyl]amino-(1-6C)alkyl, (2-6C)alkanoylamino-(1-6C) alkyl, N-(1-6C)alkyl-(2-6C)alkanoylamino-(1-6C)alkyl, (1-6C)alkoxycarbonylamino-(1-6C)alkyl, carbamoyl-(1-6C) alkyl, N-(1-6C)alkylcarbamoyl-(1-6C)alkyl, N,N-di-[(1-6C) alkyl]carbamoyl-(1-6C)alkyl, (2-6C)alkanoyl-(1-6C)alkyl, (2-6C)alkanoyloxy-(1-6C)alkyl or (1-6C)alkoxycarbonyl-(1-6C)alkyl, and from a group of the formula:

$$—X^8—Q^6$$

wherein $X^8$ is a direct bond or is selected from O, $SO_2$, $N(R^{31})$ and CO, wherein $R^{31}$ is hydrogen or (1-6C)alkyl, and $Q^6$ is (3-7C)cycloalkyl, (3-7C)cycloalkyl-(1-6C)alkyl, heterocyclyl or heterocyclyl-(1-6C)alkyl, which optionally bears one or more (for example 1, 2 or 3) substituents, which may be the same or different selected from halogeno, hydroxy, (1-4C)alkyl and (1-4C)alkoxy, and wherein $R^{11}$, $R^{21}$, $R^{22}$, $R^{23}$ and $R^{24}$ optionally bears on carbon one or more (for example 1, 2 or 3) $R^{29}$ substituents, which may be the same or different;

each of $R^{14}$, $R^{15}$, $R^{16}$ and $R^{17}$, which may be the same or different, is selected from halogeno, hydroxy, cyano, (1-6C) alkoxy and $NR^{27}R^{28}$, wherein $R^{27}$ and $R^{28}$, which may be the same or different, are selected from hydrogen, formyl, (1-4C) alkyl, (2-4C)alkenyl, (2-4C)alkynyl and (2-4C)alkanoyl, and wherein any of $R^{14}$, $R^{15}$, $R^{16}$ and $R^{17}$ optionally bears on carbon one or more (for example 1, 2 or 3) $R^{30}$ substituents, which may be the same or different;

$R^{29}$, $R^{30}$ and $R^{36}$, which may be the same or different, are selected from halogeno, hydroxy, cyano, amino, methylamino, dimethylamino, methoxy, ethoxy, vinyl, allyl and ethynyl;

or a pharmaceutically acceptable salt thereof.

In an embodiment, there is provided a quinazoline derivative of the formula I wherein $R^1$, $R^2$, $R^3$, $R^{3a}$, $R^6$, $R^7$, Z, a, p and m have any of the meanings defined hereinbefore;

q is 1;

$R^{5a}$ is hydrogen; and $R^5$ is selected from hydrogen, (1-4C)alkyl, (2-4C)alkenyl, and (2-4C)alkynyl, and wherein $R^5$ optionally bears on carbon one or more $R^{16}$ substituents, which may be the same or different, wherein $R^{16}$ is as hereinbefore defined;

or a pharmaceutically acceptable salt thereof.

In this specification the generic term "alkyl" includes both straight-chain and branched-chain alkyl groups such as propyl, isopropyl and tert-butyl, and (3-7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl]amino includes dimethylamino, diethylamino, N-cyclobutyl-N-methylamino and N-cyclohexyl-N-ethylamino.

It is to be understood that, insofar as certain of the compounds of formula I defined above may exist in optically active or racemic forms by virtue of one or more asymmetric carbon atoms, or as geometric isomers (E- and Z-isomers). The invention includes in its definition any such optically active or racemic form or geometric isomers which possesses the above-mentioned activity. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ratio 50:50. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above and hereinafter include those set out below.

A suitable value for any substituent when it is (3-7C)cycloalkyl or for a (3-7C)cycloalkyl group within a substituent is, for example, cyclopropyl, cyclobutyl, cyclopentyl, cyclohexyl, cycloheptyl or bicyclo[2.2.1]heptyl and a suitable value for a substituent when it is (3-7C)cycloalkenyl or for a (3-7C)cycloalkenyl group within a substituent is, for example, cyclobutenyl, cyclopentenyl, cyclohexenyl or cycloheptenyl.

Were reference is made herein to, for example, $R^3$ and $R^{3a}$ together with the carbon atom to which they are attached forming a (3-7C)cycloalkyl ring herein, the ring so formed is a (3-7C)cycloalkylidene group, for example a cyclopropylidene group of the formula:

wherein * represent the bonds from the cyclopropylidene group to the quinazoline and the group $NR^4$.

A suitable value for "aryl" herein is aromatic hydrocarbon rings such as phenyl or naphthyl.

A suitable value for "heteroaryl" herein is an aromatic 5- or 6-membered monocyclic ring or an aromatic 9- or 10-membered bicyclic ring with up to five ring heteroatoms selected from oxygen, nitrogen and sulfur, which may, unless otherwise specified, be carbon or nitrogen linked. Particularly "heteroaryl" refers to an aromatic 5 or 6-membered monocyclic ring with 1, 2 or 3 ring heteroatoms selected from nitrogen, sulfur or oxygen, which may, unless otherwise specified, be carbon or nitrogen linked. Examples of suitable values of heteroaryl rings include for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, dibenzofuranyl, indolyl, benzothienyl, dibenzothienyl, benzoxazolyl, benzimidazolyl, benzothiazolyl, indazolyl, furazanyl, benzofurazanyl, quinolyl, isoquinolyl, quinazolinyl, quinoxalinyl, cinnolinyl or naphthyridinyl.

A suitable value for the term "heterocyclyl" used herein is a saturated (i.e. ring systems with the maximum degree of saturation) or partially saturated (i.e. ring systems retaining some, but not the full, degree of unsaturation) 3 to 10 membered monocyclic or bicyclic ring with up to five heteroatoms selected from oxygen, nitrogen and sulfur, which, unless specified otherwise, may be carbon or nitrogen linked. A particular heterocyclyl group includes for example a saturated or partially saturated 4-, 5- or 6-membered monocyclic rings or a saturated or partially saturated 9- or 10-membered bicyclic ring with up to five ring heteroatoms selected from oxygen, nitrogen and sulfur, which may, unless otherwise specified, be carbon or nitrogen linked. A further particular heterocyclyl group is a saturated or partially saturated 4-, 5 or 6-membered monocyclic ring with 1 or 2 ring heteroatoms selected from nitrogen, sulfur or oxygen, which may, unless otherwise specified, be carbon or nitrogen linked. Examples of suitable values of heterocyclyl groups include oxiranyl, oxetanyl, azetidinyl, tetrahydrofuranyl, 1,3-dioxolanyl, tetrahydropyranyl, 1,4-dioxanyl, oxepanyl, pyrrolinyl, pyrrolidinyl, morpholinyl, thiomorpholinyl, 1,1-dioxothiomorpholinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, decahydroisoquinolinyl, decahydroquinolinyl, 2,3-dihydrobenzofuranyl, indolinyl or isoindolinyl, particularly tetrahydrofuranyl, tetrahydropyranyl, pyrrolidinyl, morpholinyl, 1,4-oxazepanyl, thiomorpholinyl 1,1-dioxothiomorpholinyl, piperidinyl or piperazinyl, more particularly tetrahydrofuran-3-yl, tetrahydropyran-4-yl, tetrahydrothien-3-yl, tetrahydrothiopyran-4-yl, pyrrolidin-1-yl pyrrolidin-2-yl, pyrrolidin-3-yl, morpholino, morpholin-2-yl, piperidino, piperidin-4-yl, piperidin-3-yl, piperidin-2-yl or piperazin-1-yl. A nitrogen or sulfur atom within a heterocyclyl group may be oxidized to give the corresponding N or S oxide, for example 1,1-dioxotetrahydrothienyl, 1-oxotetrahydrothienyl, 1,1-dioxotetrahydrothiopyranyl or 1-oxotetrahydrothiopyranyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for "heterocyclyl-(1-6C)alkyl" as used herein is, for example, heterocyclylmethyl, 2-heterocyclylethyl and 3-heterocyclylpropyl. The invention comprises corresponding suitable values for substituents when, for example, rather than a heterocyclyl-(1-6C)alkyl group, an heteroaryl-(1-6C)alkyl, an aryl-(1-6C)alkyl group, an (3-7C)cycloalkyl-(1-6C)alkyl or (3-7C)cycloalkenyl-(1-6C)alkyl is present.

When $R^5$ and $R^{5a}$ together with the nitrogen atom to which they are attached form a heterocyclyl group, the group so formed is a saturated (i.e. ring systems with the maximum degree of saturation) or partially saturated (i.e. ring systems retaining some, but not the full, degree of unsaturation) 4 to 7 membered monocyclic ring which ring contains 1 nitrogen heteroatom and optionally 1, 2 or 3 additional heteroatoms selected from oxygen, nitrogen and sulfur, which ring is linked to the group C=Z in formula I by a ring nitrogen. Examples of heterocyclyl groups formed by $R^5$ and $R^{5a}$ together with the nitrogen atom to which they are attached include the nitrogen containing monocyclic heterocyclyl groups mentioned above which contain at least 1 nitrogen heteroatom, for example azetidin-1-yl, pyrrolidin-1-yl, 2-pyrrolin-1-yl, 3-pyrrolin-1-yl, piperidino, piperazin-1-yl, morpholino, homopiperidino. The heterocyclyl rings so formed may be substituted as defined hereinbefore.

When $R^6$ and $R^7$ together with the carbon atom to which they are attached form a (3-7C)cycloalkyl, (3-7C)cycloalkenyl or heterocyclyl group, the ring so formed is linked to the $NR^4$ group in formula I by a ring carbon atom, and the amide or thioamide group $R^{5a}R^5NC(Z)$ is attached to the same ring carbon atom. For example when $R^6$ and $R^7$ together with the carbon atom to which they are attached form a (3-7C)cycloalkyl group the substituent at the 6-position on the quinazoline ring so formed in formula I when q is 1 and $R^{5a}$ is hydrogen is of the formula:

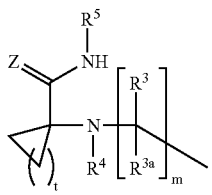

wherein t is 1 to 5 and the (3-7C)cycloalkyl group is optionally substituted as defined above. Similarly, when $R^6$ and $R^7$ together with the carbon atom to which they are attached form a heterocyclyl group the substituent at the 6-position on the quinazoline ring in formula I so formed is when q is 1 and $R^{5a}$ is hydrogen of the formula:

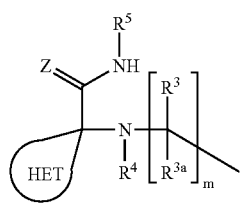

wherein HET is a heterocyclyl group. Examples of suitable heterocyclyl groups are as defined above and the heterocyclyl group HET is optionally substituted by one or more $R^{22}$ substituents as defined above. Particular values for HET include 4, 5 or 6 membered non-aromatic monocyclic heterocyclyl rings containing 1, 2 or 3 heteroatoms selected from O, S and N, for example azetidinyl, pyrrolidinyl, piperidinyl or tetrahydropyranyl.

When $R^7$ and the group $R^{5a}R^5NC(Z)$ together with the carbon atom to which they are attached form a heterocyclyl group, the amide or thioamide group $[NR^aC(Z)]$ forms part of the ring structure of the heterocyclyl group so formed, which heterocyclyl group is linked to $NR^4$ by a ring carbon atom. For example when $R^7$ and the group $R^{5a}R^5NC(Z)$ together with the carbon atom to which they are attached form a heterocyclyl group, $R^{5a}$ is hydrogen and q is 1, the substituent at the 6-position in formula I so formed is of the formula Ia:

Ia

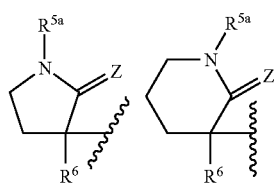

wherein A is a heterocyclyl group incorporating the group NHC(Z) in the ring, and wherein the heterocyclyl group A is optionally substituted by one or more $R^{23}$ as defined hereinbefore. In one embodiment of the invention, the NH group in the heterocyclyl group A is unsubstituted. The heterocyclyl group A is a saturated (i.e. ring systems with the maximum degree of saturation) or partially saturated (i.e. ring systems retaining some, but not the full, degree of unsaturation) 4 to 10 membered monocyclic or bicyclic ring with up to five heteroatoms selected from oxygen, nitrogen and sulfur. Examples of heterocyclyl groups which may be formed by $R^7$ and the group $R^{5a}R^5NC(Z)$ together with the carbon atom to which they are attached include:

wherein the rings above optionally bear on a ring carbon atom one or more $R^{23}$ as defined hereinbefore and wherein ～ represents the attachment point to the group $[C(R^6)(R^7)]_{q-1}N(R^4)$ in formula I. In an embodiment $R^{5a}$ in the ring is hydrogen.

When $R^4$ and the group $R^{5a}R^5NC(Z)$ together with the atoms to which they are attached form a heterocyclyl group, the ring so formed incorporates the nitrogen of the $NR^4$ group and the $NR^{5a}C(Z)$ group into the ring structure. The heterocyclyl group so formed A is a saturated (i.e. ring systems with the maximum degree of saturation) or partially saturated (i.e. ring systems retaining some, but not the full, degree of unsaturation) 4 to 10 (such as 5 to 10) membered monocyclic or bicyclic ring with up to five heteroatoms selected from oxygen, nitrogen and sulfur, which ring optionally bears one or more $R^{24}$. In an embodiment $R^{5a}$ in the $NR^{5a}C(Z)$ group in the ring so formed is hydrogen such that the ring so formed contains a group in the ring of the formula $R^5NHC(Z)$.

For example when $R^4$ and the group $R^{5a}R^5NC(Z)$ together with the atoms to which they are attached form a heterocyclyl group the substituent at the 6-position in formula I so formed when q is 1 and $R^{5a}$ is hydrogen is of the formula Ib:

Ib

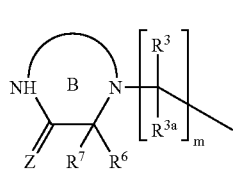

wherein the heterocyclyl group B optionally bears one or more $R^{24}$ as hereinbefore defined. In an embodiment the NH group in heterocyclyl B is unsubstituted.

Suitable values for any of the substituents herein (for example one of the 'R' groups) or for various groups within such substituent include:— for halogeno fluoro, chloro, bromo and iodo;
for (1-6C)alkyl: methyl, ethyl, propyl, isopropyl and tert-butyl;
for (2-8C)alkenyl: vinyl, isopropenyl, allyl and but-2-enyl;
for (2-8C)alkynyl: ethynyl, 2-propynyl and but-2-ynyl;
for (1-6C)alkoxy: methoxy, ethoxy, propoxy, isopropoxy and butoxy;
for (2-6C)alkenyloxy: vinyloxy and allyloxy;
for (2-6C)alkynyloxy: ethynyloxy and 2-propynyloxy;
for (1-6C)alkylthio: methylthio, ethylthio and propylthio;
for (1-6C)alkylsulfinyl: methylsulfinyl and ethylsulfinyl;
for (1-6C)alkylsulfonyl: methylsulfonyl and ethylsulfonyl;
for (1-6C)alkylamino: methylamino, ethylamino, propylamino, isopropylamino and butylamino;
for di-[(1-6C)alkyl]amino: dimethylamino, diethylamino, N-ethyl-N-methylamino and diisopropylamino;
for (1-6C)alkoxycarbonyl: methoxycarbonyl, ethoxycarbonyl, propoxycarbonyl and tert-butoxycarbonyl;
for N-(1-6C)alkylcarbamoyl: N-methylcarbamoyl, N-ethylcarbamoyl and N-propylcarbamoyl;
for N,N-di-[(1-6C)alkyl]carbamoyl: N,N-dimethylcarbamoyl, N-ethyl-N-methylcarbamoyl and N,N-diethylcarbamoyl;
for (2-6C)alkanoyl: acetyl, propionyl, butyryl and isobuyryl;
for (2-6C)alkanoyloxy: acetoxy and propionyloxy;
for (2-6C)alkanoylamino: acetamido and propionamido;
for N-(1-6C)alkyl-(2-6C)alkanoylamino: N-methylacetamido and N-methylpropionamido;
for N-(1-6C)alkylsulfamoyl: N-methylsulfamoyl and N-ethylsulfamoyl;
for N,N-di-[(1-6C)alkyl]sulfamoyl: N,N-dimethylsulfamoyl;
for (1-6C)alkanesulfonylamino: methanesulfonylamino and ethanesulfonylamino;
for N-(1-6C)alkyl-(1-6C)alkanesulfonylamino: N-methylmethanesulfonylamino and N-methylethanesulfonylamino;
for amino-(1-6C)alkyl: aminomethyl, 2-aminoethyl, 1-aminoethyl and 3-aminopropyl;
for (1-6C)alkylamino-(1-6C)alkyl: methylaminomethyl, ethylaminomethyl, 1-methylaminoethyl, 2-methylaminoethyl, 2-ethylaminoethyl and 3-methylaminopropyl;
for di-[(1-6C)alkyl]amino-(1-6C)alkyl: dimethylaminomethyl, diethylaminomethyl, 1-dimethylaminoethyl, 2-dimethylaminoethyl and 3-dimethylaminopropyl;
for halogeno-(1-6C)alkyl: chloromethyl, 2-chloroethyl, 1-chloroethyl and 3-chloropropyl;
for hydroxy-(1-6C)alkyl: hydroxymethyl, 2-hydroxyethyl, 1-hydroxyethyl and 3-hydroxypropyl;
for (1-6C)alkoxy-(1-6C)alkyl: methoxymethyl, ethoxymethyl, 1-methoxyethyl, 2-methoxyethyl, 2-ethoxyethyl and 3-methoxypropyl;
for carboxy-(1-6C)alkyl: carboxymethyl and 2-carboxyethyl;
for cyano-(1-6C)alkyl: cyanomethyl, 2-cyanoethyl, 1-cyanoethyl and 3-cyanopropyl;
for (1-6C)alkylthio-(1-6C)alkyl: methylthiomethyl, ethylthiomethyl, 2-methylthioethyl, 1-methylthioethyl and 3-methylthiopropyl;

for (1-6C)alkylsulfinyl-(1-6C)alkyl: methylsulfinylmethyl, ethylsulfinylmethyl, 2-methylsulfinylethyl, 1-methylsulfinylethyl and 3-methylsulfinylpropyl;
for (1-6C)alkylsulfonyl-(1-6C)alkyl: methylsulfonylmethyl, ethylsulfonylmethyl, 2-methylsulfonylethyl, 1-methylsulfonylethyl and 3-methylsulfonylpropyl;
for (2-6C)alkanoylamino-(1-6C)alkyl: acetamidomethyl, propionamidomethyl and 2-acetamidoethyl;
for N-(1-6C)alkyl-(2-6C)alkanoylamino-(1-6C)alkyl: N-methylacetamidomethyl, 2-(N-methylacetamido)ethyl and 2-(N-methylpropionamido)ethyl;
for (1-6C)alkoxycarbonylamino-(1-6C)alkyl: methoxycarbonylaminomethyl, ethoxycarbonylaminomethyl, tert-butoxycarbonylaminomethyl and 2-methoxycarbonylaminoethyl;
(2-6C)alkanoyloxy-(1-6C)alkyl: acetoxymethyl, 2-acetoxyethyl and 2-propionyloxyethyl;
for carbamoyl-(1-6C)alkyl: carbamoylmethyl, 1-carbamoylethyl, 2-carbamoylethyl and 3-carbamoylpropyl;
for (2-6C)alkanoyl-(1-6C)alkyl: acetylmethyl and 2-acetylethyl;
for N-(1-6C)alkylcarbamoyl-(1-6C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;
for N,N-di[(1-6C)alkyl]carbamoyl-(1-6C)alkyl: N,N-dimethylcarbamoylmethyl, N,N-diethylcarbamoylmethyl, 2-(N,N-dimethylcarbamoyl)ethyl, and 3-(N,N-dimethylcarbamoyl)propyl;
for hydroxy-(2-6C)alkanoyl: hydroxyacetyl, 3-hydroxypropionyl and 2-hydroxypropionyl; and
for (1-6C)alkoxy(2-6C)alkanoyl: methoxyacetyl, ethoxyacetyl, isopropyloxyacetyl, 2-methoxypropionyl and 3-methoxypropionyl.

As will be understood, references herein to the anilino group in the quinazoline of formula I refer to the group located at the 4-position of the quinazoline ring of the formula:

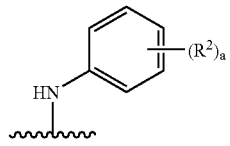

When herein optional substituents are chosen from "one or more" groups it is to be understood that this definition includes all the substituents being chosen from one of the specified groups or the substituents being chosen from two or more of the specified groups.

When, as defined hereinbefore a $CH_2\!=\!CH\!-$ or $HC\!\equiv\!C\!-$ group within a $R^7$ substituent bears at the terminal $CH_2\!=$ or $HC\!\equiv$ position a substituent of the formula $Q^4\!-\!X^5\!-$ and $X^5$ is $N(R^{19})CO$, the $N(R^{19})$ group is attached to $Q^4$ and the carbonyl group is attached at the terminal $CH_2\!=$ or $HC\!\equiv$ group. The same convention is applied to other groups defined herein. For example, when a $CH_3$, within a $R^7$ substituent is substituted by a group of the formula $-X^6\!-\!Q^5$ and $X^6$ is $C(R^{20})_2O$, the $C(R^{20})_2$ group is attached to the carbon of the $CH_3$ group to give a $CH_2\ C(R^{20})_2$ group and the oxygen is attached to the $Q^5$ group to give a $CH_2\ C(R^{20})_2OQ^5$ group.

As defined hereinbefore, adjacent carbon atoms in any (2-6C)alkylene chain within, for example, a $R^1$ substituent may be optionally separated by the insertion into the chain of a group such as O, CON($R^8$), N($R^8$) or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido) ethoxy group. It is to be understood that the term (2-6C) alkylene chain refers to any $CH_2CH_2$ group within, for example, an $R^1$ or $R^7$ substituent and includes, for example alkylene chains within a (1-6C)alkyl, (1-6C)alkoxy, (2-6C) alkenyl, (2-6C)alkenyloxy, (2-6C)alkynyl and (2-6C)alkynyloxy group. For example the insertion of a N($CH_3$) group between the third and fourth carbon atoms in a hex-5-enyloxy group in $R^1$ gives rise to a 3-(N-methyl-N-allylamino)propoxy group.

When, as defined hereinbefore, any $CH_2$=CH— or HC≡C— group within, for example a $R^1$ substituent optionally bears at the terminal $CH_2$= or HC≡ position a substituent such as a group of the formula $Q^2$—$X^2$— wherein $X^2$ is, for example, NHCO and $Q^2$ is a heterocyclyl-(1-6C)alkyl group, suitable $R^1$ substituents so formed include, for example, N-[heterocyclyl-(1-6C)alkyl]carbamoylvinyl groups such as N-(2-pyrrolidin-1-ylethyl)carbamoylvinyl or N-[heterocyclyl-(1-6C)alkyl]carbamoylethynyl groups such as N-(2-pyrrolidin-1-ylethyl)carbamoylethynyl.

When reference is made herein to a $CH_2$ or $CH_3$ group optionally bearing on each said $CH_2$ or $CH_3$ group one or more halogeno or (1-6C)alkyl substituents, there are suitably 1 or 2 halogeno or (1-6C)alkyl substituents present on each said $CH_2$ group and there are suitably 1, 2 or 3 such substituents present on each said $CH_3$ group.

Where reference is made herein to any $CH_2$ or $CH_3$ group optionally bearing on each said $CH_2$ or $CH_3$ group a substituent as defined herein, suitable substituents so formed include, for example, hydroxy-substituted heterocyclyl-(1-6C)alkoxy groups such as 2-hydroxy-3-piperidinopropoxy and 2-hydroxy-3-morpholinopropoxy, hydroxy-substituted heterocyclyl-(1-6C)alkylamino groups such as 2-hydroxy-3-piperidinopropylamino and 2-hydroxy-3-morpholinopropylamino, and hydroxy-substituted (2-6C)alkanoyl groups such as hydroxyacetyl, 2-hydroxypropionyl and 2-hydroxybutyryl.

Where reference is made herein to "any $CH_2$ or $CH_3$ group, other than a $CH_2$ group within a heterocyclyl group, optionally bearing a substituent", it is to be understood that such a statement is present only to distinguish between optional substituents that may be present on, for example, a $CH_3$ group in an alkyl group from substituents that may be present on carbon atoms of a heterocyclyl group. Accordingly, it is to be understood, that this statement does not exclude other substituents being present on ring carbon atoms in a heterocyclyl group when it is stated herein that said heterocyclyl group may also optionally bear one or more substituents. For example, if $R^1$ is 3-(pyrrolidin-1-yl)propoxy and herein it is stated that a $CH_2$ or $CH_3$ group within, for example, a $R^1$ substituent, other than a $CH_2$ group within a heterocyclyl group, optionally bears a hydroxy substituent, and that any heterocyclyl group within $R^1$ optionally bears an alkyl substituent, then the optional hydroxy substituent may be present on a $CH_2$ of the propoxy group to give for example a 2-hydroxy-3-(pyrrolidin-1-yl)propoxy group. Similarly an alkyl group such as methyl may be present on the pyrrolidinyl ring to give, for example, a 3-(3-methylpyrrolidin-1-yl)propoxy group. Equally, the propoxy group may be substituted by a hydroxy group and the pyrrolidinyl ring may be substituted by a methyl group to give, for example, a 2-hydroxy-3-(3-methylpyrrolidin-1-yl)propoxy group.

For the avoidance of doubt, when herein reference is made to a $CH_2$ optionally bearing an oxo substituent, a $CH_2$ group is substituted by 0 to give a C(O) group.

The quinazoline derivative of formula I is unsubstituted at the 2-position on the quinazoline ring.

It is to be understood that certain compounds of the formula I may exist in solvated as well as unsolvated forms such as, for example, hydrated forms. It is to be understood that the invention encompasses all such solvated forms which exhibit an inhibitory effect on an erbB receptor tyrosine kinase.

It is also to be understood that certain compounds of the formula I may exhibit polymorphism, and that the invention encompasses all such forms which exhibit an inhibitory effect on an erbB receptor tyrosine kinase.

It is also to be understood that the invention relates to all tautomeric forms of the compounds of the formula I forms which exhibit an inhibitory effect on an erbB receptor tyrosine kinase.

A suitable pharmaceutically-acceptable salt of a compound of the formula I is, for example, an acid-addition salt of a compound of the formula I, for example an acid-addition salt with an inorganic or organic acid such as hydrochloric, hydrobromic, sulfuric, trifluoroacetic, citric or maleic acid; or, for example, a salt of a compound of the formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinazoline derivatives of the formula I, or pharmaceutically-acceptable salts thereof, wherein, unless otherwise stated, each of $R^1$, $R^2$, $R^3$, $R^{3a}$, $R^4$, $R^5$, $R^{5a}$, $R^6$, $R^7$, a, m, p, q and Z has any of the meanings defined hereinbefore or in paragraphs (a) to (ccccc) hereinafter:—

(a) $R^1$ is selected from hydrogen, hydroxy, (1-6C)alkoxy, (2-6C)alkenyloxy, (2-6C)alkynyloxy, or from a group of the formula:

$Q^1$—$X^1$— wherein $X^1$ is a direct bond or is O, and $Q^1$ is (3-7C)cycloalkyl, (3-7C)cycloalkyl-(1-6C)alkyl, heterocyclyl or heterocyclyl-(1-6C)alkyl, and wherein adjacent carbon atoms in any (2-6C)alkylene chain within a $R^1$ substituent are optionally separated by the insertion into the chain of a group selected from O, N($R^8$), CON($R^8$), N($R^8$)CO, CH=CH and C≡C wherein $R^8$ is hydrogen or (1-6C)alkyl, and wherein any $CH_2$=CH— or HC≡C— group within a $R^1$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$Q^2$—$X^2$— wherein $X^3$ is a direct bond or is selected from CO and N($R^9$)CO, wherein $R^9$ is hydrogen or (1-6C)alkyl, and $Q^3$ is heterocyclyl or heterocyclyl-(1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)

alkylamino, di-[(1-6C)alkyl]amino, N-(1-6C)alkylcarbamoyl and N,N-di-[(1-6C)alkyl]carbamoyl, or from a group of the formula:

$$—X^3—Q^3$$

wherein $X^3$ is a direct bond or is selected from O, $N(R^{10})$, $CON(R^{10})$, $N(R^{10})CO$ and $C(R^{10})_2O$, wherein $R^{10}$ is hydrogen or (1-6C)alkyl, and $Q^3$ is heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, cyano, nitro, hydroxy, amino, carbamoyl, (1-6C)alkyl, (2-8C)alkenyl, (2-8C)alkynyl, (1-6C)alkoxy, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, or from a group of the formula:

$$—X^7—R^{25}$$

wherein $X^7$ is a direct bond or is selected from O and $N(R^{26})$, wherein $R^{26}$ is hydrogen or (1-6C)alkyl, and $R^{25}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl and N,N-di-[(1-6C)alkyl]carbamoyl-(1-6C)alkyl, and wherein any heterocyclyl group within a substituent on $R^1$ optionally bears 1 or 2 oxo substituents;

(b) $R^1$ is selected from hydrogen, hydroxy, (1-6C)alkoxy, (2-6C)alkenyloxy, (2-6C)alkynyloxy, or from a group of the formula:

$$Q^1—X^1—$$

wherein $X^1$ is a direct bond or is O, and $Q^1$ is heterocyclyl or heterocyclyl-(1-6C)alkyl, and wherein adjacent carbon atoms in any (2-6C)alkylene chain within a $R^1$ substituent are optionally separated by the insertion into the chain of a group selected from O, $N(R^8)$, $CON(R^8)$, $N(R^8)CO$, CH=CH and C≡C wherein $R^8$ is hydrogen or (1-6C)alkyl, and wherein any $CH_2$=CH— or HC≡C— group within a $R^1$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, N-(1-6C)alkylcarbamoyl and N,N-di-[(1-6C)alkyl]carbamoyl, or from a group of the formula:

$$—X^3—Q^3$$

wherein $X^3$ is a direct bond or is selected from O, $N(R^{10})$, $CON(R^{10})$, $N(R^{10})CO$ and $C(R^{10})_2O$, wherein $R^{10}$ is hydrogen or (1-6C)alkyl, and $Q^3$ is heterocyclyl or heterocyclyl-(1-6C)alkyl, and wherein any heterocyclyl group within a substituent on $R^1$ optionally bears 1, 2 or 3 substituents, which may be the same or different, selected from halogeno, trifluoromethyl, hydroxy, cyano, amino, carbamoyl, (1-6C)alkyl, (2-8C)alkenyl, (2-8C)alkynyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, or from a group of the formula:

$$—X^7—R^{25}$$

wherein $X^7$ is a direct bond or is selected from O, C(O) and $N(R^{26})$, wherein $R^{26}$ is hydrogen or (1-6C)alkyl, and $R^{25}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl and di-[(1-6C)alkyl]amino-(1-6C)alkyl, and wherein any heterocyclyl group within a substituent on $R^1$ optionally bears 1 or 2 oxo substituents;

(c) p is 1, $R^1$ is located at the 5- or 7-position (particularly the 7-position) and $R^1$ is selected from hydrogen, hydroxy, (1-6C)alkoxy, (2-6C)alkenyloxy and (2-6C)alkynyloxy, and wherein adjacent carbon atoms in any (2-6C)alkylene chain within a $R^1$ substituent are optionally separated by the insertion into the chain of a group selected from O, $N(R^8)$, $CON(R^8)$, $N(R^8)CO$, CH=CH and C≡C wherein $R^8$ is hydrogen or (1-6C)alkyl, and wherein any $CH_2$ or $CH_3$ group within a $R^1$ substituent optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, N-(1-6C)alkylcarbamoyl and N,N-di-[(1-6C)alkyl]carbamoyl;

(d) p is 1, $R^1$ is located at the 5- or 7-position (particularly the 7-position) and $R^1$ is selected from hydrogen, hydroxy, methoxy, ethoxy, propoxy, isopropyloxy, 2-hydroxyethoxy, 2-fluoroethoxy, cyclopropylmethoxy, 2-cyclopropylethoxy, vinyloxy, allyloxy, ethynyloxy, 2-propynyloxy, tetrahydrofuran-3-yloxy, tetrahydropyran-3-yloxy, tetrahydropyran-4-yloxy, tetrahydrofurfuryloxy, tetrahydrofuran-3-ylmethoxy, 2-(tetrahydrofuran-2-yl)ethoxy, 3-(tetrahydrofuran-2-yl)propoxy, 2-(tetrahydrofuran-3-yl)ethoxy, 3-(tetrahydrofuran-3-yl)propoxy, tetrahydropyranylmethoxy, 2-tetrahydropyranylethoxy, 3-tetrahydropyranylpropoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, pyrrolidin-1-yl, morpholino, piperidino and piperazin-1-yl, and wherein adjacent carbon atoms in any (2-6C)alkylene chain within a $R^1$ substituent are optionally separated by the insertion into the chain of a group selected from O, NH, $N(CH_3)$, CH=CH and C≡C (for example O, NH or $N(CH_3)$), and when $R^1$ is a vinyloxy, allyloxy, ethynyloxy or 2-propynyloxy group, the $R^1$ substituent optionally bears at the terminal $CH_2$= or HC≡ position a substituent selected from N-methylcarbamoyl, N-ethylcarbamoyl, N-propylcarbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$$Q^2—X^2—$$

wherein X² is a direct bond or is NHCO or N(CH₃)CO and Q² is pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any CH₂ group which is attached to 2 carbon atoms (other than a CH₂ group within a heterocyclyl ring) or any CH₃ group which is attached to a carbon atom within a R¹ substituent optionally bears on each said CH₂ or CH₃ group a substituent selected from hydroxy, amino, methoxy, ethoxy, methylsulfonyl, methylamino and dimethylamino, and wherein any heterocyclyl group within a substituent on R¹ optionally bears 1 or 2 substituents, which may be the same or different, selected from fluoro, chloro, trifluoromethyl, hydroxy, amino, methylamino, ethylamino, dimethylamino, diethylamino, carbamoyl, methyl, ethyl, n-propyl, isopropyl and methoxy, and any piperidin-3-ylmethyl, piperidin-4-ylmethyl, 2-piperazin-1-ylethylamino, 3-piperazin-1-ylpropylamino, or piperazin-1-yl group within a R¹ substituent is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, acetyl, hydroxyacetyl, methoxyacetyl, propionyl, 2-hydroxypropionyl, 2-methoxypropionyl, or methylsulfonyl, and wherein any heterocyclyl group within a substituent on R¹ optionally bears 1 or 2 oxo substituents;

(e) p is 1, R¹ is located at the 7-position and R¹ is selected from hydrogen, hydroxy, (1-6C)alkoxy, (3-7C)cycloalkyl-oxy and (3-7C)cycloalkyl-(1-6C)alkoxy, and wherein any CH₂ or CH₃ group within a R¹ substituent optionally bears on each said CH₂ or CH₃ group one or more halogeno or (1-6C)alkyl substituents, or a substituent selected from hydroxy, cyano, amino, carboxy, carbamoyl, sulfamoyl, oxo, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, N-(1-6C)alkylsulfamoyl and N,N-di-[(1-6C)alkyl]sulfamoyl, (1-6C)alkanesulfonylamino and N-(1-6C)alkyl-(1-6C)alkanesulfonylamino;

(f) p is 1, R¹ is located at the 7-position and R¹ is selected from hydrogen, hydroxy, (1-6C)alkoxy, (3-7C)cycloalkyl-oxy and (3-7C)cycloalkyl-(1-6C)alkoxy, and wherein any CH₂ or CH₃ group within a R¹ substituent optionally bears on each said CH₂ or CH₃ group one or more fluoro or chloro substituents, or a substituent selected from hydroxy, amino, (1-4C)alkoxy, (1-4C)alkylamino and di-[(1-4C)alkyl]amino;

(g) p is 1, R¹ is located at the 7-position and R¹ is (1-6C)alkoxy and wherein any CH₂ or CH₃ group within a R¹ substituent optionally bears on each said CH₂ or CH₃ group one or more fluoro or chloro substituents, or a substituent selected from hydroxy, amino, (1-4C)alkoxy, (1-4C)alkylamino and di-[(1-4C)alkyl]amino;

(h) p is 1, R¹ is located at the 7-position and R¹ is selected from hydrogen, hydroxy, (1-6C)alkoxy, (3-7C)cycloalkyl-oxy and (3-7C)cycloalkyl-(1-6C)alkoxy, and wherein adjacent carbon atoms in any (2-6C)alkylene chain within a R¹ substituent are optionally separated by the insertion into the chain of an O atom, and wherein any CH₂ or CH₃ group within a R¹ substituent optionally bears on each said CH₂ or CH₃ group one or more fluoro or chloro substituents, or a substituent selected from hydroxy and (1-3C)alkoxy;

(i) p is 1, R¹ is located at the 7-position and R¹ is selected from hydrogen, (1-6C)alkoxy, cyclopropyl-(1-4C)alkoxy, cyclobutyl-(1-4C)alkoxy, cyclopentyl-(1-4C)alkoxy, cyclohexyl-(1-6C)alkoxy, tetrahydrofuranyl-(1-4C)alkoxy and tetrahydropyranyl-(1-4C)alkoxy, and wherein adjacent carbon atoms in any (2-6C)alkylene chain within a R¹ substituent are optionally separated by the insertion into the chain of an O atom, and wherein any CH₂ or CH₃ group within a R¹ substituent optionally bears on each said CH₂ or CH₃ group one or more fluoro or chloro substituents, or a substituent selected from hydroxy and (1-3C)alkoxy;

(j) p is 1, R¹ is located at the 7-position and R¹ is selected from hydrogen, (1-6C)alkoxy, cyclopropylmethoxy and 2-cyclopropylethoxy, and wherein any CH₂ or CH₃ group within a R¹ substituent optionally bears on each said CH₂ or CH₃ group one or more fluoro or chloro substituents, or a substituent selected from hydroxy, methoxy and ethoxy;

(k) p is 1, R¹ is located at the 7-position and R¹ is selected from hydrogen methoxy, ethoxy, propoxy, isopropyloxy, cyclopropylmethoxy, 2-hydroxyethoxy, 2-fluoroethoxy, 2-methoxyethoxy, 2-ethoxyethoxy, 2,2-difluoroethoxy and 2,2,2-trifluoroethoxy;

(l) p is 1, R¹ is located at the 7-position and R¹ is selected from (1-3C)alkoxy, hydroxy-(2-3C)alkoxy and (1-3C)alkoxy-(2-3C)alkoxy, for example R¹ is selected from methoxy, ethoxy, isopropyloxy, 2-hydroxyethoxy, 2-methoxy-ethoxy;

(m) p is 1, R¹ is located at the 7-position and R¹ is selected from hydrogen and (1-3C)alkoxy;

(n) R¹ is hydrogen;

(o) p is 1, R¹ is located at the 7-position and R¹ is (1-3C) alkoxy (for example methoxy, ethoxy or isopropyloxy);

(p) each R², which may be the same or different, is selected from halogeno, cyano, nitro, hydroxy, amino, carboxy, trifluoromethyl, trifluoromethoxy, (1-6C)alkyl, (2-8C)alkenyl, (2-8C)alkynyl, (1-6C)alkoxy, (1-6C)alkylamino, di-[(1-6C)alkyl]amino, (2-6C)alkanoyl, (2-6C)alkanoyloxy, and a group of the formula:

wherein X⁴ is a direct bond or is selected from O and N(R¹³), wherein R¹³ is hydrogen or (1-6C)alkyl, and R¹² is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl;

(q) each R², which may be the same or different, is selected from halogeno, hydroxy, nitro, cyano, trifluoromethyl, amino, (1-4C)alkyl, (2-4C)alkenyl, (2-4C)alkynyl, (1-4C)alkoxy, (1-4C)alkylamino and di-[(1-4C)alkyl]amino;

(r) each R², which may be the same or different, is selected from fluoro, chloro, bromo, iodo, cyano, hydroxy, trifluoromethyl, (1-4C)alkyl, (2-4C)alkenyl, (2-4C)alkynyl and (1-4C)alkoxy;

(s) each $R^2$, which may be the same or different, is selected from halogeno (for example fluoro, chloro or bromo) and (2-4C)alkynyl (for example ethynyl);

(t) each $R^2$, which may be the same or different, is selected from fluoro, chloro, bromo, iodo, cyano, hydroxy, trifluoromethyl, methyl, ethyl, isopropyl, methoxy, ethoxy, vinyl, allyl, ethynyl, 1-propynyl and 2-propynyl;

(u) each $R^2$, which may be the same or different, is selected from fluoro, chloro, bromo, hydroxy, cyano, trifluoromethyl, methyl, ethyl, isopropyl, methoxy, ethoxy, vinyl, allyl, ethynyl, 1-propynyl, and 2-propynyl;

(v) each $R^2$, which may be the same or different, is selected from fluoro, chloro, bromo, trifluoromethyl, methyl, ethyl, methoxy, ethoxy and ethynyl;

(w) each $R^2$, which may be the same or different, is selected from halogeno (particularly fluoro, chloro and bromo);

(x) a is 1, 2 or 3 and one $R^2$ is at the meta (3-) position on the anilino group;

(y) a is 1, 2 or 3 (particularly 1 or 2) and each $R^2$, which may be the same or different, is as defined in any of (p) to (w) above;

(z) a is 1, 2 or 3, one $R^2$ is at the meta (3-) position on the anilino group and is halogeno (for example chloro or bromo), and when a is 2 or 3 the other $R^2$ group(s), which may be the same or different, are as defined in any of any of (p) to (w) above;

(aa) a is 1, 2 or 3, each $R^2$, which may be the same or different, is halogeno (for example selected from fluoro, chloro and bromo), and wherein one $R^2$ is at the meta (3-) position on the anilino group;

(bb) a is 1 or 2, each $R^2$, which may be the same or different, is halogeno (particularly fluoro, chloro or bromo) and wherein one $R^2$ is at the 3-position and the other $R^2$ is at the 2- or 4-position on the anilino group;

(cc) a is 2, each $R^2$, which may be the same or different, is halogeno (particularly fluoro, chloro or bromo, more particularly fluoro or chloro) and wherein one $R^2$ is at the 3-position and the other $R^2$ is at the 2-position on the anilino group;

(dd) a is 1 or 2, one $R^2$ is at the 3-position on the anilino group and is chloro, and when a is 2 the other $R^2$ group(s), which may be the same or different, are selected from fluoro, chloro and bromo;

(ee) the anilino group at the 4-position on the quinazoline ring in formula I is selected from 3-chloro-4-fluoroanilino, 3,4-difluoroanilino, 3-chloro-2-fluoroanilino, 2-fluoro-5-chloroanilino, 3-bromoanilino, 3-methylanilino and 3-ethynylanilino;

(ff) the anilino group at the 4-position on the quinazoline ring in formula I is selected from 3-chloro-2-fluoroanilino, 3-chloro-4-fluoroanilino, 3-bromo-2-fluoroanilino, 3-chloro-2,4-difluoroanilino, 3-chloro-2,6-difluoroanilino and 3-chloro-5-fluoroanilino;

(gg) the anilino group at the 4-position on the quinazoline ring in formula I is selected from 3-chloro-2-fluoroanilino, 3-chloro-4-fluoroanilino and 3-bromo-2-fluoroanilino;

(hh) the anilino group at the 4-position on the quinazoline ring in formula I is 3-chloro-4-fluoroanilino;

(ii) the anilino group at the 4-position on the quinazoline ring in formula I is 3-chloro-2-fluoroanilino;

(jj) the anilino group at the 4-position on the quinazoline ring in formula I is 3-bromo-2-fluoroanilino;

(kk) the anilino group at the 4-position on the quinazoline ring in formula I is 3-ethynylanilino;

(ll) m is 1;

(mm) m is 2;

(nn) each of $R^3$ and $R^{3a}$, which may be the same or different, is selected from selected from hydrogen and (1-3C)alkyl, or
$R^3$ and $R^{3a}$ together with the carbon atom to which they are attached form a cyclopropyl, cyclobutyl, cyclopentyl or cyclohexyl ring,
and wherein any $R^3$ or $R^{3a}$ optionally bears on carbon one or more (for example 1, 2 or 3) $R^{14}$ substituents, which may be the same or different,
wherein $R^{14}$ is selected from halogeno, amino, hydroxy, cyano, (1-3C)alkoxy and $NR^{27}R^{28}$, wherein $R^{27}$ and $R^{28}$, which may be the same or different, are selected from hydrogen, (1-3C)alkyl, (2-3C)alkenyl and (2-3C)alkynyl;
and wherein any carbon atom not attached to nitrogen, oxygen or sulfur in any of $R^{14}$, $R^{15}$, $R^{16}$ and $R^{17}$ optionally bears one or more (for example 1, 2 or 3) $R^{30}$ substituents, which may be the same or different as hereinabove defined;

(oo) each of $R^3$ and $R^{3a}$, which may be the same or different, is selected from selected from hydrogen and (1-3C)alkyl,
and wherein any $R^3$ or $R^{3a}$ optionally bears on carbon one or more (for example 1, 2 or 3) substituents, which may be the same or different, selected from fluoro, chloro, amino, hydroxy, cyano, methoxy, ethoxy, methylamino, ethylamino, dimethylamino, diethylamino, hydroxyethylamino and methoxyethylamino;

(pp) $R^{3a}$ is hydrogen and $R^3$ is selected from hydrogen and (1-3C)alkyl, and wherein $R^3$ optionally bears a substituent, selected from fluoro, chloro, amino, hydroxy, methoxy, ethoxy, methylamino, ethylamino, dimethylamino and diethylamino;

(qq) $R^{3a}$ is hydrogen and $R^3$ is selected from hydrogen and (1-3C)alkyl, and wherein $R^3$ optionally bears a substituent, selected from fluoro, chloro, amino, hydroxy, methoxy, ethoxy, provided that when m is 2 one $R^3$ is hydrogen;

(rr) m is 1 or 2 (particularly, m is 1), each $R^{3a}$ is hydrogen and when m is 1 $R^3$ is selected from methyl and ethyl, and when m is 2 one $R^3$ is hydrogen and the other $R^3$ is selected from methyl and ethyl and wherein $R^3$ optionally bears on carbon a substituent, selected from fluoro, hydroxy and methoxy;

(ss) m is 1 and $R^3$ and $R^{3a}$, which may be the same or different, are selected from hydrogen and methyl (for example $R^3$ and $R^{3a}$ are both hydrogen or $R^{3a}$ is hydrogen and $R^3$ is methyl);

(tt) $R^4$ is selected from hydrogen, (1-6C)alkyl, (2-6C)alkenyl, (2-6C)alkynyl, carbamoyl, N-(1-6C)alkylcarbamoyl, N,N-di-[(1-6C)alkyl]carbamoyl, (2-6C)alkanoyl, and (1-6C)alkylsulfonyl,
and wherein a $R^4$ substituent optionally bears on carbon one or more (for example 1, 2 or 3) $R^{15}$ substituents as hereinbefore defined, which may be the same or different;

(uu) $R^4$ is selected from (1-6C)alkyl, (2-6C)alkenyl, (2-6C)alkynyl, carbamoyl, N-(1-6C)alkylcarbamoyl, N,N-di-[(1-6C)alkyl]carbamoyl, (2-6C)alkanoyl, and (1-6C)alkylsulfonyl,
and wherein a $R^4$ substituent optionally bears on carbon one or more (for example 1, 2 or 3) $R^{15}$ substituents as hereinbefore defined, which may be the same or different;

(vv) $R^4$ is selected from hydrogen, (1-6C)alkyl, carbamoyl, N-(1-6C)alkylcarbamoyl, N,N-di-[(1-6C)alkyl]carbamoyl, (2-6C)alkanoyl, and (1-6C)alkylsulfonyl, and wherein a $R^4$ substituent optionally bears on carbon one or more (for example 1, 2 or 3) $R^{15}$ substituents, which may be the same or different, wherein $R^{15}$ is selected from halogeno, hydroxy, cyano, (1-6C)alkoxy and $NR^{27}R^{28}$, wherein $R^{27}$ and $R^{28}$, which may be the same or different, are selected from hydrogen, (1-4C)alkyl, (2-4C)alkenyl and (2-4C)alkynyl, and wherein $R^{15}$ optionally bears on carbon one or more (for example 1, 2 or 3) substituents, which may be the same or different selected from halogeno, hydroxy, cyano, amino, methylamino, dimethylamino, methoxy and ethoxy;

(vv) $R^4$ is selected from hydrogen, (1-4C)alkyl, carbamoyl, N-(1-4C)alkylcarbamoyl, N,N-di-[(1-4C)alkyl]carbamoyl, (2-4C)alkanoyl, and (1-4C)alkylsulfonyl, and wherein $R^4$ optionally bears on carbon one or more (for example 1, 2 or 3) $R^{15}$ substituents, which may be the same or different, wherein $R^{15}$ is selected from halogeno, hydroxy, cyano, (1-3C)alkoxy and $NR^{27}R^{28}$, wherein $R^{27}$ and $R^{28}$, which may be the same or different, are selected from hydrogen and (1-3C)alkyl, and wherein any carbon atom not attached to nitrogen or oxygen in any $R^{15}$ substituent optionally bears one or more (for example 1, 2 or 3) substituents, which may be the same or different, selected from fluoro, chloro, hydroxy, methoxy and ethoxy;

(ww) $R^4$ is selected from hydrogen, methyl, ethyl, propyl, isopropyl, vinyl, allyl, ethynyl, 2-propynyl, carbamoylmethyl, N-methylcarbamoylmethyl, N-ethylcarbamoylmethyl, N,N-dimethylcarbamoylmethyl, N,N-diethylcarbamoylmethyl, cyanomethyl, 2-hydroxyethyl, 2-aminoethyl, 2-(N-methylamino)ethyl, 2-(N,N-dimethylamino)ethyl, 2-methoxyethyl, 2-ethoxyethyl, 2-cyanoethyl, 2-carbamoylethyl, 2-(N-methylcarbamoyl)ethyl, 2-(N-ethylcarbamoyl)ethyl, 2-(N,N-dimethylcarbamoyl)ethyl, 2-(N,N-diethylcarbamoyl)ethyl, acetyl, propionyl, hydroxyacetyl, methoxyacetyl, ethoxyacetyl, aminoacetyl, N-methylaminoacetyl, N,N-dimethylaminoacetyl, N-ethylaminoacetyl, N,N-diethylaminoacetyl, N-(2-hydroxyethyl)aminoacetyl, N-(2-methoxyethyl)aminoacetyl, 3-hydroxypropionyl, 2-hydroxypropionyl, 3-methoxypropionyl, 2-methoxypropionyl, 3-aminopropionyl, 3-(N-methylamino)propionyl, 3-(N,N-dimethylamino)propionyl, 3-(N-ethylamino)propionyl, 3-(N,N-diethylamino)propionyl, 3-[N-(2-hydroxyethyl)amino]propionyl, 3-[N-(2-methoxyethyl)amino]propionyl, carbamoyl, N-methylcarbamoyl, N-ethylcarbamoyl, N,N-dimethylcarbamoyl, N,N-diethylcarbamoyl, methylsulfonyl and ethylsulfonyl;

(xx) $R^4$ is selected from hydrogen, methyl, ethyl, 2-hydroxyethyl, 2-aminoethyl, 2-(N-methylamino)ethyl, 2-(N,N-dimethylamino)ethyl, 2-methoxyethyl, 2-ethoxyethyl, cyanoethyl, allyl, 2-propynyl, acetyl, propionyl, hydroxyacetyl, methoxyacetyl, ethoxyacetyl, aminoacetyl, N-methylaminoacetyl, N,N-dimethylaminoacetyl, N-ethylaminoacetyl, N,N-diethylaminoacetyl, N-(2-hydroxyethyl)aminoacetyl, N-(2-methoxyethyl)aminoacetyl, 3-hydroxypropionyl, 2-hydroxypropionyl, 3-methoxypropionyl, 2-methoxypropionyl, 3-aminopropionyl, 3-(N-methylamino)propionyl, 3-(N,N-dimethylamino)propionyl, 3-(N-ethylamino)propionyl, 3-(N,N-diethylamino)propionyl, 3-[N-(2-hydroxyethyl)amino]propionyl, 3-[N-(2-methoxyethyl)amino]propionyl, carbamoyl, N-methylcarbamoyl, N-ethylcarbamoyl, N,N-dimethylcarbamoyl, N,N-diethylcarbamoyl and methylsulfonyl;

(yy) $R^4$ is (1-4C)alkyl, wherein $R^4$ optionally bears on any carbon one or more (for example 1, 2 or 3) substituents, which may be the same or different, selected from fluoro, chloro, hydroxy, methoxy, cyano, amino, methylamino and dimethylamino;

(zz) $R^4$ is (1-4C)alkyl, wherein $R^4$ optionally bears on any carbon one or more (for example 1, 2 or 3, particularly 1) substituents, which may be the same or different, selected from hydroxy, (1-3C)alkoxy and cyano;

(aaa) $R^4$ is selected from methyl, ethyl, isopropyl, butyl, 2-cyanoethyl, 2-hydroxyethyl, 2-methoxyethyl and 3-methoxyprop-2-yl;

(bbb) $R^4$ is hydrogen;

(ccc) $R^4$ is (1-3C)alkyl, wherein $R^4$ optionally bears on any carbon atom not attached to nitrogen a substituent selected from fluoro, hydroxy and methoxy;

(ddd) $R^4$ is methyl or ethyl;

(eee) $R^4$ is methyl;

(fff) $R^5$ is selected from hydrogen, (1-4C)alkyl, (2-4C)alkenyl, (2-4C)alkynyl, heterocyclyl, (3-7C)cycloalkyl, heterocyclyl-(1-4C)alkyl and (3-7C)cycloalkyl-(1-4C)alkyl, and wherein and wherein any $CH_2$ or $CH_3$, other than a $CH_2$ group within a heterocyclyl ring, within a $R^5$ substituent optionally bears on each said $CH_2$ or $CH_3$ one or more substituents (for example 1, 2 or 3), which may be the same or different, selected from halogeno, hydroxy, cyano and (1-3C)alkoxy, amino, (1-3C)alkylamino and di-[(1-3C)alkyl]amino, and wherein any heterocyclyl group in $R^5$ is a 4, 5 or 6 membered monocyclic ring containing 1, 2 or 3 heteroatoms selected from O, S and N and which optionally bears 1, 2 or 3 substituents, which may be the same or different, selected from halogeno, (1-4C)alkyl, (2-4C)alkanoyl, hydroxy-(2-4C)alkanoyl, (1-4C)alkoxy-(2-4C)alkanoyl and (1-4C)alkylsulfonyl;

(ggg) $R^5$ is selected from hydrogen, (1-4C)alkyl, (2-4C)alkenyl, (2-4C)alkynyl, tetrahydrofuranyl, tetrahydropyranyl, tetrahydrofuranyl-(1-4C)alkyl and tetrahydropyranyl-(1-4C)alkyl, and wherein and wherein any $CH_2$ or $CH_3$, other than a $CH_2$ group within a heterocyclyl ring, within a $R^5$ substituent optionally bears on each said $CH_2$ or $CH_3$ one or more substituents (for example 1, 2 or 3), which may be the same or different, selected from halogeno, hydroxy, cyano and (1-3C)alkoxy, and wherein any heterocyclyl group within a $R^5$ substituent optionally bears 1 or 2 oxo substituents;

(hhh) $R^5$ is selected from hydrogen, (1-4C)alkyl, (2-4C)alkenyl, and (2-4C)alkynyl, and wherein $R^5$ optionally bears on carbon one or more substituents (for example 1, 2 or 3), which may be the same or different, selected from halogeno, hydroxy, cyano, (1-3C)alkoxy, amino, (1-3C)alkylamino and di-[(1-3C)alkyl]amino;

(iii) $R^5$ is selected from hydrogen, (1-4C)alkyl, (2-4C)alkenyl, and (2-4C)alkynyl, and wherein $R^5$ optionally bears on carbon one or more substituents (for example 1, 2 or 3), which may be the same or different, selected from hydroxy and (1-3C)alkoxy;

(jjj) $R^5$ is selected from hydrogen, (1-3C)alkyl, (2-3C)alkenyl, and (2-3C)alkynyl, and wherein $R^5$ optionally bears on carbon one or more substituents (for example 1, 2 or 3), which may be the same or different, selected from fluoro, hydroxy, cyano, methoxy, and ethoxy;

(kkk) $R^5$ is selected from hydrogen, methyl, ethyl, isopropyl, butyl, allyl, vinyl, ethynyl, 2-propynyl, cyanomethyl, 2-cyanoethyl, 2-hydroxyethyl and 2-methoxyethyl;

(lll) $R^5$ is selected from hydrogen, methyl and ethyl;

(mmm) $R^5$ is selected from hydrogen and methyl;

(nnn) $R^5$ is hydrogen;

(ooo) $R^{5a}$ is selected from hydrogen and (1-4C)alkyl and $R^5$ is as defined in any of (fff) to (nnn);

(ppp) $R^{5a}$ is selected from hydrogen and methyl and $R^5$ is as defined in any of (fff) to (nnn);

(qqq) $R^{5a}$ is hydrogen and $R^5$ is as defined in any of (fff) to (nnn);

(rrr) $R^5$ and $R^{5a}$ are both hydrogen;

(sss) $R^6$ is selected from hydrogen and (1-4C)alkyl, and wherein $R^6$ optionally bears on carbon one or more (for example 1, 2 or 3) $R^{17}$ substituents, which may be the same or different selected from halogeno, hydroxy, cyano, (1-3C)alkoxy, amino, (1-3C)alkylamino and di-[(1-3C)alkyl]amino;

(ttt) $R^6$ is selected from hydrogen and (1-4C)alkyl, and wherein $R^6$ optionally bears on carbon one or more (for example 1, 2 or 3) $R^{17}$ substituents, which may be the same or different selected from fluoro, chloro, hydroxy, methoxy, cyano, amino, methylamino and dimethylamino;

(uuu) $R^6$ is selected from hydrogen, methyl, ethyl, allyl, 2-propynyl, cyanomethyl, hydroxymethyl, 2-hydroxyethyl, methoxymethyl, 2-methoxyethyl, aminomethyl, N-methylaminomethyl, N,N-dimethylaminomethyl, 2-aminoethyl, 2-(N-methylamino)ethyl and 2-(N,N-dimethylamino)ethyl;

(vvv) $R^6$ is hydrogen or methyl;

(www) $R^6$ is hydrogen;

(xxx) $R^6$ is (1-3C)alkyl (for example $R^6$ is methyl);

(yyy) Z is O;

(zzz) Z is S;

(aaaa) $R^7$ is selected from hydrogen, (1-6C)alkyl, (2-6C)alkenyl, (2-6C)alkynyl, aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl and heterocyclyl-(1-6C)alkyl, provided that when $R^7$ is heterocyclyl or heteroaryl and q is 1, $R^7$ is linked to the carbon carrying $R^6$ and the $R^{5a}R^5NC(Z)$ group by a ring carbon, and wherein adjacent carbon atoms in any (2-6C)alkylene chain within a $R^7$ substituent are optionally separated by the insertion into the chain of a group selected from O, S, N($R^{18}$), CON($R^{18}$), N($R^{18}$)CO, CH=CH and C≡C wherein $R^{18}$ is hydrogen or (1-6C)alkyl, and wherein any $CH_2$=CH— or HC≡C— group within a $R^7$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^4—X^5—$$

wherein $X^5$ is a direct bond or is selected from CO and N($R^{19}$)CO, wherein $R^{19}$ is hydrogen or (1-6C)alkyl, and $Q^4$ is heteroaryl, heteroaryl-(1-6C)alkyl, heterocyclyl or heterocyclyl-(1-6C)alkyl, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, or from a group of the formula:

$$—X^6—Q^5$$

wherein $X^6$ is a direct bond or is selected from O, S, N($R^{20}$), CON($R^{20}$), N($R^{20}$)CO and C($R^{20}$)$_2$O, wherein $R^{20}$ is hydrogen or (1-6C)alkyl, and $Q^5$ is aryl, aryl-(1-6C)alkyl, (3-7C)cycloalkyl, (3-7C)cycloalkyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^7$ optionally bears one or more (for example 1, 2 or 3) $R^{21}$ substituents, which may be the same or different, as hereinabove defined, and wherein any heterocyclyl group within a $R^7$ substituent optionally bears 1 or 2 oxo or thioxo substituents;

or $R^6$ and $R^7$ together with the carbon atom to which they are attached form a (3-7C)cycloalkyl or heterocyclyl group, which group optionally bears one or more (for example 1, 2 or 3) $R^{22}$ substituents, which may be the same or different, as hereinabove defined, and wherein any heterocyclyl group formed by $R^6$ and $R^7$ together with the carbon atom to which they are attached, optionally bears 1 or 2 oxo or thioxo substituents;

or $R^7$ and the group $R^{5a}R^5NC(Z)$ together with the carbon atom to which they are attached form a heterocyclyl group, which group optionally bears one or more (for example 1, 2 or 3) $R^{23}$ substituents, which may be the same or different, as hereinbefore defined;

(bbbb) $R^7$ is selected from hydrogen, (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, provided that when $R^7$ is heterocyclyl and q is 1, $R^7$ is linked to the carbon carrying $R^6$ and the $R^{5a}R^5NC(Z)$ group by a ring carbon, and wherein adjacent carbon atoms in any (2-6C)alkylene chain within a $R^7$ substituent are optionally separated by the insertion into the chain of a group selected from O, S, N($R^{18}$), CON($R^{18}$), N($R^{18}$)CO, CH=CH and C≡C wherein $R^{18}$ is hydrogen or (1-6C)alkyl, and wherein any $CH_2$=CH— or HC≡C— group within a $R^7$ substituent optionally bears at the terminal $CH_2$= or HC≡ position a substituent selected from carbamoyl, N-(1-6C)alkylcarbamoyl, N,N-di-[(1-6C)alkyl]carbamoyl, amino-(1-6C)alkyl, (1-6C)alkylamino-(1-6C)alkyl and di-[(1-6C)alkyl]amino-(1-6C)alkyl or from a group of the formula:

$$Q^4—X^5—$$

wherein $X^5$ is a direct bond or is selected from CO and N($R^{19}$)CO, wherein $R^{19}$ is hydrogen or (1-6C)alkyl, and $Q^4$ is heterocyclyl or heterocyclyl-(1-6C)alkyl, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, or from a group of the formula:

—$X^6$—$Q^5$ wherein $X^6$ is a direct bond or is selected from O, S, $N(R^{20})$, $CON(R^{20})$, $N(R^{20})CO$ and $C(R^{20})_2O$, wherein $R^{20}$ is hydrogen or (1-6C)alkyl, and $Q^5$ is (3-7C)cycloalkyl, (3-7C)cycloalkyl-(1-6C)alkyl, heterocyclyl or heterocyclyl-(1-6C)alkyl, and wherein any heterocyclyl group within a substituent on R optionally bears one or more (for example 1, 2 or 3) $R^{21}$ substituents, which may be the same or different, as hereinabove defined, and wherein any heterocyclyl group within a $R^7$ substituent optionally bears 1 or 2 oxo or thioxo substituents;

or $R^6$ and $R^7$ together with the carbon atom to which they are attached form a (3-7C)cycloalkyl, (3-7C)cycloalkenyl or heterocyclyl group, which group optionally bears one or more (for example 1, 2 or 3) $R^{22}$ substituents, which may be the same or different, as hereinabove defined, and wherein any heterocyclyl group formed by $R^6$ and $R^7$ together with the carbon atom to which they are attached, optionally bears 1 or 2 oxo substituents;

or $R^7$ and the group $R^{5a}R^5NC(Z)$ together with the carbon atom to which they are attached form a heterocyclyl group, which group optionally bears one or more (for example 1, 2 or 3) $R^{23}$ substituents, which may be the same or different, as hereinbefore defined;

(cccc) $R^7$ is selected from hydrogen, (1-6C)alkyl, (2-6C)alkenyl, (2-6C)alkynyl, aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl and heterocyclyl-(1-6C)alkyl, provided that when $R^7$ is heterocyclyl or heteroaryl and q is 1, $R^7$ is linked to the carbon carrying $R^6$ and the $R^{5a}R^5NC(Z)$ group by a ring carbon, and wherein adjacent carbon atoms in any (2-6C)alkylene chain within a $R^7$ substituent are optionally separated by the insertion into the chain of a group selected from O, S, $N(R^{18})$, $CON(R^{18})$, $N(R^{18})CO$, CH=CH and C≡C wherein $R^{18}$ is hydrogen or (1-6C)alkyl, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, or from a group of the formula:

—$X^6$—$Q^5$ wherein $X^6$ is a direct bond or is selected from O, S, $N(R^{20})$, $CON(R^{20})$, $N(R^{20})CO$ and $C(R^{20})_2O$, wherein $R^{20}$ is hydrogen or (1-6C)alkyl, and $Q^5$ is aryl, aryl-(1-6C)alkyl, (3-7C)cycloalkyl, (3-7C)cycloalkyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^7$ optionally bears one or more (for example 1, 2 or 3) $R^{21}$, wherein each $R^{21}$, which may be the same or different, is selected from halogeno, trifluoromethyl, cyano, nitro, hydroxy, amino, carbamoyl, formyl, (1-6C)alkyl, (2-8C)alkenyl, (2-8C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoylamino and N-(1-6C)alkyl-(2-6C)alkanoylamino, a group of the formula:

—$X^7$—$R^{25}$ wherein $X^7$ is a direct bond or is selected from O, $N(R^{26})$ and C(O), wherein $R^{26}$ is hydrogen or (1-6C)alkyl, and $R^{25}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl or (2-6C)alkanoyl-(1-6C)alkyl, and from a group of the formula:

—$X^8$—$Q^6$ wherein $X^8$ is a direct bond or is selected from O, $N(R^{31})$ and CO, wherein $R^{31}$ is hydrogen or (1-6C)alkyl, and $Q^6$ is (3-7C)cycloalkyl, (3-7C)cycloalkyl-(1-6C)alkyl, heterocyclyl or heterocyclyl-(1-6C)alkyl, which optionally bears one or more (for example 1, 2 or 3) substituents, which may be the same or different selected from halogeno, hydroxy, (1-4C)alkyl and (1-4C)alkoxy, and wherein any $R^{21}$ optionally bears on carbon one or more (for example 1, 2 or 3) $R^{29}$ substituents, which may be the same or different, selected from fluoro, hydroxy, cyano, amino, methylamino, dimethylamino, methoxy, ethoxy, vinyl, allyl and ethynyl, and wherein any heterocyclyl group within a $R^7$ substituent optionally bears 1 oxo substituent;

or $R^6$ and $R^7$ together with the carbon atom to which they are attached form a (3-6C)cycloalkyl or heterocyclyl group, which heterocyclyl group is a 4 to 7 membered monocyclic, saturated or partially saturated monocyclic ring with 1 or 2 heteroatoms selected from oxygen, nitrogen and sulfur, and wherein the group formed by $R^6$ and $R^7$ together with the carbon to which they are attached optionally bears one or more (for example 1, 2 or 3) $R^{22}$ substituents, which may be the same or different, as hereinabove defined, and wherein any heterocyclyl group formed by $R^6$ and $R^7$ together with the carbon atom to which they are attached, optionally bears 1 oxo substituent, or $R^7$ and the group $R^{5a}R^5NC(Z)$ together with the carbon atom to which they are attached form a heterocyclyl group, which heterocyclic group is a 4 to 7 membered monocyclic, saturated or partially saturated monocyclic ring which optionally contains 1 further heteroatom selected from oxygen, nitrogen and sulfur, and wherein the group formed by $R^7$ and the group $R^{5a}R^5NC(Z)$ together with the carbon atom to which they are attached optionally bears one or more (for example 1, 2 or 3) $R^{23}$ substituents, which may be the same or different, as hereinabove defined (In a particular embodiment $R^{5a}$ is hydrogen in the $NR^{5a}C(Z)$ group in the ring so formed);

(dddd) $R^7$ is selected from hydrogen, (1-6C)alkyl, (2-6C)alkenyl, (2-6C)alkynyl, aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl and heterocyclyl-(1-6C)alkyl, provided that when $R^7$ is heterocyclyl or heteroaryl and q is 1, $R^7$ is linked to the carbon carrying $R^6$ and the $R^{5a}R^5NC(Z)$ group by a ring carbon, and wherein adjacent carbon atoms in any (2-6C)alkylene chain within a $R^7$ substituent are optionally separated by the insertion into the chain of a group selected from O, S, $N(R^{18})$, $CON(R^{18})$, $N(R^{18})CO$, CH=CH and C≡C wherein $R^{18}$ is hydrogen or (1-6C)alkyl, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, or from a group of the formula:

$$-X^6-Q^5$$

wherein $X^6$ is a direct bond or is selected from O, S, N($R^{20}$), CON($R^{20}$), N($R^{20}$)CO and C($R^{20}$)$_2$O, wherein $R^{20}$ is hydrogen or (1-6C)alkyl, and $Q^5$ is aryl, aryl-(1-6C)alkyl, (3-7C)cycloalkyl, (3-7C)cycloalkyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^7$ optionally bears one or more (for example 1, 2 or 3) $R^{21}$, wherein each $R^{21}$, which may be the same or different, is selected from halogeno, trifluoromethyl, cyano, nitro, hydroxy, amino, carbamoyl, formyl, (1-6C)alkyl, (2-8C)alkenyl, (2-8C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoylamino and N-(1-6C)alkyl-(2-6C)alkanoylamino, a group of the formula:

$$-X^7-R^{25}$$

wherein $X^7$ is a direct bond or is selected from O, N($R^{26}$) and C(O), wherein $R^{26}$ is hydrogen or (1-6C)alkyl, and $R^{25}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl or (2-6C)alkanoyl-(1-6C)alkyl, and from a group of the formula:

$$-X^8-Q^6$$

wherein $X^8$ is a direct bond or is selected from O, N($R^{31}$) and CO, wherein $R^{31}$ is hydrogen or (1-6C)alkyl, and $Q^6$ is (3-7C)cycloalkyl, (3-7C)cycloalkyl-(1-6C)alkyl, heterocyclyl or heterocyclyl-(1-6C)alkyl, which optionally bears one or more (for example 1, 2 or 3) substituents, which may be the same or different selected from halogeno, hydroxy, (1-4C)alkyl and (1-4C)alkoxy, and wherein any $R^{21}$ optionally bears on carbon one or more (for example 1, 2 or 3) $R^{29}$ substituents, which may be the same or different, selected from fluoro, hydroxy, cyano, amino, methylamino, dimethylamino, methoxy, ethoxy, vinyl, allyl and ethynyl, and wherein any heterocyclyl group within a $R^7$ substituent optionally bears 1 oxo substituent;

or $R^6$ and $R^7$ together with the carbon atom to which they are attached form a (3-6C)cycloalkyl or heterocyclyl group, which heterocyclyl group is a 4 to 7 membered monocyclic, saturated or partially saturated monocyclic ring with 1 or 2 heteroatoms selected from oxygen, nitrogen and sulfur, and wherein the group formed by $R^6$ and $R^7$ together with the carbon to which they are attached optionally bears one or more (for example 1, 2 or 3) $R^{22}$ substituents, which may be the same or different, selected from halogeno, trifluoromethyl, hydroxy, amino, carbamoyl, (1-4C)alkyl, (1-4C)alkoxy, (1-4C)alkylsulfonyl, (1-4C)alkylamino, di-[(1-4C)alkyl]amino, N-(1-4C)alkylcarbamoyl, N,N-di-[(1-4C)alkyl]carbamoyl and (2-4C)alkanoyl, and wherein any heterocyclyl group formed by $R^6$ and $R^7$ together with the carbon atom to which they are attached, optionally bears 1 oxo substituent, and wherein any $R^{22}$ optionally bears on carbon one or more (for example 1, 2 or 3) substituents, which may be the same or different, selected from fluoro, hydroxy, cyano, amino, methylamino, dimethylamino, methoxy, ethoxy, vinyl, allyl and ethynyl;

(eeee) $R^7$ is selected from hydrogen, (1-6C)alkyl, (2-6C)alkenyl, (2-6C)alkynyl, (3-7C)cycloalkyl, (3-7C)cycloalkyl-(1-6C)alkyl, heterocyclyl and heterocyclyl-(1-6C)alkyl, provided that when $R^7$ is heterocyclyl and q is 1, $R^7$ is linked to the carbon carrying $R^6$ and the $R^{5a}R^5NC(Z)$ group by a ring carbon, and wherein adjacent carbon atoms in any (2-6C)alkylene chain within a $R^7$ substituent are optionally separated by the insertion into the chain of a group selected from O, S, N($R^-$), CH=CH and C≡C wherein $R^{18}$ is hydrogen or (1-4C)alkyl, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, or from a group of the formula:

$$-X^6-Q^5$$

wherein $X^6$ is a direct bond or is selected from O, S, N($R^{20}$), CON($R^{20}$), N($R^{20}$)CO and C($R^{20}$)$_2$O, wherein $R^{20}$ is hydrogen or (1-6C)alkyl, and $Q^5$ is aryl, aryl-(1-6C)alkyl, (3-7C)cycloalkyl, (3-7C)cycloalkyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^7$ optionally bears one or more (for example 1, 2 or 3) $R^{21}$ substituents, wherein each $R^{21}$, which may be the same or different, is selected from halogeno, trifluoromethyl, cyano, nitro, hydroxy, amino, carbamoyl, formyl, (1-6C)alkyl, (2-8C)alkenyl, (2-8C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoylamino and N-(1-6C)alkyl-(2-6C)alkanoylamino, a group of the formula:

$$-X^7-R^{25}$$

wherein $X^7$ is a direct bond or is selected from O, N($R^{26}$) and C(O), wherein $R^{26}$ is hydrogen or (1-4C)alkyl, and $R^{25}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl or (2-6C)alkanoyl-(1-6C)alkyl, and from a group of the formula:

$$-X^8-Q^6$$

wherein $X^8$ is a direct bond or is selected from O, N($R^{31}$) and CO, wherein $R^{31}$ is hydrogen or (1-6C)alkyl, and $Q^6$ is (3-7C)cycloalkyl, (3-7C)cycloalkyl-(1-6C)alkyl, heterocyclyl or heterocyclyl-(1-6C)alkyl, which optionally bears one or more (for example 1, 2 or 3) substituents, which may be the same or different selected from halogeno, hydroxy, (1-4C)alkyl and (1-4C)alkoxy, and wherein any $R^{21}$ optionally bears on carbon one or more (for example 1, 2 or 3) $R^{29}$ substituents, which may be the same or different, selected from fluoro, hydroxy, cyano, amino, methylamino, dimethylamino, methoxy, ethoxy, vinyl, allyl and ethynyl, and wherein any heterocyclyl group within a $R^7$ substituent optionally bears 1 oxo substituent;

(ffff) $R^7$ is selected from hydrogen, (1-6C)alkyl, hydroxy-(1-6C)alkyl, (1-4C)alkoxy-(1-6C)alkyl, amino-(1-6C)alkyl, (1-4C)alkylamino-(1-6C)alkyl, di-[(1-4C)alkyl]amino-(1-6C)alkyl, heterocyclyl and heterocyclyl-(1-6C)alkyl, which heterocyclyl is a 4 to 6 membered monocyclic, saturated or partially saturated monocyclic ring with 1 or 2 heteroatoms selected from oxygen, nitrogen and sulfur, provided that when $R^7$ is heterocyclyl and q is 1, $R^7$ is linked to the carbon carrying $R^6$ and the $R^{5a}R^5NC(Z)$ group by a ring carbon, and wherein any heterocyclyl group within a substituent on R optionally bears one or more (for example 1, 2 or 3) $R^{21}$ substituents, which may be the same or different, and wherein any heterocyclyl group within a $R^7$ substituent optionally bears 1 oxo substituent;

or $R^6$ and $R^7$ together with the carbon atom to which they are attached form a (3-6C)cycloalkyl, (3-6C)cycloalkenyl or heterocyclyl, which heterocyclyl is a 4 to 6 membered monocyclic, saturated or partially saturated monocyclic ring with 1 or 2 heteroatoms selected from oxygen, nitrogen and sulfur, and wherein the group formed by $R^6$ and $R^7$ together with the carbon to which they are attached optionally bears one or more (for example 1, 2 or 3) $R^{22}$ substituents, which may be the same or different, and wherein any heterocyclyl group formed by $R^6$ and $R^7$ together with the carbon atom to which they are attached, optionally bears 1 oxo substituent, and wherein each $R^{21}$ and $R^{22}$, which may be the same or different, is selected from halogeno, cyano, hydroxy, carbamoyl, (1-6C)alkyl, (2-6C)alkenyl, (2-6C)alkynyl, (1-6C)alkoxy, (1-6C)alkylsulfonyl, N-(1-6C)alkylcarbamoyl, N,N-di-[(1-6C)alkyl]carbamoyl, (2-6C)alkanoyl, hydroxy-(2-6C)alkanoyl, (1-4C)alkoxy-(2-6C)alkanoyl, carbamoyl-(1-6C)alkyl, N-(1-6C)alkylcarbamoyl-(1-6C)alkyl and N,N-di-[(1-6C)alkyl]carbamoyl-(1-6C)alkyl;

or $R^7$ and the group $R^{5a}R^5NC(Z)$ together with the carbon atom to which they are attached form a heterocyclyl group selected from a group of the formula:

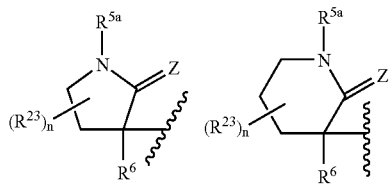

wherein Z is O, $R^6$ is as defined hereinabove (particularly $R^6$ is hydrogen or (1-4C)alkyl, for example $R^6$ is hydrogen), $R^{5a}$ is hydrogen or (1-4C)alkyl (for example $R^{5a}$ is hydrogen or methyl, particularly $R^{5a}$ is hydrogen), n is 0, 1 or 2 and each $R^{23}$, which may be the same or different, is selected from (1-4C)alkyl;

(gggg) $R^7$ is selected from hydrogen, methyl, ethyl, propyl, isopropyl, butyl, iso-butyl, tert-butyl, 1-methylpropyl, vinyl, isopropenyl, allyl, ethynyl, 2-propynyl, phenyl, benzyl, 2-phenylethyl, cyclopropyl, cyclobutyl, cyclopentyl, cyclohexyl, cyclopropylmethyl, cyclobutylmethyl, cyclopentylmethyl, cyclohexylmethyl, 2-(cyclopropyl)ethyl, 2-(cyclobutyl)ethyl, 2-(cyclopentyl)ethyl, 2-(cyclohexyl)ethyl, 2- or 3-furanyl, 2- or 3-pyrrolyl, 2- or 3-thienyl, 2-, 4- or 5-imidazolyl, 3-, 4- or 5-isoxazolyl, 2-, 4- or 5-oxazolyl, 2-, 3- or 4-pyridyl, 3-indolyl, 2- or 3-furanylmethyl, 2- or 3-pyrrolylmethyl, 2- or 3-thienylmethyl, 1-,2-, 4- or 5-imidazolylmethyl, 3-, 4- or 5-isoxazolylmethyl, 2-, 4- or 5-oxazolylmethyl, 2-, 3- or 4-pyridylmethyl, 3-indolylmethyl, 2-(2- or 3-furanyl)ethyl, 2-(2- or 3-pyrrolyl)ethyl, 2-(2- or 3-thienyl)ethyl, 2-(1-, 2-, 4- or 5-imidazolyl)ethyl, 2-(3-, 4- or 5-isoxazolyl)ethyl, 2-(2-, 4- or 5-oxazolyl)ethyl, 2-(2-, 3- or 4-pyridyl)ethyl, 2-(3-indolyl)ethyl, tetrahydrofuranyl, tetrahydropyranyl, azetidin-2-yl, azetidin-3-yl, pyrrolidin-2-yl, pyrrolidin-3-yl, piperidin-2-yl, piperidin-3-yl, piperidin-4-yl, piperazin-2-yl, piperazin-3-yl, homopiperidin-2-yl, homopiperidin-3-yl, homopiperidin-4-yl, homopiperazin-2-yl, homopiperazin-3-yl, morpholin-2-yl, morpholin-3-yl, thiomorpholin-2-yl, thiomorpholin-3-yl, tetrahydrofuranylmethyl, tetrahydropyranylmethyl, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, piperazin-2-ylmethyl, piperazin-3-ylmethyl, homopiperidin-1-ylmethyl, homopiperidin-2-ylmethyl, homopiperidin-3-ylmethyl, homopiperidin-4-ylmethyl, homopiperazin-1-ylmethyl, homopiperazin-2-ylmethyl, homopiperazin-3-ylmethyl, morpholinomethyl, morpholin-2-ylmethyl, morpholin-3-ylmethyl, thiomorpholin-2-ylmethyl, thiomorpholin-3-ylmethyl, 2-(tetrahydrofuranyl)ethyl, 2-(tetrahydropyranyl)ethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl, 2-(piperazin-2-yl)ethyl, 2-(piperazin-3-yl)ethyl, 2-(homopiperidin-1-yl)ethyl, 2-(homopiperidin-2-yl)ethyl, 2-(homopiperidin-3-yl)ethyl, 2-(homopiperidin-4-yl)ethyl, 2-(homopiperazin-1-yl)ethyl, 2-(homopiperazin-2-yl)ethyl, 2-(homopiperazin-3-yl)ethyl, 2-(morpholino)ethyl, 2-(morpholin-2-yl)ethyl, 2-(morpholin-3-yl)ethyl, 2-(thiomorpholin-2-yl)ethyl, 2-(thiomorpholin-3-yl)ethyl, 2-(azetidin-1-yl)propyl, 3-(azetidin-2-yl)propyl, 3-(azetidin-3-yl)propyl, 3-(pyrrolidin-1-yl)propyl, 3-(pyrrolidin-2-yl)propyl, 3-(pyrrolidin-3-yl)propyl, 3-(piperidino)propyl, 3-(piperidin-2-yl)propyl, 3-(piperidin-3-yl)propyl, 3-(piperidin-4-yl)propyl, 3-(piperazino)propyl, 3-(piperazin-2-yl)propyl, 3-(piperazin-3-yl)propyl, 3-(homopiperidin-1-yl)propyl, 3-(homopiperidin-2-yl)propyl, 3-(homopiperidin-3-yl)propyl, 3-(homopiperidin-4-yl)propyl, 3-(homopiperazin-1-yl)propyl, 3-(homopiperazin-2-yl)propyl, 3-(homopiperazin-3-yl)propyl, 3-(morpholino)propyl, 3-(morpholin-2-yl)propyl and 3-(morpholin-3-yl)propyl, and wherein adjacent carbon atoms in any (2-6C)alkylene chain within a $R^7$ substituent are optionally separated by the insertion into the chain of a group selected from O, S, NH, $N(CH_3)$, CH=CH and C≡C, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-3C)alkyl substituents or a substituent selected from hydroxy, cyano, amino, (1-3C)alkoxy, (1-3C)alkylsulfonyl, (1-3C)alkylamino and di-[(1-3C)alkyl]amino, or from a group of the formula:

—$X^6$—$Q^5$ wherein X⁶ is a direct bond or is selected from O, S, NH, CONH, NHCO and CH₂O, wherein Q⁵ is cyclopropyl, cyclobutyl, cyclopentyl, cyclohexyl, cyclopropylmethyl, cyclobutylmethyl, cyclopentylmethyl, cyclohexylmethyl, tetrahydrofuranyl, tetrahydropyranyl, azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, morpholino, tetrahydrofuranylmethyl, tetrahydropyranylmethyl, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, morpholinomethyl, morpholin-2-ylmethyl, morpholin-3-ylmethyl, 2-(tetrahydrofuranyl)ethyl, 2-(tetrahydropyranyl)ethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl or 2-(morpholino)ethyl, and wherein any aryl, heteroaryl or heterocyclyl group within a substituent on R⁷ optionally bears 1, 2 or 3 R²¹ substituents, which may be the same or different, selected from halogeno, trifluoromethyl, cyano, nitro, hydroxy, amino, carbamoyl, (1-3C)alkyl, vinyl, allyl, ethynyl, 2-propynyl, (1-3C)alkoxy, (1-3C)alkylsulfonyl, (1-3C)alkylamino, di-[(1-3C)alkyl]amino, N-(1-3C)alkylcarbamoyl, N,N-di-[(1-3C)alkyl]carbamoyl, (2-3C)alkanoyl, a group of the formula:

wherein X⁷ is a direct bond or is selected from O, NH and C(O), wherein R²⁵ is halogeno-(1-3C)alkyl, hydroxy-(1-3C)alkyl, (1-3C)alkoxy-(1-3C)alkyl, cyano-(1-3C)alkyl, amino-(1-3C)alkyl, (1-3C)alkylamino-(1-3C)alkyl, di-[(1-3C)alkyl]amino-(1-3C)alkyl, carbamoyl-(1-3C)alkyl, N-(1-3C)alkylcarbamoyl-(1-3C)alkyl or N,N-di-[(1-3C)alkyl]carbamoyl-(1-3C)alkyl, and from a group of the formula:

wherein X⁸ is a direct bond or is selected from O, NH and CO, wherein Q⁶ is cyclopropyl, cyclobutyl, cyclopentyl, cyclohexyl, cyclopropylmethyl, cyclobutylmethyl, cyclopentylmethyl, cyclohexylmethyl, azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, morpholino, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, morpholinomethyl, morpholin-2-ylmethyl, morpholin-3-ylmethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl or 2-(morpholino)ethyl, and wherein Q⁶ optionally bears 1, 2 or 3 substituents, which may be the same or different, selected from fluoro, chloro, hydroxy, methyl, ethyl, methoxy and ethoxy, and wherein any R²¹ optionally bears on carbon one or more (for example 1, 2 or 3) R²⁹ substituents, which may be the same or different, selected from fluoro, hydroxy, cyano, amino, methylamino, dimethylamino, methoxy, ethoxy, vinyl, allyl and ethynyl, and wherein any heterocyclyl group within a R⁷ substituent optionally bears 1 oxo substituent, or R⁶ and R⁷ together with the carbon atom to which they are attached form a cyclopropyl, cyclobutyl, cyclopentyl, cyclohexyl, azetidin-3-yl, pyrrolidin-3-yl, piperidin-4-yl, tetrahydrofuran-3-yl, tetrahydropyran-3-yl or tetrahydropyran-4-yl group (particularly a cyclopropyl, cyclobutyl, cyclopentyl, cyclohexyl, piperidin-4-yl or tetrahydropyran-4-yl group), which group optionally bears 1, 2 or 3 substituents, which may be the same or different, selected from fluoro, chloro, hydroxy, amino, carbamoyl, (1-3C)alkyl, vinyl, allyl, ethynyl, 2-propynyl, (1-3C)alkoxy, (1-3C)alkylsulfonyl, (1-3C)alkylamino, di-[(1-3C)alkyl]amino, N-(1-3C)alkylcarbamoyl, N,N-di-[(1-3C)alkyl]carbamoyl, (2-3C)alkanoyl, a group of the formula:

wherein X⁷ is a direct bond or is selected from O, NH and C(O), wherein R²⁵ is halogeno-(1-3C)alkyl, hydroxy-(1-3C)alkyl, (1-3C)alkoxy-(1-3C)alkyl, cyano-(1-3C)alkyl, amino-(1-3C)alkyl, (1-3C)alkylamino-(1-3C)alkyl, di-[(1-3C)alkyl]amino-(1-3C)alkyl, carbamoyl-(1-3C)alkyl, N-(1-3C)alkylcarbamoyl-(1-3C)alkyl or N,N-di-[(1-3C)alkyl]carbamoyl-(1-3C)alkyl, and wherein any heterocyclyl group formed by R⁶ and R⁷ together with the carbon atom to which they are attached, optionally bears 1 oxo substituent, or R⁷ and the group R⁵ᵃR⁵NC(Z) together with the carbon atom to which they are attached form a heterocyclyl group selected from a group of the formula:

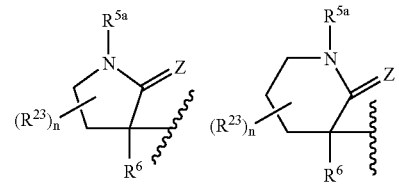

wherein Z is O or S (particularly Z is O), R⁶ is as defined hereinabove (particularly R⁶ is hydrogen or (1-3C)alkyl, more particularly hydrogen), R⁵ᵃ is hydrogen, n is 0, 1 or 2 and each R²³, which may be the same or different, is selected from fluoro, chloro, hydroxy, amino, carbamoyl, (1-3C)alkyl, (1-3C)alkoxy, (1-3C)alkylamino, di-[(1-3C)alkyl]amino, N-(1-3C)alkylcarbamoyl, N,N-di-[(1-3C)alkyl]carbamoyl, (2-3C)alkanoyl and a group of the formula:

wherein X⁷ is a direct bond or is O, and R²⁵ is halogeno-(1-3C)alkyl, hydroxy-(1-3C)alkyl, (1-3C)alkoxy-(1-3C)alkyl, cyano-(1-3C)alkyl, amino-(1-3C)alkyl, (1-3C)alkylamino-(1-3C)alkyl, di-[(1-3C)alkyl]amino-(1-3C)alkyl, carbamoyl-(1-3C)alkyl, N-(1-3C)alkylcarbamoyl-(1-3C)alkyl or N,N-di-[(1-3C)alkyl]carbamoyl-(1-3C)alkyl;

(hhhh) R⁷ is selected from hydrogen, methyl, ethyl, propyl, isopropyl, butyl, iso-butyl, tert-butyl, 1-methylpropyl, cyclopropyl, cyclobutyl, cyclopentyl, cyclohexyl, cyclopropylmethyl, cyclobutylmethyl, cyclopentylmethyl, cyclohexylmethyl, tetrahydrofuranyl, tetrahydropyranyl, azetidin-2-yl, azetidin-3-yl, pyrrolidin-2-yl, pyrrolidin-3-yl, piperidin-2-yl, piperidin-3-yl, piperidin-4-yl, piperazin-2-yl, piperazin-3-yl, homopiperidin-2-yl, homopiperidin-3-yl, homopiperidin-4-yl, homopiperazin-2-yl, homopiperazin-3-yl, morpholin-2-yl, morpholin-3-yl, thiomorpholin-2-yl, thiomorpholin-3-yl, tetrahydrofuranylmethyl, tetrahydropyranylmethyl, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, piperazin-2-ylmethyl, piperazin-3-ylmethyl, homopiperidin-1-ylmethyl homopiperidin-2-ylmethyl, homopiperidin-3-ylmethyl, homopiperidin-4-ylmethyl, homopiperazin-1-ylmethyl, homopiperazin-2-ylmethyl, homopiperazin-3-ylmethyl, morpholinomethyl, morpholin-2-ylmethyl, morpholin-3-ylmethyl, thiomorpholin-2-ylmethyl, thiomorpholin-3-ylmethyl, 2-(tetrahydrofuranyl)ethyl, 2-(tetrahydropyranyl)ethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl, 2-(piperazin-2-yl)ethyl, 2-(piperazin-3-yl)ethyl, 2-(homopiperidin-1-yl)ethyl, 2-(homopiperidin-2-yl)ethyl, 2-(homopiperidin-3-yl)ethyl, 2-(homopiperidin-4-yl)ethyl, 2-(homopiperazin-1-yl)ethyl, 2-(homopiperazin-2-yl)ethyl, 2-(homopiperazin-3-yl)ethyl, 2-(morpholino)ethyl, 2-(morpholin-2-yl)ethyl, 2-(morpholin-3-yl)ethyl, 2-(thiomorpholin-2-yl)ethyl, 2-(thiomorpholin-3-yl)ethyl, 2-(azetidin-1-yl)propyl, 3-(azetidin-2-yl)propyl, 3-(azetidin-3-yl)propyl, 3-(pyrrolidin-1-yl)propyl, 3-(pyrrolidin-2-yl)propyl, 3-(pyrrolidin-3-yl)propyl, 3-(piperidino)propyl, 3-(piperidin-2-yl)propyl, 3-(piperidin-3-yl)propyl, 3-(piperidin-4-yl)propyl, 3-(piperazino)propyl, 3-(piperazin-2-yl)propyl, 3-(piperazin-3-yl)propyl, 3-(homopiperidin-1-yl)propyl, 3-(homopiperidin-2-yl)propyl, 3-(homopiperidin-3-yl)propyl, 3-(homopiperidin-4-yl)propyl, 3-(homopiperazin-1-yl)propyl, 3-(homopiperazin-2-yl)propyl, 3-(homopiperazin-3-yl)propyl, 3-(morpholino)propyl, 3-(morpholin-2-yl)propyl and 3-(morpholin-3-yl)propyl, and wherein adjacent carbon atoms in any (2-6C)alkylene chain within a $R^7$ substituent are optionally separated by the insertion into the chain of a group selected from O, S, NH, N(CH$_3$), CH=CH and C≡C, and wherein any CH$_2$ or CH$_3$, other than a CH$_2$ group within a heterocyclyl ring, within a $R^7$ substituent optionally bears on each said CH$_2$ or CH$_3$ group one or more fluoro, chloro, methyl or ethyl substituents or a substituent selected from hydroxy, cyano, amino, methoxy, ethoxy, methylsulfonyl, ethylsulfonyl, methylamino, ethylamino, dimethylamino, diethylamino, or from a group of the formula:

$$-X^6-Q^5$$

wherein $X^6$ is a direct bond or is selected from O, S and NH, wherein $Q^5$ is cyclopropyl, cyclobutyl, cyclopentyl, cyclohexyl, cyclopropylmethyl, cyclobutylmethyl, cyclopentylmethyl, cyclohexylmethyl, tetrahydrofuranyl, tetrahydropyranyl, azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, morpholino, tetrahydrofuranylmethyl, tetrahydropyranylmethyl, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, morpholinomethyl, morpholin-2-ylmethyl, morpholin-3-ylmethyl, 2-(tetrahydrofuranyl)ethyl, 2-(tetrahydropyranyl)ethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl or 2-(morpholino)ethyl, and wherein any heterocyclyl group within a substituent on $R^7$ optionally bears 1, 2 or 3 $R^{21}$ substituents, which may be the same or different, selected from fluoro, chloro, trifluoromethyl, cyano, nitro, hydroxy, amino, carbamoyl, methyl, ethyl, vinyl, allyl, ethynyl, 2-propynyl, methoxy, ethoxy, methylsulfonyl, methylamino, ethylamino, dimethylamino, diethylamino, N-methylcarbamoyl, N-ethylcarbamoyl, N,N-dimethylcarbamoyl, N,N-diethylcarbamoyl, carbamoylmethyl, N-methylcarbamoylmethyl, N-ethylcarbamoylmethyl, N,N-dimethylcarbamoylmethyl, N,N-diethylcarbamoylmethyl, cyanomethyl, 2-hydroxyethyl, 2-aminoethyl, 2-(N-methylamino)ethyl, 2-(N,N-dimethylamino)ethyl, 2-methoxyethyl, 2-ethoxyethyl, 2-cyanoethyl, 2-carbamoylethyl, 2-(N-methylcarbamoyl)ethyl, 2-(N-ethylcarbamoyl)ethyl, 2-(N,N-dimethylcarbamoyl)ethyl, 2-(N,N-diethylcarbamoyl)ethyl, 2-hydroxyethoxy, 2-aminoethoxy, 2-(N-methylamino)ethoxy, 2-(N,N-dimethylamino)ethoxy, 2-methoxyethoxy, 2-ethoxyethoxy, acetyl, propionyl, hydroxyacetyl, methoxyacetyl, ethoxyacetyl, aminoacetyl, N-methylaminoacetyl, N,N-dimethylaminoacetyl, N-ethylaminoacetyl, N,N-diethylaminoacetyl, N-(2-hydroxyethyl)aminoacetyl, N-(2-methoxyethyl)aminoacetyl, 3-hydroxypropionyl, 2-hydroxypropionyl, 3-methoxypropionyl, 2-methoxypropionyl, 3-aminopropionyl, 3-(N-methylamino)propionyl, 3-(N,N-dimethylamino)propionyl, 3-(N-ethylamino)propionyl, 3-(N,N-diethylamino)propionyl, 3-[N-(2-hydroxyethyl)amino]propionyl, 3-[N-(2-methoxyethyl)amino]propionyl, and from a group of the formula:

$$-X^8-Q^6$$

wherein $X^8$ is a direct bond or is selected from O, NH and CO, wherein $Q^6$ is cyclopropyl, cyclobutyl, cyclopentyl, cyclohexyl, cyclopropylmethyl, cyclobutylmethyl, cyclopentylmethyl, cyclohexylmethyl, azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, morpholino, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, morpholinomethyl, morpholin-2-ylmethyl, morpholin-3-ylmethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl or 2-(morpholino)ethyl, and wherein $Q^6$ optionally bears 1, 2 or 3 substituents, which may be the same or different, selected from fluoro, chloro, hydroxy, methyl, ethyl, methoxy and ethoxy, and wherein any heterocyclyl group within a $R^7$ substituent optionally bears 1 oxo substituent, or $R^6$ and $R^7$ together with the carbon atom to which they are attached form a cyclopropyl, cyclobutyl, cyclopentyl, cyclohexyl, piperidin-4-yl or tetrahydropyran-4-yl group, which group optionally bears 1, 2 or 3 substituents, which may be the same or different, selected from fluoro, chloro, hydroxy, methyl, ethyl, methoxy, ethoxy, amino, carbamoyl, methylsulfonyl, acetyl, methylamino, dimethylamino, N-methylcarbamoyl, N-ethylcarbamoyl, N,N-dimethylcarbamoyl, hydroxymethyl, methoxymethyl, 2-hydroxyethyl, 2-methoxyethyl, 2-hydroxyethoxy, 2-methoxyethoxy, hydroxyacetyl, methoxyacetyl, or R⁷ and the group R⁵ᵃR⁵NC(Z) together with the carbon atom to which they are attached form a heterocyclyl group selected from a group of the formula:

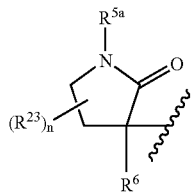 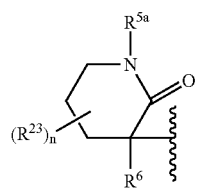

wherein R⁶ and R⁵ᵃ are hydrogen, n is 0, 1 or 2 and each R²³, which may be the same or different, is selected from fluoro, chloro, hydroxy, amino, methyl, ethyl, methoxy, ethoxy, methylamino, dimethylamino, hydroxymethyl, methoxymethyl, 2-hydroxyethyl, 2-methoxyethyl, 2-hydroxyethoxy and 2-methoxyethoxy;

(iiii) R⁷ is selected from hydrogen, methyl, ethyl, propyl, isopropyl, butyl, iso-butyl, tert-butyl, 1-methylpropyl, cyclopropyl, cyclobutyl, cyclopentyl, cyclohexyl, cyclopropylmethyl, cyclobutylmethyl, cyclopentylmethyl, cyclohexylmethyl, tetrahydrofuranyl, tetrahydropyranyl, azetidin-2-yl, azetidin-3-yl, pyrrolidin-2-yl, pyrrolidin-3-yl, piperidin-2-yl, piperidin-3-yl, piperidin-4-yl, piperazin-2-yl, piperazin-3-yl, homopiperidin-2-yl, homopiperidin-3-yl, homopiperidin-4-yl, homopiperazin-2-yl, homopiperazin-3-yl, morpholin-2-yl, morpholin-3-yl, thiomorpholin-2-yl, thiomorpholin-3-yl, tetrahydrofuranylmethyl, tetrahydropyranylmethyl, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, piperazin-2-ylmethyl, piperazin-3-ylmethyl, homopiperidin-1-ylmethyl homopiperidin-2-ylmethyl, homopiperidin-3-ylmethyl, homopiperidin-4-ylmethyl, homopiperazin-1-ylmethyl, homopiperazin-2-ylmethyl, homopiperazin-3-ylmethyl, morpholinomethyl, morpholin-2-ylmethyl, morpholin-3-ylmethyl, thiomorpholin-2-ylmethyl, thiomorpholin-3-ylmethyl, 2-(tetrahydrofuranyl)ethyl, 2-(tetrahydropyranyl)ethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl, 2-(piperazin-2-yl)ethyl, 2-(piperazin-3-yl)ethyl, 2-(homopiperidin-1-yl) ethyl, 2-(homopiperidin-2-yl)ethyl, 2-(homopiperidin-3-yl) ethyl, 2-(homopiperidin-4-yl)ethyl, 2-(homopiperazin-1-yl) ethyl, 2-(homopiperazin-2-yl)ethyl, 2-(homopiperazin-3-yl) ethyl, 2-(morpholino)ethyl, 2-(morpholin-2-yl)ethyl, 2-(morpholin-3-yl)ethyl, 2-(thiomorpholin-2-yl)ethyl, 2-(thiomorpholin-3-yl)ethyl, 2-(azetidin-1-yl)propyl, 3-(azetidin-2-yl)propyl, 3-(azetidin-3-yl)propyl, 3-(pyrrolidin-1-yl)propyl, 3-(pyrrolidin-2-yl)propyl, 3-(pyrrolidin-3-yl)propyl, 3-(piperidino)propyl, 3-(piperidin-2-yl)propyl, 3-(piperidin-3-yl)propyl, 3-(piperidin-4-yl)propyl, 3-(piperazino)propyl, 3-(piperazin-2-yl)propyl, 3-(piperazin-3-yl)propyl, 3-(homopiperidin-1-yl)propyl, 3-(homopiperidin-2-yl)propyl, 3-(homopiperidin-3-yl)propyl, 3-(homopiperidin-4-yl)propyl, 3-(homopiperazin-1-yl)propyl, 3-(homopiperazin-2-yl)propyl, 3-(homopiperazin-3-yl)propyl, 3-(morpholino)propyl, 3-(morpholin-2-yl)propyl and 3-(morpholin-3-yl)propyl, and wherein adjacent carbon atoms in any (2-6C)alkylene chain within a R⁷ substituent are optionally separated by the insertion into the chain of a group selected from O, S, NH, N(CH₃), CH=CH and C≡C, and wherein any CH₂ or CH₃, other than a CH₂ group within a heterocyclyl ring, within a R⁷ substituent optionally bears on each said CH₂ or CH₃ group one or more fluoro, chloro, methyl or ethyl substituents or a substituent selected from hydroxy, cyano, amino, methoxy, ethoxy, methylsulfonyl, ethylsulfonyl, methylamino, ethylamino, dimethylamino, diethylamino, or from a group of the formula:

—X⁶—Q⁵ wherein X⁶ is a direct bond or is selected from O, S and NH, wherein Q⁵ is cyclopropyl, cyclobutyl, cyclopentyl, cyclohexyl, cyclopropylmethyl, cyclobutylmethyl, cyclopentylmethyl, cyclohexylmethyl, tetrahydrofuranyl, tetrahydropyranyl, azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, morpholino, tetrahydrofuranylmethyl, tetrahydropyranylmethyl, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, morpholinomethyl, morpholin-2-ylmethyl, morpholin-3-ylmethyl, 2-(tetrahydrofuranyl)ethyl, 2-(tetrahydropyranyl)ethyl, 2-(azetidin-1-yl)ethyl, 2-(azetidin-2-yl)ethyl, 2-(azetidin-3-yl)ethyl, 2-(pyrrolidin-1-yl) ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl or 2-(morpholino)ethyl, and wherein any heterocyclyl group within a substituent on R⁷ optionally bears 1, 2 or 3 R²¹ substituents, which may be the same or different, selected from fluoro, chloro, trifluoromethyl, cyano, nitro, hydroxy, amino, carbamoyl, methyl, ethyl, vinyl, allyl, ethynyl, 2-propynyl, methoxy, ethoxy, methylsulfonyl, methylamino, ethylamino, dimethylamino, diethylamino, N-methylcarbamoyl, N-ethylcarbamoyl, N,N-dimethylcarbamoyl, N,N-diethylcarbamoyl, carbamoylmethyl, N-methylcarbamoylmethyl, N-ethylcarbamoylmethyl, N,N-dimethylcarbamoylmethyl, N,N-diethylcarbamoylmethyl, cyanomethyl, hydroxymethyl, methoxymethyl, 2-hydroxyethyl, 2-aminoethyl, 2-(N-methylamino)ethyl, 2-(N,N-dimethylamino)ethyl, 2-methoxyethyl, 2-ethoxyethyl, 2-cyanoethyl, 2-carbamoylethyl, 2-(N-methylcarbamoyl) ethyl, 2-(N-ethylcarbamoyl)ethyl, 2-(N,N-dimethylcarbamoyl)ethyl, 2-(N,N-diethylcarbamoyl)ethyl, 2-hydroxyethoxy, 2-aminoethoxy, 2-(N-methylamino)ethoxy, 2-(N,N-dimethylamino)ethoxy, 2-methoxyethoxy, 2-ethoxyethoxy, acetyl, propionyl, hydroxyacetyl, methoxyacetyl, ethoxyacetyl, aminoacetyl, N-methylaminoacetyl, N,N-dimethylaminoacetyl, N-ethylaminoacetyl, N,N-diethylaminoacetyl, N-(2-hydroxyethyl)aminoacetyl, N-(2-methoxyethyl)aminoacetyl, 3-hydroxypropionyl, 2-hydroxypropionyl, 3-methoxypropionyl, 2-methoxypropionyl, 3-aminopropionyl, 3-(N-methylamino)propionyl, 3-(N,N-dimethylamino)propionyl, 3-(N-ethylamino)propionyl, 3-(N,N-diethylamino) propionyl, 3-[N-(2-hydroxyethyl)amino]propionyl, 3-[N-(2-methoxyethyl)amino]propionyl, and from a group of the formula:

—X⁸—Q⁶ wherein X⁸ is a direct bond or is selected from O, NH and CO, wherein Q⁶ is cyclopropyl, cyclobutyl, cyclopentyl, cyclohexyl, cyclopropylmethyl, cyclobutylmethyl, cyclopentylmethyl, cyclohexylmethyl, azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, morpholino, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, morpholinomethyl, morpholin-2-ylmethyl, morpholin-3-ylmethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl or 2-(morpholino)ethyl, and wherein $Q^6$ optionally bears 1, 2 or 3 substituents, which may be the same or different, selected from fluoro, chloro, hydroxy, methyl, ethyl, methoxy and ethoxy, and wherein any heterocyclyl group within a $R^7$ substituent optionally bears 1 oxo substituent, or $R^6$ and $R^7$ together with the carbon atom to which they are attached form a cyclopropyl, cyclobutyl, cyclopentyl or cyclohexyl, azetidin-3-yl, piperidin-3-yl, piperidin-4-yl, tetrahydropyran-3-yl or tetrahydropyran-4-yl group, which group optionally bears 1, 2 or 3 substituents, which may be the same or different, selected from fluoro, chloro, hydroxy, methyl, ethyl, methoxy, ethoxy, amino, carbamoyl, acetyl, methylsulfonyl, methylamino, dimethylamino, N-methylcarbamoyl, N-ethylcarbamoyl, N,N-dimethylcarbamoyl, hydroxymethyl, methoxymethyl, 2-hydroxyethyl, 2-methoxyethyl, 2-hydroxyethoxy, 2-methoxyethoxy, hydroxyacetyl and methoxyacetyl, (jjjj) $R^7$ is selected from hydrogen and (1-6C)alkyl, and wherein adjacent carbon atoms in any (2-6C)alkylene chain within a $R^7$ substituent are optionally separated by the insertion into the chain of a group selected from O, S, and $N(R^{18})$ wherein $R^{18}$ is hydrogen or (1-3C)alkyl, and wherein $R^7$ optionally bears on carbon one or more (for example 1, 2 or 3) fluoro, chloro or (1-3C)alkyl substituents or a substituent selected from hydroxy, cyano, amino, (3-6C)-cycloalkyl, (3-6C)-cycloalkyl-oxy, (1-3C)alkoxy, (1-3C)alkylsulfonyl, (1-3C)alkylamino and di-[(1-3C)alkyl]amino, or $R^6$ and $R^7$ together with the carbon atom to which they are attached form a cyclopropyl, cyclobutyl, cyclopentyl, cyclohexyl, azetidin-3-yl, piperidin-3-yl, piperidin-4-yl, tetrahydropyran-3-yl or tetrahydropyran-4-yl group, which group optionally bears 1 or 2 substituents, which may be the same or different, selected from fluoro, chloro, hydroxy, oxo, methyl, ethyl, methoxy and ethoxy, or $R^7$ and the group $R^{5a}R^5NC(Z)$ together with the carbon atom to which they are attached form a heterocyclyl group selected from a group of the formula:

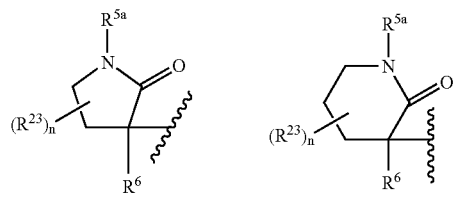

wherein $R^6$ is hydrogen,
$R^{5a}$ is hydrogen, n is 0, 1 or 2 and each $R^{23}$, which may be the same or different, is selected from fluoro, chloro, hydroxy, methyl, ethyl, methoxy and ethoxy;

(kkkk) $R^7$ is selected from hydrogen, methyl, ethyl, propyl, isopropyl, butyl, iso-butyl, tert-butyl, hydroxymethyl, 2-hydroxyethyl, 2-hydroxypropyl, 3-hydroxypropyl, methoxymethyl, 2-methoxyethyl, 2-methoxypropyl, 3-methoxypropyl, ethoxymethyl, 2-ethoxyethyl, 3-ethoxypropyl, isopropoxymethyl, 2-isopropoxyethyl, 3-isopropoxypropyl, (2-hydroxyethoxy)methyl, (2-methoxyethoxy)methyl, (2-ethoxyethoxy)methyl, 2-(2-hydroxyethoxy)ethyl, 2-(2-methoxyethoxy)ethyl, 2-(2-ethoxyethoxy)ethyl, cyclopropyloxymethyl and 2-(cyclopropyloxy)ethyl;

(llll) $R^7$ is selected from hydrogen and (1-3C)alkyl substituted by a group selected from azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, homopiperidin-1-yl, homopiperidin-2-yl, homopiperidin-3-yl, homopiperidin-4-yl, homopiperazin-1-yl, homopiperazin-2-yl, homopiperazin-3-yl, morpholino, morpholin-2-yl, morpholin-3-yl, $NR^{32}R^{33}$, $C(O)NR^{34}R^{35}$, (2-3C)alkanoylamino, N-(1-3C)alkyl-(2-3C)alkanoylamino, and a group of the formula:

$$-X^6-Q^5$$

wherein $X^6$ is selected from O and $N(R^{20})$, wherein $R^{20}$ is hydrogen or methyl and $Q^5$ is selected from azetidin-1-yl-(1-3C)alkyl, azetidin-2-yl-(1-3C)alkyl, azetidin-3-yl-(1-3C)alkyl, pyrrolidin-1-yl-(1-3C)alkyl, pyrrolidin-2-yl-(1-3C)alkyl, pyrrolidin-3-yl-(1-3C)alkyl, piperidino-(1-3C)alkyl, piperidin-2-yl-(1-3C)alkyl, piperidin-3-yl-(1-3C)alkyl, piperidin-4-yl-(1-3C)alkyl, piperazino-(1-3C)alkyl, piperazin-2-yl-(1-3C)alkyl, piperazin-3-yl-(1-3C)alkyl, homopiperidin-1-yl-(1-3C)alkyl, homopiperidin-2-yl-(1-3C)alkyl, homopiperidin-3-yl-(1-3C)alkyl, homopiperidin-4-yl-(1-3C)alkyl, homopiperazin-1-yl-(1-3C)alkyl, homopiperazin-2-yl-(1-3C)alkyl, homopiperazin-3-yl-(1-3C)alkyl, morpholino-(1-3C)alkyl, morpholin-2-yl-(1-3C)alkyl, morpholin-3-yl-(1-3C)alkyl, wherein each of $R^{32}$, $R^{33}$, $R^{34}$ and $R^{35}$, which may be the same or different, is selected from hydrogen, (1-3C)alkyl, (2-3C)alkenyl and (2-3C)alkynyl, and wherein any of $R^{32}$, $R^{33}$, $R^{34}$ and $R^{35}$ optionally bears on carbon one or more (for example 1, 2 or 3) $R^{36}$ substituents, which may be the same or different, selected from fluoro hydroxy, cyano, methoxy and ethoxy, and wherein any heterocyclyl group within $R^7$ optionally bears one or more (for example 1, 2 or 3) $R^{21}$ substituents, which may be the same or different, selected from fluoro, chloro, trifluoromethyl, cyano, nitro, hydroxy, amino, carbamoyl, methyl, ethyl, vinyl, allyl, ethynyl, 2-propynyl, methoxy, ethoxy, methylsulfonyl, ethylsulfonyl, methylamino, ethylamino, dimethylamino, diethylamino, N-methylcarbamoyl, N-ethylcarbamoyl, N,N-dimethylcarbamoyl, N,N-diethylcarbamoyl, carbamoylmethyl, N-methylcarbamoylmethyl, N-ethylcarbamoylmethyl, N,N-dimethylcarbamoylmethyl, N,N-diethylcarbamoylmethyl, cyanomethyl, hydroxymethyl, methoxymethyl, 2-hydroxyethyl, 2-aminoethyl, 2-(N-methylamino)ethyl, 2-(N,N-dimethylamino)ethyl, 2-methoxyethyl, 2-ethoxyethyl, 2-cyanoethyl, 2-carbamoylethyl, 2-(N-methylcarbamoyl)ethyl, 2-(N-ethylcarbamoyl)ethyl, 2-(N,N-dimethylcarbamoyl)ethyl, 2-(N,N-diethylcarbamoyl)ethyl, 2-hydroxyethoxy, 2-aminoethoxy, 2-(N-methylamino)ethoxy, 2-(N,N-dimethylamino)ethoxy, 2-methoxyethoxy, 2-ethoxyethoxy, acetyl, propionyl, hydroxyacetyl, methoxyacetyl, ethoxyacetyl, aminoacetyl, N-methylaminoacetyl, N,N-dimethylaminoacetyl, N-ethylaminoacetyl, N,N-diethylaminoacetyl, N-(2-hydroxyethyl)aminoacetyl, N-(2-methoxyethyl)aminoacetyl, 3-hydroxypropionyl, 2-hydroxypropionyl, 3-methoxypropionyl, 2-methoxypropionyl, 3-aminopropionyl, 3-(N-methylamino)propionyl, 3-(N,N-dimethylamino)propionyl, 3-(N-ethylamino)propionyl, 3-(N,N-diethylamino)propionyl, 3-[N-(2-hydroxyethyl)amino]propionyl, 3-[N-(2-methoxyethyl)amino]propionyl, and from a group of the formula:

$$-X^8-Q^6$$

wherein $X^8$ is CO, wherein $Q^6$ is cyclopropyl, cyclobutyl, cyclopentyl, cyclohexyl, cyclopropylmethyl, cyclobutylmethyl, cyclopentylmethyl, cyclohexylmethyl, azetidin-1-ylmethyl, azetidin-2-ylmethyl, azetidin-3-ylmethyl, pyrrolidin-1-ylmethyl, pyrrolidin-2-ylmethyl, pyrrolidin-3-ylmethyl, piperidinomethyl, piperidin-2-ylmethyl, piperidin-3-ylmethyl, piperidin-4-ylmethyl, piperazinomethyl, morpholinomethyl, morpholin-2-ylmethyl, morpholin-3-ylmethyl, 2-(azetidin-1-yl)ethyl, 2-(azetidin-2-yl)ethyl, 2-(azetidin-3-yl)ethyl, 2-(pyrrolidin-1-yl)ethyl, 2-(pyrrolidin-2-yl)ethyl, 2-(pyrrolidin-3-yl)ethyl, 2-(piperidino)ethyl, 2-(piperidin-2-yl)ethyl, 2-(piperidin-3-yl)ethyl, 2-(piperidin-4-yl)ethyl, 2-(piperazino)ethyl or 2-(morpholino)ethyl, and wherein $Q^6$ optionally bears 1, 2 or 3 substituents, which may be the same or different, selected from fluoro, chloro, hydroxy, methyl, ethyl, methoxy and ethoxy, and wherein any heterocyclyl group within a $R^7$ substituent optionally bears 1 oxo substituent;

(mmmm) $R^7$ is (1-3C)alkyl (for example methyl or ethyl) substituted by a group selected from azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, homopiperidin-1-yl, homopiperidin-2-yl, homopiperidin-3-yl, homopiperidin-4-yl, homopiperazin-1-yl, homopiperazin-2-yl, homopiperazin-3-yl, morpholino, morpholin-2-yl, morpholin-3-yl, $NR^{32}R^{33}$ and $C(O)NR^{34}R^{35}$, wherein each of $R^{32}$, $R^{33}$, $R^{34}$ and $R^{35}$, which may be the same or different, is selected from hydrogen and (1-3C)alkyl, and wherein any of $R^{32}$, $R^{33}$, $R^{34}$ and $R^{35}$ optionally bears on carbon one or more (for example 1, 2 or 3) fluoro substituent or a substituent selected from hydroxy, cyano, methoxy and ethoxy, and wherein any heterocyclyl group within $R^7$ optionally bears one or more (for example 1, 2 or 3) $R^{21}$ substituents, which may be the same or different, selected from fluoro, chloro, trifluoromethyl, cyano, nitro, hydroxy, amino, carbamoyl, methyl, ethyl, vinyl, allyl, ethynyl, 2-propynyl, methoxy, ethoxy, methylsulfonyl, ethylsulfonyl, methylamino, ethylamino, dimethylamino, diethylamino, N-methylcarbamoyl, N-ethylcarbamoyl, N,N-dimethylcarbamoyl, N,N-diethylcarbamoyl, carbamoylmethyl, N-methylcarbamoylmethyl, N-ethylcarbamoylmethyl, N,N-dimethylcarbamoylmethyl, N,N-diethylcarbamoylmethyl, cyanomethyl, hydroxymethyl, 2-hydroxyethyl, 2-aminoethyl, 2-(N-methylamino)ethyl, 2-(N,N-dimethylamino)ethyl, methoxymethyl, 2-methoxyethyl, 2-ethoxyethyl, 2-cyanoethyl, 2-carbamoylethyl, 2-(N-methylcarbamoyl)ethyl, 2-(N-ethylcarbamoyl)ethyl, 2-(N,N-dimethylcarbamoyl)ethyl, 2-(N,N-diethylcarbamoyl)ethyl, acetyl, propionyl, hydroxyacetyl, methoxyacetyl, ethoxyacetyl, aminoacetyl, N-methylaminoacetyl, N,N-dimethylaminoacetyl, N-ethylaminoacetyl, N,N-diethylaminoacetyl, 3-hydroxypropionyl, 2-hydroxypropionyl, 3-methoxypropionyl, 2-methoxypropionyl, 3-aminopropionyl, 3-(N-methylamino)propionyl, 3-(N,N-dimethylamino)propionyl, 3-(N-ethylamino)propionyl and 3-(N,N-diethylamino)propionyl, and wherein any heterocyclyl group within a $R^7$ substituent optionally bears 1 oxo substituent;

(nnnn) $R^7$ is (1-3C)alkyl (for example methyl or ethyl) substituted by a group selected from
azetidin-1-yl, azetidin-2-yl, azetidin-3-yl, pyrrolidin-1-yl, pyrrolidin-2-yl, pyrrolidin-3-yl, piperidino, piperidin-2-yl, piperidin-3-yl, piperidin-4-yl, piperazino, piperazin-2-yl, piperazin-3-yl, homopiperidin-1-yl, homopiperidin-2-yl, homopiperidin-3-yl, homopiperidin-4-yl, homopiperazin-1-yl, homopiperazin-2-yl, homopiperazin-3-yl, morpholino, morpholin-2-yl, morpholin-3-yl, amino, methylamino ethylamino, dimethylamino, diethylamino, carbamoyl, N-methylcarbamoyl, N-ethylcarbamoyl, N,N-dimethylcarbamoyl, N,N-diethylcarbamoyl, and wherein any heterocyclyl group within $R^7$ optionally bears on a ring nitrogen a substituent selected from methyl, ethyl, allyl, 2-propynyl, methylsulfonyl, ethylsulfonyl, carbamoylmethyl, N-methylcarbamoylmethyl, N-ethylcarbamoylmethyl, N,N-dimethylcarbamoylmethyl, N,N-diethylcarbamoylmethyl, cyanomethyl, 2-hydroxyethyl, 2-methoxyethyl, 2-ethoxyethyl, 2-cyanoethyl, 2-carbamoylethyl, 2-(N-methylcarbamoyl)ethyl, 2-(N-ethylcarbamoyl)ethyl, 2-(N,N-dimethylcarbamoyl)ethyl, 2-(N,N-diethylcarbamoyl)ethyl, acetyl, propionyl, hydroxyacetyl, methoxyacetyl, ethoxyacetyl, aminoacetyl, N-methylaminoacetyl, N,N-dimethylaminoacetyl, N-ethylaminoacetyl, N,N-diethylaminoacetyl, 3-hydroxypropionyl, 2-hydroxypropionyl, 3-methoxypropionyl, 2-methoxypropionyl, 3-aminopropionyl, 3-(N-methylamino)propionyl, 3-(N,N-dimethylamino)propionyl, 3-(N-ethylamino)propionyl and 3-(N,N-diethylamino)propionyl, and wherein any heterocyclyl group within $R^7$ is optionally substituted on carbon by 1 or 2 substituents selected from fluoro, chloro, hydroxy, carbamoyl, methyl, ethyl, methoxy, ethoxy, N-methylcarbamoyl, N-ethylcarbamoyl, N,N-dimethylcarbamoyl, and N,N-diethylcarbamoyl, and wherein any heterocyclyl group within a $R^7$ substituent optionally bears 1 oxo substituent;

(oooo) $R^7$ is selected from hydrogen, methyl, ethyl, isopropyl, hydroxymethyl, methoxymethyl, isopropyloxymethyl, 2-hydroxyethyl, 2-methoxyethyl, aminomethyl, 2-aminoethyl, methylaminomethyl, 2-(methylamino)ethyl, dimethylaminomethyl, 2-(dimethylamino)ethyl, pyrrolidin-3-yl and 1-methylpyrrolidin-3-yl, or $R^6$ and $R^7$ together with the carbon atom to which they are attached form a cyclopropyl, cyclobutyl, cyclopentyl, cyclohexyl, cyclopent-3-en-1-yl, azetidin-3-yl, piperidin-3-yl, piperidin-4-yl, tetrahydropyran-3-yl or tetrahydropyran-4-yl group, which group optionally bears 1 or 2 substituents, which may be the same or different, selected from (1-4C)alkyl, hydroxy-(1-4C)alkyl, (1-3C)alkoxy-(1-4C)alkyl, (2-4C)alkanoyl, hydroxy-(2-4C)alkanoyl, (1-3C)alkoxy-(2-4C)alkanoyl, (1-4C)alkylsulfonyl, carbamoyl-(1-4C)alkyl, N-(1-4C)alkylcarbamoyl-(1-4C)alkyl and N,N-di-[(1-4C)alkyl]carbamoyl-(1-4C)alkyl, or $R^7$ and the group $R^{5a}R^5NC(Z)$ together with the carbon atom to which they are attached form a heterocyclyl group selected from a group of the formula:

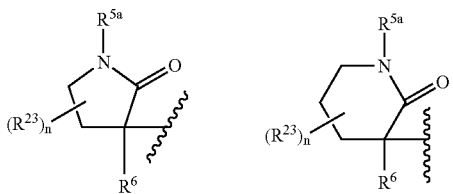

wherein $R^6$ is hydrogen, and $R^{5a}$ is selected from hydrogen, methyl and ethyl (particularly $R^{5a}$ is hydrogen);

n is 0, 1 or 2 and each $R^{23}$, which may be the same or different, is methyl (particularly n is 0);

(pppp) $R^7$ is selected from hydrogen, methyl, ethyl, isopropyl, hydroxymethyl, methoxymethyl, isopropyloxymethyl, 2-hydroxyethyl, 2-methoxyethyl, aminomethyl, 2-aminoethyl, methylaminomethyl, 2-(methylamino)ethyl, dimethylaminomethyl, 2-(dimethylamino)ethyl, pyrrolidin-3-yl and 1-methylpyrrolidin-3-yl, or $R^6$ and $R^7$ together with the carbon atom to which they are attached form a cyclopropyl, cyclobutyl, cyclopentyl, cyclohexyl, cyclopent-3-en-1-yl, azetidin-3-yl, piperidin-3-yl, piperidin-4-yl, tetrahydropyran-3-yl or tetrahydropyran-4-yl group, which group formed by $R^6$ and $R^7$ together with the carbon atom to which they are attached optionally bears on an available nitrogen atom a substituent selected from, methyl, ethyl, isopropyl, cyclopropylmethyl, 2-hydroxyethyl, 2-methoxyethyl, methylsulfonyl, carbamoylmethyl, 2-carbamoylethyl, N-methylcarbamoylmethyl, N,N-dimethylcarbamoylmethyl, 2-(N-methylcarbamoyl)ethyl, 2-(N,N-dimethylcarbamoyl)ethyl, 3-(N,N-dimethylcarbamoyl)prop-2-yl, acetyl, propionyl, hydroxyacetyl, methoxyacetyl, ethoxyacetyl, 3-hydroxypropionyl, 2-hydroxypropionyl, 3-methoxypropionyl and 2-methoxypropionyl, which group formed by $R^6$ and $R^7$ together with the carbon atom to which they are attached optionally bears on an available carbon atom 1 or 2 methyl substituents;

(qqqq) $R^6$ and $R^7$ together with the carbon atom to which they are attached form a (3-7C)cycloalkyl, (3-7C)cycloalkenyl or heterocyclyl group, which group optionally bears one or more (for example 1, 2 or 3) $R^{22}$ substituents, which may be the same or different, as defined hereinbefore, and wherein any heterocyclyl group formed by $R^6$ and $R^7$ together with the carbon atom to which they are attached, optionally bears 1 or 2 oxo or thioxo substituents, or $R^7$ and the group $R^{5a}R^5NC(Z)$ together with the carbon atom to which they are attached form a heterocyclyl group selected from a group of the formula:

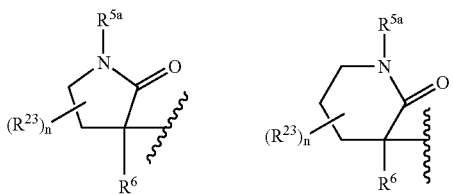

wherein $R^6$ is hydrogen, and $R^{5a}$ is selected from hydrogen, methyl and ethyl (particularly $R^{5a}$ is hydrogen);

n is 0, 1 or 2 and each $R^{23}$, which may be the same or different, is methyl (particularly n is 0);

(rrrr) $R^6$ and $R^7$ together with the carbon atom to which they are attached form a cyclopropyl, cyclobutyl, cyclopentyl, cyclohexyl, cyclopent-3-en-1-yl, azetidin-3-yl, piperidin-3-yl, piperidin-4-yl, tetrahydropyran-3-yl or tetrahydropyran-4-yl group, which group optionally bears 1 or 2 substituents, which may be the same or different, selected from (1-4C)alkyl, hydroxy-(1-4C)alkyl, (1-3C)alkoxy-(1-4C)alkyl, (2-4C)alkanoyl, hydroxy-(2-4C)alkanoyl, (1-3C)alkoxy-(2-4C)alkanoyl, (1-4C)alkylsulfonyl, carbamoyl-(1-4C)alkyl, N-(1-4C)alkylcarbamoyl-(1-4C)alkyl and N,N-di-[(1-4C)alkyl]carbamoyl-(1-4C)alkyl;

(ssss) $R^7$ and the group $R^{5a}R^5NC(Z)$ together with the carbon atom to which they are attached form a heterocyclyl group selected from a group of the formula:

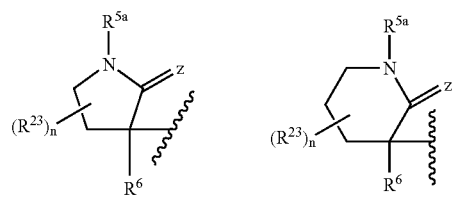

wherein Z is O, $R^6$ is as defined hereinabove (particularly $R^6$ is hydrogen or (1-3C)alkyl, more particularly $R^6$ is hydrogen), $R^{5a}$ is as defined hereinabove (particularly $R^{5a}$ is hydrogen), n is 0, 1 or 2 (particularly n is 0) and each $R^{23}$, which may be the same or different, is as hereinbefore defined (for example $R^{23}$ is methyl);

(tttt) $R^7$ is as defined in any of (aaaa) to (ssss) above except $R^7$ is not hydrogen;

(uuuu) $R^6$ is hydrogen and $R^7$ is as defined in any of (aaaa) to (ssss) above;

(wwww) $R^7$ is selected from hydrogen and (1-3C)alkyl (for example $R^7$ is methyl or ethyl);

(xxxx) $R^6$ and $R^7$, which may be the same or different are selected from hydrogen, (1-4C)alkyl, hydroxy-(1-4C)alkyl and (1-3C)alkoxy-(1-4C)alkyl (particularly $R^6$ and $R^7$ are not both hydrogen);

(yyyy) $R^6$ is hydrogen or methyl (particularly hydrogen), $R^7$ is selected from (1-4C)alkyl, hydroxy-(1-4C)alkyl and (1-3C)alkoxy-(1-4C)alkyl (for example $R^7$ is methyl, ethyl, hydroxymethyl, methoxymethyl, 2-hydroxyethyl or 2-methoxyethyl), and $R^4$ is selected from hydrogen and (1-3C)alkyl (for example $R^4$ is methyl);

(zzzz) $R^6$ is hydrogen and $R^7$ is selected from methyl, ethyl, hydroxymethyl, methoxymethyl, 2-hydroxyethyl and 2-methoxyethyl, or $R^6$ and $R^7$ together with the carbon atoms to which they are attached form a cyclopropyl group; and $R^4$ is hydrogen, methyl, ethyl or isopropyl (for example $R^4$ is methyl);

(aaaaa) $R^{5a}$ is hydrogen or (1-3C)alkyl, and $R^5$ is selected from (2-4C)alkenyl, (2-4C)alkynyl, (3-7C)cycloalkyl, (3-7C)cycloalkyl-(1-4C)alkyl, (3-7C)cycloalkenyl, (3-7C)cycloalkenyl-(1-4C)alkyl, heterocyclyl, heterocyclyl-(1-4C)alkyl and (1-4C)alkyl substituted by one or more (for example 1 or 2), $R^{16}$ substituents as hereinbefore defined, which may be the same or different, and wherein and wherein any $CH_2$ or $CH_3$, other than a $CH_2$ group within a heterocyclyl ring, within a $R^5$ or $R^{5a}$ substituent optionally bears on each said $CH_2$ or $CH_3$ one or more $R^{16}$ substituents as hereinbefore defined, which may be the same or different, and wherein any heterocyclyl group within a substituent on $R^5$ or $R^{5a}$ optionally bears one or more (for example 1, 2 or 3) substituents, which may be the same or different, selected from halogen, (1-4C)alkyl, (2-4C)alkanoyl, hydroxy-(2-4C)alkanoyl, (1-4C)alkoxy-(2-4C)alkanoyl and (1-4C)alkylsulfonyl, and wherein any heterocyclyl group within a $R^5$ or $R^{5a}$ substituent optionally bears 1 or 2 oxo substituents;

(bbbbb) $R^{5a}$ is hydrogen or (1-3C)alkyl (for example $R^{5a}$ is hydrogen), and $R^5$ is selected from hydroxy-(2-4C)alkyl, (1-3C)alkoxy-(2-4C)alkyl, (2-4C)alkenyl, and (2-4C)alkynyl; and (ccccc) $R^{5a}$ is hydrogen, $R^5$ is hydrogen or methyl and $R^4$ is (1-4C)alkyl.

A particular embodiment of the present invention is a quinazoline derivative of the formula I wherein:

p is 1 and $R^1$ is located at the 7-position;

$R^1$ is selected from (1-6C)alkoxy, (3-7C)cycloalkyl-oxy and (3-7C)cycloalkyl-(1-6C)alkoxy, and wherein adjacent carbon atoms in any (2-6C)alkylene chain within a $R^1$ substituent are optionally separated by the insertion into the chain of an O atom, and wherein any $CH_2$ or $CH_3$ group within a $R^1$ substituent optionally bears on each said $CH_2$ or $CH_3$ group one or more fluoro or chloro substituents, or a substituent selected from hydroxy and (1-3C)alkoxy;

a is 1, 2 or 3;

each $R^2$, which may be the same or different, is selected from halogeno (for example fluoro, chloro or bromo) and, (2-3C)alkynyl;

m is 1 or 2;

$R^{3a}$ is hydrogen;

$R^3$ is selected from hydrogen and (1-4C)alkyl, or $R^3$ and $R^{3a}$ together with the carbon atom to which they are attached form a (3-6C)cycloalkyl ring, and wherein any $R^3$ or $R^{3a}$ optionally bears on carbon one or more (for example 1, 2 or 3) $R^{14}$ substituents, which may be the same or different;

$R^4$ is selected from is (1-6C)alkyl, and wherein a $R^4$ substituent optionally bears on carbon one or more (for example 1, 2 or 3) $R^{15}$ substituents, which may be the same or different;

$R^{5a}$ is hydrogen or (1-3C)alkyl (for example $R^{5a}$ is hydrogen);

$R^5$ is selected from hydrogen, (1-4C)alkyl, (2-4C)alkenyl, (2-4C)alkynyl, (3-7C)cycloalkyl, (3-7C)cycloalkyl-(1-4C)alkyl, (3-7C)cycloalkenyl, (3-7C)cycloalkenyl-(1-4C)alkyl, heterocyclyl and heterocyclyl-(1-4C)alkyl, and wherein and wherein any $CH_2$ or $CH_3$, other than a $CH_2$ group within a heterocyclyl ring, within a $R^5$ substituent optionally bears on each said $CH_2$ or $CH_3$ one or more $R^{16}$ substituents, which may be the same or different, and wherein any heterocyclyl group within a substituent on $R^5$ optionally bears one or more (for example 1, 2 or 3) substituents, which may be the same or different, selected from halogeno, (1-4C)alkyl, (2-4C)alkanoyl, hydroxy-(2-4C)alkanoyl, (1-4C)alkoxy-(2-4C)alkanoyl and (1-4C)alkylsulfonyl, and wherein any heterocyclyl group within a $R^5$ substituent optionally bears 1 or 2 oxo substituents, or $R^5$ and $R^{5a}$ together with the nitrogen atom to which they are attached form a azetidin-1-yl, pyrrolidin-1-yl, piperidino, morpholino or piperazin-1yl group, which group optionally bears one or more substituents (for example 1, 2 or 3), which may be the same or different, selected from halogeno, (1-4C)alkyl, (2-4C)alkanoyl, hydroxy-(2-4C)alkanoyl, (1-4C)alkoxy-(2-4C)alkanoyl and (1-4C)alkylsulfonyl, and wherein any heterocyclyl group formed by $R^5$ and $R^{5a}$ together with the nitrogen atom to which they are attached, optionally bears 1 or 2 oxo substituents;

Z is O;

q is 1;

each $R^6$, which may be the same or different, is selected from hydrogen and (1-4C)alkyl, and wherein $R^6$ optionally bears on carbon one or more (for example 1, 2 or 3) $R^{17}$ substituents, which may be the same or different (for example $R^6$ is hydrogen);

each $R^7$, which may be the same or different, is selected from (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, provided that when $R^7$ is heterocyclyl, $R^7$ is linked to the carbon carrying $R^6$ and the $R^{5a}R^5NC(Z)$ group by a ring carbon, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, carboxy, carbamoyl, (1-6C)alkoxy, $NR^{32}R^{33}$, $C(O)NR^{34}R^{35}$ and (2-6C)alkanoyl, wherein each of $R^{32}$, $R^{33}$, $R^{34}$ and $R^{35}$, which may be the same or different, is selected from hydrogen (1-6C)alkyl, (2-6C)alkenyl and (2-6C)alkynyl, and wherein any of $R^{32}$, $R^{33}$, $R^{34}$ and $R^{35}$ optionally bears on carbon one or more (for example 1, 2 or 3) $R^{36}$ substituents, which may be the same or different, and wherein any heterocyclyl group within a substituent on R optionally bears one or more (for example 1, 2 or 3) $R^{21}$ substituents, which may be the same or different, and wherein any heterocyclyl group within a $R^7$ substituent optionally bears 1 or 2 oxo substituents;

or $R^6$ and $R^7$ together with the carbon atom to which they are attached form a (3-7C)cycloalkyl, (3-7C)cycloalkenyl or heterocyclyl group, which group optionally bears one or more (for example 1, 2 or 3) $R^{22}$ substituents, which may be the same or different, and wherein any heterocyclyl group formed by $R^6$ and $R^7$ together with the carbon atom to which they are attached, optionally bears 1 or 2 oxo substituents;

or $R^7$ and the group $R^{5a}R^5NC(Z)$ together with the carbon atom to which they are attached form a heterocyclyl group, which group optionally bears one or more (for example 1, 2 or 3) $R^{23}$ substituents, which may be the same or different;

each $R^{21}$, $R^{22}$ and $R^{24}$, which may be the same or different, is selected from halogeno, trifluoromethyl, cyano, nitro, hydroxy, amino, carboxy, carbamoyl, formyl, mercapto, sulfamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, N-(1-6C)alkylsulfamoyl, N,N-di-[(1-6C)alkyl]sulfamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, a group of the formula:

—$X^7$—$R^{25}$ wherein $X^7$ is a direct bond or is selected from O, $N(R^{26})$ and C(O), wherein $R^{26}$ is hydrogen or (1-6C)alkyl, and $R^{25}$ is halogeno-(1-6C)alkyl, hydroxy-(1-6C)alkyl, carboxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl, (2-6C)alkanoyloxy-(1-6C)alkyl or (1-6C)alkoxycarbonyl-(1-6C)alkyl, and from a group of the formula:

$$-X^8-Q^6$$

wherein $X^8$ is a direct bond or is selected from O, $SO_2$, $N(R^{31})$ and CO, wherein $R^{31}$ is hydrogen or (1-6C)alkyl, and $Q^6$ is (3-7C)cycloalkyl, (3-7C)cycloalkyl-(1-6C)alkyl, heterocyclyl or heterocyclyl-(1-6C)alkyl, which optionally bears one or more (for example 1, 2 or 3) substituents, which may be the same or different selected from halogeno, hydroxy, (1-4C)alkyl and (1-4C)alkoxy, and wherein $R^{21}$, $R^{22}$ and $R^{23}$ optionally bears on carbon one or more (for example 1, 2 or 3) $R^{29}$ substituents, which may be the same or different;

each of $R^{14}$, $R^{15}$, $R^{16}$ and $R^{17}$, which may be the same or different, is selected from halogeno, hydroxy, cyano and (1-4C)alkoxy, and wherein any of $R^{14}$, $R^{15}$, $R^{16}$ and $R^{17}$ optionally bears on carbon one or more (for example 1, 2 or 3) $R^{30}$ substituents, which may be the same or different;

$R^{29}$, $R^{30}$ and $R^{36}$, which may be the same or different, are selected from halogeno, hydroxy, cyano, amino, methylamino, dimethylamino, methoxy, ethoxy, vinyl, allyl and ethynyl;

or a pharmaceutically acceptable salt thereof.

Another embodiment is a quinazoline derivative of the formula I wherein:

p is 1;

$R^1$ is located at the 7-position and is selected from hydrogen, hydroxy, (1-6C)alkoxy, (3-7C)cycloalkyl-oxy and (3-7C)cycloalkyl-(1-6C)alkoxy, and wherein adjacent carbon atoms in any (2-6C)alkylene chain within a $R^1$ substituent are optionally separated by the insertion into the chain of an O atom, and wherein any $CH_2$ or $CH_3$ group within a $R^1$ substituent optionally bears on each said $CH_2$ or $CH_3$ group one or more fluoro or chloro substituents, or a substituent selected from hydroxy and (1-3C)alkoxy;

a is 1, 2 or 3;

each $R^2$, which may be the same or different, is selected from fluoro, chloro, bromo, iodo, cyano, hydroxy, trifluoromethyl, (1-4C)alkyl, (2-4C)alkenyl, (2-4C)alkynyl and (1-4C)alkoxy;

m is 1 or 2 (for example m is 1);

$R^{3a}$ is hydrogen;

$R^3$ is selected from hydrogen and (1-3C)alkyl, and wherein $R^3$ optionally bears on carbon a substituent, selected from fluoro, hydroxy and methoxy (for example $R^3$ is hydrogen or methyl);

$R^4$ is selected from hydrogen, (1-4C)alkyl, (2-4C)alkanoyl, and (1-4C)alkylsulfonyl (for example $R^4$ is selected from (1-4C)alkyl, (2-4C)alkanoyl, and (1-4C)alkylsulfonyl, such as methyl);

q is 1;

$R^{5a}$ is hydrogen;

$R^5$ is selected from hydrogen and (1-3C)alkyl;

Z is O;

$R^6$ is selected from hydrogen and (1-3C)alkyl (for example $R^6$ is hydrogen);

$R^7$ is selected from hydrogen, (1-6C)alkyl, (2-6C)alkenyl, (2-6C)alkynyl, aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl and heterocyclyl-(1-6C)alkyl, provided that when $R^7$ is heterocyclyl or heteroaryl, $R^7$ is linked to the carbon carrying $R^6$ and the $R^5NHC(Z)$ group by a ring carbon, and wherein adjacent carbon atoms in any (2-6C)alkylene chain within a $R^7$ substituent are optionally separated by the insertion into the chain of a group selected from O, S, $N(R^{18})$, $CON(R^{18})$, $N(R^{18})CO$, CH=CH and C≡C wherein $R^{18}$ is hydrogen or (1-6C)alkyl, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, or from a group of the formula:

$$-X^6-Q^5$$

wherein $X^6$ is a direct bond or is selected from O, S, $N(R^{20})$, $CON(R^{20})$, $N(R^{20})CO$ and $C(R^{20})_2O$, wherein $R^{20}$ is hydrogen or (1-6C)alkyl, and $Q^5$ is aryl, aryl-(1-6C)alkyl, (3-7C)cycloalkyl, (3-7C)cycloalkyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^7$ optionally bears one or more (for example 1, 2 or 3) $R^{21}$, wherein each $R^{21}$, which may be the same or different, is selected from halogeno, trifluoromethyl, cyano, nitro, hydroxy, amino, carbamoyl, formyl, (1-6C)alkyl, (2-8C)alkenyl, (2-8C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoylamino and N-(1-6C)alkyl-(2-6C)alkanoylamino, a group of the formula:

$$-X^7-R^{25}$$

wherein $X^7$ is a direct bond or is selected from O, $N(R^{26})$ and C(O), wherein $R^{26}$ is hydrogen or (1-6C)alkyl, and $R^{25}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl or (2-6C)alkanoyl-(1-6C)alkyl, and from a group of the formula:

$$-X^8-Q^6$$

wherein $X^8$ is a direct bond or is selected from O, $N(R^{31})$ and CO, wherein $R^{31}$ is hydrogen or (1-6C)alkyl, and $Q^6$ is (3-7C)cycloalkyl, (3-7C)cycloalkyl-(1-6C)alkyl, heterocyclyl or heterocyclyl-(1-6C)alkyl, which optionally bears one or more (for example 1, 2 or 3) substituents, which may be the same or different selected from halogeno, hydroxy, (1-4C)alkyl and (1-4C)alkoxy, and wherein any $R^{21}$ optionally bears on carbon one or more (for example 1, 2 or 3) $R^{29}$ substituents, which may be the same or different, selected from fluoro, hydroxy, cyano, amino, methylamino, dimethylamino, methoxy, ethoxy, vinyl, allyl and ethynyl, and wherein any heterocyclyl group within a $R^7$ substituent optionally bears 1 oxo substituent;

or $R^6$ and $R^7$ together with the carbon atom to which they are attached form a (3-6C)cycloalkyl or heterocyclyl group, which heterocyclyl group is a 4 to 7 membered monocyclic, saturated or partially saturated monocyclic ring with 1 or 2 heteroatoms selected from oxygen, nitrogen and sulfur, and wherein the group formed by $R^6$ and $R^7$ together with the carbon to which they are attached optionally bears one or more (for example 1, 2 or 3) $R^{22}$ substituents, which may be the same or different, as hereinabove defined, and wherein any heterocyclyl group formed by $R^6$ and $R^7$ together with the carbon atom to which they are attached, optionally bears 1 oxo substituent, or $R^7$ and the group $R^5$NHC(Z) together with the carbon atom to which they are attached form a heterocyclyl group, which heterocyclic group is a 4 to 7 membered monocyclic, saturated or partially saturated monocyclic ring which optionally contains 1 further heteroatom selected from oxygen, nitrogen and sulfur, and wherein the group formed by $R^7$ and the group $R^5$NHC(Z) together with the carbon atom to which they are attached optionally bears one or more (for example 1, 2 or 3) $R^{23}$ substituents, which may be the same or different, as hereinabove defined (in particular embodiments, the NHC(Z) group in the ring so formed is not substituted);

or a pharmaceutically acceptable salt thereof.

Particular values for $R^7$ in this embodiment are any of the groups defined above in any one of paragraphs (aaaa) to (pppp). Particularly $R^7$ in this embodiment is selected from hydrogen, methyl, ethyl, propyl, isopropyl, butyl, iso-butyl, tert-butyl, hydroxymethyl, 2-hydroxyethyl, 2-hydroxypropyl, 3-hydroxypropyl, methoxymethyl, 2-methoxyethyl, 2-methoxypropyl, 3-methoxypropyl, isopropoxymethyl, 2-isopropoxyethyl, 3-isopropoxypropyl, (2-hydroxyethoxy)methyl, (2-methoxyethoxy)methyl, 2-(2-hydroxyethoxy)ethyl, 2-(2-methoxyethoxy)ethyl, cyclopropyloxymethyl and 2-(cyclopropyloxy)ethyl. Still more particularly $R^7$ in this embodiment is selected from methyl, ethyl, propyl, isopropyl, hydroxymethyl, 2-hydroxyethyl, 2-hydroxypropyl, 3-hydroxypropyl, methoxymethyl, 2-methoxyethyl, 2-methoxypropyl, 3-methoxypropyl, isopropoxymethyl, 2-isopropoxyethyl, (2-hydroxyethoxy)methyl, (2-methoxyethoxy)methyl, 2-(2-hydroxyethoxy)ethyl, 2-(2-methoxyethoxy)ethyl, cyclopropyloxymethyl and 2-(cyclopropyloxy)ethyl.

Another value for $R^7$ in this embodiment is methyl, ethyl, isopropyl, hydroxymethyl, methoxymethyl, isopropyloxymethyl, 2-hydroxyethyl, 2-methoxyethyl, aminomethyl, 2-aminoethyl, methylaminomethyl, 2-(methylamino)ethyl, dimethylaminomethyl, 2-(dimethylamino)ethyl, pyrrolidin-3-yl and 1-methylpyrrolidin-3-yl, or $R^6$ and $R^7$ together with the carbon atom to which they are attached form a cyclopropyl, cyclobutyl, cyclopentyl, cyclohexyl, cyclopent-3-en-1-yl, azetidin-3-yl, piperidin-3-yl, piperidin-4-yl, tetrahydropyran-3-yl or tetrahydropyran-4-yl group, which group formed by $R^6$ and $R^7$ together with the carbon atom to which they are attached optionally bears on an available nitrogen atom a substituent selected from, methyl, ethyl, isopropyl, 2-hydroxyethyl, 2-methoxyethyl, methylsulfonyl, carbamoylmethyl, 2-carbamoylethyl, N-methylcarbamoylmethyl, N,N-dimethylcarbamoylmethyl, 2-(N-methylcarbamoyl)ethyl, 2-(N,N-dimethylcarbamoyl)ethyl, 3-(N,N-dimethylcarbamoyl)prop-2-yl, acetyl, propionyl, hydroxyacetyl, methoxyacetyl, ethoxyacetyl, 3-hydroxypropionyl, 2-hydroxypropionyl, 3-methoxypropionyl and 2-methoxypropionyl, which group formed by $R^6$ and $R^7$ together with the carbon atom to which they are attached optionally bears on an available carbon atom 1 or 2 methyl substituents.

In this embodiment particular values for the anilino group at the 4-position on the quinazoline ring in formula I include 3-chloro-4-fluoroanilino, 3,4-difluoroanilino, 3-chloro-2-fluoroanilino, 2-fluoro-5-chloroanilino, 3-bromoanilino, 3-methylanilino and 3-ethynylanilino.

Further values in this embodiment for the anilino group at the 4-position on the quinazoline ring in formula I in this embodiment include for example 3-chloro-2-fluoroanilino, 3-chloro-4-fluoroanilino, 3-bromo-2-fluoroanilino, 3-chloro-2,4-difluoroanilino, 3-chloro-2,6-difluoroanilino and 3-chloro-5-fluoroanilino. Particularly the anilino group is 3-chloro-2-fluoroanilino, 3-chloro-2-fluoroanilino or 3-bromo-2-fluoroanilino.

Another embodiment is a quinazoline derivative of the formula I wherein:

p is 1, $R^1$ is located at the 7-position;

$R^1$ is selected from (1-3C)alkoxy, hydroxy-(2-3C)alkoxy and (1-3C)alkoxy-(2-3C)alkoxy (for example $R^1$ is selected from methoxy, ethoxy, isopropyloxy, 2-hydroxyethoxy, 2-methoxy-ethoxy);

a 1, 2 or 3;

each $R^2$, which may be the same or different is selected from fluoro, chloro and bromo;

m is 1 or 2 (for example m is 1);

$R^{3a}$ is hydrogen;

$R^3$ is hydrogen or (1-3C)alkyl (for example $R^3$ is hydrogen or methyl, particularly $R^3$ is hydrogen;

$R^4$ is (1-4C)alkyl, wherein $R^4$ optionally bears on any carbon one or more (for example 1, 2 or 3, particularly 1) substituents, which may be the same or different, selected from hydroxy, (1-3C)alkoxy and cyano (for example $R^4$ is methyl, ethyl or isopropyl);

$R^{5a}$ is hydrogen or (1-3C)alkyl (for example $R^{5a}$ is hydrogen);

$R^5$ is selected from hydrogen, (1-4C)alkyl, (2-4C)alkenyl, and (2-4C)alkynyl, and wherein $R^5$ optionally bears on carbon one or more substituents (for example 1, 2 or 3), which may be the same or different, selected from hydroxy and (1-3C)alkoxy (particularly $R^5$ is selected from methyl, ethyl and isopropyl);

q is 1 or 2 (particularly q is 1);

Z is O;

$R^6$ is hydrogen or (1-3C)alkyl (particularly $R^6$ is hydrogen);

$R^7$ is selected from hydrogen, (1-4C)alkyl, hydroxy-(1-4C)alkyl, (1-3C)alkoxy-(1-4C)alkyl, amino-(1-4C)alkyl, (1-4C)alkylamino-(1-6C)alkyl, di-[(1-4C)alkyl]amino-(1-6C)alkyl and a heterocyclyl group selected from azetidinyl, pyrrolidinyl, piperidinyl, morpholinyl, tetrahydrofuranyl and tetrahydropyranyl which heterocyclyl group is linked to the carbon atom carrying $R^6$ by a ring carbon when q is 1, and wherein said heterocyclyl group optionally bears 1 or 2 substituents, which may be the same or different, selected from (1-4C)alkyl, hydroxy-(1-4C)alkyl, (1-3C)alkoxy-(1-4C)alkyl, (2-4C)alkanoyl, hydroxy-(2-4C)alkanoyl, (1-3C)alkoxy-(2-4C)alkanoyl, (1-4C)alkylsulfonyl, carbamoyl-(1-4C)alkyl, N-(1-4C)alkylcarbamoyl-(1-4C)alkyl and N,N-di-[(1-4C)alkyl]carbamoyl-(1-4C)alkyl, or $R^6$ and $R^7$ together with the carbon atom to which they are attached form a cyclopropyl, cyclobutyl, cyclopentyl, cyclohexyl, cyclopentenyl, azetidinyl, piperidinyl, morpholinyl or tetrahydropyranyl group, which group optionally bears 1 or 2 substituents, which may be the same or different, selected from (1-4C)alkyl, hydroxy-(1-4C)alkyl, (1-3C)alkoxy-(1-4C)alkyl, (2-4C)alkanoyl, hydroxy-(2-4C)alkanoyl, (1-3C)alkoxy-(2-4C)alkanoyl, (1-4C)alkylsulfonyl, carbamoyl-(1-4C)alkyl, N-(1-4C)alkylcarbamoyl-(1-4C)alkyl and N,N-di-[(1-4C)alkyl]carbamoyl-(1-4C)alkyl, or $R^7$ and the group $R^{5a}R^5NC(Z)$ together with the carbon atom to which they are attached form a heterocyclyl group selected from a group of the formula:

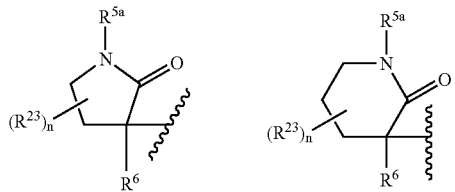

wherein $R^6$ is hydrogen, and $R^{5a}$ is selected from hydrogen, methyl and ethyl (particularly $R^{5a}$ is hydrogen), and n is 0, 1 or 2, and each $R^{23}$, which may be the same or different, is methyl (particularly n is 0); and the anilino group at the 4-position on the quinazoline ring in formula I is selected from 3-chloro-2-fluoroanilino, 3-chloro-4-fluoroanilino, 3-bromo-2-fluoroanilino, 3-chloro-2,4-difluoroanilino, 3-chloro-2,6-difluoroanilino and 3-chloro-5-fluoroanilino (for example the anilino group is 3-chloro-2-fluoroanilino, 3-chloro-2-fluoroanilino or 3-bromo-2-fluoroanilino);

or a pharmaceutically acceptable salt thereof.

In this embodiment a particular value for $R^7$ is one of the values as hereinbefore defined other than hydrogen (for example $R^7$ is (1-4C)alkyl).

Another embodiment of the present invention is a quinazoline derivative of the formula I of the formula Ic:

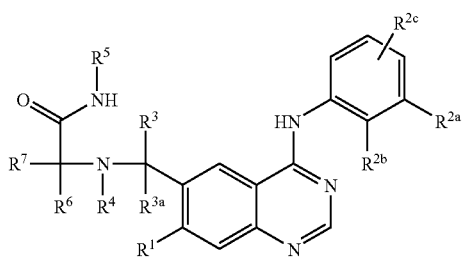

Ic wherein:

$R^1$ is selected from hydrogen, (1-3C)alkoxy, cyclopropylmethoxy and 2-cyclopropylethoxy (particularly $R^1$ is (1-3C)alkoxy), and wherein any $CH_2$ or $CH_3$ group within a $R^1$ substituent optionally bears on each said $CH_2$ or $CH_3$ group one or more fluoro substituents, or a substituent selected from hydroxy, methoxy and ethoxy;

$R^{2a}$ is halogeno (for example fluoro, chloro or bromo, particularly $R^{2a}$ is chloro or bromo);

$R^{2b}$ and $R^{2c}$ are selected from hydrogen and halogeno (for example fluoro, chloro or bromo), provided that $R^{2b}$ and $R^{2c}$ are not both halogeno;

$R^{3a}$ is hydrogen;

$R^3$ is selected from hydrogen and (1-3C)alkyl, and wherein $R^3$ optionally bears on carbon a substituent, selected from fluoro, hydroxy and methoxy (for example $R^3$ is hydrogen or methyl);

$R^4$ is selected from hydrogen, (1-4C)alkyl, (2-4C)alkanoyl, and (1-4C)alkylsulfonyl (for example $R^4$ is selected from (1-4C)alkyl, (2-4C)alkanoyl, and (1-4C)alkylsulfonyl, particularly $R^4$ is (1-4C)alkyl);

$R^5$ is selected from hydrogen and (1-3C)alkyl;

$R^6$ is selected from hydrogen and (1-3C)alkyl;

$R^7$ is selected from hydrogen, (1-6C)alkyl, (2-6C)alkenyl, (2-6C)alkynyl, aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl and heterocyclyl-(1-6C)alkyl, provided that when $R^7$ is heterocyclyl or heteroaryl, $R^7$ is linked to the carbon carrying $R^6$ and the $R^5NHC(Z)$ group by a ring carbon, and wherein adjacent carbon atoms in any (2-6C)alkylene chain within a $R^7$ substituent are optionally separated by the insertion into the chain of a group selected from O, S, N($R^{18}$), CON($R^{18}$), N($R^{18}$)CO, CH=CH and C≡C wherein $R^{18}$ is hydrogen or (1-6C)alkyl, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, or from a group of the formula:

wherein $X^6$ is a direct bond or is selected from O, S, N($R^{20}$), CON($R^{20}$), N($R^{20}$)CO and C($R^{20}$)$_2$O, wherein $R^{20}$ is hydrogen or (1-6C)alkyl, and $Q^5$ is aryl, aryl-(1-6C)alkyl, (3-7C)cycloalkyl, (3-7C)cycloalkyl-(1-6C)alkyl, heteroaryl, heteroaryl-(1-6C)alkyl, heterocyclyl or heterocyclyl-(1-6C)alkyl, and wherein any aryl, heteroaryl or heterocyclyl group within a substituent on $R^7$ optionally bears one or more (for example 1, 2 or 3) $R^{21}$, wherein each $R^{21}$, which may be the same or different, is selected from halogeno, trifluoromethyl, cyano, nitro, hydroxy, amino, carbamoyl, formyl, (1-6C)alkyl, (2-8C)alkenyl, (2-8C)alkynyl, (1-6C)alkoxy, (1-6C)alkylthio, (1-6C)alkylsulfinyl, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoylamino and N-(1-6C)alkyl-(2-6C)alkanoylamino, a group of the formula:

wherein $X^7$ is a direct bond or is selected from O, N($R^{26}$) and C(O), wherein $R^{26}$ is hydrogen or (1-6C)alkyl, and $R^{25}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl or (2-6C)alkanoyl-(1-6C)alkyl, and from a group of the formula:

wherein $X^8$ is a direct bond or is selected from O, N($R^{31}$) and CO, wherein $R^{31}$ is hydrogen or (1-6C)alkyl, and $Q^6$ is (3-7C)cycloalkyl, (3-7C)cycloalkyl-(1-6C)alkyl, heterocyclyl or heterocyclyl-(1-6C)alkyl, which optionally bears one or more (for example 1, 2 or 3) substituents, which may be the same or different selected from halogeno, hydroxy, (1-4C)alkyl and (1-4C)alkoxy, and wherein any $R^{21}$ optionally bears on carbon one or more (for example 1, 2 or 3) $R^{29}$ substituents, which may be the same or different, selected from fluoro, hydroxy, cyano, amino, methylamino, dimethylamino, methoxy, ethoxy, vinyl, allyl and ethynyl, and wherein any heterocyclyl group within a $R^7$ substituent optionally bears 1 oxo substituent;

or $R^6$ and $R^7$ together with the carbon atom to which they are attached form a (3-6C)cycloalkyl or heterocyclyl group, which heterocyclyl group is a 4 to 7 membered monocyclic, saturated or partially saturated monocyclic ring with 1 or 2 heteroatoms selected from oxygen, nitrogen and sulfur, and wherein the group formed by $R^6$ and $R^7$ together with the carbon to which they are attached optionally bears one or more (for example 1, 2 or 3) $R^{22}$ substituents, which may be the same or different, as hereinabove defined, and wherein any heterocyclyl group formed by $R^6$ and $R^7$ together with the carbon atom to which they are attached, optionally bears 1 oxo substituent, or $R^7$ and the group $R^5$NHC(O) together with the carbon atom to which they are attached form a heterocyclyl group, which heterocyclic group is a 4 to 7 membered monocyclic, saturated or partially saturated monocyclic ring which optionally contains 1 further heteroatom selected from oxygen, nitrogen and sulfur, and wherein the group formed by $R^7$ and the group $R^5$NHC(O) together with the carbon atom to which they are attached optionally bears one or more (for example 1, 2 or 3) $R^{23}$ substituents, which may be the same or different, as hereinabove defined (in particular embodiments, the NHC(O) group in the ring is not substituted);

or a pharmaceutically acceptable salt thereof.

In this embodiment particular values for $R^1$ in the compounds of formula Ic are hydrogen, methoxy, ethoxy, propyloxy, isopropyloxy, cyclopropylmethoxy, 2-hydroxyethoxy, 2-fluoroethoxy, 2-methoxyethoxy, 2-ethoxyethoxy, 2,2-difluoroethoxy and 2,2,2-trifluoroethoxy. For example $R^1$ is hydrogen or (1-3C)alkoxy. More particularly $R^1$ is (1-3C)alkoxy such as methoxy.

In another embodiment in the compounds of formula Ic $R^{2a}$ is selected from chloro and bromo; and one of $R^{2b}$ and $R^{2c}$ is hydrogen and the other of $R^{2b}$ and $R^{2c}$ is selected from hydrogen, fluoro and chloro.

In a further embodiment the anilino group in the compound of formula Ic 3-chloro-4-fluoroanilino, 3-bromo-2-fluoroanilino and 3-chloro-2-fluoroanilino, particularly 3-chloro-2-fluoroanilino.

A particular value for $R^4$ in the compounds of formula Ic is (1-3C)alkyl such as methyl.

A particular value for $R^5$ in the compounds of formula Ic is hydrogen or methyl.

A particular value for $R^6$ in the compounds of formula Ic is hydrogen or methyl, more particularly hydrogen.

A particular compound of the formula Ic is one wherein one of $R^6$ or $R^7$ is not hydrogen.

Particular values for $R^7$ in the compounds of formula Ic are any of the groups defined above in any one of paragraphs (aaaa) to (pppp). Particularly $R^7$ in this embodiment is selected from hydrogen, methyl, ethyl, propyl, isopropyl, butyl, iso-butyl, tert-butyl, hydroxymethyl, 2-hydroxyethyl, 2-hydroxypropyl, 3-hydroxypropyl, methoxymethyl, 2-methoxyethyl, 2-methoxypropyl, 3-methoxypropyl, isopropoxymethyl, 2-isopropoxyethyl, 3-isopropoxypropyl, (2-hydroxyethoxy)methyl, (2-methoxyethoxy)methyl, 2-(2-hydroxyethoxy)ethyl, 2-(2-methoxyethoxy)ethyl, cyclopropyloxymethyl and 2-(cyclopropyloxy)ethyl. More particularly in this embodiment $R^7$ is not hydrogen. For example $R^7$ in this embodiment is selected from methyl, ethyl, propyl, isopropyl, hydroxymethyl, 2-hydroxyethyl, 2-hydroxypropyl, 3-hydroxypropyl, methoxymethyl, 2-methoxyethyl, 2-methoxypropyl, 3-methoxypropyl, isopropoxymethyl, 2-isopropoxyethyl, (2-hydroxyethoxy)methyl, (2-methoxyethoxy)methyl, 2-(2-hydroxyethoxy)ethyl, 2-(2-methoxyethoxy)ethyl, cyclopropyloxymethyl and 2-(cyclopropyloxy) ethyl.

In another embodiment in the compounds of formula Ic $R^6$ and $R^7$ together with the carbon atom to which they are attached form a (3-6C)cycloalkyl, (3-6)cycloalkenyl or heterocyclyl, which heterocyclyl is a 4 to 6 membered monocyclic, saturated or partially saturated monocyclic ring with 1 or 2 heteroatoms selected from oxygen, nitrogen and sulfur, and wherein the group formed by $R^6$ and $R^7$ together with the carbon to which they are attached optionally bears one or more (for example 1, 2 or 3) $R^{22}$ substituents, which may be the same or different, and wherein any heterocyclyl group formed by $R^6$ and $R^7$ together with the carbon atom to which they are attached, optionally bears 1 oxo substituent, and wherein each $R^{22}$, which may be the same or different, is selected from halogeno, cyano, hydroxy, carbamoyl, (1-6C)alkyl, (2-6C)alkenyl, (2-6C)alkynyl, (1-6C)alkoxy, (1-6C)alkylsulfonyl, N-(1-6C)alkylcarbamoyl, N,N-di-[(1-6C)alkyl]carbamoyl, (2-6C)alkanoyl, hydroxy-(2-6C)alkanoyl, (1-4C)alkoxy-(2-6C)alkanoyl, carbamoyl-(1-6C)alkyl, N-(1-6C)alkylcarbamoyl-(1-6C)alkyl and N,N-di-[(1-6C)alkyl]carbamoyl-(1-6C)alkyl;

or $R^7$ and the group $R^5$HNC(O) together with the carbon atom to which they are attached form a heterocyclyl group selected from a group of the formula:

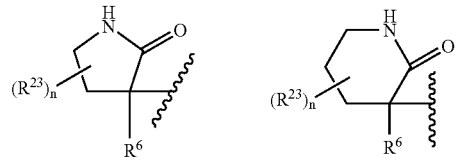

wherein $R^6$ is as defined hereinabove (particularly $R^6$ is hydrogen or (1-4C)alkyl, for example $R^6$ is hydrogen), n is 0, 1 or 2 and each $R^{23}$, which may be the same or different, is selected from (1-4C)alkyl (particularly n is 0).

Another embodiment of the present invention is a quinazoline derivative of the formula I of the formula Ic as defined hereinabove wherein:

$R^1$ is selected from hydrogen and (1-3C)alkoxy. More particularly $R^1$ is (1-3C)alkoxy such as methoxy;

$R^{2a}$ is chloro, $R^{2b}$ is fluoro and $R^{2c}$ is hydrogen, or;

$R^{2a}$ is chloro, $R^{2b}$ is hydrogen and $R^{2c}$ is fluoro (for example 4-fluoro);

$R^4$ is (1-3C)alkyl such as methyl;

$R^5$ is selected from hydrogen, methyl and ethyl (particularly $R^5$ is hydrogen or methyl);

$R^6$ is hydrogen;

$R^7$ is as defined hereinabove in relation to the compound of formula Ic, in particular $R^7$ is selected from methyl, ethyl, propyl, isopropyl, hydroxymethyl, 2-hydroxyethyl, 2-hydroxypropyl, 3-hydroxypropyl, methoxymethyl, 2-methoxyethyl, 2-methoxypropyl, 3-methoxypropyl, isopropoxymethyl, 2-isopropoxyethyl, (2-hydroxyethoxy)methyl, (2-methoxyethoxy)methyl, 2-(2-hydroxyethoxy)ethyl, 2-(2-methoxyethoxy)ethyl, cyclopropyloxymethyl and 2-(cyclopropyloxy)ethyl;

or a pharmaceutically acceptable salt thereof.

In this embodiment a particular values include $R^{2a}$ is chloro, $R^{2b}$ is fluoro and $R^{2c}$ is hydrogen.

In this embodiment a particular value for $R^7$ is selected from methyl, ethyl, isopropyl, hydroxymethyl, methoxymethyl, isopropyloxymethyl, 2-hydroxyethyl and 2-methoxyethyl.

Another particular embodiment is a quinazoline derivative of the formula I of the formula Ic as hereinbefore defined wherein:

$R^1$ is selected from (1-3C)alkoxy, hydroxy-(2-3C)alkoxy and (1-3C)alkoxy-(2-3C)alkoxy (for example $R^1$ is selected from methoxy, ethoxy, isopropyloxy, 2-hydroxyethoxy, 2-methoxyethoxy);

$R^{2a}$ is selected from fluoro, chloro and bromo;

one of $R^{2b}$ and $R^{2c}$ is selected from fluoro, chloro and bromo, and the other of $R^{2b}$ and $R^{2c}$ is hydrogen;

$R^{3a}$ is hydrogen;

$R^3$ is selected from hydrogen and (1-3C)alkyl;

$R^4$ is (1-3C)alkyl;

$R^5$ is selected from hydrogen and (1-3C)alkyl;

$R^6$ is selected from hydrogen and (1-3c) alkyl (particularly $R^6$ is hydrogen);

$R^7$ is selected from methyl, ethyl, isopropyl, hydroxymethyl, methoxymethyl, isopropyloxymethyl, 2-hydroxyethyl, 2-methoxyethyl, aminomethyl, 2-aminoethyl, methylaminomethyl, 2-(methylamino)ethyl, dimethylaminomethyl, 2-(dimethylamino)ethyl, pyrrolidin-3-yl and 1-methylpyrrolidin-3-yl, or $R^6$ and $R^7$ together with the carbon atom to which they are attached form a cyclopropyl, cyclobutyl, cyclopentyl, cyclohexyl, cyclopent-3-en-1-yl, azetidin-3-yl, piperidin-3-yl, piperidin-4-yl, tetrahydropyran-3-yl or tetrahydropyran-4-yl group, which group optionally bears 1 or 2 substituents, which may be the same or different, selected from (1-4C)alkyl, hydroxy-(1-4C)alkyl, (1-3C)alkoxy-(1-4C)alkyl, (2-4C)alkanoyl, hydroxy-(2-4C)alkanoyl, (1-3C)alkoxy-(2-4C)alkanoyl, (1-4C)alkylsulfonyl, carbamoyl-(1-4C)alkyl, N-(1-4C)alkylcarbamoyl-(1-4C)alkyl and N,N-di-[(1-4C)alkyl]carbamoyl-(1-4C)alkyl, or $R^7$ and the group $R^5NHC(O)$ together with the carbon atom to which they are attached form a heterocyclyl group selected from a group of the formula:

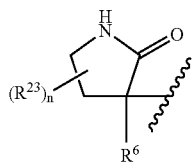 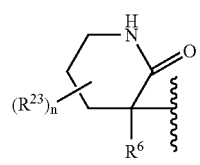

wherein $R^6$ is hydrogen;

n is 0, 1 or 2 and each $R^{23}$, which may be the same or different, is methyl (particularly n is 0);

or a pharmaceutically acceptable salt thereof.

In this embodiment a particular value for $R^7$ is selected from methyl, ethyl and isopropyl, or $R^6$ and $R^7$ together with the carbon atom to which they are attached form a cyclopropyl group; and the anilino group in the compound of formula Ic is selected from 3-chloro-4-fluoroanilino, 3-bromo-2-fluoroanilino and 3-chloro-2-fluoroanilino, particularly 3-chloro-2-fluoroanilino or 3-bromo-2-fluoroanilino.

Another embodiment is a quinazoline derivative of the formula I of the formula Id:

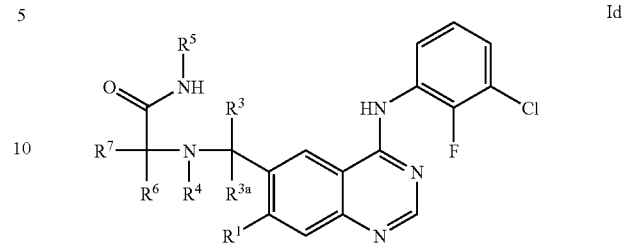

wherein:

$R^1$ is selected from (1-3C)alkoxy, hydroxy-(2-3C)alkoxy and (1-3C)alkoxy-(2-3C)alkoxy (for example $R^1$ is selected from methoxy, ethoxy, isopropyloxy, 2-hydroxyethoxy, 2-methoxyethoxy);

$R^{3a}$ is hydrogen;

$R^3$ is hydrogen or (1-3C)alkyl (for example $R^3$ is hydrogen or methyl, particularly $R^3$ is hydrogen), or $R^3$ and $R^{3a}$ together with the carbon atom to which they are attached form a cyclopropyl ring;

$R^4$ is selected from methyl, ethyl and isopropyl (particularly $R^4$ is methyl or ethyl, more particularly $R^4$ is methyl);

$R^5$ is selected from hydrogen and methyl (particularly $R^5$ is hydrogen);

$R^6$ is hydrogen;

$R^7$ is selected from hydrogen, methyl, ethyl, isopropyl, hydroxymethyl, methoxymethyl, isopropyloxymethyl, 2-hydroxyethyl, 2-methoxyethyl, aminomethyl, 2-aminoethyl, methylaminomethyl, 2-(methylamino)ethyl, dimethylaminomethyl, 2-(dimethylamino)ethyl, pyrrolidin-3-yl and 1-methylpyrrolidin-3-yl;

or $R^6$ and $R^7$ together with the carbon atom to which they are attached form a cyclopropyl, cyclobutyl, cyclopentyl, cyclohexyl, cyclopent-3-en-1-yl, azetidin-3-yl, piperidin-3-yl, piperidin-4-yl, tetrahydropyran-3-yl or tetrahydropyran-4-yl group, which group formed by $R^6$ and $R^7$ together with the carbon atom to which they are attached optionally bears on an available nitrogen atom a substituent selected from, methyl, ethyl, isopropyl, 2-hydroxyethyl, 2-methoxyethyl, methylsulfonyl, carbamoylmethyl, 2-rbamoylethyl, N-methylcarbamoylmethyl, N,N-dimethylcarbamoylmethyl, 2-(N-methylcarbamoyl)ethyl, 2-(N,N-dimethylcarbamoyl)ethyl, 3-(N,N-dimethylcarbamoyl)prop-2-yl, acetyl, propionyl, hydroxyacetyl, methoxyacetyl, ethoxyacetyl, 3-hydroxypropionyl, 2-hydroxypropionyl, 3-methoxypropionyl and 2-methoxypropionyl, which group formed by $R^6$ and $R^7$ together with the carbon atom to which they are attached optionally bears on an available carbon atom 1 or 2 methyl substituents;

or a pharmaceutically acceptable salt thereof.

In a particular compound of formula Id, $R^{3a}$ is hydrogen; $R^3$ is hydrogen or (1-3C)alkyl and $R^1$, $R^4$, $R^5$, $R^6$ and $R^7$ have any of the values defined above in relation to the compound of formula Id.

Another embodiment is a quinazoline derivative of the formula I of the formula Id as hereinbefore defined wherein:

$R^1$ is selected from (1-3C)alkoxy and (1-3C)alkoxy-(2-3C)alkoxy (for example $R^1$ is selected from methoxy and 2-methoxyethoxy);

$R^{3a}$ is hydrogen;

$R^3$ is hydrogen or methyl (particularly $R^3$ is hydrogen);

$R^4$ is selected from methyl and ethyl (particularly $R^4$ is methyl);

$R^5$ is selected from hydrogen and methyl (particularly $R^5$ is hydrogen);

$R^6$ is hydrogen;

$R^7$ is selected from methyl, ethyl, hydroxymethyl, methoxymethyl, pyrrolidin-3-yl and 1-methylpyrrolidin-3-yl;

or $R^6$ and $R^7$ together with the carbon atom to which they are attached form a cyclopropyl, cyclopent-3-en-1-yl, azetidin-3-yl, piperidin-3-yl or piperidin-4-yl group, which group formed by $R^6$ and $R^7$ together with the carbon atom to which they are attached optionally bears on an available nitrogen atom a substituent selected from, methyl, ethyl, isopropyl, 2-hydroxyethyl and 2-methoxyethyl (particularly methyl and 2-methoxyethyl); or a pharmaceutically acceptable salt thereof.

Another embodiment is a quinazoline derivative of the formula I of the formula Id as hereinbefore defined wherein:

$R^1$ is selected from (1-3C)alkoxy and (1-3C)alkoxy-(2-3C)alkoxy (for example $R^1$ is selected from methoxy and 2-methoxyethoxy);

$R^{3a}$ is hydrogen;

$R^3$ is hydrogen or methyl (particularly $R^3$ is hydrogen);

$R^4$ is selected from methyl, ethyl and isopropyl (particularly $R^4$ is methyl);

$R^5$ is selected from hydrogen and methyl (particularly $R^5$ is hydrogen);

$R^6$ is hydrogen;

$R^7$ is methyl or $R^6$ and $R^7$ together with the carbon atom to which they are attached form a cyclopropyl group;

or a pharmaceutically acceptable salt thereof

A particular compound of the invention is, for example, a quinazoline derivative of the formula I selected from:

$N^2$-({4-[(3-chloro-2-fluorophenyl)amino]-7-methoxyquinazolin-6-yl}methyl)-$N^2$-methylglycinamide;

$N^2$-({4-[(3-chloro-2-fluorophenyl)amino]-7-methoxyquinazolin-6-yl}methyl)-$N^2$-methyl-D-alaninamide;

$N^2$-({4-[(3-chloro-2-fluorophenyl)amino]-7-methoxyquinazolin-6-yl}methyl)-$N^2$-methyl-L-alaninamide;

$N^2$-({4-[(3-chloro-2-fluorophenyl)amino]-7-methoxyquinazolin-6-yl}methyl)-$N^2$-methyl-L-serinamide;

$N^2$-({4-[(3-chloro-2-fluorophenyl)amino]-7-methoxyquinazolin-6-yl}methyl)-D-alaninamide;

$N^2$-({4-[(3-chloro-2-fluorophenyl)amino]-7-methoxyquinazolin-6-yl}methyl)glycinamide;

$N^2$-({4-[(3-chloro-2-fluorophenyl)amino]-7-methoxyquinazolin-6-yl}methyl)-$N^2$,O-dimethyl-L-serinamide;

$N^2$-({4-[(3-chloro-2-fluorophenyl)amino]-7-methoxyquinazolin-6-yl}methyl)-$N^2$,O-dimethyl-D-serinamide;

$N^2$-({4-[(3-chloro-2-fluorophenyl)amino]-7-methoxyquinazolin-6-yl}methyl)-$N^2$,O-dimethyl-L-homoserinamide;

$N^2$-({4-[(3-chloro-4-fluorophenyl)amino]-7-methoxyquinazolin-6-yl}methyl)-$N^2$,O-dimethyl-L-serinamide; and $N^2$-({4-[(3-chloro-4-fluorophenyl)amino]-7-methoxyquinazolin-6-yl}methyl)-$N^2$-methyl-D-alaninamide;

or a pharmaceutically acceptable salt thereof.

Another particular compound of the invention is, for example, a quinazoline derivative of the formula I selected from:

3-[({4-[(3-chloro-2-fluorophenyl)amino]-7-methoxyquinazolin-6-yl}methyl)(methyl)amino]-1-isopropylazetidine-3-carboxamide;

3-[({4-[(3-chloro-2-fluorophenyl)amino]-7-methoxyquinazolin-6-yl}methyl)(methyl)amino]-1-methylazetidine-3-carboxamide;

1-[({4-[(3-chloro-2-fluorophenyl)amino]-7-methoxyquinazolin-6-yl}methyl)(methyl)amino]cyclopropanecarboxamide;

3-[({4-[(3-chloro-2-fluorophenyl)amino]-7-methoxyquinazolin-6-yl}methyl)(methyl)amino]-1-methylpiperidine-3-carboxamide;

1-[({4-[(3-chloro-2-fluorophenyl)amino]-7-methoxyquinazolin-6-yl}methyl)(methyl)amino]cyclopent-3-ene-1-carboxamide;

4-[({4-[(3-chloro-2-fluorophenyl)amino]-7-methoxyquinazolin-6-yl}methyl)(methyl)amino]-N,1-dimethylpiperidine-4-carboxamide;

4-[({4-[(3-chloro-2-fluorophenyl)amino]-7-methoxyquinazolin-6-yl}methyl)(methyl)amino]-1-methylpiperidine-4-carboxamide;

$N^2$-{[4-[(3-chloro-2-fluorophenyl)amino]-7-(2-methoxyethoxy)quinazolin-6-yl]methyl}-$N^2$-methyl-D-alaninamide;

3-[({4-[(3-chloro-2-fluorophenyl)amino]-7-methoxyquinazolin-6-yl}methyl)(methyl)amino]-1-(2-methoxyethyl)azetidine-3-carboxamide;

$N^2$-({4-[(3-chloro-2-fluorophenyl)amino]-7-methoxyquinazolin-6-yl}methyl)-$N^2$-ethyl-D-alaninamide;

2-[({4-[(3-chloro-2-fluorophenyl)amino]-7-methoxyquinazolin-6-yl}methyl)(methyl)amino]-2-(1-methylpyrrolidin-3-yl)acetamide;

$N^2$-({4-[(3-chloro-2-fluorophenyl)amino]-7-methoxyquinazolin-6-yl}methyl)-$N^1$,$N^2$-dimethyl-D-alaninamide;

1-[({4-[(3-chloro-2-fluorophenyl)amino]-7-methoxyquinazolin-6-yl}methyl)(ethyl)amino]cyclopropanecarboxamide; and $N^2$-(1-{4-[(3-chloro-2-fluorophenyl)amino]-7-methoxyquinazolin-6-yl}ethyl)-$N^2$-methyl-D-alaninamide;

or a pharmaceutically acceptable salt thereof

A quinazoline derivative of the formula I, or a pharmaceutically-acceptable salt thereof, may be prepared by any process known to be applicable to the preparation of chemically-related compounds. Information on the preparation of necessary starting materials or related compounds (which may be adapted to form necessary starting materials) may also be found in the following Patent and Application Publications, the contents of the relevant process sections of which are hereby incorporated herein by reference: WO 95/03283, WO 96/33977, WO 96/33978, WO 96/33979, WO 96/33980, WO 96/33981, WO 97/30034, WO 97/38994, WO01/66099, EP 520 722, EP 566 226, EP 602 851 and EP 635 507.

Such processes, when used to prepare a quinazoline derivative of the formula I are provided as a further feature of the invention and are illustrated by the following representative process variants in which, unless otherwise stated, $R^1$, $R^2$, $R^3$, $R^{3a}$, $R^4$, $R^5$, $R^6$, $R^7$, a, m, p and Z have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

Process (a):

The reaction of a compound of formula II:

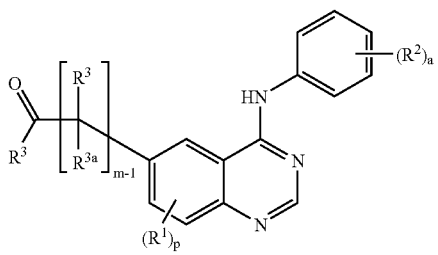

II wherein $R^1$, $R^2$, $R^3$, $R^{3a}$, a, m and p are as hereinbefore defined, except that any functional group is protected if necessary, with a compound of the formula III:

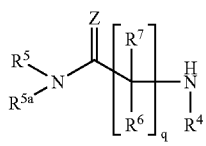

III wherein $R^4$, $R^5$, $R^{5a}$, $R^6$, $R^7$, q and Z have any of the meanings defined hereinbefore, except that any functional group is protected if necessary; or Process (b)

the reaction of a compound of the formula IV:

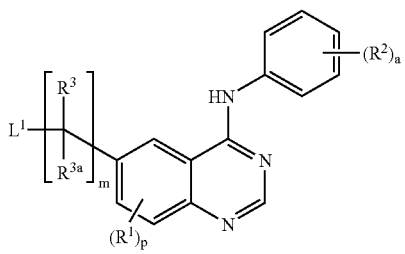

IV wherein $R^1$, $R^2$, $R^3$, $R^{3a}$, a, m and p are as hereinbefore defined, except that any functional group is protected if necessary, and $L^1$ is a suitable leaving group, with a compound of the formula III as hereinbefore defined; or Process (c):

for the preparation of those quinazolines of formula I in which Z is O, the coupling of a compound of the formula V, or a reactive derivative thereof:

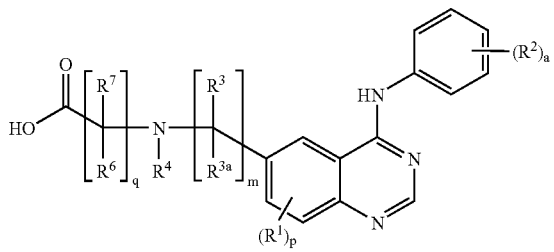

V wherein $R^1$, $R^2$, $R^3$, $R^{3a}$, $R^4$, $R^6$, $R^7$, a, m and p are as hereinbefore defined, except that any functional group is protected if necessary, with an amine of the formula VI, or salt thereof:

$NHR^5R^{5a}$   VI wherein $R^5$ and $R^{5a}$ are as hereinbefore defined, except that any functional group is protected if necessary; or Process (d):

the reductive amination of a quinazoline derivative of the formula I which contains an NH group with an appropriate aldehyde or ketone; or Process (e):

for the preparation of those quinazoline derivatives of the formula I wherein $R^1$ is linked to the quinazoline ring by an oxygen atom, by coupling a compound of the formula VII:

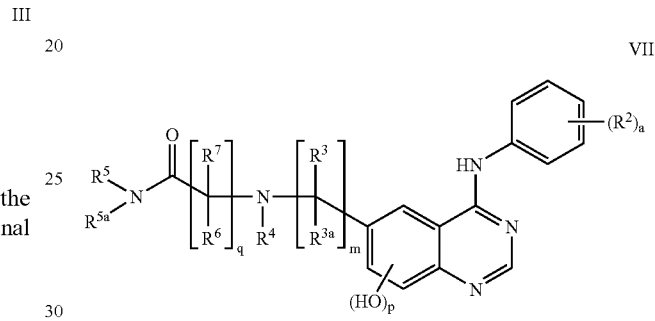

VII wherein $R^2$, $R^3$, $R^{3a}$, $R^4$, $R^5$, $R^{5a}$ $R^6$, $R^7$, a, m and p are as hereinbefore defined, except that any functional group is protected if necessary, with a compound of the formula $R^{1'}OH$ wherein $R^{1'}O$ is one of the oxygen linked groups as hereinbefore defined for $R^1$ (for example $Q^1$—O—) except that any functional group is protected if necessary; or Process (f)

the reaction of a compound of the formula VII as hereinbefore defined with a compound of the formula $R^{1'}L^3$, wherein $R^{1'}O$ is one of the oxygen linked groups as hereinbefore defined for $R^1$ (for example when $R^1$ is (1-3C)alkoxy (2-4C)alkoxy, $R^{1'}$ is (1-3C)alkoxy(2-4C)alkyl) except that any functional group is protected if necessary, and $L^3$ is a suitable displaceable group;

and thereafter, if necessary:

(i) converting a quinazoline derivative of the formula I into another quinazoline derivative of the formula I;

(ii) removing any protecting group that is present by conventional means;

(iii) forming a pharmaceutically acceptable salt.

Specific conditions for the above reactions are as follows:

Process (a)

The reductive amination reaction is suitably carried out in the presence of a reducing agent, in particular a Lewis acid such as a boron compound, or hydrogen. A particular examples of suitable reducing agents include sodium triacteoxyborohydride, sodium cyanoborohydride, sodium borohydride or polymer supported borohydride. The reaction is suitably effected in an organic solvent such as tetrahydrofuran (THF), dichloromethane, 1,2-dichloroethane, or an alkyl alcohol such as methanol or ethanol. Moderate temperatures for example of from 0-60° C., and conveniently at ambient temperature, are suitably employed. The reaction may also be preformed in the presence of a drying or dehydrating agent, typically magnesium sulfate or molecular sieves as this which helps drive the forward reaction.

If desired, optically active or resolved forms of compounds of formula III may be employed, to produce optically active compounds of formula I.

Preparation of Starting Materials for Process (a):

Compounds of formula II may be prepared using conventional methods, for example by oxidising a compound of formula Ia:

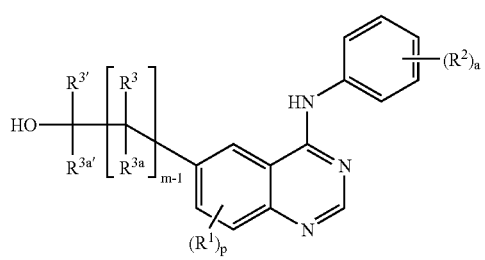

wherein $R^1$, $R^2$, $R^3$, $R^{3a}$, a, m and p are as hereinbefore defined, except that any functional group is protected if necessary, $R^{3'}$ is as hereinbefore defined for $R^3$ and $R^{3a'}$ is hydrogen, and whereafter any protecting group that is present is removed by conventional means. The oxidation reaction is suitably carried out in the presence of a suitable oxidising agent such as manganese oxide or tetrapropylammonium perruthenate (TPAP/N) together with methylmorpholine N-oxide. Alternatively oxidation under Swern conditions may be used (e.g oxidation promoted by oxalyl chloride activation of dimethyl sulfoxide (DMSO) upon the addition of a base such as tri-ethylamine). The reaction is conveniently carried out in the presence of an inert solvent or diluent, for example an inert organic solvent such as methylene chloride, methanol, dioxane, dichloromethane, 1,2 dichloroethane or tetrahydrofuran. The reaction is suitably carried out at moderate temperatures, for example of from 0-50° C. and conveniently ambient temperatures are suitably employed. The reaction is continued for a sufficient period of time to allow oxidation to take place. If necessary, the product can be separated using column chromatography, for example on a silica column.

Compounds of formula Ia wherein $R^{3'}$ is hydrogen may be prepared by, for example, reduction of a compound of formula IIb:

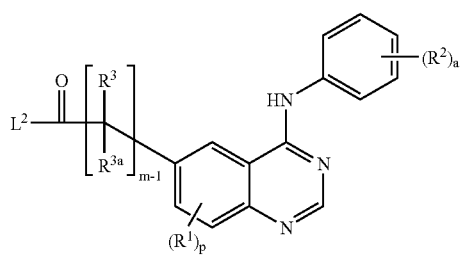

wherein $R^1$, $R^2$, $R^3$, $R^{3a}$, a, m and p are as hereinbefore defined, except that any functional group is protected if necessary, and $L^2$ is hydroxy or a suitable displaceable group (for example (1-6C)alkoxy or halogeno such as chloro), and whereafter any protecting group that is present is removed by conventional means if necessary.

The reduction is suitably carried out using a reducing agent such as lithium aluminium hydride (LiAlH$_4$), diisobutylaluminum hydride (DIBAL-H), sodium borohydride (NaBH$_4$) or BH$_3$.S(CH$_3$)$_2$. A particular reducing agent which may be used in this process is Red-Al, a compound of formula IIc $$([CH_2OCH_2OCH_2)_2AlH_2]Na \qquad IIc$$

which is obtainable as a solution, for example of 65-70% w/w in organic solvents such as hexane, or toluene. The reaction is suitably effected in an organic solvent such as THF, at low or moderate temperatures, for example of from −100-60° C. At the end of the reaction with Red-AL, the reaction may be quenched, for example sodium hydrogen tartrate in water.

Compounds of formula Ia wherein $R^{3'}$ is (1-6C)alkyl may also be prepared by, for example, addition of an (1-6C)alkyl lithium or (1-6C)alkyl Grignard reagent to a compound of formula IIb as hereinbefore defined wherein $L^2$ is a suitable displaceable group (for example (1-6C)alkoxy). The addition is suitably carried out using an (1-6C)alkyl metal reagent such as methyl lithium, methyl magnesium bromide or isopropyl magnesium chloride. A particular metal reagent is methylmagnesium bromide. Suitably the reaction is carried out in an organic solvent such as tetrahydrofuran or diethyl ether and at low or moderate temperatures, for example of from −100 to 60° C. Following reaction any excess reagent may be quenched, for example using sodium hydrogen tartrate in water.

Compounds of formula IIb where m is 1 and $L^2$ is (1-6C) alkoxy may be prepared by hydrocarboxylation of a compound of formula IId:

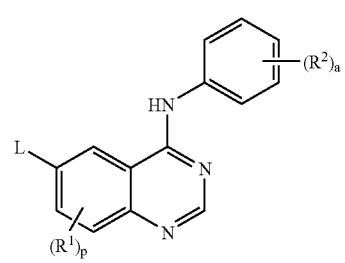

wherein $R^1$, $R^2$, p and a are as hereinbefore defined, except that any functional group is protected if necessary, and L is a suitable leaving group, and whereafter any protecting group that is present is removed by conventional means.

The hydrocarboxylation reaction may be carried out by, for example, reacting the compound of formula IId with carbon monoxide and a (1-6C)alkyl alcohol, in the presence of a palladium catalyst such as palladium acetate, which is suitably combined with a strong electron donor, such as diphenylphosphinopropane and a base such as triethylamine. The reaction is suitably carried out in the presence of an inert solvent such as N,N-dimethylformamide (DMF), to give a compound of formula IIb wherein $L^2$ is (1-6C)alkoxy. The hydrocarboxylation may be carried out at room temperature or at elevated temperatures for example up to about 70° C. Optionally the reaction may be carried out at elevated pressure in a suitable pressure vessel such as an autoclave, for example at a pressure of from 1 to 15, for example about 13 bar.

Suitable leaving groups, L, in formula IId include for example, an alkyl- or aryl-sulfonyloxy group (such as trifluoromethanesulfonyloxy or tosylate) or halogeno (such as chloro, bromo or iodo).

Compounds of formula IId wherein L is halogeno may be prepared by, for example, reacting a compound of formula IIe:

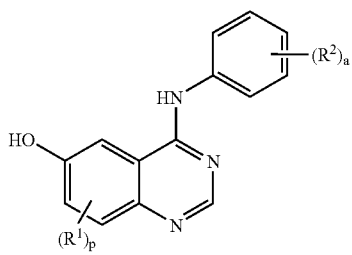

IIe wherein $R^1$, $R^2$, p and a are as hereinbefore defined, except that any functional group is protected if necessary, with a halogenating agent, and whereafter any protecting group that is present is removed if necessary by conventional means. Suitable halogenating agents include for example HCl, HBr, phosphorus tribromide or thionyl chloride. If required the halogenation may be carried out in a suitable inert solvent such as dichloromethane.

Compounds of the formula IId wherein L is an alkyl- or aryl-sulfonyloxy group, may be prepared by reaction of a compound of formula IIe with a suitable sulfonic acid or acid anhydride such as trifluoromethanesulfonic acid anhydride (triflic anhydride). The reaction is suitably carried out in an inert organic solvent such as methylene chloride, THF or 1,2-dichloroethane in the presence of a base such as pyridine, triethylamine, diisopropylethylamine or 4-dimethylaminopyridine. Low temperatures, for example of from −20 to 20° C., and such as about 0° C. are suitably employed.

Compounds of formula IIb where m is 2, $R^{3'}$ and $R^{3a}$ are hydrogen and $L^2$ is (1-6C)alkyl can be prepared by, for example, reacting a compound of formula IId wherein L is a leaving group such as a triflate group, with a compound of formula IIf:

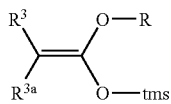

IIf wherein $R^3$ and $R^{3a}$ are as hereinbefore defined, R is (1-6C) alkyl and tms is a trimethylsilyl group, in the presence of a palladium catalyst using a method analogous to that described in J. Organic Chemistry 1991, 56(1) p 261.

Alternatively, a compound of formula Ia wherein m is 2 and $R^{3'}$ and $R^{3a'}$ are hydrogen, can be prepared by reduction of a compound of formula IIg:

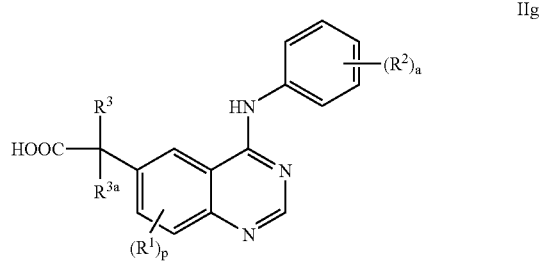

IIg wherein $R^1$, $R^2$, $R^3$, $R^{3'}$, a and p are as hereinbefore defined, except that any functional group is protected if necessary, and whereafter any protecting group that is present is removed by conventional means if necessary.

Suitable conditions for the reduction of the compound of formula IIg are analogous to those described above for the reduction of the compound of formula IIb.

Compounds of formula IIg wherein $R^3$ and $R^{3a}$ are hydrogen can be prepared by subjecting a compound of formula IIh:

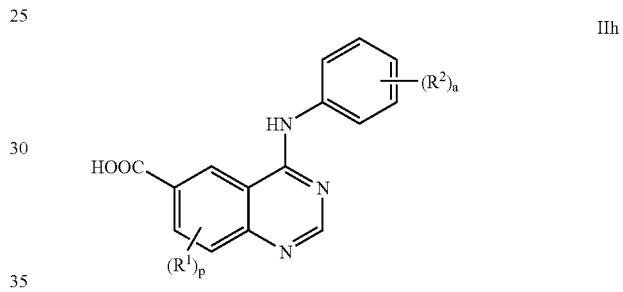

IIh wherein $R^1$, $R^2$, p and a are as hereinbefore defined, except that any functional group is protected if necessary, to an Arndt-Eistert homologation, as described for example by H. Meier et al., Chem Int Ed. Engl., 1975, 14, 32, and whereafter any protecting group that is present is removed by conventional means if necessary.

The Arndt-Eistert homologation reaction comprises:

i) acid chloride formation (for example using $(COCl)_2$/N,N-dimethylformamide/$CH_2Cl_2$ at 0° C. to room temperature;

ii) diazoketone formation (for example using diazomethane or TMS diazomethane/diethyl ether/tetrahydrofuran at 0° C.-room temperature; and iii) a Wolff rearrangement using $H_2O$, and heat in the presence of an $Ag_2O$ catalyst.

Compounds of formula IIh are suitably prepared by hydrolysis of a compound of formula IIb wherein m is 1 and $L^2$ is (1-6C)alkoxy. Hydrolysis may suitably be carried out using an alkyl alcohol such as methanol, in the presence of a base such as sodium or lithium hydroxide in an organic solvent such as THF. Temperatures ranging from ambient temperatures to the reflux temperature of the solvent are suitably employed for the hydrolysis.

Compounds of formula II wherein m is 1 and $R^3$ and $R^{3a}$ are hydrogen may also be prepared by, for example, hydroformylation of a compound of formula IId as defined hereinabove. The hydroformylation reaction is suitably carried out by reacting a compound of formula IId with carbon monoxide and a reducing agent such as trioctyl silane or triethyl silane, in the presence of a palladium catalyst such as palladium acetate, which is suitably combined with a strong electron donor, such as diphenylphosphinopropane and a base such as triethylamine. The reaction may be carried out at ambient temperature or at elevated temperatures, for example from about 25 to about 80° C., for example about 70° C. The reaction is optionally carried out at elevated pressure in a sutable pressure vessel such as an autoclave, for example at a pressure of from 1 to 15 bar, such as about 13 bar. The reaction is suitably carried out in the presence of an inert solvent such as a polar aprotic solvent, for example N,N-dimethylformamide, N,N-dimethylacetamide N-methylpyrrolidin-2-one or dimethylsulfoxide.

ably carried out at elevated temperature, for example at about 80° C. Following the coupling reaction the protecting group is removed by conventional means, for example when Pg is an alkyl group by acid hydrolysis.

Compounds of formula III, IIc, IIe, IIf and IIg used in the above processes are commercially available compounds or they are known in the literature, or they can be can be prepared by standard processes known in the art known compounds or they can be prepared from known compounds by conventional methods, for example as illustrated by the Examples herein. For example, the compounds of the formula IIe may be prepared in accordance with Reaction Scheme 1:

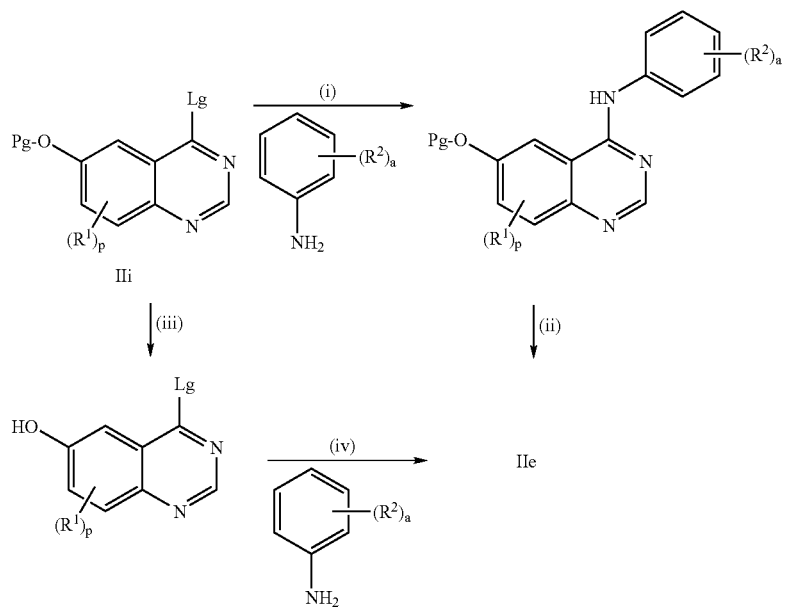

Reaction Scheme 1

Compounds of the formula II wherein m is 1, $R^{3a}$ is hydrogen and $R^3$ is (1-6C) alkyl optionally substituted by $R^{14}$ as hereinbefore defined may also be prepared by coupling a compound of the formula IId, wherein L is a suitable leaving group such as triflate with a compound of the formula IIg:

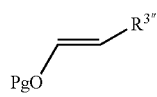

IIg wherein Pg is a suitable hydroxy protecting group (for example tert-butyl) and $R^{3''}$ is (1-5C)alkyl optionally substituted by $R^{14}$, and thereafter removing the protecting group Pg. The reaction is suitably preformed in the presence of a suitable catalyst such as a palladium catalyst, for example palladium acetate, which is suitably combined with a strong electron donor such as 1,3-(diphenylphosphino)propane. The reaction is suitably performed in an inert solvent or diluent such as such as a polar aprotic solvent, for example N,N-dimethylformamide, N,N-dimethylacetamide N-methylpyrrolidin-2-one or dimethylsulfoxide. The reaction is favourwherein $R^1$, $R^2$, p and a are as hereinbefore defined, except that any functional groups are protected if necessary, Pg is a hydroxy protecting group.

(i) Reaction suitably in an inert protic solvent (such as an alkanol for example iso-propanol), an aprotic solvent (such as dioxane) or a dipolar aprotic solvent (such as N,N-dimethylacetamide) in the presence of an acid, for example hydrogen chloride gas in diethyl ether or dioxane, or hydrochloric acid.

Alternatively the reaction may be carried out in one of the above inert solvents conveniently in the presence of a base, for example potassium carbonate. The above reactions are conveniently carried out at a temperature in the range, for example, 0 to 150° C., suitably at or near the reflux temperature of the reaction solvent.

(ii) Cleavage of Pg may be performed under standard conditions for such reactions. For example when Pg is an alkanoyl group such as acetyl, it may be cleaved by heating in the presence of a methanolic ammonia solution.

(iii) Cleavage of Pg, under analogous conditions to (ii).

(iv) Aniline coupling under analogous conditions to (iii).

Compounds of formula IIi are known or can be prepared using known processes for the preparation of analogous compounds by procedures which are selected from standard chemical techniques, techniques which are analogous to the synthesis of known, structurally similar compounds, or techniques which are analogous to the procedures described in the Examples. For example, standard chemical techniques are as described in Houben Weyl. By way of example the compound of the formula IIj in which the $R^1$ is 7-methoxy, Lg is chloro and Pg is acetyl may be prepared using the process illustrated in Reaction Scheme 2:

the formula $NHR^{5a}R^5$, or a salt thereof. The coupling reaction is conveniently carried out in the presence of a suitable coupling agent, such as a suitable peptide coupling agent, for example O-(7-azabenzotriazol-1-yl)-N,N,N',N'-tetramethyluronium hexafluoro-phosphate (HATU) or O-(1H-Benzotriazol-1-yl)-N,N,N'N'-tetramethyluronium tetrafluoroborate (TBTU); or a carbodiimide such as dicyclohexylcarbodiimide or 1-[3-(dimethyaminopropyl]-3-ethylcarbodiimide

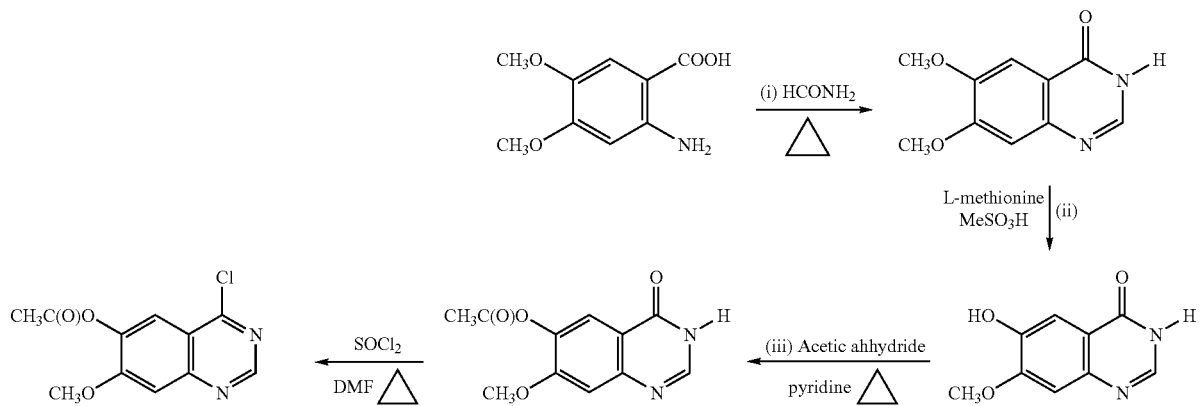

Reaction scheme 2

Reaction Scheme 2 may be generalised by the skilled man to apply to compounds within the present specification which are not specifically illustrated (for example to introduce a substituent other than methoxy at the 7-position in the quinazoline ring).

Compounds of the formula III wherein Z is O may be prepared using conventional methods for the conversion of amino acids to amides for example by using the process illustrated in Reaction scheme 3

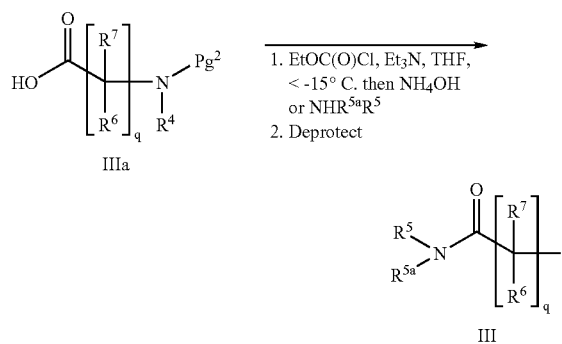

Reaction Scheme 3 wherein $R^4$, $R^5$, $R^{5a}$, $R^6$, $R^7$ and q are as hereinbefore defined, except that any functional groups are protected if necessary, $Pg^2$ is a suitable amino protecting group for example tert-butoxycarbonyl.

Other acid to amide conversions may also be used to prepare compounds of the formula III, and are well known in the art. For example, by coupling of a carboxylic acid of the formula IIIa, or a reactive derivative thereof with an amine of hydrochloride, optionally in the presence of a catalyst such as 1-hydroxybenzotriazole (HOBT), dimethylaminopyridine or 4-pyrrolidinopyridine.

The coupling reaction is conveniently carried out in the presence of a suitable base. A suitable base is, for example, an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate, calcium carbonate.

The coupling reaction is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, from 0 to 120° C., conveniently at or near ambient temperature.

By the term "reactive derivative" of the carboxylic acid of the formula IIIa is meant a carboxylic acid derivative that will react with the amine of the formula $NHR^{5a}R^5$ to give the corresponding amide. A suitable reactive derivative of a carboxylic acid of the formula IIIa is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; or an acyl azide, for example an azide formed by the reaction of the acid and azide such as diphenylphosphoryl azide; an acyl cyanide, for example a cyanide formed by the reaction of an acid and a cyanide such as diethylphosphoryl cyanide.

Compounds of the formula III wherein $R^6$ and $R^7$ together with the carbon atom to which they are attached form a monocyclic heterocyclyl group containing an NH group may be prepared by for example the process illustrated in Reaction Scheme 4:

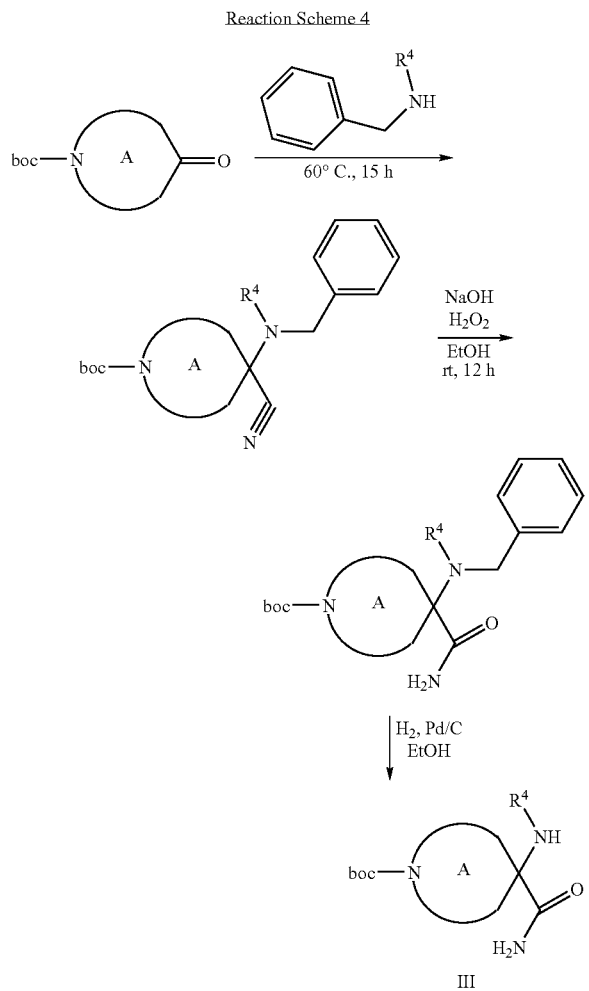

wherein A is a monocyclic heterocyclyl group containing a ring NH group, $R^5$ is as hereinbefore defined and boc is tert-butoxycarbonyl. As will be realised, alternative protecting groups may be used to protect the nitrogen atoms in Reaction Scheme 4.

If required further functional group modifications may be made to the compounds of formula IIIa or formula III (or the $Pg^2$ protected amide formed following step 1 in Reaction Scheme 3) to give further compounds of the formula III. Such functional group modifications are well known in the art, for example (1-6C)alkylation of a hydroxy or amino group with a suitable alkylating agent as illustrated hereinafter in the examples to give, for example, a corresponding (1-6C)alkoxy or (1-6C)alkylamino substituent.

Reaction Conditions for Process (b)

A suitable leaving group, L, in the compound of formula IV is, for example an alkyl or arylsulfonyloxy group (such as mesylate triflate or tosylate) or halogeno such as chloro. The reaction is conveniently carried out in the presence of a suitable base. Suitable bases include, for example, an organic amine base such as pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate, calcium carbonate. Generally the reaction is carried out in a suitable inert solvent or diluent for example an inert organic solvent such as dichloromethane, dichloroethane, N,N-dimethylformamide or N,N-dimethylacetamide. Suitably the reaction is carried out at temperatures in the range of from about 0° C. to about 200° C., conveniently at or near boiling point of the solvent used.

Preparation of Starting Materials for Process (b)

Compounds of formula IV can be prepared by conventional methods, for example by reacting a compound of formula Ia as described above, with a halogenating agent (such as thionyl chloride) or an alkyl or aryl sulfonic acid or acid anhydride using an analogous process to that described above for the preparation of compounds of the formula IId described hereinabove. The preparation of compounds of the formula Ia are as described hereinbefore. Alternatively a compound of formula Ia may be prepared by the reduction of a compound of the formula II. Suitable reduction conditions are well known, for example as described herein in relation to the reduction of a compound of formula IIb.

Reaction Conditions for Process (c)

The coupling reaction is suitably carried out under analogous conditions to those used for the preparation of compounds of the formula III. For example the compound of formula V is coupled with the amine of the formula VI in the presence of a suitable coupling agent such as O-(1H-Benzotriazol-1-yl)-N,N,N'N'-tetramethyluronium tetrafluoroborate (TBTU) or O-(7-azabenzotriazol-1-yl)-N,N,N',N'-tetramethyluronium hexafluoro-phosphate (HATU). Alternatively a carbodiimide coupling agent may be used such as 1-[3-(dimethyaminopropyl]-3-ethylcarbodiimide hydrochloride and 1-hydroxybenzotriazole (HOBT). The coupling reaction is conveniently carried out in the presence of a suitable base as hereinbefore mentioned such as an organic amine base, for example di-isopropylethylamine or N-methylmorpholine. The reaction is suitably carried out in an inert solvent or diluent, for example a halogenated solvent or dipolar aprotic solvent as defined hereinbefore. The reaction is conveniently carried out at a temperature in the range, for example, from 0 to 120° C., for example at or near ambient temperature.

By the term "reactive derivative" of the acid of the formula V is meant a carboxylic acid derivative that will react with the amine formula VI to give the corresponding amide. Suitable reactive derivatives of the carboxylic acid function are as described above in relation to the preparation of compounds of the formula III.

Preparation of Starting Materials for Process (c)

Compounds of the formula V may be prepared using conventional methods, for example as illustrated in Reaction Scheme 5:

Reaction Scheme 5

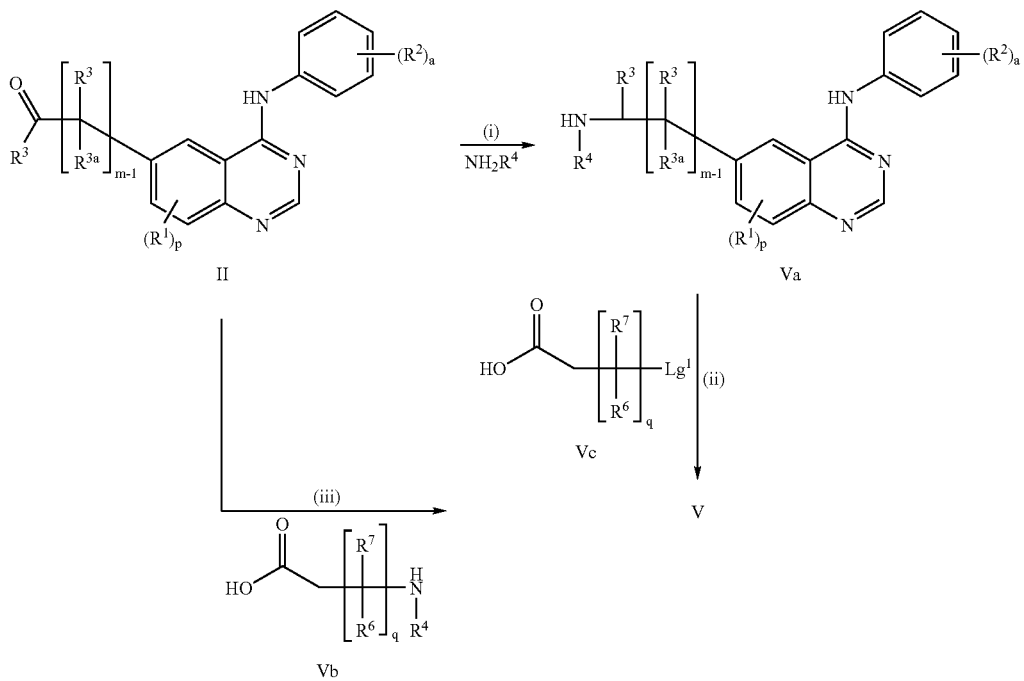

wherein $R^1$, $R^2$, $R^3$, $R^{3a}$, $R^4$, $R^5$, $R^{5a}$ $R^6$, $R^7$, a, m and p are as hereinbefore defined except that any functional group is protected if necessary, and $Lg^1$ is a suitable leaving group, for example halogeno (such as chloro), an alkyl or arylsulfonyloxy group (such as mesylate triflate or tosylate).

Notes for Reaction Scheme 5:

Steps (i) and (iii): Analogous conditions to Process (a).

Step (ii): analogous conditions to Process (b). In step (b) the carboxylic acid of the formula Vc may be protected by a suitable carboxy protecting group such as (1-4C)alkyl. The protecting group may then be removed using conventional methods, such as alkaline hydrolysis.

Compounds of the formulae Vb and Vc are known or can be prepared using conventional techniques or analogous processes to those described in the prior art or as illustrated in the examples herein.

Reaction Conditions for Process (d)

Suitable reductive amination conditions are well known in the art, for example, as described in relation to Process (a) herein. A quinazoline derivative of the formula I, which contains an NH group (for example when $R^6$ and $R^7$ together with the carbon atom to which they are attached form a piperid-4-yl group) is reacted with an appropriate aldehyde or ketone to give an optionally substituted ring N(alkyl) group. Appropriate aldehydes and ketones will be apparent, for example for the production of those quinazoline derivatives of the Formula I wherein $Q^a$ contains a ring N-methyl, the corresponding compound containing a ring N—H group may be reacted with paraformaldehyde or aqueous formaldehyde in the presence of a suitable reducing agent. Similarly to give an optionally substituted ring N(alkyl) group a suitable aldehyde or ketone is used for example acetaldehyde, propionaldehyde, (1-4C)alkoxyacetaldehyde, such as methoxyacetaldehyde, or acetone (to give an isopropyl group).

A suitable reducing agent is, for example, a hydride reducing agent, for example an alkali metal aluminium hydride such as lithium aluminium hydride, or, suitably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is suitably performed under acidic conditions in the presence of a suitable acid such as hydrogen chloride or acetic acid, a buffer may also be used to maintain pH at the desired level during the reaction. When the reducing agent is formic acid the reaction is conveniently carried out using an aqueous solution of the formic acid. The reaction is performed at a temperature in the range, for example, −20 to 100° C., such as −10 to 50° C., conveniently, at or near ambient temperature.

Reaction Conditions for Process (e)

The coupling reaction is conveniently carried out under Mitsunobu conditions. Suitable Mitsunobu conditions are well known and include, for example, reaction in the presence of a suitable tertiary phosphine and a di-alkylazodicarboxylate in an organic solvent such as THF, or suitably dichloromethane and in the temperature range 0° C. to 100° C., for example 0° C. to 60° C., but suitably at or near ambient temperature. A suitable tertiary phosphine includes for example tri-n-butylphosphine or particularly tri-phenylphosphine. A suitable di-alkylazodicarboxylate includes, for example, diethyl azodicarboxylate (DEAD) or suitably di-tert-butyl azodicarboxylate (DTAD). Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

Preparation of Starting Materials for Process (e)

The compound of formula VII used as starting material may be prepared by, for example, the cleavage of a quinazoline derivative of the formula I, wherein $R^1$ is, for example, methoxy. The cleavage reaction may conveniently be carried out by any of the many procedures known for such a transformation. A particularly suitable cleavage reaction is the treatment of a quinazoline derivative of the Formula I wherein $R^1$ is a (1-6C)alkoxy group with an alkali metal halide such as lithium iodide or magnesium bromide in the presence of pyridine (for example pyridinium hydrochloride), or 2,4,6-collidine (2,4,6-trimethylpyridine). The reaction is suitably carried out at a temperature in the range, for example, 10 to 170° C., particularly at elevated temperature for example 120 to 170° C., for example approximately 130° C.

Reaction Conditions for Process (f)

A suitable leaving group represented by $L^3$ in the compound of the formula compound of the formula $R^1L^3$ is, for example halogeno such as chloro or bromo. The reaction is suitably performed under analogous conditions to those of process (b) described hereinbefore.

The quinazoline derivative of the formula I may be obtained from the above processes in the form of the free base or alternatively it may be obtained in the form of a salt, an acid addition salt. When it is desired to obtain the free base from a salt of the compound of formula I, the salt may be treated with a suitable base, for example, an alkali or alkaline earth metal carbonate or hydroxide, for example sodium carbonate, potassium carbonate, calcium carbonate, sodium hydroxide or potassium hydroxide, or by treatment with ammonia for example using a methanolic ammonia solution such as 7N ammonia in methanol.

The protecting groups used in the processes above may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); lower alkanoyloxyalkyl groups (for example pivaloyloxymethyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl. For example a tert butoxycarbonyl protecting group may be removed from an amino group by an acid catalysed hydrolysis using trifluoroacetic acid.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups. It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. For example converting a quinazoline derivative of the formula I into another quinazoline derivative of the formula I as mentioned in the processes described above. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; the introduction of a (2-6C)alkanoyl group to an NH group by reacting the quinazoline of formula I with an (2-6C)alkanoyl halide, or by an amide coupling using analogous conditions to those of Process (c); the introduction of an (1-6C)alkylsulfonyl group to an NH group by reacting the quinazoline of formula I with an (1-6C)alkylsulfonyl halide; and the introduction of a halogeno group. A particular functional modification useful in the present invention is the alkylation of an NH group in a quinazoline derivative of the formula I to introduce, for example an $R^4$ group. Alkylation may be achieved using a suitable alkylating agent, for example, any agent known in the art for the alkylation of amino to alkylamino, for example an alkyl or substituted alkyl halide, for example a (1-6C)alkyl chloride, bromide or iodide or a substituted (1-6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature. A further convenient alkylation reaction suitable for introducing, for example an alkyl $R^4$ group into a quinazoline derivative of formula I is via a suitable reductive amination reaction with the corresponding aldehyde or ketone. For example, for the production of those compounds of the formula I wherein $R^4$ is methyl, the corresponding compound of formula I containing a N—H group may be reacted with formaldehyde in the presence of a suitable reducing agent. A suitable reducing agent and reaction conditions are as described above in relation to Process (a).

When a pharmaceutically-acceptable salt of a quinazoline derivative of the formula I is required, for example an acid-addition salt, it may be obtained by, for example, reaction of said quinazoline derivative with a suitable acid using a conventional procedure.

As mentioned hereinbefore some of the compounds according to the present invention may contain one of more chiral centers and may therefore exist as stereoisomers (for example when $R^6$ and $R^7$ are not the same). Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free for other stereoisomers, for example containing less than 20%, particularly less than 10% and more particularly less than 5% by weight of other stereoisomers.

In the section above relating to the preparation of the quinazoline derivative of formula I, the expression "inert solvent" refers to a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

BIOLOGICAL ASSAYS

The inhibitory activities of compounds were assessed in non-cell based protein tyrosine kinase assays as well as in cell based proliferation assays before their in vivo activity was assessed in Xenograft studies.

a) Protein Tyrosine Kinase Phosphorylation Assays

This test measures the ability of a test compound to inhibit the phosphorylation of a tyrosine containing polypeptide substrate by EGFR tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis($\beta$-aminoethyl ether) N',N',N',N'-tetraacetic acid (EGTA), plus protease inhibitors and then cleared by centrifugation.

Constitutive kinase activity of these recombinant proteins was determined by their ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 200 μl phosphate buffered saline (PBS) solution and incubated at 4° C. overnight). Plates were washed in 50 mM HEPES pH 7.4 at room temperature to remove any excess unbound synthetic peptide. EGFR or erbB2 activities were assessed by incubation in peptide coated plates for 20 minutes at room temperature in 100 mM HEPES pH 7.4 at room temperature, adenosine trisphosphate (ATP) at Km concentration for the respective enzyme, 10 mM $MnCl_2$, 0.1 mM $Na_3VO_4$, 0.2 mM DL-dithiothreitol (DTT), 0.1% Triton X-100 with test compound in DMSO (final concentration of 2.5%). Reactions were terminated by the removal of the liquid components of the assay followed by washing of the plates with PBS-T (phosphate buffered saline with 0.5% Tween 20).

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzthiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of KB cells (human naso-pharangeal carcinoma obtained from the American Type Culture Collection (ATCC)).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethylsulfoxide (DMSO) (0.1% final) before incubation for 4 days. Following the incubation period, cell numbers were determined by addition of 50 µl of 3-(4,5-Dimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 µl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) Cellular EGFR Phosphorylation Assay

This assay measures the ability of a test compound to inhibit the phosphorylation of EGFR in KB cells (human naso-pharangeal carcinoma obtained from the American Type Culture Collection (ATCC).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $2 \times 10^5$ cells per well of a 6 well plate in DMEM containing 2.5% charcoal stripped serum, 2 mM glutamine and non-essential amino acids at 37° C. in 7.5% $CO_2$ and allowed to settle for 72 hours.

Following the 72 hour incubation period, the stripped serum containing media was then replaced with serum-free media (DMEM containing 2 mM glutamine and non-essential amino acids) and incubated at 37° C. in 7.5% $CO_2$ for 72 hours. Following this incubation period, the cells were treated with or without compound at a range of concentrations in dimethylsulfoxide (DMSO) (0.1% final) in serum free DMEM. Following incubation for 1.5 hours at 37° C. in 7.5% $CO_2$, the cells were treated with EGF (final concentration of 1 µg/ml) and incubated at 37° C. in 7.5% $CO_2$ for 3 minutes. The media was then removed and the cells washed twice in ice cold Phosphate Buffered Saline before lysis of the cells with 1 ml of ice cold lysis buffer containing 120 mM $NaCl_2$, 25 mM HEPES, pH 7.6, 5 mM B-Glycerophosphate, 2.5 mM $MgCl_2$, 1 mM EGTA, 0.2 mM EDTA, 1 mM $Na_3VO_4$, 1% Triton X-100, 100 mM NaF, 1 mM DTT, 1 mM PMSF, 10 µg/ml Leupeptin and 10 µg/ml Benzamidine. The lysates were centrifuged in a microfuge at 13000 rpm for 15 minutes and the supernatants taken before analysis by sandwich Elisa.

Nunc Maxisorb F96 Immunoplates were coated with EGFR capture antibody (sc-120, Santa Cruz Biotechnology, Inc.) by incubation at a concentration of 0.16 µg/ml in 100 µl of 50 mM carbonate/bicarbonate buffer, pH 9.6. The plates were incubated at 4° C. overnight with a gentle shaking action. Following overnight incubation, the plates were washed extensively with PBS containing 0.05% Tween before blocking with Superblock (Pierce). 100 µl of lysate was then added to each well and incubated overnight at 4° C. before extensive washing with PBS containing 0.05% Tween.

The immobilised EGFR was then probed with an anti-phosphotyrosine HRP conjugated antibody (4G10, Upstate Biotechnology Inc.) at a dilution of 1 in 800 in PBS containing 0.05% Tween plus 0.5% Bovine Serum Albumen. After further washing, HRP activity in each well of the plate was measured calorimetrically using Tetra Methyl Benzidine (TMB) from Bushranger (Roche Applied Sciences) in phosphate-citrate-perborate buffer containing 10% DMSO as a substrate. This reaction was stopped by the addition of 100 ul of 1M $H_2SO_4$ after 12 minutes and quantified by measurement of the absorbance at 450 nm using a Molecular Devices ThermoMax microplate reader.

Inhibition of EGFR phosphorylation for a given compound was expressed as an $IC_{50}$ value. This was determined by calculation of the concentration of compound that was required to give 50% inhibition of phosphorylation in this assay. The range of phosphorylation was calculated from the positive (vehicle plus EGF) and negative (vehicle minus EGF) control values.

d) Clone 24 phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1 \times 10^4$ cells per well (in 100 ul) into clear bottomed 96 well plates (Packard, No. 6005182).

3 days later, Growth Medium was removed from the wells and replaced with 100 ul Assay Medium (phenol red free DMEM, 2 mM glutamine, 1.2 mg/ml G418) either with or without erbB inhibitor compound. Plates were returned to the incubator for 4 hrs and then 20 µl of 20% formaldehyde solution in PBS was added to each well and the plate was left at room temperature for 30 minutes. This fixative solution was removed with a multichannel pipette, 100 µl of PBS was added to each well and then removed with a multichannel pipette and then 50 µl PBS was added to each well. Plates were then sealed and stored for up to 2 weeks at 4° C.

Immunostaining was performed at room temperature. Wells were washed once with 200 µl PBS/Tween 20 (made by adding 1 sachet of PBS/Tween dry powder (Sigma, No. P3563) to IL of double distilled $H_2O$) using a plate washer then 200 µl Blocking Solution (5% Marvel dried skimmed milk (Nestle) in PBS/Tween 20) was added and incubated for 10 minutes. Blocking Solution was removed using a plate washer and 200 µl of 0.5% Triton X-100/PBS was added to permeabalise the cells. After 10 minutes, the plate was washed with 200 µl PBS/Tween 20 and then 200 µl Blocking Solution was added once again and incubated for 15 minutes. Following removal of the Blocking Solution with a plate washer, 30 µl of rabbit polyclonal anti-phospho ErbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 µl PBS/Tween 20 washes using a plate washer. Then 30 µl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by two 200 ul PBS/Tween 20 washes using a plate washer. Then 100 µl PBS was added to each plate, incubated for 10 minutes and then removed using a plate washer. Then a further 100 µl PBS was added to each plate and then, without prolonged incubation, removed using a plate washer. Then 50 µl of PBS was added to each well and plates were resealed with black backing tape and stored for up to 2 days at 4° C. before analysis.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

e) In Vivo Xenograft Assay

This assay measures the ability of a test compound to inhibit the growth of a LoVo tumour (colorectal adenocarcinoma obtained from the ATCC) in Female Swiss athymic mice (Alderley Park, nu/nu genotype).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. LoVo tumour cell (colorectal adenocarcinoma obtained from the ATCC) xenografts were established in the hind flank of donor mice by sub cutaneous injections of $1 \times 10^7$ freshly cultured cells in 100 µl of serum free media per animal. On day 5 post-implant, mice were randomised into groups of 7 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of study was calculated by comparison of the mean changes in tumour volume for the control and treated groups, and statistical significance between the two groups was evaluated using a Students t test.

f) hERG-Encoded Potassium Channel Inhibition Assay

This assay determines the ability of a test compound to inhibit the tail current flowing through the human ether-a-go-go-related-gene (hERG)-encoded potassium channel. Test compounds that are active in the hERG assay; may give rise to ECG (electrocardiogram) changes in vivo. Accordingly it is preferred that compounds are inactive or only weakly active in the hERG assay.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at room temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| MgCl$_2$ | 1 | 1 |
| CaCl$_2$ | — | 1.8 |
| HEPES | 10 | 10 |
| glucose | — | 10 |
| Na$_2$ATP | 5 | — |
| EGTA | 5 | — |

| Parameter | Pipette | Bath |
|---|---|---|
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency (IC$_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Although the pharmacological properties of the compounds of the formula I vary with structural change as expected, in general activity possessed by compounds of the formula I, may be demonstrated at the following concentrations or doses in one or more of the above tests (a), (b), (c), (d) and (e):—

Test (a):—IC$_{50}$ in the range, for example, 0.001-1 µM;

Test (b):—IC$_{50}$ in the range, for example, 0.001-5 µM;

Test (b):—IC$_{50}$ in the range, for example, 0.001-5 µM;

Test (d):—IC$_{50}$ in the range, for example, 0.01-5 µM;

Test (e):—activity in the range, for example, 1-200 mg/kg/day;

No physiologically unacceptable toxicity was observed in Test (e) at the effective dose for compounds tested of the present invention. Accordingly no untoward toxicological effects are expected when a compound of formula I, or a pharmaceutically-acceptable salt thereof, as defined hereinbefore is administered at the dosage ranges defined hereinafter.

By way of example, using Test (a) (for the inhibition of EGFR tyrosine kinase protein phosphorylation) and Test (b), the KB cell assay described above, representative compounds described in the Examples herein gave the IC$_{50}$ results shown below in Table A:

TABLE A

| Compound of Example | IC$_{50}$ (nM) Test (a) (Inhibition of EGFR tyrosine kinase protein phosphorylation) | IC$_{50}$ (nM) Test (b) (EGFR driven KB cell proliferation assay) |
|---|---|---|
| 4 | 17 | 23 |
| 20 | 17 | 36 |
| 29 | 27 | 54 |
| 66 | 9 | 91 |

According to a further aspect of the invention there is provided a pharmaceutical composition which comprises a quinazoline derivative of the formula I, or a pharmaceutically-acceptable thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a quinazoline derivative of the formula I will naturally vary according to the nature and severity of the conditions, the age and sex of the animal or patient and the route of administration, according to well known principles of medicine.

In using a quinazoline derivative of the formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erbB family receptor tyrosine kinase inhibitory activity, particularly inhibition of the EGF receptor (erbB1) tyrosine kinase. Furthermore, certain of the compounds according to the present invention possess substantially better potency against the EGF receptor tyrosine kinase, than against other tyrosine kinase enzymes, for example erbB2. Such compounds possess sufficient potency against the EGF receptor tyrosine kinase that they may be used in an amount sufficient to inhibit EGF receptor tyrosine kinase whilst demonstrating little, or significantly lower, activity against other tyrosine kinase enzymes such as erbB2. Such compounds are likely to be useful for the selective inhibition of EGF receptor tyrosine kinase and are likely to be useful for the effective treatment of, for example EGF driven tumours.

Accordingly, the compounds of the present invention are expected to be useful in the treatment of diseases or medical conditions mediated alone or in part by erbB receptor tyrosine kinases (especially EGF receptor tyrosine kinase), i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours, particularly solid tumours, that are sensitive to inhibition of one or more of the erbB receptor tyrosine kinases, such as EGF and/or erbB2 and/or erbB4 receptor tyrosine kinases (especially EGF receptor tyrosine kinase) that are involved in the signal transduction steps which drive proliferation and survival of these tumour cells. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancers.

According to this aspect of the invention there is provided a compound of the formula I, or a pharmaceutically acceptable salt thereof, for use as a medicament.

According to a further aspect of the invention there is provided a compound of the formula I, or a pharmaceutically acceptable salt thereof, for use in the production of an anti-proliferative effect in a warm-blooded animal such as man.

Thus according to this aspect of the invention there is provided the use of a quinazoline derivative of the formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the formula I, or a pharmaceutically acceptable salt thereof, as hereinbefore defined.

According to a further aspect of the invention there is provided the use of a quinazoline derivative of the formula I, or a pharmaceutically-acceptable salt thereof, as defined hereinbefore in the manufacture of a medicament for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further feature of this aspect of the invention there is provided a method for the prevention or treatment of those tumours which are sensitive to inhibition of one or more of the erbB family of receptor tyrosine kinases, such as EGFR and/or erbB2 and/or erbB4 (especially EGFR), that are involved in the signal transduction steps which lead to the proliferation and/or survival of tumour cells which comprises administering to said animal an effective amount of a quinazoline derivative of the formula I, or a pharmaceutically-acceptable salt thereof, as defined hereinbefore.

According to a further feature of this aspect of the invention there is provided a compound of the formula I, or a pharmaceutically acceptable salt thereof, for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further aspect of the invention there is provided the use of a quinazoline derivative of the formula I, or a pharmaceutically-acceptable salt thereof, as defined hereinbefore in the manufacture of a medicament for use in providing a EGFR and/or erbB2 and/or erbB4 (especially a EGFR) tyrosine kinase inhibitory effect.

According to a further feature of this aspect of the invention there is provided a method for providing a EGFR and/or an erbB2 and or an erbB4 (especially a EGFR) tyrosine kinase inhibitory effect which comprises administering to said animal an effective amount of a quinazoline derivative of the formula I, or a pharmaceutically-acceptable salt thereof, as defined hereinbefore.

According to a further feature of this aspect of the invention there is provided a compound of the formula I, or a pharmaceutically acceptable salt thereof, for use in providing a EGFR and/or erbB2 and/or erbB4 (especially a EGFR) tyrosine kinase inhibitory effect.

According to a further feature of the present invention there is provided the use of a quinazoline derivative of the formula I, or a pharmaceutically-acceptable salt thereof, as defined hereinbefore in the manufacture of a medicament for use in providing a selective EGFR tyrosine kinase inhibitory effect.

According to a further feature of this aspect of the invention there is provided a method for providing a selective EGFR tyrosine kinase inhibitory effect which comprises administering to said animal an effective amount of a quinazoline derivative of the formula I, or a pharmaceutically-acceptable salt thereof, as defined hereinbefore.

According to a further feature of this aspect of the invention there is provided a compound of the formula I, or a pharmaceutically acceptable salt thereof, for use in providing a selective EGFR tyrosine kinase inhibitory effect.

By "a selective EGFR kinase inhibitory effect" is meant that the quinazoline derivative of formula I is more potent against EGF receptor tyrosine kinase than it is against other kinases. In particular some of the compounds according to the invention are more potent against EGF receptor kinase than it is against other tyrosine kinases such as other erbB receptor tyrosine kinases such erbB2. For example a selective EGFR kinase inhibitor according to the invention is at least 5 times, particularly at least 10, more particularly at least 100 times more potent against EGF receptor tyrosine kinase than it is against erbB2 tyrosine kinase, as determined from the relative $IC_{50}$ values in suitable assays. For example, by comparing the $IC_{50}$ value from the Cellular EGFR phosphorylation assay (Test (c) above, a measure of the EGFR tyrosine kinase inhibitory activity) with the $IC_{50}$ value from the Clone 24 phospho-erbB2 cell assay (a measure of erb-B2 tyrosine kinase inhibitory activity) for a given test compound as described above.

According to a further aspect of the present invention there is provided the use of a quinazoline derivative of the formula I, or a pharmaceutically-acceptable salt thereof, as defined hereinbefore in the manufacture of a medicament for use in the treatment of a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

According to a further feature of this aspect of the invention there is provided a method for treating a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer) in a warm-blooded animal, such as man, in need of such treatment, which comprises administering to said animal an effective amount of a quinazoline derivative of the formula I, or a pharmaceutically-acceptable salt thereof, as defined hereinbefore.

According to a further aspect of the invention there is provided a compound of the formula I, or a pharmaceutically acceptable salt thereof, for use in the treatment of a cancer (for example selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

As mentioned above the size of the dose required for the therapeutic or prophlyactic treatment of a particular disease will necessarily be varied depending upon, amongst other things, the host treated, the route of administration and the severity of the illness being treated.

The anti-proliferative treatment/tyrosine kinase inhibitory effect defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin $α_νβ_3$ function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the formula I as defined hereinbefore and an additional anti-tumour agent as defined hereinbefore for the conjoint treatment of cancer.

Although the compounds of the formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulfate or sodium sulfate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LCMS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at the operating frequency of the NMR apparatus used (300 or 400 MHz), using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms;

(x) mass spectra (MS) were run using a Waters or Micromass electrospray LC-MS in positive or negative ion mode; values for m/z are given; generally, only ions which indicate the parent mass are reported; and unless otherwise stated, the mass ion quoted is $(MH)^+$;

(xi) where a synthesis is described as being analogous to that described in a previous example the amounts used are the millimolar ratio equivalents to those used in the previous example;

(xii) the following abbreviations have been used:
DIPEA N,N-diisopropylethylamine
DMF N,N-dimethylformamide
DMSO dimethylsulfoxide
DTAD di-tert-butyl azodicarboxylate
EtOAc ethyl acetate
HATU O-(7-azabenzotriazol-1-yl)-N,N,N',N'-tetramethyluronium hexafluoro-phosphate
NMP N-methylpyrrolidinone
THF tetrahydrofuran.

(xiii) SCX and $NH_2$ columns used to purify compounds in the examples are solid phase extraction cartridges containing a variety of different bonded silica sorbents. $NH_2$ columns are functionalised with an amino propyl side chain making them a weak anion exchange resin (pKa 9.8). SCX columns are functionalised with a benzene sulfonic acid side chain making them a strong cation exchange resin (see Handbook of Sorbent Extraction Technology (ISBN 0-9616096-0-5)); and (xiv) Where the commercially available or literature derived form of the amino acid starting material used in the examples was a salt, the free base was generated by use of an SCX column. A solution of the salt in methanol was loaded onto an SCX column and washed with methanol. The column was then be eluted with saturated methanolic ammonia solution. Appropriate fractions were combined and evaporated to afford the free base form which was used as such without further purification.

(xv) where examples refer to purification by preparative LCMS (standard acidic system) the following conditions were used:

| | |
|---|---|
| Apparatus: | Waters/Micromass |
| Column: | Xterra, Waters Sum 19 × 100 mm |
| Eluant: | Gradient of 20 to 100% Acetonitrile/H2O (2 g/l of ammonium carbonate over 7.5 minutes. |
| Flow: | 25 ml/min |
| Detection: | UV 254 nm + MS |
| Injection in: | Dimethylformamide |

The desired fractions were pooled and evaporated to dryness. The resulting solids were dried to a constant weight under high vacuum at 60° C. for 12 hours to afford the desired compound as the free base.

(xiv) where examples refer to purification by preparative LCMS (standard basic system) the following conditions were used:

| | |
|---|---|
| Apparatus: | Waters/Micromass |
| Column: | Xterra, Waters 5 um 19 × 100 mm |
| Eluant: | Gradient of 0 to 100% Acetonitrile/H2O (1% acetic acid over 7.5 minutes. |
| Flow: | 25 ml/min |
| Detection: | UV 254 nm + MS |
| Injection in: | Dimethylacetamide |

The desired fractions were pooled and evaporated to dryness. To the resulting residue was added toluene and the solvent was evaporated to dryness again. This step was repeated and the resulting solids were dried to a constant weight under high vacuum at 60° C. for 12 hours to afford the desired compound as the free base.

EXAMPLE 1

N²-({4-[(3-Chloro-2-fluorophenyl)amino]-7-methoxyquinazolin-6-yl}methyl)-N²-methylglycinamide (Process (a))

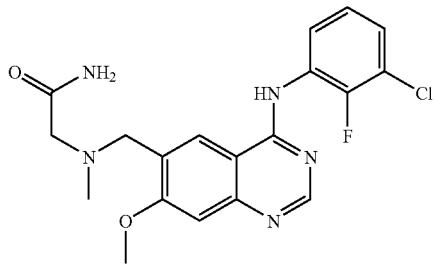

A mixture of 4-[(3-chloro-2-fluorophenyl)amino]-7-methoxyquinazoline-6-carbaldehyde (200 mg, 0.60 mmol), N-methylglycinamide (80 mg, 0.90 mmol) and 3 Å molecular sieves in 5% acetic acid in dichloromethane (12 ml) was stirred and to it added sodium triacetoxyborohydride (192 mg, 0.90 mmol) portionwise over 0.5 hours. After the final addition the reaction mixture was stirred for 1 hour, filtered and concentrated under reduced pressure. The residue was dissolved in methanol, absorbed onto an SCX column, washed with methanol and eluted with 7N ammonia in methanol. Appropriate fractions were combined and evaporated. The resulting material was purified by column chromatography on silica, eluting with increasingly polar mixtures of methanol/methylene chloride (2/98 to 5/95) to give the title product (140 mg, 57%) as a white solid; $^1$H NMR Spectrum: (DMSOd$_6$) 2.28 (s, 3H), 3.03 (s, 2H), 3.71 (s, 2H), 3.97 (s, 3H), 7.22 (s, 2H), 7.29 (t, 1H), 7.36 (brs, 1H), 7.50 (t, 1H), 7.56 (t, 1H), 8.44 (s, 2H), 9.79 (s, 1H); Mass Spectrum: (M+H)$^+$ 404.

The 4-[(3-chloro-2-fluorophenyl)amino]-7-methoxyquinazoline-6-carbaldehyde starting material was prepared as follows:

A suspension of 4-[(3-chloro-2-fluorophenyl)amino]-6-hydroxy-7-methoxyquinazoline (800 mg, prepared as described in Reference Example 2 of WO03/82831 in methylene chloride (150 ml) was cooled to 0° C. and pyridine (1.5 ml) added. Triflic anhydride (507 μl) was then added dropwise and the resulting solution left to stir to room temperature. After 18 hours the reaction mixture was washed with water and brine, dried over MgSO$_4$, filtered and evaporated under reduced pressure. The residues were then triturated with methylene chloride to give 4-[(3-chloro-2-fluorophenyl)amino]-7-methoxyquinazolin-6-yl trifluoromethanesulfonate as a white solid which was collected by filtration and dried (880 mg, 79%); $^1$H NMR Spectrum: (DMSO d$_6$) 4.13 (s, 3H), 7.37 (m, 1H), 7.56 (m, 1H), 7.64 (m, 1H), 7.66 (s, 1H), 8.86 (s, 1H), 9.06 (s, 1H), 11.7 (bs, 1H); Mass Spectrum: (M+H)$^+$ 452.

A high pressure vessel was charged with 4-[(3-chloro-2-fluorophenyl)amino]-7-methoxyquinazolin-6-yl trifluoromethanesulfonate (10 g, 22.1 mmol), palladium (II) acetate (700 mg, 3.12 mmol), triethylamine (7.6 ml, 54.5 mmol), 1,3-bis diphenylphosphinopropane (1.46 g, 3.54 mmol), trioctylsilane (13.2 ml, 29.4 mmol) and N,N-dimethylformamide (110 ml). The reaction mixture was heated at 70° C. under a carbon monoxide atmosphere (13 Bar) for 3 hours. The mixture was cooled and the lower N,N-dimethylformamide layer was separated, filtered and concentrated under reduced pressure. The residue was suspended in methanol, filtered, washed with isohexane and dried to give 4-[(3-chloro-2-fluorophenyl)amino]-7-methoxyquinazoline-6-carbaldehyde (3.0 g, 41%) as a pale orange solid; $^1$H NMR spectrum: (DMSO d$_6$) 4.07 (s, 3H), 7.29 (t, 1H), 7.36 (s, 1H), 7.51 (t, 2H), 8.52 (s, 1H), 8.95 (s, 1H), 10.36 (s, 1H), 10.45 (s, 1H); Mass Spectrum: (M+H)$^+$ 332.

EXAMPLE 2

N²-({4-[(3-Chloro-2-fluorophenyl)amino]-7-methoxyquinazolin-6-yl}methyl)-N²-methyl-D-alaninamide (Process (a))

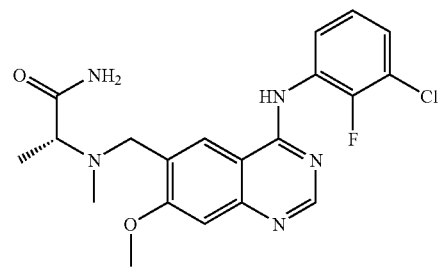

4-[(3-Chloro-2-fluorophenyl)amino]-7-methoxyquinazoline-6-carbaldehyde was coupled with N²-methyl-D-alaninamide (described in 108732-07-6P. J. Med. Chem., 1995 38(21), 4244), using an analogous method to that described for the equivalent step in Example 1 to give the title product; $^1$H NMR spectrum: (DMSO d$_6$) 1.21 (d, 3H), 2.23 (s, 3H), 3.25 (q, 1H), 3.65 (d, 1H), 3.72 (d, 1H), 3.96 (s, 3H), 7.11 (brs, 1H), 7.21 (s, 1H), 7.29 (dt, 1H), 7.39 (brs, 1H), 5.57 (m, 2H), 8.43 (m, 2H), 9.79 (s, 1H); Mass Spectrum: (M+H)$^+$ 418.

EXAMPLE 3

N²-({4-[(3-Chloro-2-fluorophenyl)amino]-7-methoxyquinazolin-6-yl}methyl)-N²-methyl-L-alaninamide (Process (a))

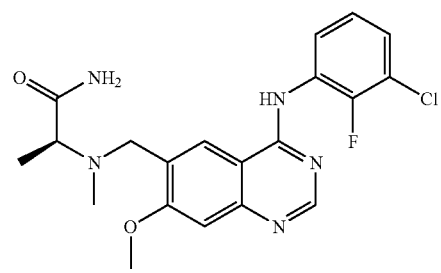

4-[3-Chloro-2-fluorophenyl)amino]-7-methoxyquinazoline-6-carbaldehyde was coupled with N²-methyl-L-alaninamide (55988-12-0P. J. Med. Chem., 1995 38(21), 4244) using an analogous process to that described for the equivalent step in Example 1 to give the title product; $^1$H NMR spectrum: (DMSO d$_6$) 1.21 (d, 3H), 2.23 (s, 3H), 3.25 (q, 1H), 3.65 (d, 1H), 3.72 (d, 1H), 3.96 (s, 3H), 7.11 (brs, 1H), 7.21 (s, 1H), 7.29 (dt, 1H), 7.39 (brs, 1H), 5.57 (m, 2H), 8.43 (m, 2H), 9.79 (s, 1H); Mass Spectrum: (M+H)$^+$ 418.

EXAMPLE 4

N²-({4-[(3-Chloro-2-fluorophenyl)amino]-7-methoxyquinazolin-6-yl}methyl)-N²-methyl-L-serinamide (Process (a))

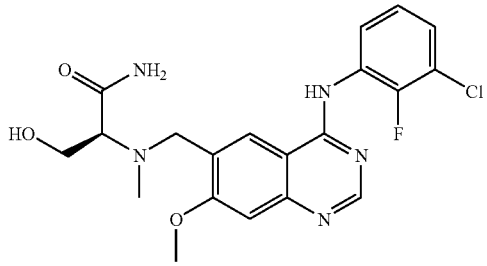

4-[(3-Chloro-2-fluorophenyl)amino]-7-methoxyquinazoline-6-carbaldehyde was coupled with N²-methyl-L-serinamide (166186-98-7P. J. Med. Chem., 1995, 38(21), 4244) using an analogous process to that described for the equivalent step in Example 1 to give the title product; $^1$H NMR spectrum: (DMSO d$_6$) 2.31 (s, 3H), 3.26 (t, 1H), 3.77 (m, 1H), 3.86 (m, 3H), 3.96 (s, 3H), 4.50 (t, 1H), 7.15 (brs, 1H), 7.21 (s, 1H), 7.29 (dt, 1H), 7.43 (brs, 1H), 7.50 (dt, 1H), 7.56 (m, 1H), 8.39 (s, 1H), 8.43 (s, 1H), 9.77 (s, 1H); Mass Spectrum: (M+H)$^+$ 434.

EXAMPLE 5

N²-({4-[(3-Chloro-2-fluorophenyl)amino]-7-methoxyquinazolin-6-yl}methyl)-D-alaninamide (Process (a))

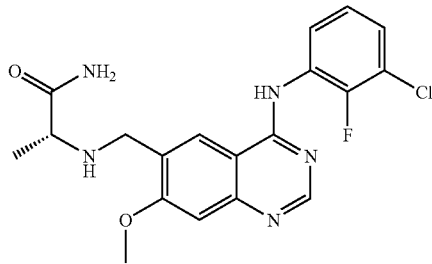

4-[(3-Chloro-2-fluorophenyl)amino]-7-methoxyquinazoline-6-carbaldehyde was coupled with D-alaninamide using an analogous process to that described for the equivalent step in Example 1 to give the title product; $^1$H NMR spectrum: (DMSO d$_6$) 1.22 (d, 3H), 2.38 (brs, 1H), 3.15 (m, 1H), 3.75 (m, 2H), 3.96 (s, 3H), 7.06 (brs, 1H), 7.20 (s, 1H), 7.29 (t, 1H), 7.42 (brs, 1H), 7.55 (m, 2H), 8.38 (s, 1H), 8.44 (s, 1H), 9.82 (s, 1H); Mass Spectrum: (M+H)$^+$ 404.

EXAMPLE 6

N²-({4-[(3-Chloro-2-fluorophenyl)amino]-7-methoxyquinazolin-6-yl}methyl)glycinamide (Process (a))

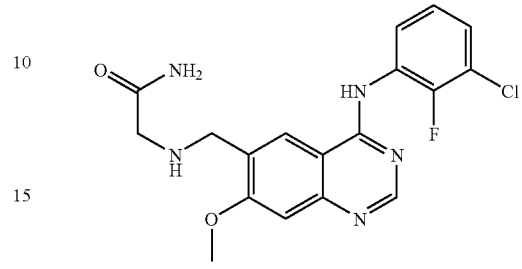

4-[(3-Chloro-2-fluorophenyl)amino]-7-methoxyquinazoline-6-carbaldehyde was coupled with glycinamide using an analogous process to that described for the equivalent step in Example 1 to give the title product; $^1$H NMR spectrum: (DMSO d$_6$) 2.55 (brs, 1H), 3.16 (s, 2H), 3.81 (s, 2H), 3.96 (s, 3H), 7.14 (brs, 1H), 7.21 (s, 1H), 7.28 (t, 1H), 7.41 (brs, 1H), 7.51 (m, 2H), 8.39 (s, 1H), 8.44 (s, 1H), 9.84 (s, 1H); Mass Spectrum: (M+H)$^+$ 390.

EXAMPLE 7

N²-({4-[(3-Chloro-2-fluorophenyl)amino]-7-methoxyquinazolin-6-yl}methyl)-N²,O-dimethyl-L-serinamide (Process (a))

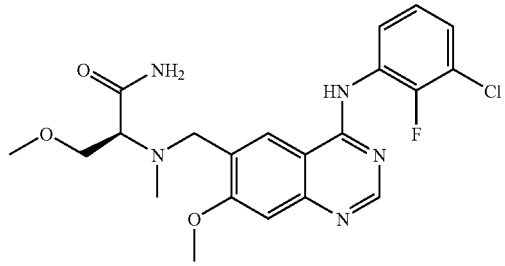

4-[(3-Chloro-2-fluorophenyl)amino]-7-methoxyquinazoline-6-carbaldehyde was coupled with N²,O-dimethyl-L-serinamide using an analogous process to that described for the equivalent step in Example 1 to give the title product; $^1$H NMR spectrum: (DMSO d$_6$) 2.28 (s, 3H), 3.29 (s, 3H), 3.42 (t, 1H), 3.71 (dd, 1H), 3.79 (m, 3H), 3.96 (s, 3H), 7.21 (s, 1H), 7.23 (d, 1H), 7.29 (t, 1H), 7.52 (m, 3H), 8.37 (s, 1H), 8.43 (s, 1H), 9.83 (s, 1H); Mass Spectrum: (M−H)$^−$ 446.

The N²,O-dimethyl-L-serinamide used as starting material was prepared as follows:

Sodium hydride (2.1 g, 52.4 mmol) was washed with isohexane under a nitrogen atmosphere. Tetrahydrofuran (20 ml) was added and the suspension cooled in an ice/water bath. A mixture of N-(tert-butoxycarbonyl)-O-methyl-L-serine (starting material obtained by converting the dicyclohexylamine salt to the free base as described above in the preamble to the Examples) (2.5 g, 11.4 mmol) and water (41 μl, 2.28 mmol) in tetrahydrofuran (15 ml) was slowly added. The resulting mixture was allowed to stir for 20 minutes and dimethylsulfate (3.3 ml, 35.3 mmol) was slowly added. The mixture was stirred for 2 hours and treated with concentrated ammonium hydroxide (15 ml). The resulting mixture was stirred for a further 2 hours, then acidified with 2M hydrochloric acid, extracted with ethyl acetate, dried (MgSO$_4$) and concentrated under reduced pressure. The residues were dissolved in methanol, absorbed onto an NH$_2$ column, washed with methanol and eluted with 7N ammonia in methanol. Appropriate fractions were combined and evaporated under reduced pressure to give N-(tert-butoxycarbonyl)-N,O-dimethyl-L-serine (1.5 g, 56%) as a viscous, colourless oil; $^1$H NMR spectrum: (DMSO d$_6$, 100° C.) 1.40 (s, 9H), 2.77 (s, 3H), 3.26 (s, 3H), 3.67 (m, 2H), 4.51 (m, 1H).

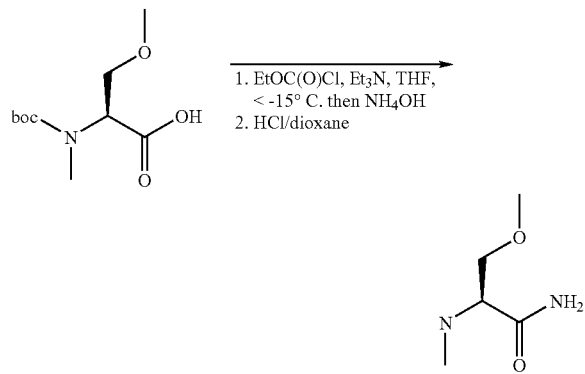

N-(tert-Butoxycarbonyl)-N,O-dimethyl-L-serine (1.5 g, 6.43 mmol) and triethylamine (0.99 ml, 7.07 mmol) in tetrahydrofuran (20 ml) were cooled to −15 to −17° C. Ethyl chloroformate (0.68 ml, 7.07 mmol) was added drop wise followed by concentrated ammonium hydroxide (12 ml). The mixture was stirred at 0 to 5° C. for 2 hours. Saturated ammonium chloride solution was added and the layers separated. The aqueous layer was re-extracted with ethyl acetate and the combined organics dried (MgSO$_4$) and concentrated under reduced pressure. The residues were dissolved in dioxane (10 ml) and 4M hydrogen chloride in dioxane (10 ml) was added and the mixture stirred for 1 hour. The mixture was evaporated and the residue dissolved in methanol, absorbed onto an SCX column, washed with methanol and eluted with 7N ammonia in methanol. Appropriate fractions were combined and evaporated to give N$^2$,O-dimethyl-L-serinamide (576 mg, 68%) as a white, crystalline solid; $^1$H NMR spectrum: (DMSO d$_6$) 1.92 (brs, 1H); 2.21 (s, 3H); 2.98 (t, 1H); 3.21 (s, 3H); 3.37 (m, 2H); 7.07 (brs, 1H); 7.30 (brs, 1H).

EXAMPLE 8

N$^2$-({4-[(3-Chloro-2-fluorophenyl)amino]-7-methoxyquinazolin-6-yl}methyl)-N$^2$,O-dimethyl-D-serinamide (Process (a))

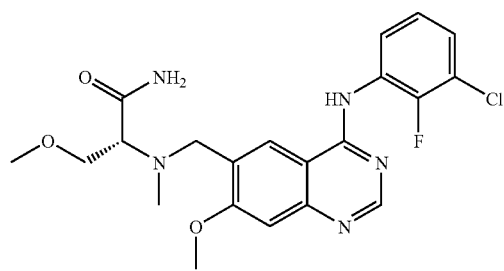

4-[(3-Chloro-2-fluorophenyl)amino]-7-methoxyquinazoline-6-carbaldehyde was coupled with N$^2$,O-dimethyl-D- serinamide using an analogous process to that described for the equivalent step in Example 1 to give the title product; $^1$H NMR spectrum: (DMSO d$_6$) 2.28 (s, 3H), 3.29 (s, 3H), 3.42 (t, 1H), 3.71 (dd, 1H), 3.79 (m, 3H), 3.96 (s, 3H), 7.21 (s, 1H), 7.23 (d, 1H), 7.29 (t, 1H), 7.52 (m, 3H), 8.37 (s, 1H), 8.43 (s, 1H), 9.83 (s, 1H); Mass Spectrum: (M−H)$^-$ 446.

The starting N$^2$,O-dimethyl-D-serinamide starting material was prepared as follows:

N-(tert-Butoxycarbonyl)-D-serine (5.0 g, 54.4 mmol) was dissolved in acetone (100 ml) and silver (I) oxide (19.8 g, 85.3 mmol) and methyl iodide (12.1 ml, 85.3 mmol) added. After 10 minutes a gel formed and more acetone was added until the mixture stirred. The mixture was stirred over night, filtered and concentrated under reduced pressure. The resulting product was purified by column chromatography on silica, eluting with methylene chloride to give methyl N-(tert-butoxycarbonyl)-O-methyl-D-serinate (2.07 g, 36%) as a colourless oil; $^1$H NMR spectrum: (DMSO d$_6$) 1.37 (s, 9H), 3.22 (s, 3H), 3.53 (m, 2H), 3.62 (s, 3H), 4.21 (m, 1H), 7.12 (d, 1H).

Methyl N-(tert-butoxycarbonyl)-O-methyl-D-serinate (2.0 g, 85.7 mmol) was dissolved in tetrahydrofuran (40 ml) and water (20 ml) and lithium hydroxide mono hydrate (1.8 g, 42.9 mmol) added. The mixture was stirred for 4 hours at room temperature, concentrated under reduced pressure to remove most of the tetrahydrofuran and then acidified by the addition of concentrated hydrochloric acid. The solution was extracted with ethyl acetate (three times). The combined organics were dried (MgSO$_4$), filtered and evaporated under reduced pressure to give N-(tert-butoxycarbonyl)-O-methyl-D-serine (1.9 g, 100%) as a colourless oil; $^1$H NMR spectrum: (DMSO d$_6$) 1.37 (s, 9H), 3.23 (s, 3H), 3.53 (m, 2H), 4.18 (m, 1H), 6.87 (d, 1H), 12.60 (brs, 1H).

N$^2$,O-dimethyl-D-serinamide was prepared by methylating N-(tert-butoxycarbonyl)-O-methyl-D-serine using an analogous method to that described in Example 7 for the methylation of N-(tert-butoxycarbonyl)-O-methyl-L-serine, to give N-(tert-butoxycarbonyl)-N,O-dimethyl-D-serine; $^1$H NMR spectrum: (DMSO d$_6$, 100° C.) 1.40 (s, 9H), 2.77 (s, 3H), 3.26 (s, 3H), 3.67 (m, 2H), 4.51 (m, 1H).

N-(tert-butoxycarbonyl)-N,O-dimethyl-D-serine was converted to the corresponding amide, followed by removal of the nitrogen protecting group using an analogous as process to that described in Example 7 for the preparation of N$^2$,O-dimethyl-L-serinamide, to give N$^2$,O-dimethyl-D-serinamide; $^1$H NMR spectrum: (DMSO d$_6$) 1.92 (brs, 1H), 2.21 (s, 3H), 2.98 (t, 1H), 3.21 (s, 3H), 3.37 (m, 2H), 7.07 (brs, 1H), 7.30 (brs, 1H).

EXAMPLE 9

N$^2$-({4-[(3-Chloro-2-fluorophenyl)amino]-7-methoxyquinazolin-6-yl}methyl)-N$^2$,O-dimethyl-L-homoserinamide

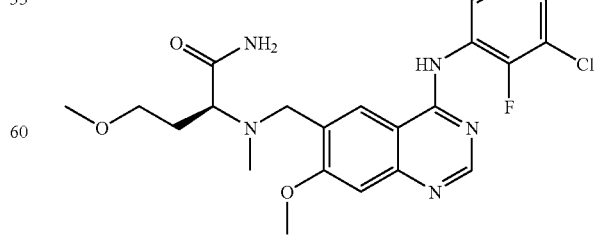

4-[(3-Chloro-2-fluorophenyl)amino]-7-methoxyquinazoline-6-carbaldehyde was coupled with N$^2$,O-dimethyl-L-homoserinamide analogously as for the equivalent step in Example 1 to give N²-({4-[(3-chloro-2-fluorophenyl)amino]-7-methoxyquinazolin-6-yl}methyl)-N²,O-dimethyl-L-homoserinamide; ¹H NMR spectrum: (DMSO d₆) 1.91 (m, 2H), 2.25 (s, 3H), 3.23 (s, 3H), 3.27 (t, 1H), 3.39 (m, 1H), 3.48 (m, 1H), 3.66 (d, 1H), 3.81 (d, 1H), 3.96 (s, 3H), 7.07 (brs, 1H), 7.20 (s, 1H), 7.29 (t, 1H), 7.38 (brs, 1H), 7.49 (t, 1H), 7.55 (t, 1H), 8.35 (s, 1H), 8.43 (s, 1H), 9.77 (s, 1H); Mass Spectrum: (M+H)⁺ 462.

The N²,O-dimethyl-L-homoserinamide used as starting material was prepared by methylating N-(tert-butoxycarbonyl)-O-methyl-L-homoserine using an analogous method to that described in Example 7 for the methylation of N-(tert-butoxycarbonyl)-O-methyl-L-serine, to give N-(tert-butoxycarbonyl)-N,O-dimethyl-L-homoserine; ¹H NMR spectrum: (DMSO d₆, 100° C.) 1.40 (s, 9H), 1.91 (m, 1H), 2.09 (m, 1H), 2.75 (s, 3H), 3.24 (s, 3H), 3.34 (m, 2H), 4.44 (m, 1H).

N-(tert-butoxycarbonyl)-N,O-dimethyl-L-homoserine was converted to the corresponding amide, followed by removal of the nitrogen protecting group using an analogous as process to that described in Example 7 for the preparation of N²,O-dimethyl-L-serinamide, to give N²,O-dimethyl-L-homoserinamide; ¹H NMR spectrum: (DMSO d₆) 1.58 (m, 1H), 1.69 (m, 1H), 1.80 (brs, 1H), 2.17 (s, 3H), 2.84 (dd, 1H), 3.20 (s, 3H), 3.34 (m, 2H), 6.93 (brs, 1H), 7.27 (brs, 1H).

EXAMPLE 10

3-[({4-[(3-chloro-2-fluorophenyl)amino]-7-methoxyquinazolin-6-yl}methyl)amino]piperidin-2-one (Process (a))

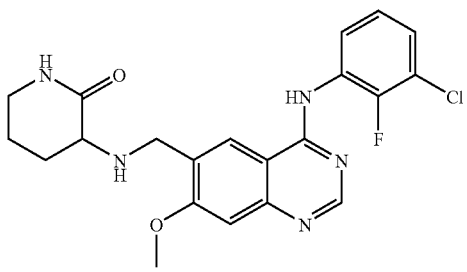

4-[(3-Chloro-2-fluorophenyl)amino]-7-methoxyquinazoline-6-carbaldehyde was coupled with 3-amino-piperidin-2-one (prepared by converting 3-amino-piperidin-2-one hydrochloride to the free-base form) using an analogous method to that described for the equivalent step in Example 1 to give the title compound; ¹H NMR spectrum: (DMSO d₆) 1.54 (m, 1H), 1.68 (m, 1H), 1.84 (m, 1H), 2.16 (m, 1H), 2.73 (brs, 1H), 3.05 (dd, 1H), 3.13 (m, 2H), 3.84 (d, 1H), 3.93 (d, 1H), 3.98 (s, 3H), 7.21 (s, 1H), 7.28 (t, 1H), 7.48 (t, 1H), 7.53 (m, 2H), 8.35 (s, 1H), 8.44 (s, 1H), 9.80 (s, 1H); Mass Spectrum: (M+H)⁺ 430.

EXAMPLE 11

3-[({4-[(3-chloro-2-fluorophenyl)amino]-7-methoxyquinazolin-6-yl}methyl)(methyl)amino]piperidin-2-one

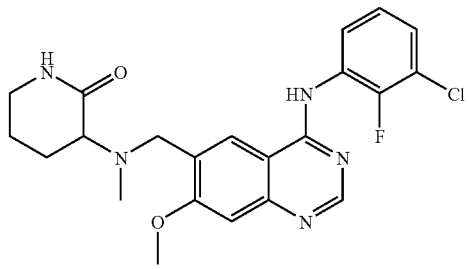

3-[({4-[(3-chloro-2-fluorophenyl)amino]-7-methoxyquinazolin-6-yl}methyl)amino]piperidin-2-one (160 mg, 0.37 mmol prepared as described in Example 10), para-formaldehyde (112 mg, 3.72 mmol) and magnesium sulfate (90 mg, 0.74 mmol) were stirred in methanol (15 ml) and sodium cyanoborohydride (94 mg, 1.49 mmol) added. The mixture was heated at 50° C. for 1.5 hours, cooled, filtered and concentrated under reduced pressure. The resulting material was purified by flash chromatography on silica, eluting with increasingly polar mixtures of methanol/methylene chloride (2/98 to 5/95) to give the title product (101 mg, 61%) as a white solid; ¹H NMR spectrum: (DMSO d₆) 1.77 (m, 3H), 2.02 (m, 1H), 2.40 (s, 3H), 3.09 (m, 2H), 3.29 (dd, 1H), 3.95 (s, 5H), 7.18 (s, 1H), 7.28 (t, 1H), 7.40 (brs, 1H), 7.48 (t, 1H), 7.55 (m, 1H), 8.35 (s, 1H), 8.42 (s, 1H), 9.76 (s, 1H); Mass Spectrum: (M+H)⁺ 444.

EXAMPLE 12

3-[({4-[(3-chloro-2-fluorophenyl)amino]-7-methoxyquinazolin-6-yl}methyl)amino]pyrrolidin-2-one (Process (a))

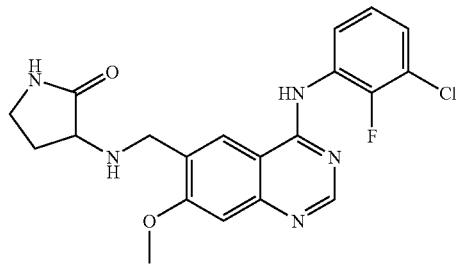

4-[(3-Chloro-2-fluorophenyl)amino]-7-methoxyquinazoline-6-carbaldehyde was coupled with 3-amino-pyrrolidin-2-one (Synthesis, 1978, 615) using an analogous method to that described for the equivalent step in Example 1 to give the title compound; ¹H NMR spectrum: (DMSO d₆) 1.79 (m, 1H); 2.36 (m, 2H); 3.14 (m, 1H); 3.22 (m, 2H); 3.90 (d, 1H); 3.95 (d, 1H); 3.98 (s, 3H); 7.21 (s, 1H); 7.28 (dt, 1H); 7.48 (dt, 1H); 7.55 (dt, 1H); 7.75 (s, 1H); 8.36 (s, 1H); 8.44 (s, 1H); 9.79 (s, 1H); Mass Spectrum: (M+H)⁺ 416.

EXAMPLE 13

3-[({4-[(3-chloro-2-fluorophenyl)amino]-7-methoxyquinazolin-6-yl}methyl)(methyl)amino]pyrrolidin-2-one (Process (a))

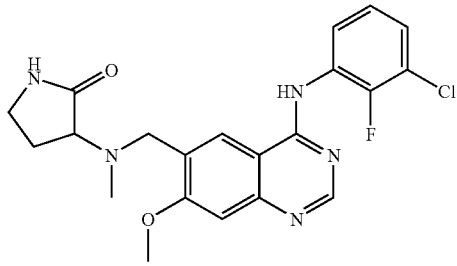

3-[({4-[(3-chloro-2-fluorophenyl)amino]-7-methoxyquinazolin-6-yl}methyl)amino]pyrrolidin-2-one (prepared as described in Example 12) was methylated by reaction with para-formaldehyde in the presence of sodium cyanoborohydride using an analogous process to that described in Example 10 to give the title compound; $^1$H NMR spectrum: (DMSO $d_6$) 2.06 (m, 1H), 2.21 (m, 1H), 2.33 (s, 3H), 3.18 (m, 2H), 3.49 (t, 1H), 3.82 (d, 1H), 3.94 (m, 4H), 7.20 (s, 1H), 7.28 (t, 1H), 7.48 (t, 1H), 7.54 (t, 1H), 7.69 (s, 1H), 8.36 (s, 1H), 8.43 (s, 1H), 9.84 (s, 1H). Mass Spectrum: (M+H)$^+$ 430.

EXAMPLE 14

$N^2$-({4-[(3-Chloro-4-fluorophenyl)amino]-7-methoxyquinazolin-6-yl}methyl)-$N^2$,O-dimethyl-L-serinamide (Process (a))

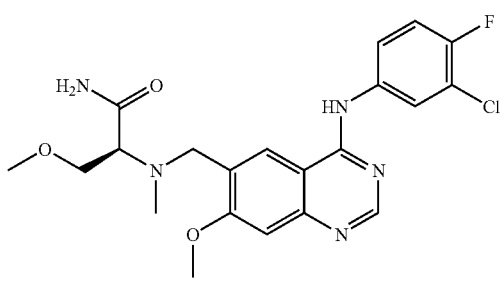

4-[(3-Chloro-4-fluorophenyl)amino]-7-methoxyquinazoline-6-carbaldehyde was coupled with $N^2$,O-dimethyl-L-serinamide (prepared as described in Example 7) using an analogous method to that described for the equivalent step in Example 1 to give the title compound; $^1$H NMR Spectrum: (DMSO $d_6$+CD$_3$COOD) 2.25 (s, 3H), 3.26 (s, 3H), 3.41 (t, 1H), 3.65-3.90 (m, 4H), 3.94 (s, 3H), 7.20 (s, 1H), 7.40 (m, 1H), 7.70-7.85 (m, 1H), 8.10 (dd, 1H), 8.37 (s, 1H), 8.53 (s, 1H); Mass Spectrum: (M+H)$^+$ 448.

The 4-[(3-chloro-4-fluorophenyl)amino]-7-methoxyquinazoline-6-carbaldehyde starting material was prepared as follows:

4-[(3-Chloro-4-fluorophenyl)amino]-7-methoxyquinazolin-6-ol (described in U.S. Pat. No. 5,770,599, Example 1) was reacted with triflic anhydride using an analogous method to that described in Example 1, preparation of starting materials to give 4-[(3-chloro-4-fluorophenyl)amino]-7-methoxyquinazolin-6-yl trifluoromethanesulfonate; $^1$H NMR Spectrum: (DMSO $d_6$) 4.14 (s, 3H), 7.51 (s, 1H), 7.57 (m, 1H), 7.68 (m, 1H), 8.00 (m, 1H), 8.82 (s, 1H), 8.93 (s, 1H), 11.13 (bs, 1H); Mass Spectrum: (M+H)$^+$ 452; (M−H)$^−$ 450.

4-[(3-chloro-4-fluorophenyl)amino]-7-methoxyquinazolin-6-yl trifluoromethanesulfonate was reduced under an atmosphere of carbon monoxide using an analogous method to that described in Example 1, preparation of starting materials, to give 4-[(3-chloro-4-fluorophenyl)]-7-methoxyquinazoline-6-carbaldehyde; $^1$H NMR Spectrum: (DMSO $d_6$) 4.03 (s, 3H), 7.30 (s, 1H), 7.43 (m, 1H), 7.73-7.90 (m, 1H), 8.08-8.22 (m, 1H), 8.59 (s, 1H), 8.95 (s, 1H), 10.21 (s, 1H), 10.42 (s, 1H); Mass Spectrum: (M+H)$^+$ 332; (M−H)$^−$ 330.

EXAMPLE 15

$N^2$-({4-[(3-Chloro-4-fluorophenyl)amino]-7-methoxyquinazolin-6-yl}methyl)-$N^2$-methyl-D-alaninamide (Process (a))

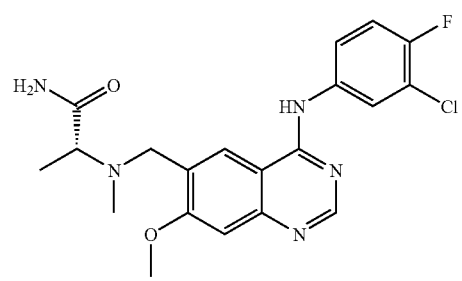

4-[(3-chloro-4-fluorophenyl)amino]-7-methoxyquinazoline-6-carbaldehyde was coupled with $N^2$-methyl-D-alaninamide using an analogous method to that described for the equivalent step in Example 1 to give the title compound; $^1$H NMR Spectrum: (DMSO $d_6$) 1.18 (d, 3H), 2.20 (s, 3H), 3.20-3.35 (m, 1H+H$_2$O), 3.68 (q, 2H); 3.93 (s, 3H), 7.10 (bs, 1H), 7.20 (s, 1H); 7.32-7.50 (m, 2H), 7.70-7.85 (m, 1H), 8.05-8.15 (m, 1H), 8.43 (s, 1H); 8.52 (s, 1H), 9.70 (s, 1H); Mass Spectrum: (M+H)$^+$ 418.

EXAMPLE 16

4-[({4-[(3-chloro-2-fluorophenyl)amino]-7-methoxyquinazolin-6-yl}methyl)(methyl)amino]piperidine-4-carboxamide (Process (c))

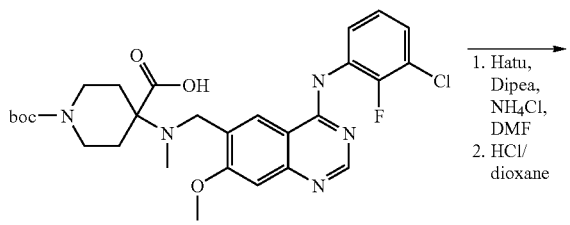

-continued

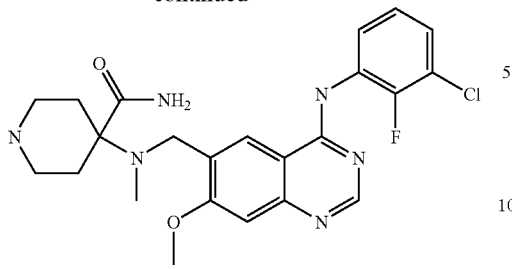

1-(tert-Butoxycarbonyl)-4-[({4-[(3-chloro-2-fluorophenyl)amino]-7-methoxyquinazolin-6-yl}methyl)(methyl)amino]piperidine-4-carboxylic acid (280 mg, 0.49 mmol) was dissolved in N,N-dimethylformamide (2 ml) and O-(7-azabenzotriazol-1-yl)-N,N,N',N'-tetramethyluronium hexafluorophosphate (278 mg, 0.73 mmol) and N,N-diisopropylethylamine (425 μl, 2.44 mmol) added. After a few minutes, ammonium chloride (39 mg, 0.73 mmol) was added and the mixture stirred for 1.5 hours at room temperature. The mixture was diluted with ethyl acetate, washed with brine (×2), dried over magnesium sulfate, filtered and concentrated under reduced pressure. The residues were purified by column chromatography on silica, eluting with 2% methanol in dichloromethane to give a white solid; Mass Spectrum: (M+H)+ 573.

This was stirred in 4M hydrogen chloride in dioxane (15 ml) for 2 hours, concentrated under reduced pressure, the residue dissolved in methanol, absorbed onto an Isolute SCX column, washed with methanol and eluted with ammonia in methanol. Appropriate fractions were combined and concentrated to give the title product (110 mg, 48%); $^1$H NMR Spectrum: (DMSO-d$_6$+D$_2$O) 1.77 (m, 2H); 1.98 (m, 2H); 2.15 (s, 3H); 2.64 (m, 2H); 2.95 (m, 2H); 3.60 (s, 2H); 3.92 (s, 3H); 7.16 (s, 1H); 7.29 (t, 1H); 7.49 (m, 2H); 8.32 (s, 1H); 8.38 (s, 1H). Mass Spectrum: (M+H)+ 473.

The 1-(tert-Butoxycarbonyl)-4-[({4-[(3-chloro-2-fluorophenyl)amino]-7-methoxyquinazolin-6-yl}methyl)(methyl)amino]piperidine-4-carboxylic acid used as starting material was prepared as follows:

4-(3-Chloro-2-fluoroanilino)-7-methoxyquinazoline-6-carbaldehyde was coupled with 4-amino-1-(tert-butoxycarbonyl)piperidine-4-carboxylic acid using an analogous method to that described for the equivalent step in Example 1 to give 1-(tert-butoxycarbonyl)-4-[({4-[(3-chloro-2-fluorophenyl)amino]-7-methoxyquinazolin-6-yl}methyl)amino]piperidine-4-carboxylic acid; $^1$H NMR Spectrum: (DMSO d$_6$) 1.39 (s, 9H); 1.70 (m, 2H); 1.86 (m, 2H); 3.43 (m, 4H); 3.76 (s, 2H); 3.96 (s, 3H); 7.19 (s, 1H); 7.28 (t, 1H); 7.48 (t, 1H); 7.55 (t, 1H); 8.37 (s, 1H); 8.43 (s, 1H); 9.78 (s, 1H); Mass Spectrum: (M+H)+ 560.

1-(tert-Butoxycarbonyl)-4-[({4-[(3-chloro-2-fluorophenyl)amino]-7-methoxyquinazolin-6-yl}methyl)amino]piperidine-4-carboxylic acid was reacted with paraformaldehyde using an analogous method to that described for the equivalent step in Example 11 to give 1-(tert-butoxycarbonyl)-4-[({4-[(3-chloro-2-fluorophenyl)amino]-7-methoxyquinazolin-6-yl}methyl)(methyl)amino]piperidine-4-carboxylic acid; $^1$H NMR Spectrum: (DMSO-d$_6$) 1.39 (s, 9H); 1.80 (m, 2H); 2.00 (m, 2H); 2.26 (s, 3H); 3.18 (m, 2H); 3.62 (m, 2H); 3.73 (s, 2H); 3.94 (s, 3H); 7.20 (s, 1H); 7.29 (t, 1H); 7.50 (t, 1H); 7.56 (t, 1H); 8.30 (s, 1H); 8.43 (s, 1H); 9.73 (s, 1H); 12.70 (brs, 1H). Mass Spectrum: (M+H)+ 574.

EXAMPLE 17

4-[({4-[(3-chloro-2-fluorophenyl)amino]-7-methoxyquinazolin-6-yl}methyl)(methyl)amino]-1-methylpiperidine-4-carboxamide (Process (d))

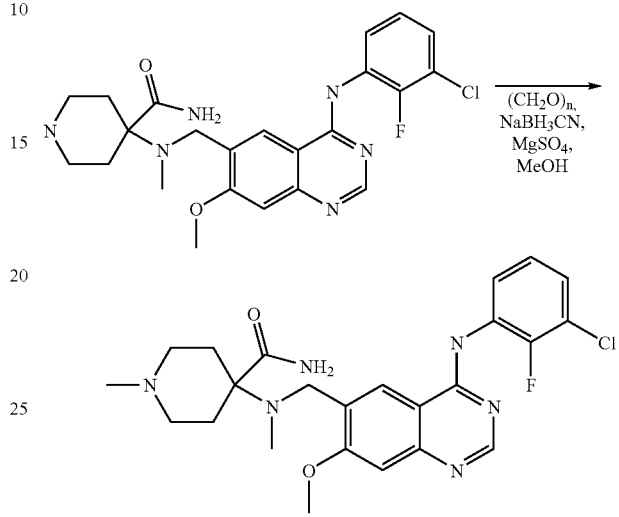

4-[({4-[(3-Chloro-2-fluorophenyl)amino]-7-methoxyquinazolin-6-yl}methyl)(methyl)amino]piperidine-4-carboxamide (Example 16) was reacted with paraformaldehyde using an analogous method to that described for the equivalent step in Example 11 to give 4-[({4-[(3-chloro-2-fluorophenyl)amino]-7-methoxyquinazolin-6-yl}methyl)(methyl)amino]-1-methylpiperidine-4-carboxamide; $^1$H NMR Spectrum: (DMSO d$_6$) 1.80 (m, 2H); 2.03-2.17 (m, 10H); 2.66 (m, 2H); 3.64 (s, 2H); 3.95 (s, 3H); 7.08 (s, 1H); 7.17 (m, 2H); 7.30 (t, 1H); 7.51 (m, 1H); 7.57 (m, 1H); 8.34 (s, 1H); 8.42 (s, 1H); 9.68 (s, 1H). Mass Spectrum: (M+H)+ 487.

EXAMPLE 18

4-[({4-[(3-chloro-2-fluorophenyl)amino]-7-methoxyquinazolin-6-yl}methyl)(methyl)amino]-1-glycoloylpiperidine-4-carboxamide (Process (c))

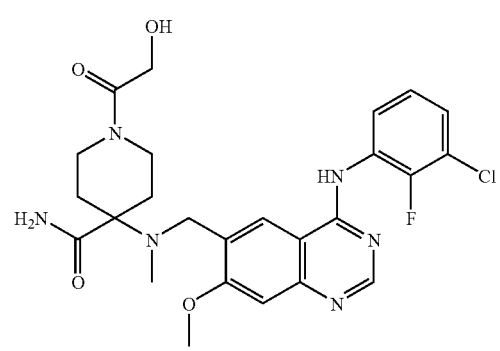

Triethylamine (360 μl, 2.58 mmol) was added to a stirred, cooled (0° C.) suspension of 4-[({4-[(3-chloro-2-fluorophenyl)amino]-7-methoxyquinazolin-6-yl}methyl)(methyl) amino]piperidine-4-carboxamide (300 mg, 0.63 mmol) (Example 16) in NMP (5 ml). Acetoxyacetyl chloride (100 μl 0.93 mmol) was then added drop wise and the reaction mixture left to warm to room temperature over a period of 2 hours. This was then partitioned between saturated aqueous sodium hydrogen carbonate solution and ethyl acetate. The organic phase was washed with saturated aqueous ammonium chloride solution followed by brine, dried over magnesium sulfate, filtered and evaporated to give 2-{4-(aminocarbonyl)-4-[({4-[(3-chloro-2-fluorophenyl)amino]-7-methoxyquinazolin-6-yl}methyl)(methyl)amino]piperidin-1-yl}-2-oxoethyl acetate as a dry film (250 mg). Mass spectrum: (M+H)+ 573.

This was dissolved in 7M ammonia in methanol (5 ml) and left to stand overnight. The resulting solution was evaporated to dryness and the residues were purified by column chromatography on silica, eluting with 7M ammonia in methanol/ methylene chloride (16/84). Fractions containing the desired product were combined and evaporated. The residues were triturated with diethyl ether to give the title product as a white solid (191 mg, 57%); ¹H NMR Spectrum: (DMSO-d₆) 1.70-1.90 (m, 2H), 1.96-2.06 (d, 2H), 2.18 (s, 3H), 3.05-3.24 (m, 1H), 3.15 (d, 1H), 3.54-3.68 (m, 3H), 3.92 (s, 3H), 3.97-4.10 (m, 3H), 4.40 (t, 1H), 7.18 (s, 1H), 7.22-7.29 (m, 3H), 7.43-7.57 (m, 2H), 8.32 (s, 1H), 8.39 (s, 1H), 9.67 (s, 1H); Mass Spectrum: (M+H)+ 531.

EXAMPLE 19

4-[({4-[(3-chloro-2-fluorophenyl)amino]-7-methoxyquinazolin-6-yl}methyl)(methyl)amino]-1-(2-hydroxyethyl)piperidine-4-carboxamide

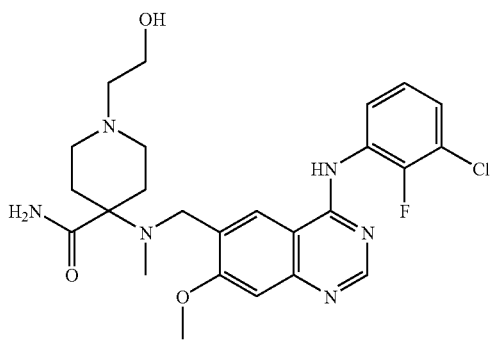

2-Bromoethanol (47 μl, 0.66 mmol) was added to a stirred suspension of 4-[({4-[(3-chloro-2-fluorophenyl)amino]-7-methoxyquinazolin-6-yl}methyl)(methyl)amino]piperidine-4-carboxamide (250 mg, 0.53 mmol) (Example 16) and anhydrous potassium carbonate (150 mg, 1.08 mmol) in tetrahydrothiophene 1,1-dioxide (Sulfolane) (5 ml). The mixture was heated at 90° C. for 3 hours and partitioned between saturated aqueous sodium hydrogen carbonate and ethyl acetate. The organic phase was washed with brine and evaporated. The residues were purified by column chromatography on silica, eluting with 7M ammonia in methanol/methylene chloride (16/84). Fractions containing the desired product were combined and evaporated to a foam. This was triturated with diethyl ether to give the title product as a white solid (43 mg, 16%); ¹H NMR Spectrum: (DMSO-d₆+CD₃COOD) 2.13-2.21 (m, 2H), 2.25 (s, 3H), 2.26-2.33 (m, 2H), 3.13-3.17 (t, 2H), 3.17-3.25 (m, 2H), 3.42-3.49 (m, 2H), 3.71-3.77 (m, 4H), 3.94 (s, 3H), 7.18-7.22 (m, 1H), 7.23 (s, 1H), 7.33-7.38 (m, 1H), 7.58-7.63 (m, 1H), 8.28 (s, 1H), 8.39 (s, 1H); Mass Spectrum: (M+H)+ 517.

EXAMPLE 20

4-[({4-[(3-chloro-2-fluorophenyl)amino]-7-methoxyquinazolin-6-yl}methyl)(methyl)amino]-N,1-dimethylpiperidine-4-carboxamide

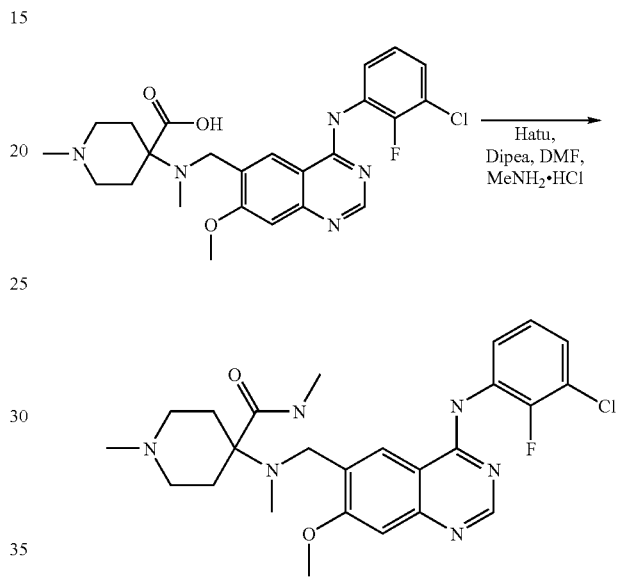

4-[({4-[(3-Chloro-2-fluorophenyl)amino]-7-methoxyquinazolin-6-yl}methyl)(methyl)amino]-1-methylpiperidine-4-carboxylic acid (50 mg, 0.1 mmol) was dissolved in N,N-dimethylformamide (2 ml) and O-(7-azabenzotriazol-1-yl)-N,N,N',N'-tetramethyluronium hexafluorophosphate (59 mg, 0.15 mmol) and N,N-diisopropylethylamine (89 μl, 0.51 mmol) were added. After a few minutes methylamine hydrochloride (10 mg, 0.15 mmol) was added and the mixture stirred for 1 hour at room temperature. The mixture was absorbed onto an Isolute SCX column, washed with methanol and eluted with ammonia in methanol. Appropriate fractions were combined and concentrated. The residue was purified by column chromatography on silica, eluting with 5% 7N ammonia in methanol/dichloromethane, to give the title product (40 mg, 77%) as a white solid; ¹H NMR Spectrum: (DMSO d₆) 1.82 (m, 2H); 2.02 (m, 2H); 2.13 (m, 8H); 2.65 (m, 5H); 3.60 (s, 2H); 3.94 (s, 3H); 7.18 (s, 1H); 7.30 (t, 1H); 7.50 (m, 1H); 7.58 (m, 2H); 8.32 (s, 1H); 8.73 (s, 1H); 9.68 (s, 1H). Mass Spectrum: (M+H)+ 501.

The 4-[({4-[(3-chloro-2-fluorophenyl)amino]-7-methoxyquinazolin-6-yl}methyl)(methyl)amino]-1-methylpiperidine-4-carboxylic acid used as starting material was prepared as follows:

1-(tert-butoxycarbonyl)-4-[({4-[(3-chloro-2-fluorophenyl)amino]-7-methoxyquinazolin-6-yl}methyl)(methyl) amino]piperidine-4-carboxylic acid (prepared as described in Example 16) was deprotected by treating the compound with hydrogen chloride in dioxane using an analogous method to that described for the equivalent step in Example 7 to give 4-[({4-[(3-chloro-2-fluorophenyl)amino]-7-methoxyquinazolin-6-yl}methyl)(methyl)amino]piperidine-4-carboxylic acid; $^1$H NMR Spectrum: (DMSO-d$_6$+CD$_3$COOD) 2.06 (m, 2H); 2.15 (m, 2H); 2.26 (s, 3H); 3.04 (m, 2H); 3.27 (m, 2H); 3.75 (s, 2H); 3.96 (s, 3H); 7.21 (s, 1H); 7.28 (m, 1H); 7.48 (m, 1H); 7.54 (m, 1H); 8.32 (s, 1H); 8.42 (S, 1H). Mass Spectrum: (M+H)$^+$ 474.

4-[({4-[(3-Chloro-2-fluorophenyl)amino]-7-methoxyquinazolin-6-yl}methyl)(methyl)amino]piperidine-4-carboxylic acid was reacted with para-formaldehyde using an analogous method to that described for the equivalent step in Example 11 to give 4-[({4-[(3-chloro-2-fluorophenyl)amino]-7-methoxyquinazolin-6-yl}methyl)(methyl)amino]-1-methylpiperidine-4-carboxylic acid; $^1$H NMR Spectrum: (DMSO-d$_6$+CD$_3$COOD) 2.04 (m, 2H); 2.17 (m, 2H); 2.27 (s, 3H); 2.45-2.55 (m, 3H+ DMSO; 2.68 (m, 2H); 3.06 (m, 2H); 3.72 (s, 2H); 3.95 (s, 3H); 7.20 (s, 1H); 7.28 (t, 1H); 7.48 (t, 1H); 7.57 (t, 1H); 8.32 (s, 1H); 8.42 (s, 1H); Mass Spectrum: (M+H)$^+$ 488.

EXAMPLE 21

4-[({4-[(3-chloro-2-fluorophenyl)amino]-7-methoxyquinazolin-6-yl}methyl)(methyl)amino]-N,N,1-trimethylpiperidine-4-carboxamide (Process (c))

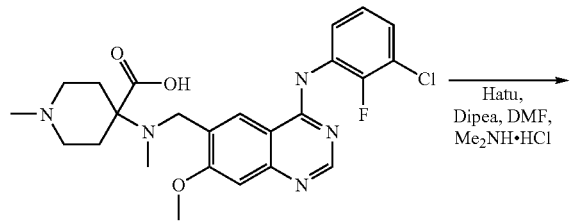

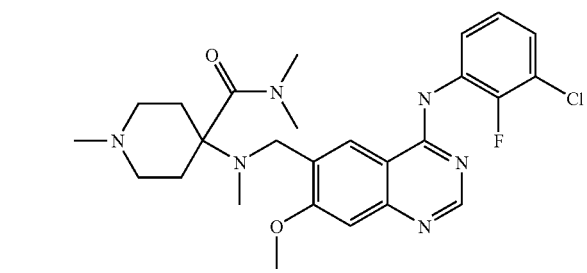

4-[({4-[(3-Chloro-2-fluorophenyl)amino]-7-methoxyquinazolin-6-yl}methyl)(methyl)amino]-1-methylpiperidine-4-carboxylic acid (Example 20) was coupled with dimethylamine hydrochloride using an analogous method to that described for the equivalent step in Example 20 to give the title product; $^1$H NMR Spectrum: (DMSO-d$_6$,100° C.) 1.93 (m, 2H); 2.17 (m, 10H); 2.72 (m, 2H); 3.09 (s, 6H); 3.72 (s, 2H); 3.97 (s, 3H); 7.19 (s, 1H); 7.25 (t, 1H); 7.39 (t, 1H); 7.60 (brs, 1H); 8.20 (s, 1H); 8.42 (brs, 1H); 9.40 (brs, 1H). Mass Spectrum: (M+H)$^+$ 514.

EXAMPLE 22

4-[({4-[(3-chloro-2-fluorophenyl)amino]-7-methoxyquinazolin-6-yl}methyl)(methyl)amino]-1-isopropylpiperidine-4-carboxamide (Process b))

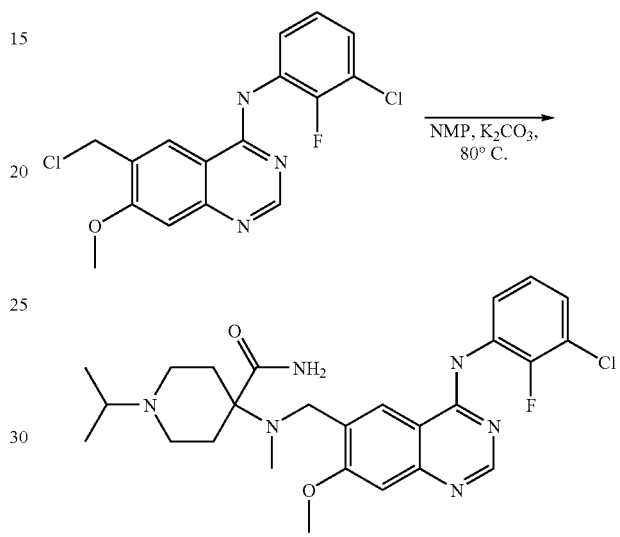

N-(3-Chloro-2-fluorophenyl)-6-(chloromethyl)-7-methoxyquinazolin-4-amine hydrochloride (Example 62 preparation of starting materials) (200 mg, 0.52 mmol), 1-isopropyl-4-(methylamino)piperidine-4-carboxamide (113 mg, 0.57 mmol) and potassium carbonate (157 mg, 1.13 mmol) in 1-methyl-2-pyrrolidinone (5 ml) were heated at 80° C. for 2 hours. The mixture was cooled, absorbed onto an Isolute SCX column, washed with methanol and eluted with 3.5M ammonia in methanol. Appropriate fractions were combined and evaporated. The residues were purified by column chromatography on silica, eluting with increasingly polar mixtures of methanol/dichloromethane (2/98-5/95) to give the title product (37 mg, 14%); $^1$H NMR Spectrum: (DMSO-d$_6$) 0.94 (d, 6H); 1.77 (m, 2H); 2.18 (m, 7H); 2.62 (m, 1H); 2.72 (m, 2H); 3.65 (s, 2H); 3.95 (s, 3H); 7.05 (s, 1H); 7.15 (s, 1H); 7.18 (s, 1H); 7.30 (t, 1H); 7.53 (m, 2H); 8.35 (s, 1H); 8.41 (s, 1H); 9.69 (s, 1H). Mass Spectrum: (M+H)$^+$ 515.

The 1-isopropyl-4-(methylamino)piperidine-4-carboxamide used as starting material was prepared as follows: 1-benzyl-4-(methylamino)piperidine-4-carboxamide (J Med Chem., 1998, 41(25), 5084) may be deprotected by hydrogenation using an analogous method to that described for the equivalent step in Example 74 to give 4-(methylamino)piperidine-4-carboxamide; $^1$H NMR Spectrum: 1.35 (m, 2H); 1.68 (m, 2H); 1.93 (brs, 1H); 2.06 (s, 3H), 2.59 (m, 2H); 2.71 (m, 2H); 6.81 (s, 1H); 7.14 (s, 1H).

4-(methylamino)piperidine-4-carboxamide (250 mg, 1.59 mmol), potassium carbonate (264 mg, 1.91 mmol) and 2-bromopropane (0.179 ml, 1.91 mmol) in acetonitrile (10 ml) were heated at reflux for 1.5 hours. The mixture was cooled, filtered and concentrated under reduced pressure. The residues were purified by column chromatography on silica eluting with ammonia in methanol/dichloromethane (90/10) to give 1-isopropyl-4-(methylamino)piperidine-4-carboxamide (153 mg, 48%) as a white solid. $^1$H NMR Spectrum: (DMSO-$d_6$) 0.92 (d, 6H); 1.45 (m, 2H); 1.77 (m, 2H); 1.86 (s, 1H); 2.06 (s, 3H); 2.38 (m, 4H); 2.59 (m, 1H); 6.82 (s, 1H); 7.15 (s, 1H).

EXAMPLE 23

4-[({4-[(3-chloro-2-fluorophenyl)amino]-7-methoxyquinazolin-6-yl}methyl)(methyl)amino]-1-(2-methoxyethyl)piperidine-4-carboxamide (Process (b))

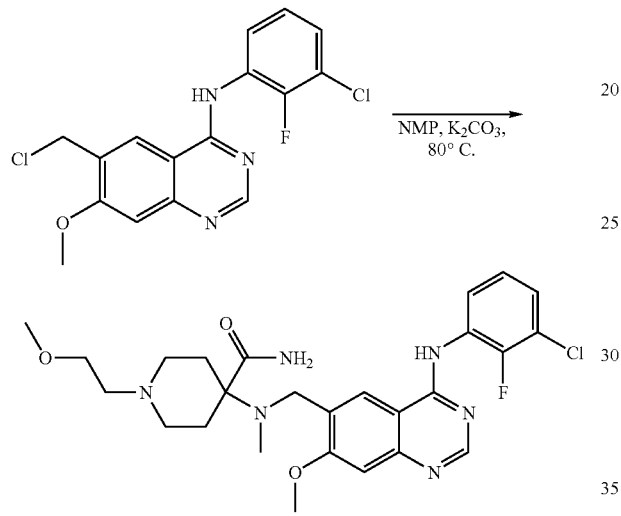

N-(3-Chloro-2-fluorophenyl)-6-(chloromethyl)-7-methoxyquinazolin-4-amine hydrochloride was coupled with 1-(2-methoxyethyl)-4-(methylamino)piperidine-4-carboxamide using an analogous method to that described for the equivalent step in Example 22 to give the title product; $^1$H NMR Spectrum: (DMSO-$d_6$+$CD_3COOD$) 1.93 (m, 2H); 2.13 (m, 2H); 2.19 (s, 3H); 2.44 (m, 2H); 2.69 (t, 2H); 2.97 (m, 2H); 3.24 (s, 3H); 3.49 (t, 2H); 3.65 (s, 2H); 3.95 (s, 3H); 7.19 (s, 1H); 7.29 (t, 1H); 7.50 (t, 1H); 7.57 (t, 1H); 8.34 (s, 1H); 8.42 (s, 1H). Mass Spectrum: (M+H)$^+$ 531.

The 1-(2-methoxyethyl)-4-(methylamino)piperidine-4-carboxamide used as starting material was prepared as follows:

4-Carbamoyl-4-methylaminopiperidine was coupled with 2-bromoethylmethyl ether using an analogous method to that described for the equivalent step in Example 22 to give 1-(2-methoxyethyl)-4-(methylamino)piperidine-4-carboxamide as a white crystalline solid; $^1$H NMR Spectrum: (DMSO-$d_6$) 1.44 (m, 2H); 1.78 (m, 2H); 1.89 (s, 1H); 2.05 (s, 3H); 2.28-2.44 (m, 6H); 3.21 (s, 3H); 3.38 (t, 2H); 6.84 (s, 1H); 7.16 (s, 1H).

EXAMPLE 24

4-[({4-[(3-chloro-2-fluorophenyl)amino]-7-methoxyquinazolin-6-yl}methyl)(ethyl)amino]-N-methyltetrahydro-2H-pyran-4-carboxamide (Process (c))

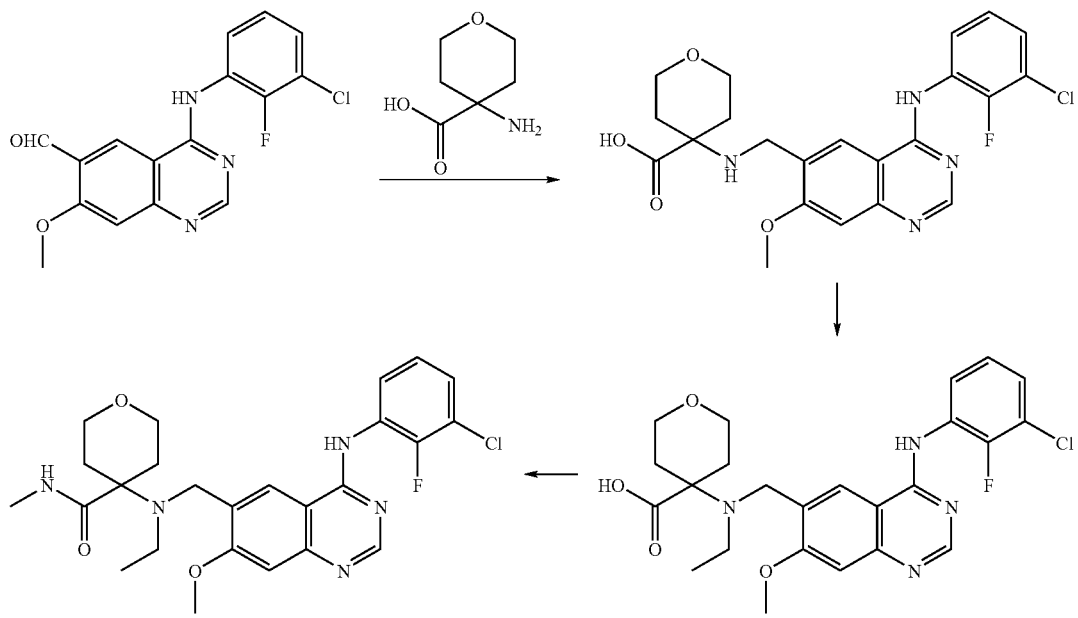

Example 24

4-[({4-[(3-chloro-2-fluorophenyl)amino]-7-methoxyquinazolin-6-yl}methyl)(ethyl)amino]tetrahydro-2H-pyran-4-carboxylic acid was coupled with methylamine using an analogous method to that described for the equivalent step in Example 20 to give the title product; $^1$H NMR Spectrum: (DMSO-d$_6$) δ0.82 (t, 3H); 1.70-1.88 (m, 2H), 1.95-2.15 (m, 2H), 2.50-2.80 (m, 5H), 3.20-3.45 (m, 2H), 3.70-3.85 (m, 4H), 3.95 (s, 3H), 7.16 (s, 1H), 7.30 (m, 1H), 7.50 (m, 1H), 7.62 (m, 1H), 7.69 (m, 1H), 8.41 (s, 2H), 9.61 (s, 1H); Mass Spectrum: (M+H)$^+$ 502.

The starting material 4-[({4-[(3-chloro-2-fluorophenyl)amino]-7-methoxyquinazolin-6-yl}methyl)(ethyl)amino]tetrahydro-2H-pyran-4-carboxylic acid was prepared as follows:

4-(3-Chloro-2-fluoroanilino)-7-methoxyquinazoline-6-carbaldehyde was coupled with 4-aminotetrahydro-2H-pyran-4-carboxylic acid using an analogous method to that described for the equivalent step in Example 1 to give 4-[({4-[(3-chloro-2-fluorophenyl)amino]-7-methoxyquinazolin-6-yl}methyl)amino]tetrahydro-2H-pyran-4-carboxylic acid; $^1$H NMR Spectrum: (DMSO-d$_6$) 1.62-1.74 (m, 2H), 1.92-2.03 (m, 2H), 3.46-3.56 (m, 2H), 3.76 (s, 2H), 3.76-3.85 (m, 2H), 3.94 (s, 3H), 7.18 (s, 1H), 7.23-7.31 (m, 1H), 7.43-7.57 (m, 2H), 8.38 (s, 1H), 8.42 (s, 1H), 9.81 (brs, 1H). Mass Spectrum: (M+H)$^+$ 461.

1M HCl in diethyl ether (1.4 ml) was added to a stirred suspension of 4-[({4-[(3-chloro-2-fluorophenyl)amino]-7-methoxyquinazolin-6-yl}methyl)amino]tetrahydro-2H-pyran-4-carboxylic acid (0.66 g, 1.43 mmol), acetaldehyde (1.6 ml, 28.6 mmol) and anhydrous magnesium sulfate (0.34 g, 2.83 mmol) in methanol (10 ml). Sodium cyanoborohydride (0.36 g, 5.71 mmol) was added and the resulting mixture heated at 40° C. for 4 hours. The reaction mixture was then filtered and evaporated. The residues were purified by column chromatography on silica, eluting with 7M ammonia in methanol/methylene chloride (16/84). Fractions containing the desired product were combined and evaporated. The resulting gum was triturated with diethyl ether to give 4-[({4-[(3-chloro-2-fluorophenyl)amino]-7-methoxyquinazolin-6-yl}methyl)(ethyl)amino]tetrahydro-2H-pyran-4-carboxylic acid as a white solid (440 mg, 63%); $^1$H NMR Spectrum: (DMSO-d$_6$) δ 0.79 (t, 3H), 1.71-1.84 (m, 2H), 2.07-2.11 (d, 2H), 2.67-2.76 (q, 2H), 3.23-3.33 (t, 2H), 3.80-3.88 (m, 2H), 3.89-3.95 (m, 5H), 7.16 (s, 1H), 7.22-7.29 (m, 1H), 7.43-7.49 (m, 1H), 7.52-7.57 (dd, 1H), 8.38 (s, 1H), 8.41 (s, 1H); Mass Spectrum: (M+H)$^+$ 489.

EXAMPLE 25

4-[({4-[(3-chloro-2-fluorophenyl)amino]-7-methoxyquinazolin-6-yl}methyl)(methyl)amino]-N-methyltetrahydro-2H-pyran-4-carboxamide (Process (c))

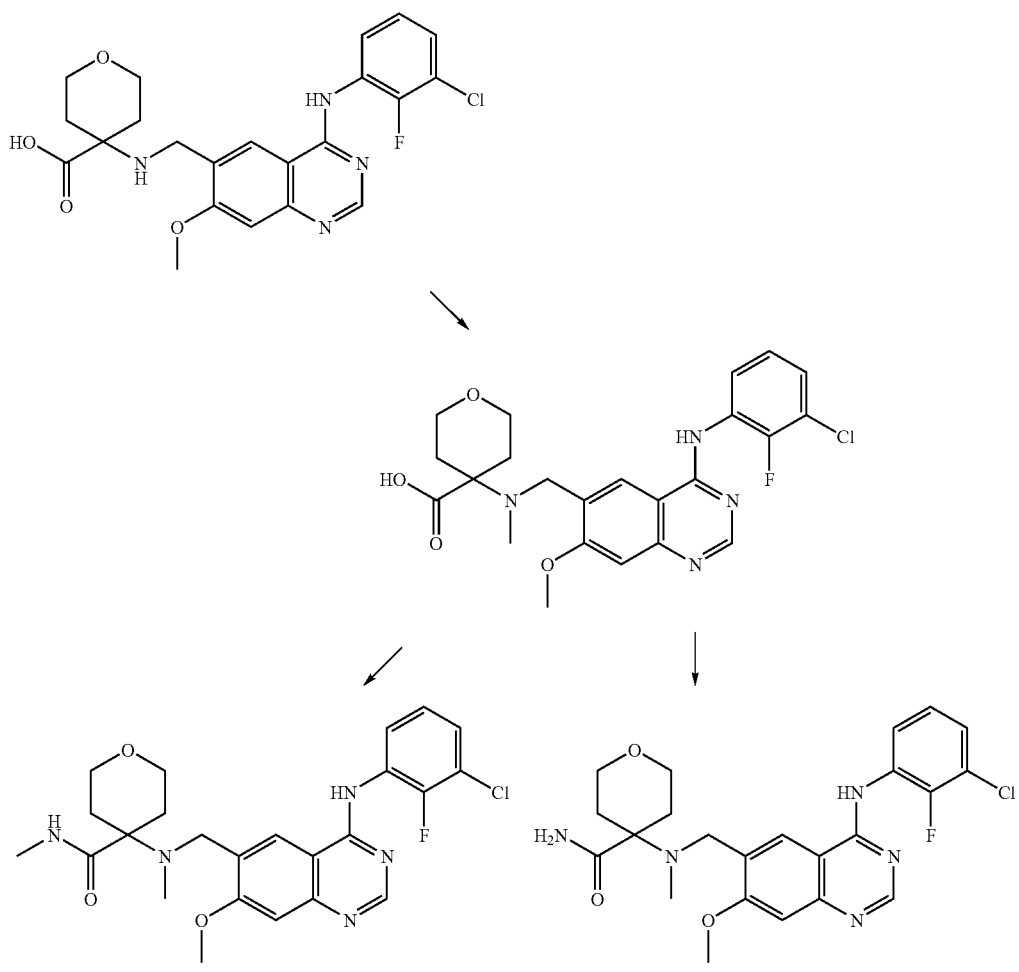

Example 25  Example 26

4-[({4-[(3-chloro-2-fluorophenyl)amino]-7-methoxyquinazolin-6-yl}methyl)(methyl)amino]tetrahydro-2H-pyran-4-carboxylic acid was coupled with methylamine hydrochloride using an analogous method to that described for the equivalent step in Example 20 to give the title product: $^1$H NMR Spectrum: (DMSO-$d_6$) δ1.73-1.90 (m, 2H), 2.00-2.20 (m, 2H), 2.12 (s, 3H), 2.67 (d, 3H), 3.23-3.47 (m, 2H+ $H_2O$), 3.58 (s, 2H), 3.73-3.90 (m, 2H), 3.95 (s, 3H), 7.18 (s, 1H), 7.29 (dd, 1H), 7.49 (dd, 1H), 7.55 (dd, 1H), 7.65 (m, 1H), 8.30 (s, 1H), 8.41 (s, 1H), 9.70 (s, 1H); Mass Spectrum: (M+H)$^+$ 488.

The starting material 4-[({4-[(3-chloro-2-fluorophenyl)amino]-7-methoxyquinazolin-6-yl}methyl)(methyl)amino]tetrahydro-2H-pyran-4-carboxylic acid was prepared as follows:

4-[({4-[(3-chloro-2-fluorophenyl)amino]-7-methoxyquinazolin-6-yl}methyl)amino]tetrahydro-2H-pyran-4-carboxylic acid was coupled with paraformaldehyde using an analogous method to that described for the equivalent step in Example 11 to give 4-[({4-[(3-chloro-2-fluorophenyl)amino]-7-methoxyquinazolin-6-yl}methyl)(methyl)amino]tetrahydro-2H-pyran-4-carboxylic acid; $^1$H NMR Spectrum: (DMSO-$d_6$) 1.70-1.89 (m, 2H), 2.05-2.19 (m, 2H), 2.20 (s, 3H), 3.10-3.60 (m, 2H+ $H_2O$), 3.70 (s, 2H), 3.88 (m, 2H), 3.93 (s, 3H), 7.18 (s, 1H), 7.28 (m, 1H), 7.40-7.60 (m, 2H), 8.30 (s, 1H), 8.41 (s, 1H), 9.76 (brs, 1H). Mass Spectrum: (M+H)$^+$ 475.

EXAMPLE 26

4-[({4-[(3-chloro-2-fluorophenyl)amino]-7-methoxyquinazolin-6-yl}methyl)(methyl)amino]tetrahydro-2H-pyran-4-carboxamide (Process (c))

4-[({4-[(3-chloro-2-fluorophenyl)amino]-7-methoxyquinazolin-6-yl}methyl)(methyl)amino]tetrahydro-2H-pyran-4-carboxylic acid (prepared as described in Example 25) was coupled with ammonium chloride using an analogous method to that described for the equivalent step in Example 16 to give the title product: $^1$H NMR Spectrum: (DMSO-$d_6$+ $CD_3COOD$) 1.70-1.90 (m, 2H+CDH$_2$COOH), 2.00-2.17 (m, 2H), 2.20 (s, 3H), 3.40 (t, 2H), 3.66 (s, 2H), 3.83 (m, 2H), 3.93 (s, 3H), 7.10-7.35 (m, 2H), 7.45-7.60 (m, 2H), 8.37 (s, 1H), 8.43 (s, 1H); Mass Spectrum: (M+H)$^+$ 474.

EXAMPLE 27

1-[({4-[(3-chloro-2-fluorophenyl)amino]-7-methoxyquinazolin-6-yl}methyl)(methyl)amino]cyclopropanecarboxamide (Process (c))

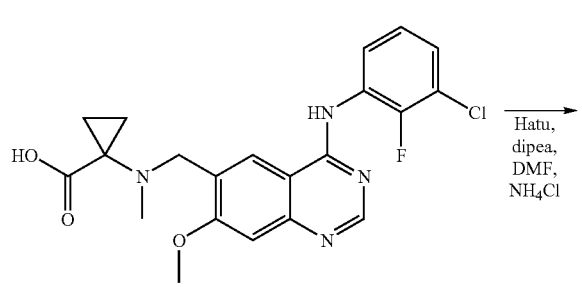

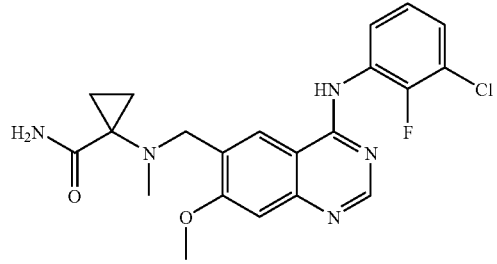

1-[({4-[(3-Chloro-2-fluorophenyl)amino]-7-methoxyquinazolin-6-yl}methyl)amino]cyclopropanecarboxylic acid was coupled with ammonium chloride using an analogous method to that described for the equivalent step in Example 16 to give the title product; $^1$H NMR Spectrum: (DMSO-$d_6$) 1.07 (s, 4H); 2.28 (s, 3H); 3.83 (s, 2H); 3.97 (s, 3H); 7.08 (s, 1H); 7.21 (s, 1H); 7.29 (m, 2H); 7.52 (m, 2H); 8.31 (s, 1H); 8.44 (s, 1H); 9.77 (s, 1H). Mass Spectrum: (M+H)$^+$ 430.

The 1-[({4-[(3-chloro-2-fluorophenyl)amino]-7-methoxyquinazolin-6-yl}methyl)(methyl)amino]cyclopropanecarboxylic acid used as starting material was prepared as follows:

4-(3-Chloro-2-fluoroanilino)-7-methoxyquinazoline-6-carbaldehyde was coupled with 1-aminocyclopropanecarboxylic acid using an analogous method to that described for the equivalent step in Example 1 to give 1-[({4-[(3-chloro-2-fluorophenyl)amino]-7-methoxyquinazolin-6-yl}methyl)amino]cyclopropanecarboxylic acid; $^1$H NMR Spectrum: (DMSO $d_6$) 0.90-1.00 (m, 2H); 1.10-1.20 (m, 2H); 3.93 (s, 2H); 3.96 (s, 3H); 7.14 (s, 1H); 7.28 (m, 1H); 7.40-7.55 (m, 2H); 8.29 (s, 1H); 8.40 (s, 1H); Mass Spectrum: (M+H)$^+$ 417.

1-[({4-[(3-Chloro-2-fluorophenyl)amino]-7-methoxyquinazolin-6-yl}methyl)amino]cyclopropanecarboxylic acid reacted with para-formaldehyde using an analogous method to that described for the equivalent step in Example 11 to give 1-[({4-[(3-chloro-2-fluorophenyl)amino]-7-methoxyquinazolin-6-yl}methyl)(methyl)amino]cyclopropanecarboxylic acid; $^1$H NMR Spectrum: (DMSO-$d_6$) 1.08 (m, 2H); 1.21 (m, 2H); 2.43 (s, 3H); 3.94 (s, 3H); 4.08 (s, 2H); 7.17 (s, 1H); 7.28 (t, 1H); 7.52 (m, 2H); 8.21 (s, 1H); 8.42 (s, 1H); 9.73 (s, 1H); Mass Spectrum: (M+H)$^+$ 431

EXAMPLE 28

1-[({4-[(3-chloro-2-fluorophenyl)amino]-7-methoxyquinazolin-6-yl}methyl) (methyl)amino]-N-methylcyclopropanecarboxamide (Process (c))

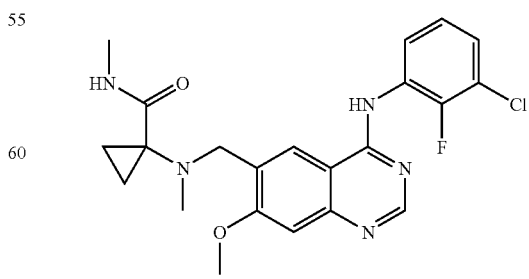

1-[({4-[(3-Chloro-2-fluorophenyl)amino]-7-methoxyquinazolin-6-yl}methyl)amino]cyclopropanecarboxylic acid (prepared as described in Example 27) was coupled with methylamine hydrochloride using an analogous method to that described for the equivalent step in Example 20 to give the title product; $^1$H NMR Spectrum: (DMSO-d$_6$) 0.90-1.15 (m, 4H); 2.25 (s, 3H); 2.63 (d, 3H); 3.75 (s, 2H), 3.98 (s, 3H); 7.20 (s, 1H); 7.29 (s, 1H); 7.40-7.60 (m, 2H); 7.80 (m, 1H); 8.30 (s, 1H); 8.42 (s, 1H); 9.70 (s, 1H); Mass Spectrum: (M+H)$^+$ 444.

EXAMPLE 29

N$^2$-({4-[(3-chloro-2-fluorophenyl)amino]-7-methoxyquinazolin-6-yl}methyl)-N$^1$,N$^2$-dimethyl-D-alaninamide (Process (c))

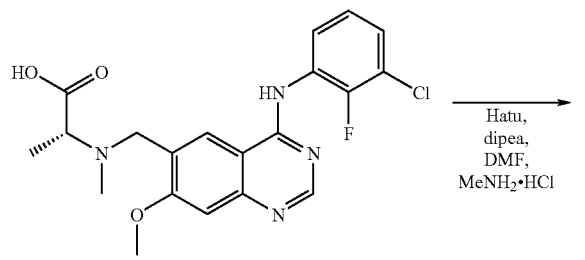

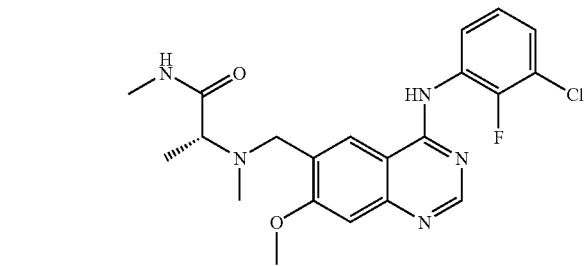

N-({4-[(3-Chloro-2-fluorophenyl)amino]-7-methoxyquinazolin-6-yl}methyl)-N-methyl-D-alanine was coupled with methylamine hydrochloride using an analogous method to that described for the equivalent step in Example 20 to give the title product; $^1$H NMR Spectrum: (DMSO-d$_6$) 1.61 (d, 3H); 2.22 (s, 3H); 2.66 (d, 3H); 3.31 (q, 1H); 3.64 (d, 1H); 3.73 (d, 1H); 3.97 (s, 3H); 7.22 (s, 1H); 7.30 (m, 1H); 7.50 (m, 1H); 7.57 (m, 1H); 7.82 (m, 1H); 8.41 (s, 1H); 8.44 (s, 1H); 9.76 (s, 1H); Mass Spectrum: (M+H)$^+$ 432.

The N-({4-[(3-chloro-2-fluorophenyl)amino]-7-methoxyquinazolin-6-yl}methyl)-N-methyl-D-alanine used as starting material was prepared as follows: 4-(3-Chloro-2-fluoroanilino)-7-methoxyquinazoline-6-carbaldehyde was coupled with N-methyl-D-alanine using an analogous method to that described for the equivalent step in Example 1 to give N-({4-[(3-chloro-2-fluorophenyl)amino]-7-methoxyquinazolin-6-yl}methyl)-N-methyl-D-alanine; $^1$H NMR Spectrum: (DMSO-d$_6$) 1.30 (d, 3H); 2.34 (s, 3H); 3.47 (q, 1H); 3.81 (d, 1H); 3.90 (d, 1H); 3.95 (s, 3H); 7.19 (s, 1H); 7.27 (t, 1H); 7.49 (m, 2H); 8.37 (s, 1H); 8.42 (s, 1H); 9.86 (brs, 1H); Mass Spectrum: (M+H)$^+$ 419.

EXAMPLE 30

N$^2$-({4-[(3-chloro-2-fluorophenyl)amino]-7-methoxyquinazolin-6-yl}methyl)-N$^1$,N$^1$,N$^2$-trimethyl-D-alaninamide (Process (c))

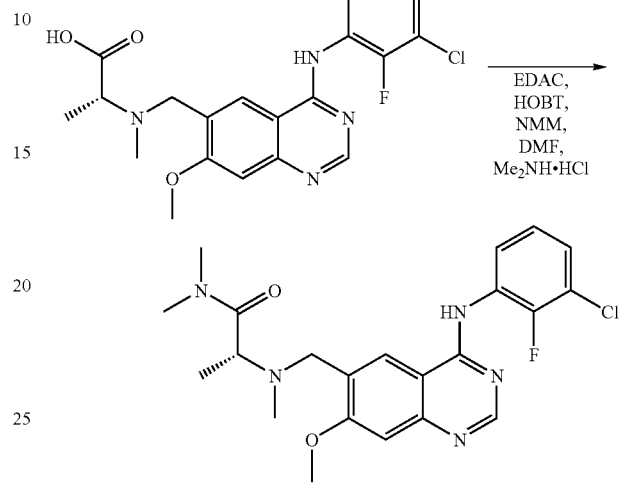

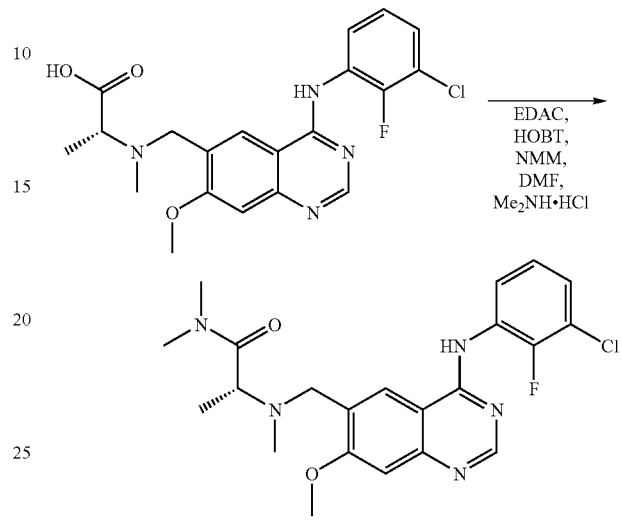

N-({4-[(3-Chloro-2-fluorophenyl)amino]-7-methoxyquinazolin-6-yl}methyl)-N-methyl-D-alanine (100 mg, 0.24 mmol prepared as described in Example 29), 1-[3-(dimethylaminopropyl]-3-ethylcarbodiimide hydrochloride (69 mg, 0.36 mmol) and 1-hydroxybenzotriazole (48 mg, 0.36 mmol) were suspended in N,N-dimethylformamide (2 ml). N-methylmorpholine (121 mg, 1.19 mmol) was added followed by dimethylamine hydrochloride (29 mg, 0.36 mmol). The reaction mixture was stirred over night and then concentrated under reduced pressure. The residue was dissolved in ethyl acetate and washed with saturated aqueous sodium bicarbonate solution, dried over magnesium sulfate and concentrated under reduced pressure. The residues were purified by column chromatography on silica eluting with methanol/dichloromethane (5/95) to give the title product (10 mg); $^1$H NMR Spectrum: (DMSO-d$_6$) 1.15 (d, 3H); 2.18 (s, 3H); 2.82 (s, 3H); 3.03 (s, 3H); 3.66 (d, 1H); 3.73 (d, 1H); 3.83 (q, 1H); 3.94 (s, 3H); 7.20 (s, 1H); 7.28 (m, 1H); 7.49 (m, 1H); 7.56 (m, 1H); 8.29 (s, 1H); 8.44 (s, 1H); 9.77 (s, 1H). Mass Spectrum: (M+Na)$^+$ 468.

EXAMPLES 31 to 39

(Process (c))

Compounds of the formula:

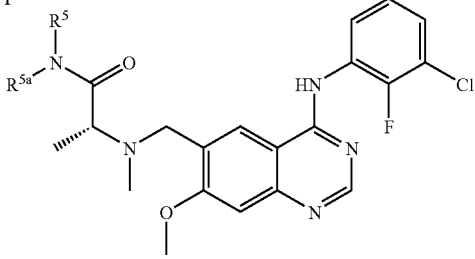

wherein the group NR$^5$R$^{5a}$ is as shown in Table 1 below, were prepared by coupling the hydrochloride salt of an amine of the formula NHR$^5$R$^{5a}$ using an analogous method to that described for the equivalent step in Example 20 to give the title compound.

TABLE 1

| Example | NR⁵R⁵ᵃ | Characterising Data |
|---|---|---|
| 31<br>N²-({4-[(3-chloro-2-fluorophenyl)amino]-7-methoxyquinazolin-6-yl}methyl)-N¹-ethyl-N²-methyl-D-alaninamide | ethylamino | ¹H NMR Spectrum: (DMSO-d₆ + D₂O) 0.99 (t, 3H); 1.21 (d, 3H); 2.25 (s, 3H); 3.09 (q, 2H); 3.24 (q, 1H); 3.65 (d, 1H); 3.75 (d, 1H); 3.97 (s, 3H); 7.21 (s, 1H); 7.29 (t, 1H); 7.51 (m, 2H); 7.92 (s, 1H); 8.45 (m, 2H); 9.83 (s, 1H); Mass Spectrum: (M−H)⁻ 444. |
| 32<br>N-(3-chloro-2-fluorophenyl)-7-methoxy-6-({methyl[(1R)-1-methyl-2-oxo-2-pyrrolidin-1-ylethyl]amino}methyl)quinazolin-4-amine | pyrrolidin-1-yl | ¹H NMR Spectrum: (DMSO-d₆) 1.15 (d, 3H); 1.75 (m, 4H); 2.23 (s, 3H); 3.23 (m, 3H); 3.69 (d, 4H); 3.94 (s, 3H); 7.20 (s, 1H); 7.28 (t, 1H); 7.51 (m, 2H); 8.29 (s, 1H); 8.44 (s, 1H); 9.78 (s, 1H); Mass Spectrum: (M+Na)⁺ 494. |
| 33<br>6-{[[(1R)-2-azetidin-1-yl-1-methyl-2-oxoethyl](methyl)amino]methyl}-N-(3-chloro-2-fluorophenyl)-7-methoxyquinazolin-4-amine | azetidin-1-yl | ¹H NMR Spectrum: (DMSO-d₆) 1.14 (d, 3H); 2.13 (m, 2H); 2.23 (s, 3H); 3.42 (q, 1H); 3.67 (d, 1H); 3.74 (d, 1H); 3.84 (m, 2H); 3.99 (m, 4H); 4.16 (m, 1H); 7.21 (s, 1H); 7.28 (m, 1H); 7.50 (m, 2H); 8.31 (s, 1H); 8.44 (s, 1H); 9.81 (s, 1H). Mass Spectrum: (M+Na)⁺ 480. |
| 34<br>N-(3-chloro-2-fluorophenyl)-7-methoxy-6-({methyl[(1R)-1-methyl-2-morpholin-4-yl-2-oxoethyl]amino}methyl)quinazolin-4-amine | morpholin-4-yl | ¹H NMR Spectrum: (CDCl₃) 1.27 (d, 3H); 2.26 (s, 3H); 3.53 (m, 7H); 3.69 (m, 4H): 3.91 (s, 3H); 7.09 (m, 3H); 7.49 (s, 1H); 7.74 (s, 1H); 8.52 (m, 1H); 8.68 (s, 1H). Mass Spectrum: (M+Na)⁺ 510. |
| 35<br>N²-({4-[(3-chloro-2-fluorophenyl)amino]-7-methoxyquinazolin-6-yl}methyl)-N²-methyl-N¹-prop-2-yn-1-yl-D-alaninamide | prop-2-yn-1-ylamino | ¹H NMR Spectrum: (DMSO-d₆) 1.22 (d, 3H); 2.23 (s, 3H); 3.03 (t, 1H); 3.36 (q, 1H); 3.65 (d, 1H); 3.76 (d, 1H); 3.92 (m, 2H); 3.98 (s, 3H); 7.22 (s, 1H); 7.29 (t, 1H); 7.52 (m, 2H); 8.24 (t, 1H); 8.42 (s, 1H); 8.44 (s, 1H); 9.76 (s, 1H). Mass Spectrum: (M+Na)⁺ 456. |

TABLE 1-continued

| Example | NR⁵R⁵ᵃ | Characterising Data |
|---|---|---|
| 36<br>N²-({4-[(3-chloro-2-fluorophenyl)amino]-7-methoxyquinazolin-6-yl}methyl)-N¹-(2-methoxyethyl)-N²-methyl-D-alaninamide | | ¹H NMR Spectrum: (CDCl₃) 1.29 (d, 3H); 2.21 (s, 3H); 3.10 (s, 3H); 3.29 (q, 1H); 3.42 (m, 4H); 3.59 (d, 1H); 3.70 (d, 1H); 3.93 (s, 3H); 7.11 (m, 3H); 7.71 (s, 1H); 7.78 (s, 1H); 7.89 (s, 1H); 8.26 (m, 1H); 8.65 (s, 1H). Mass Spectrum: (M+Na)⁺ 498. |
| 37<br>N²-({4-[(3-chloro-2-fluorophenyl)amino]-7-methoxyquinazolin-6-yl}methyl)-N¹-(2-methoxyethyl)-N¹,N²-dimethyl-D-alaninamide | | ¹H NMR Spectrum: (DMSO-d₆+ CD₃COOD, 120° C.) 1.20 (d, 3H); 2.28 (s, 3H); 2.96 (brs, 3H); 3.19 (s, 3H); 3.38 (m, 3H); 3.60 (brs, 1H); 3.75 (d, 1H); 3.80 (d, 1H); 3.85 (q, 1H); 3.97 (s, 3H); 7.21 (m, 2H); 7.36 (m, 1H); 7.61 (m, 1H); 8.24 (s,1H); 8.40 (s, 1H); Mass Spectrum: (M+Na)⁺ 512. |
| 38<br>N²-({4-[(3-chloro-2-fluorophenyl)amino]-7-methoxyquinazolin-6-yl}methyl)-N²-methyl-N¹-(tetrahydro-2H-pyran-4-yl)-D-alaninamide | | ¹H NMR Spectrum: (CDCl₃) 1.26 (d, 3H); 1.34 (m, 2H); 1.77 (m, 2H); 2.20 (s, 3H); 3.27 (q, 1H); 3.38 (m, 2H); 3.68 (d, 1H); 3.73 (d, 1H); 3.85 (m, 3H); 3.95 (s, 3H); 7.10 (m, 3H); 7.24 (s, 3H); 7.46 (m, 1H); 7.68 (s, 1H); 8.48 (m, 1H); 8.69 (s,1H); Mass Spectrum: (M+Na)⁺ 424. |

EXAMPLE 39

1-[({4-[(3-chloro-2-fluorophenyl)amino]-7-methoxyquinazolin-6-yl}methyl)(methyl)amino]cyclopent-3-ene-1-carboxamide (Process (c))

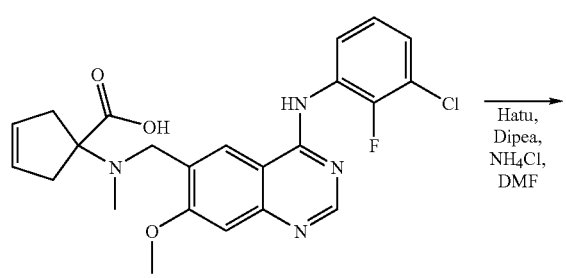

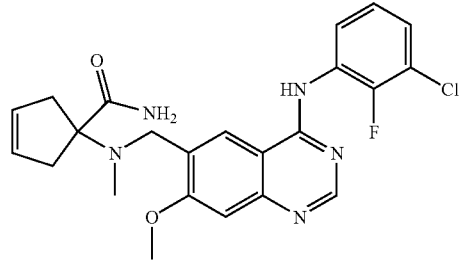

-continued

1-[({4-[(3-Chloro-2-fluorophenyl)amino]-7-methoxyquinazolin-6-yl}methyl)(methyl)amino]cyclopent-3-ene-1-carboxylic acid was coupled with ammonium chloride using an analogous method to that described for the equivalent step in Example 16 to give the title product; ¹H NMR Spectrum: (DMSO-d₆) 2.09 (s, 3H); 2.58 (d, 2H); 2.88 (d, 2H); 3.51 (s, 2H); 3.95 (s, 3H); 5.69 (s, 2H); 7.21 (s, 2H); 7.31 (t, 1H); 7.38 (s, 1H); 7.53 (m, 1H); 7.58 (t, 1H); 8.43 (s, 1H); 8.47 (s, 1H); 9.75 (s, 1H); Mass Spectrum: (M+H)⁺ 456.

The 1-[({4-[(3-chloro-2-fluorophenyl)amino]-7-methoxyquinazolin-6-yl}methyl)(methyl)amino]cyclopent-3-ene-1-carboxylic acid used as starting material was prepared as follows:

4-(3-Chloro-2-fluoroanilino)-7-methoxyquinazoline-6-carbaldehyde was coupled with 1-aminocyclopent-3-ene carboxylic acid using an analogous method to that described for the equivalent step in Example 1 to give 1-[({4-[(3-chloro-2-fluorophenyl)amino]-7-methoxyquinazolin-6-yl}methyl)amino]cyclopent-3-ene-1-carboxylic acid; $^1$H NMR Spectrum: (DMSO-$d_6$) 2.63 (d, 2H); 2.93 (d, 2H); 3.91 (s, 2H); 3.97 (s, 3H); 5.68 (s, 2H); 7.21 (s, 1H); 7.27 (t, 1H); 7.50 (m, 2H); 8.45 (s, 1H); 8.50 (s, 1H); 10.09 (s, 1H); Mass Spectrum: (M+H)$^+$ 443.

1-[({4-[(3-Chloro-2-fluorophenyl)amino]-7-methoxyquinazolin-6-yl}methyl)amino]cyclopent-3-ene-1-carboxylic acid was methylated by reaction with paraformaldehyde using an analogous method to that described for the equivalent step in Example 11 to give 1-[({4-[(3-chloro-2-fluorophenyl)amino]-7-methoxyquinazolin-6-yl}methyl)(methyl)amino]cyclopent-3-ene-1-carboxylic acid; $^1$H NMR Spectrum: (DMSO-$d_6$) 2.21 (s, 3H); 2.62 (d, 2H); 2.99 (d, 2H); 3.73 (s, 2H); 3.95 (s, 3H); 5.71 (s, 2H); 7.20 (s, 1H); 7.29 (t, 1H); 7.52 (m, 2H); 8.34 (s, 1H); 8.42 (s, 1H); 9.77 (s, 1H); Mass Spectrum: (M+H)$^+$ 457.

EXAMPLES 40 and 41

(Cis) (1s,3R,4S)-1-[({4-[(3-chloro-2-fluorophenyl)amino]-7-methoxyquinazolin-6-yl}methyl)(methyl)amino]-3,4-dihydroxycyclopentanecarboxamide; and (trans) (1r,3R,4S)-1-[({4-[(3-chloro-2-fluorophenyl)amino]-7-methoxyquinazolin-6-yl}methyl)(methyl)amino]-3,4-dihydroxycyclopentanecarboxamide 1-[({4-[(3-Chloro-2-fluorophenyl)amino]-7-methoxyquinazolin-6-yl}methyl)(methyl)amino]cyclopent-3-ene-1-carboxamide (100 mg, 0.22 mmol, Example 39) in acetone (3 ml) was added to osmium tetroxide (10 μl of a 2.5 weight % solution in water) and N-methylmorpholine (28 mg, 0.24 mmol) in water (3 ml) and stirred at room temperature over night. The mixture was concentrated under reduced pressure and the residue partitioned between ethyl acetate and brine. The organic layer was dried over magnesium sulfate, filtered and concentrated under reduced pressure. The residues were purified by column chromatography on silica eluting with 5% 3.5N ammonia in methanol/dichloromethane to give, in order of elution, Isomer 1 (cis) (1s,3R,4S)-1-[({4-[(3-chloro-2-fluorophenyl)amino]-7-methoxyquinazolin-6-yl}methyl)(methyl)amino]-3,4-dihydroxycyclopentanecarboxamide (48 mg, 45%) as a white solid; $^1$H NMR Spectrum: (DMSO-$d_6$) 1.98 (dd, 2H); 2.14 (m, 5H); 3.53 (s, 2H); 3.94 (m, 5H); 4.52 (d, 2H); 7.21 (s, 1H); 7.31 (m, 1H); 7.45 (s, 1H); 7.54 (m, 3H); 8.41 (s, 1H); 8.43 (s, 1H); 9.76 (s, 1H); Mass Spectrum: (M+H)$^+$ 490; and Isomer 2 (trans) (1r,3R,4S)-1-[({4-[(3-chloro-2-fluorophenyl)amino]-7-methoxyquinazolin-6-yl}methyl)(methyl)amino]-3,4-dihydroxycyclopentanecarboxamide (32 mg, 30%) as a white solid; $^1$H NMR Spectrum: (DMSO-$d_6$) 1.92 (dd, 2H); 2.13 (m, 5H); 3.62 (s, 2H); 3.87 (m, 2H); 3.96 (s, 3H); 4.45 (d, 2H); 7.05 (m, 1H); 7.20 (s, 1H); 7.31 (m, 2H); 7.26 (m, 2H); 8.42 (s, 1H); 8.44 (s, 1H); 9.75 (s, 1H); Mass Spectrum: (M+H)$^+$ 490.

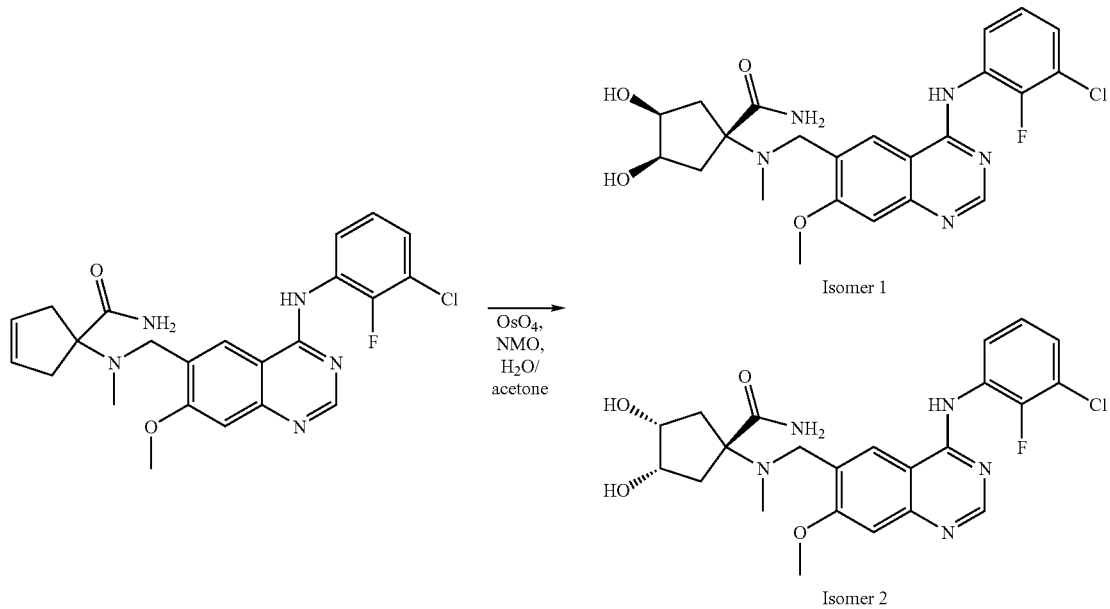

EXAMPLE 42

N³-({4-[(3-chloro-2-fluorophenyl)amino]-7-methoxyquinazolin-6-yl}methyl)-β-alaninamide (Process (a))

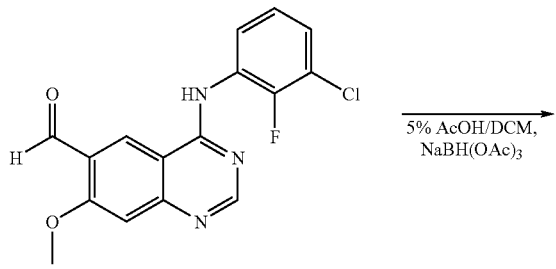

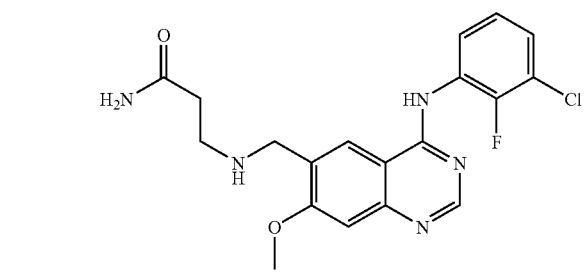

4-(3-Chloro-2-fluoroanilino)-7-methoxyquinazoline-6-carbaldehyde was coupled with β-alaninamide using an analogous method to that described for the equivalent step in Example 1 to give the title product; ¹H NMR Spectrum: (DMSO-$d_6$) 2.15 (brs, 1H); 2.28 (t, 2H); 2.78 (t, 2H); 3.82 (s, 2H); 3.96 (s, 3H); 6.83 (brs, 1H); 7.20 (s, 1H); 7.28 (t, 1H); 7.49 (m, 3H); 8.35 (s, 1H); 8.44 (s, 1H); 9.80 (s, 1H); Mass Spectrum: (M+H)⁺ 403.

EXAMPLE 43

N³-({4-[(3-chloro-2-fluorophenyl)amino]-7-methoxyquinazolin-6-yl}methyl)-N³-methyl-β-alaninamide (Process (a))

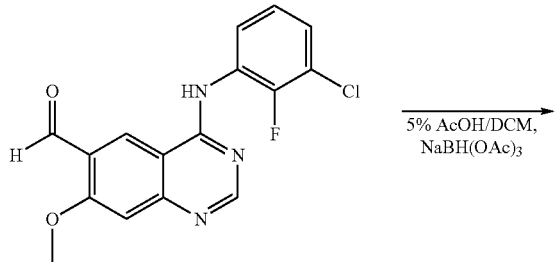

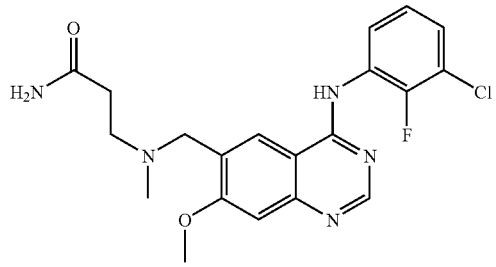

4-(3-Chloro-2-fluoroanilino)-7-methoxyquinazoline-6-carbaldehyde was coupled with N³-methyl-β-alaninamide using an analogous method to that described for the equivalent step in Example 1 to give the title product; ¹H NMR Spectrum: (DMSO-$d_6$) 2.27 (s, 3H); 2.33 (t, 2H); 2.65 (t, 2H); 3.60 (s, 2H); 3.94 (s, 3H); 6.88 (s, 1H); 7.18 (s, 1H); 7.25 (dt, 1H); 7.48 (m, 3H); 8.35 (s, 1H); 8.42 (s, 1H); 9.80 (s, 1H). Mass Spectrum: (M+H)⁺ 418.

The N³-methyl-β-alaninamide used as starting material was prepared as follows:

N-(tert-Butoxycarbonyl)-β-alanine was methylated using an analogous method to that described for the equivalent step in Example 7 to give N-(tert-butoxycarbonyl)-N-methyl-β-alanine ¹H NMR Spectrum: (DMSO-$d_6$) 1.37 (s, 9H); 2.30 (t, 2H); 2.75 (s, 3H); 3.32 (t, 2H).

N-(tert-Butoxycarbonyl)-N-methyl-β-alanine was converted to an amide and deprotected using an analogous method to that described for the equivalent step in Example 7 to give N³-methyl-β-alaninamide; ¹H NMR Spectrum: (DMSO-$d_6$) 2.16 (t, 2H); 2.24 (s, 3H); 2.61 (t, 2H); 6.68 (brs, 1H); 7.31 (brs, 1H).

EXAMPLE 44

N²-({4-[(3-chloro-2-fluorophenyl)amino]-7-methoxyquinazolin-6-yl}methyl)-N²-(2-cyanoethyl)glycinamide (Process (c))

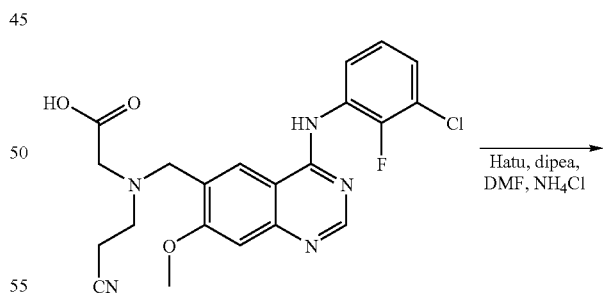

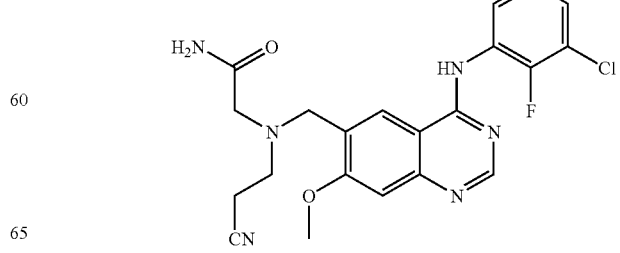

N-({4-[(3-Chloro-2-fluorophenyl)amino]-7-methoxyquinazolin-6-yl}methyl)-N-(2-cyanoethyl)glycine was coupled with ammonium chloride using an analogous method to that described for the equivalent step in Example 16 to give the title product; $^1$H NMR Spectrum: (DMSO-$d_6$) 2.84 (t, 2H); 2.95 (t, 2H); 3.27 (s, 2H); 3.93 (s, 2H); 4.07 (s, 3H); 7.32 (s, 2H); 7.39 (m, 2H); 7.59 (t, 1H); 7.66 (t, 1H); 8.47 (s, 1H); 8.55 (s, 1H); 9.80 (s, 1H); Mass Spectrum: (M+H)$^+$ 443.

The N-({4-[(3-chloro-2-fluorophenyl)amino]-7-methoxyquinazolin-6-yl}methyl)-N-(2-cyanoethyl)glycine used as starting material was prepared as follows:

4-(3-Chloro-2-fluoroanilino)-7-methoxyquinazoline-6-carbaldehyde was coupled with N-(2-cyanoethyl)glycine using an analogous method to that described for the equivalent step in Example 1 to give N-({4-[(3-chloro-2-fluorophenyl)amino]-7-methoxyquinazolin-6-yl}methyl)-N-(2-cyanoethyl)glycine; $^1$H NMR Spectrum: (DMSO-$d_6$) 2.70 (t, 2H); 3.04 (t, 2H); 3.40 (s, 2H); 3.95 (m, 5H); 7.20 (s, 1H); 7.27 (t, 1H); 7.48 (t, 1H); 7.55 (t, 1H); 8.36 (s, 1H); 8.44 (s, 1H); 9.69 (brs, 1H); Mass Spectrum: (M+H)$^+$ 444.

EXAMPLE 45

$N^2$-butyl-$N^2$-({4-[(3-chloro-2-fluorophenyl)amino]-7-methoxyquinazolin-6-yl}methyl)glycinamide (Process (c))

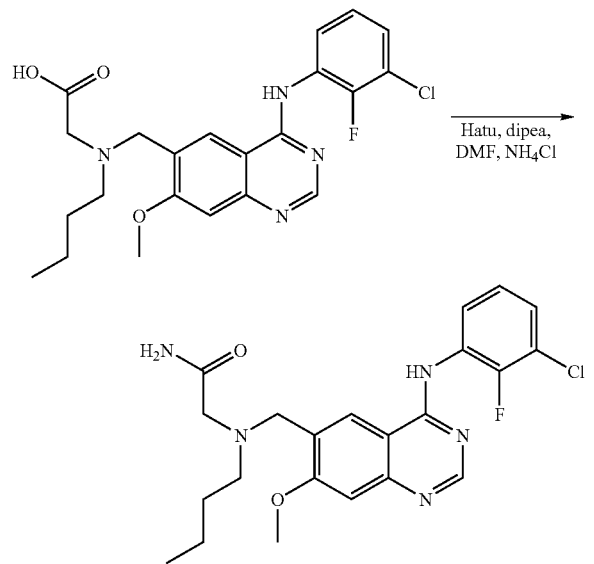

N-Butyl-N-({4-[(3-chloro-2-fluorophenyl)amino]-7-methoxyquinazolin-6-yl}methyl)glycine glycine was coupled with ammonium chloride using an analogous method to that described for the equivalent step in Example 16 to give the title product; $^1$H NMR Spectrum: (DMSO-$d_6$) 0.82 (t, 3H); 1.27 (m, 2H); 1.47 (m, 2H); 2.48 (m, 2H); 3.02 (s, 2H); 3.74 (s, 2H); 3.96 (s, 3H); 7.20 (s, 1H); 7.22 (s, 1H); 7.30 (m, 2H); 7.50 (t, 1H); 7.58 (t, 1H); 8.41 (s, 1H); 8.45 (s, 1H); 9.74 (s, 1H); Mass Spectrum: (M+H)$^+$ 446.

The N-butyl-N-({4-[(3-chloro-2-fluorophenyl)amino]-7-methoxyquinazolin-6-yl}methyl)glycine used as starting material was prepared as follows:

4-(3-Chloro-2-fluoroanilino)-7-methoxyquinazoline-6-carbaldehyde was coupled with N-butylglycine using an analogous method to that described for the equivalent step in Example 1 to give N-butyl-N-({4-[(3-chloro-2-fluorophenyl)amino]-7-methoxyquinazolin-6-yl}methyl)glycine; $^1$H NMR Spectrum: (DMSO-$d_6$) 0.83 (t, 3H); 1.27 (m, 2H); 1.46 (m, 2H); 2.70 (t, 2H); 3.33 (s, 2H); 3.95 (s, 5H); 7.20 (s, 1H); 7.28 (t, 1H); 7.47 (m, 1H); 7.55 (m, 1H); 8.36 (s, 1H); 8.43 (s, 1H); 9.82 (s, 1H); Mass Spectrum: (M+H)$^+$ 447.

EXAMPLE 46

$N^2$-({4-[(3-chloro-2-fluorophenyl)amino]-7-methoxyquinazolin-6-yl}methyl)-$N^2$-(2-morpholin-4-ylethyl)-L-alaninamide (Process (c))

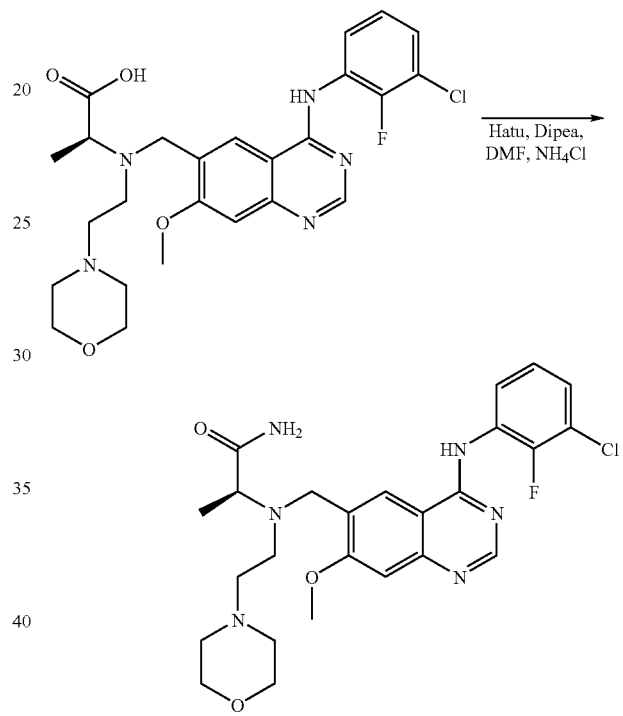

N-({4-[(3-Chloro-2-fluorophenyl)amino]-7-methoxyquinazolin-6-yl}methyl)-N-(2-morpholin-4-ylethyl)-L-alanine was coupled with ammonium chloride using a procedure analogous to the equivalent step in Example 16 to give the title product; $^1$H NMR Spectrum: (DMSO-$d_6$) 1.18 (d, 3H); 2.28 (m, 4H); 2.38 (m, 1H); 2.50 (m, 1H); 2.60 (m, 2H); 3.42 (q, 1H); 3.48 (m, 4H); 3.76 (s, 2H); 3.96 (s, 3H); 7.08 (s, 1H); 7.21 (s, 1H); 7.30 (t, 1H); 7.51 (t, 1H); 7.58 (t, 1H); 7.65 (s, 1H); 8.38 (s, 1H); 8.44 (s, 1H); 9.71 (s, 1H); Mass Spectrum: (M+H)$^+$ 517.

The N-({4-[(3-chloro-2-fluorophenyl)amino]-7-methoxyquinazolin-6-yl}methyl)-N-(2-morpholin-4-ylethyl)-L-alanine used as starting material was prepared as follows:

4-(3-Chloro-2-fluoroanilino)-7-methoxyquinazoline-6-carbaldehyde was coupled with (2-morpholin-4-ylethyl)amine using an analogous method to that described for the equivalent step in Example 1 to give N-(3-chloro-2-fluorophenyl)-7-methoxy-6-{[(2-morpholin-4-ylethyl)amino]methyl}quinazolin-4-amine; $^1$H NMR Spectrum: (DMSO-$d_6$) 2.14 (brs, 1H); 2.31 (m, 4H); 2.42 (t, 2H); 2.66 (t, 2H); 3.55 (m, 4H); 3.85 (s, 2H); 3.97 (s, 3H); 7.21 (s, 1H); 7.28 (t, 1H); 7.48 (t, 1H); 7.54 (t, 1H); 8.32 (s, 1H); 8.44 (s, 1H); 9.77 (s, 1H); Mass Spectrum: (M+H)$^+$ 446.

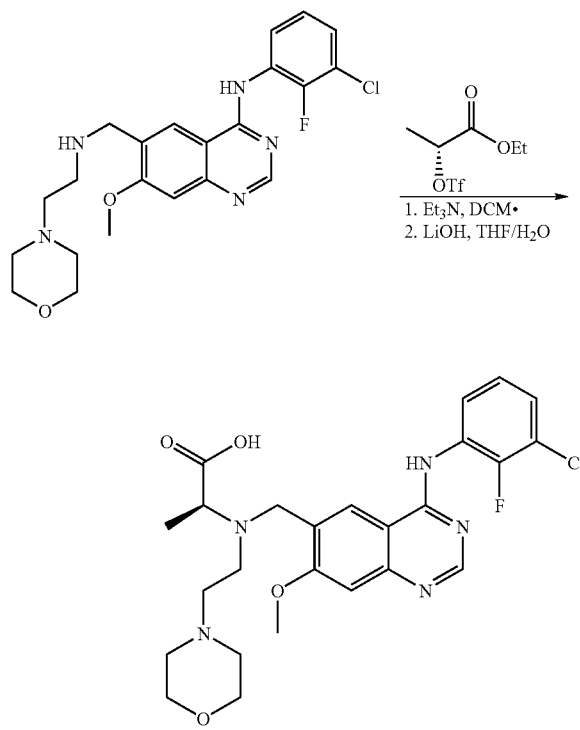

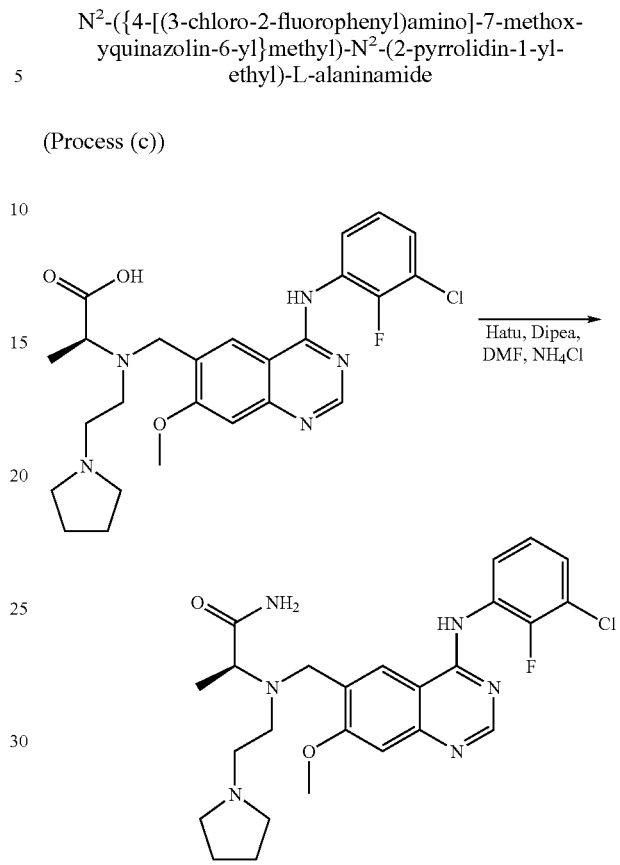

EXAMPLE 47

N²-({4-[(3-chloro-2-fluorophenyl)amino]-7-methoxyquinazolin-6-yl}methyl)-N²-(2-pyrrolidin-1-yl-ethyl)-L-alaninamide (Process (c))

N-(3-Chloro-2-fluorophenyl)-7-methoxy-6-{[(2-morpholin-4-ylethyl)amino]methyl}quinazolin-4-amine (200 mg, 0.45 mmol) was dissolved in dichloromethane (10 ml) and triethylamine (0.075 ml, 0.54 mmol) added. Ethyl O-trifluoromethanesulfonyl-D-lactate (135 mg, 0.54 mmol) (Journal of the American Chemical Society, 125(14), 4166-4173; 2003) in dichloromethane (1 ml) was added drop-wise and the mixture stirred at room temperature for 2 hours. The reaction mixture was washed with saturated, aqueous sodium hydrogen carbonate solution, dried over magnesium sulfate, filtered and concentrated under reduced pressure. The residues were purified by column chromatography on silica eluting with 2.5% methanol/dichloromethane to give a yellow oil (230 mg). This was dissolved in a mixture of tetrahydrofuran (5 ml), water (2.5 ml) and methanol (a few drops) and lithium hydroxide monohydrate (75 mg, 1.79 mmol) added. The mixture was stirred at room temperature over night, neutralised with 2N aqueous hydrochloric acid, concentrated, dissolved in methanol and absorbed onto an Isolute SCX column. After washing with methanol, the product was eluted with 7N ammonia in methanol. Fractions containing the desired material were combined and evaporated. The residues were purified by column chromatography on silica eluting with increasingly polar mixtures of 7N ammonia in methanol/dichloromethane (12/88-15/85) to give N-({4-[(3-chloro-2-fluorophenyl)amino]-7-methoxyquinazolin-6-yl}methyl)-N-(2-morpholin-4-ylethyl)-L-alanine (154 mg, 66%) as a white foam. $^1$H NMR Spectrum: (DMSO-$d_6$) 1.28 (d, 3H); 2.31 (m, 5H); 2.46 (m, 1H); 2.79 (m, 2H); 3.49 (m, 4H); 3.57 (q, 1H); 3.86 (d, 1H); 3.91 (d, 1H); 3.95 (s, 3H); 7.19 (s, 1H); 7.28 (t, 1H); 7.48 (m, 1H); 7.55 (m, 1H); 8.37 (s, 1H); 8.43 (s, 1H); 9.74 (brs, 1H). Mass Spectrum: (M+H)⁺ 518.

N-({4-[(3-Chloro-2-fluorophenyl)amino]-7-methoxyquinazolin-6-yl}methyl)-N-(2-pyrrolidin-1-ylethyl)-L-alanine was coupled with ammonium chloride using a procedure analogous to the equivalent step in Example 16 to give the title product; $^1$H NMR Spectrum: (DMSO-$d_6$) 1.18 (d, 3H); 1.60 (m, 4H); 2.35 (m, 4H); 2.60 (m, 4H); 3.40 (q, 1H); 3.75 (s, 2H); 3.96 (s, 3H); 7.05 (s, 1H); 7.21 (s, 1H); 7.30 (t, 1H); 7.50 (t, 1H); 7.58 (t, 1H); 7.63 (s, 1H); 8.40 (s, 1H); 8.44 (s, 1H); 9.70 (s, 1H). Mass Spectrum: (M+H)⁺ 501.

The N-({4-[(3-chloro-2-fluorophenyl)amino]-7-methoxyquinazolin-6-yl}methyl)-N-(2-pyrrolidin-1-ylethyl)-L-alanine used as starting material was prepared as follows:

4-(3-Chloro-2-fluoroanilino)-7-methoxyquinazoline-6-carbaldehyde was coupled with (2-pyrrolidin-1-ylethyl)amine using an analogous method to that described for the equivalent step in Example 1 to give N-(3-chloro-2-fluorophenyl)-7-methoxy-6-{[(2-pyrrolidin-1-ylethyl)amino]methyl}quinazolin-4-amine; $^1$H NMR Spectrum: (DMSO-$d_6$) 1.66 (m, 4H); 2.40 (m, 4H); 2.55 (t, 2H); 2.67 (t, 2H); 3.85 (s, 2H); 3.96 (s, 3H); 7.21 (s, 1H); 7.28 (t, 1H); 7.51 (m, 2H); 8.32 (s, 1H); 8.44 (s, 1H); 9.78 (s, 1H); Mass Spectrum: (M+H)⁺ 430.

N-(3-Chloro-2-fluorophenyl)-7-methoxy-6-{[(2-pyrrolidin-1-ylethyl)amino]methyl}quinazolin-4-amine was coupled with ethyl O-trifluoromethanesulfonyl-D-lactate and hydrolysed using analogous methods to those described for the equivalent steps in Example 46 to give N-({4-[(3-chloro-2-fluorophenyl)amino]-7-methoxyquinazolin-6-yl}methyl)-N-(2-pyrrolidin-1-ylethyl)-L-alanine; $^1$H NMR Spectrum: (DMSO-$d_6$) 1.27 (d, 3H); 1.83 (m, 4H); 2.86 (m, 8H); 3.44 (q, 1H); 3.84 (d, 1H); 3.94 (d, 1H); 4.01 (s, 3H); 7.25 (s, 1H); 7.33

(t, 1H); 7.53 (m, 1H); 7.63 (m, 1H); 8.42 (s, 1H); 8.48 (s, 1H); 9.78 (brs, 1H; Mass Spectrum: (M+H)+ 502.

EXAMPLE 48

N²-({4-[(3-chloro-2-fluorophenyl)amino]-7-methoxyquinazolin-6-yl}methyl)-N²-(2-pyrrolidin-1-yl-ethyl)-D-alaninamide (Process (c))

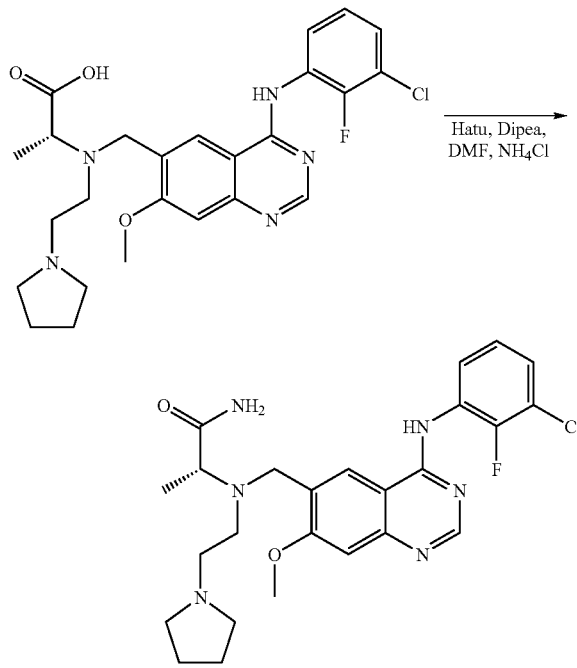

N-({4-[(3-Chloro-2-fluorophenyl)amino]-7-methoxyquinazolin-6-yl}methyl)-N-(2-pyrrolidin-1-ylethyl)-D-alanine was coupled with ammonium chloride using a procedure analogous to the equivalent step in Example 16 to give the title product; ¹H NMR Spectrum: (DMSO-d₆) 1.18 (d, 3H); 1.60 (m, 4H); 2.35 (m, 4H); 2.60 (m, 4H); 3.40 (q, 1H); 3.75 (s, 2H); 3.96 (s, 3H); 7.05 (s, 1H); 7.21 (s, 1H); 7.30 (t, 1H); 7.50 (t, 1H); 7.58 (t, 1H); 7.63 (s, 1H); 8.40 (s, 1H); 8.44 (s, 1H); 9.70 (s, 1H); Mass Spectrum: (M+H)+ 501.

The N-({4-[(3-Chloro-2-fluorophenyl)amino]-7-methoxyquinazolin-6-yl}methyl)-N-(2-pyrrolidin-1-ylethyl)-D-alanine used as starting material was prepared as follows:

N-(3-Chloro-2-fluorophenyl)-7-methoxy-6-{[(2-pyrrolidin-1-ylethyl)amino]methyl}quinazolin-4-amine (prepared as described in Example 47) was coupled with ethyl O-trifluoromethanesulfonyl-L-lactate and hydrolysed using analogous methods to those described for the equivalent steps in Example 46 to give N-({4-[(3-chloro-2-fluorophenyl)amino]-7-methoxyquinazolin-6-yl}methyl)-N-(2-pyrrolidin-1-ylethyl)-D-alanine; ¹H NMR Spectrum: (DMSO-d₆) 1.27 (d, 3H); 1.83 (m, 4H); 2.86 (m, 8H); 3.44 (q, 1H); 3.84 (d, 1H); 3.94 (d, 1H); 4.01 (s, 3H); 7.25 (s, 1H); 7.33 (t, 1H); 7.53 (m, 1H); 7.63 (m, 1H); 8.42 (s, 1H); 8.48 (s, 1H); 9.78 (brs, 1H); Mass Spectrum: (M+H)+ 502.

EXAMPLE 49

N²-({4-[(3-chloro-2-fluorophenyl)amino]-7-methoxyquinazolin-6-yl}methyl)-N²-[2-(dimethylamino)ethyl]-L-alaninamide (Process (c))

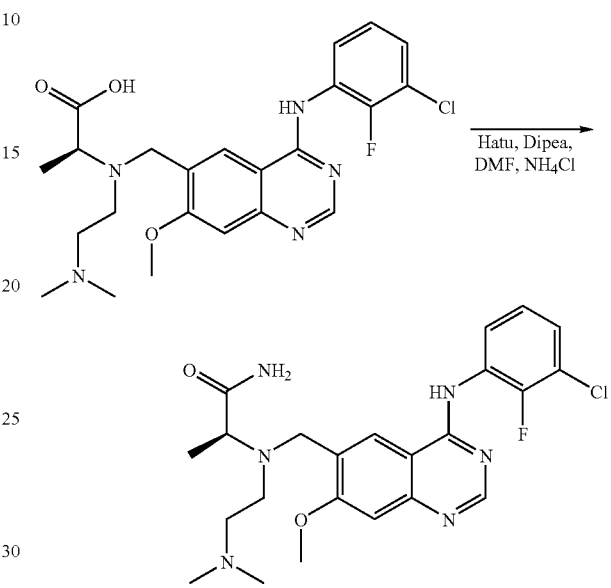

N-({4-[(3-Chloro-2-fluorophenyl)amino]-7-methoxyquinazolin-6-yl}methyl)-N-[2-(dimethylamino)ethyl]-L-alanine was coupled with ammonium chloride using a procedure analogous to the equivalent step in Example 16 to give the title product; ¹H NMR Spectrum: (DMSO-d₆) 1.18 (d, 3H); 2.07 (s, 6H); 2.39 (m, 2H); 2.56 (m, 2H); 3.41 (q, 1H); 3.75 (m, 2H); 3.96 (s, 3H); 7.05 (s, 1H); 7.21 (s, 1H); 7.30 (t, 1H); 7.51 (t, 1H); 7.59 (m, 2H); 8.41 (s, 1H); 8.44 (s, 1H); 9.69 (s, 1H); Mass Spectrum: (M−H)− 473.

The N-({4-[(3-chloro-2-fluorophenyl)amino]-7-methoxyquinazolin-6-yl}methyl)-N-[2-(dimethylamino)ethyl]-L-alanine used as starting material was prepared as follows:

4-(3-Chloro-2-fluoroanilino)-7-methoxyquinazoline-6-carbaldehyde was coupled with N,N-dimethylethane-1,2-diamine using an analogous method to that described for the equivalent step in Example 1 to give N'-({4-[(3-chloro-2-fluorophenyl)amino]-7-methoxyquinazolin-6-yl}methyl)-N,N-dimethylethane-1,2-diamine; ¹H NMR Spectrum: (DMSO-d₆) 2.12 (s, 6H); 2.37 (t, 2H); 2.65 (t, 2H); 3.85 (s, 2H); 3.97 (s, 3H); 7.21 (s, 1H); 7.28 (t, 1H); 7.51 (m, 2H); 8.32 (s, 1H); 8.43 (s, 1H); 9.78 (s, 1H); Mass Spectrum: (M+H)+ 404.

N'-({4-[(3-Chloro-2-fluorophenyl)amino]-7-methoxyquinazolin-6-yl}methyl)-N,N-dimethylethane-1,2-diamine was coupled with ethyl O-trifluoromethanesulfonyl-D-lactate and hydrolysed using analogous methods to those described for the equivalent steps in Example 46 to give N-({4-[(3-chloro-2-fluorophenyl)amino]-7-methoxyquinazolin-6-yl}methyl)-N-[2-(dimethylamino)ethyl]-L-alanine; ¹H NMR Spectrum: (DMSO-d₆) 1.24 (d, 3H); 2.36 (s, 6H); 2.63 (m, 2H); 2.77 (m, 1H); 2.86 (m, 1H); 3.41 (q, 1H); 3.80 (d, 1H); 3.89 (d, 1H); 3.96 (s, 3H); 7.21 (s, 1H); 7.29 (t, 1H); 7.49 (t, 1H); 7.60 (t, 1H); 8.36 (s, 1H); 8.44 (s, 1H); 9.71 (brs, 1H); Mass Spectrum: (M+H)+ 476.

EXAMPLE 50

N²-({4-[(3-chloro-2-fluorophenyl)amino]-7-methoxyquinazolin-6-yl}methyl)-N²-(2-methoxyethyl)-L-alaninamide (Process (c))

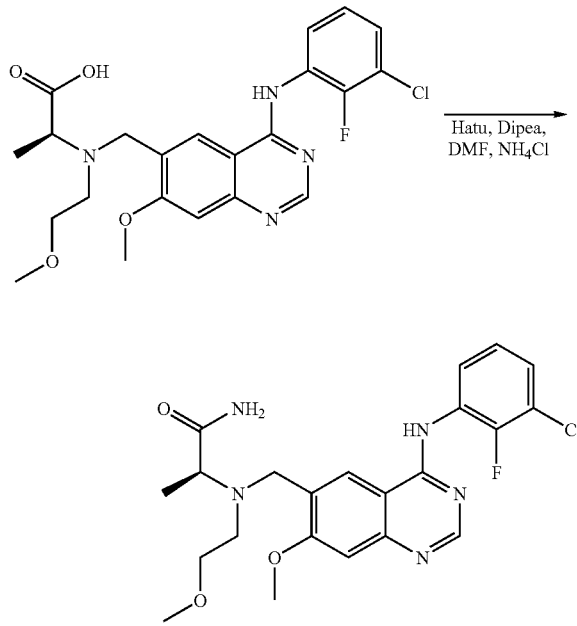

N-({4-[(3-Chloro-2-fluorophenyl)amino]-7-methoxyquinazolin-6-yl}methyl)-N-(2-methoxyethyl)-L-alanine was coupled with ammonium chloride using a procedure analogous to the equivalent step in Example 16 to give the title product; ¹H NMR Spectrum: (DMSO-d₆) 1.18 (d, 3H); 2.68 (m, 2H); 3.18 (s, 3H); 3.44 (m, 3H); 3.77 (m, 2H); 3.97 (s, 3H); 7.07 (s, 1H); 7.21 (s, 1H); 7.30 (t, 1H); 7.42 (s, 1H); 7.51 (t, 1H); 7.59 (t, 1H); 8.41 (s, 1H); 8.44 (s, 1H); 9.70 (s, 1H). Mass Spectrum: (M−H)⁻ 460.

The N-({4-[(3-chloro-2-fluorophenyl)amino]-7-methoxyquinazolin-6-yl}methyl)-N-(2-methoxyethyl)-L-alanine used as starting material was prepared as follows:

4-(3-Chloro-2-fluoroanilino)-7-methoxyquinazoline-6-carbaldehyde was coupled with aminoethylmethyl ether using an analogous method to that described for the equivalent step in Example 1 to give N-(3-chloro-2-fluorophenyl)-7-methoxy-6-{[(2-methoxyethyl)amino]methyl}quinazolin-4-amine; ¹H NMR Spectrum: (DMSO-d₆) 2.15 (brs, 1H); 2.76 (t, 2H); 3.25 (s, 3H); 3.46 (t, 2H); 3.85 (s, 2H); 3.97 (s, 3H); 7.21 (s, 1H); 7.28 (t, 1H); 7.51 (m, 2H); 8.33 (s, 1H); 8.44 (s, 1H); 9.78 (s, 1H); Mass Spectrum: (M+H)⁺ 391.

N-(3-Chloro-2-fluorophenyl)-7-methoxy-6-{[(2-methoxyethyl)amino]methyl}quinazolin-4-amine was coupled with ethyl O-trifluoromethanesulfonyl-D-lactate and hydrolysed using analogous methods to those described for the equivalent steps in Example 46 to give N-({4-[(3-chloro-2-fluorophenyl)amino]-7-methoxyquinazolin-6-yl}methyl)-N-(2-methoxyethyl)-L-alanine; ¹H NMR Spectrum: (DMSO-d₆) 1.28 (d, 3H); 2.85 (t, 2H); 3.13 (s, 3H); 3.34 (m, 2H); 3.56 (q, 1H); 3.93 (m, 5H); 7.18 (s, 1H); 7.28 (t, 1H); 7.48 (t, 1H); 7.57 (m, 1H); 8.41 (m, 2H); 9.70 (brs, 1H); Mass Spectrum: (M+H)⁺ 463.

EXAMPLE 51

N²-({4-[(3-chloro-2-fluorophenyl)amino]-7-methoxyquinazolin-6-yl}methyl)-N²-(2-methoxyethyl)-D-alaninamide (Process (c))

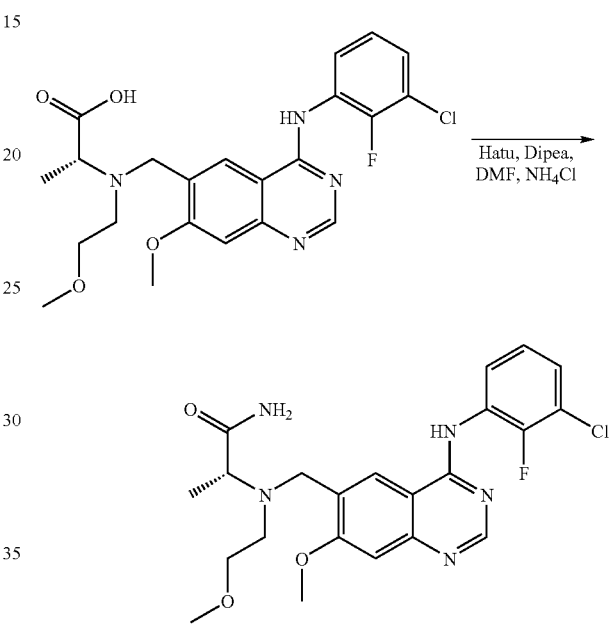

N-({4-[(3-Chloro-2-fluorophenyl)amino]-7-methoxyquinazolin-6-yl}methyl)-N-(2-methoxyethyl)-D-alanine was coupled with ammonium chloride using a procedure analogous to the equivalent step in Example 16 to give the title product; ¹H NMR Spectrum: (DMSO-d₆) 1.18 (d, 3H); 2.68 (m, 2H); 3.18 (s, 3H); 3.44 (m, 3H); 3.77 (m, 2H); 3.97 (s, 3H); 7.07 (s, 1H); 7.21 (s, 1H); 7.30 (t, 1H); 7.42 (s, 1H); 7.51 (t, 1H); 7.59 (t, 1H); 8.41 (s, 1H); 8.44 (s, 1H); 9.70 (s, 1H); Mass Spectrum: (M+H)⁺ 462.

The N-({4-[(3-chloro-2-fluorophenyl)amino]-7-methoxyquinazolin-6-yl}methyl)-N-(2-methoxyethyl)-D-alanine used as starting material was prepared as follows:

N-(3-Chloro-2-fluorophenyl)-7-methoxy-6-{[(2-methoxyethyl)amino]methyl}quinazolin-4-amine (prepared as described in Example 50) was coupled with ethyl O-trifluoromethanesulfonyl-L-lactate and hydrolysed using analogous methods to those described for the equivalent steps in Example 46 to give N-({4-[(3-chloro-2-fluorophenyl)amino]-7-methoxyquinazolin-6-yl}methyl)-N-(2-methoxyethyl)-D-alanine; ¹H NMR Spectrum: (DMSO-d₆) 1.28 (d, 3H); 2.85 (t, 2H); 3.13 (s, 3H); 3.34 (m, 2H); 3.56 (q, 1H); 3.93 (m, 5H); 7.18 (s, 1H); 7.28 (t, 1H); 7.48 (t, 1H); 7.57 (m, 1H); 8.41 (m, 2H); 9.70 (brs, 1H); Mass Spectrum: (M+H)⁺ 463.

EXAMPLE 52

(Process (c))

N²-({4-[(3-chloro-2-fluorophenyl)amino]-7-methoxyquinazolin-6-yl}methyl)-N²-[(1S)-2-methoxy-1-methylethyl]-D-alaninamide

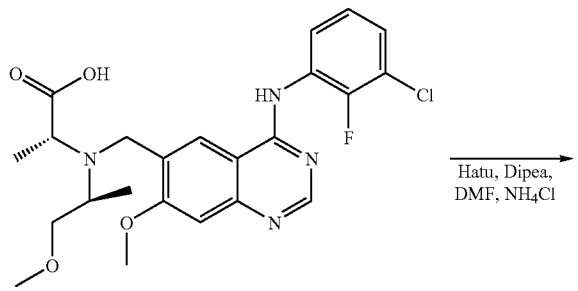

N-({4-[(3-Chloro-2-fluorophenyl)amino]-7-methoxyquinazolin-6-yl}methyl)-N-[(1S)-2-methoxy-1-methylethyl]-D-alanine was coupled with ammonium chloride using a procedure analogous to the equivalent step in Example 16 to give the title product; ¹H NMR Spectrum: (DMSO-$d_6$) 1.07 (d, 3H); 1.24 (d, 3H); 2.99 (m, 1H); 3.18 (m, 4H); 3.47 (m, 2H); 3.83 (d, 1H); 3.89 (d, 1H); 3.97 (s, 3H); 6.98 (m, 1H); 7.21 (s, 1H); 7.30 (dt, 1H); 7.50 (m, 1H); 7.60 (m, 2H); 8.37 (s, 1H); 8.44 (s, 1H); 9.64 (s, 1H); Mass Spectrum: (M+H)⁺ 476.

The N-({4-[(3-chloro-2-fluorophenyl)amino]-7-methoxyquinazolin-6-yl}methyl)-N-[(1S)-2-methoxy-1-methylethyl]-D-alanine used as starting material was prepared as follows:

4-(3-Chloro-2-fluoroanilino)-7-methoxyquinazoline-6-carbaldehyde was coupled with S-(+)-1-methoxy-2-propylamine using an analogous method to that described for the equivalent step in Example 1 to give N-(3-chloro-2-fluorophenyl)-7-methoxy-6-({[(1S)-2-methoxy-1-methylethyl]amino}methyl)quinazolin-4-amine; ¹H NMR Spectrum: (DMSO-$d_6$) 1.03 (d, 3H); 2.07 (brs, 1H); 2.85 (m, 1H); 3.24 (m, 5H); 3.81 (d, 1H); 3.92 (d, 1H); 3.97 (s, 3H); 7.21 (s, 1H); 7.28 (t, 1H); 7.48 (t, 1H); 7.54 (t, 1H); 8.32 (s, 1H); 8.44 (s, 1H); 9.76 (s, 1H); Mass Spectrum: (M+H)⁺ 405.

N-(3-Chloro-2-fluorophenyl)-7-methoxy-6-({[(1S)-2-methoxy-1-methylethyl]amino}methyl)quinazolin-4-amine was coupled with ethyl O-trifluoromethanesulfonyl-L-lactate and hydrolysed using analogous methods to those described for the equivalent steps in Example 46 to give N-({4-[(3-chloro-2-fluorophenyl)amino]-7-methoxyquinazolin-6-yl}methyl)-N-[(1S)-2-methoxy-1-methylethyl]-D-alanine; ¹H NMR Spectrum: (DMSO-$d_6$) 1.08 (d, 3H); 1.32 (d, 3H); 3.04 (m, 1H); 3.14 (s, 3H); 3.22 (dd, 1H); 3.43 (dd, 1H); 3.69 (q, 1H); 3.96 (m, 4H); 4.05 (d, 1H); 7.19 (s, 1H); 7.29 (t, 1H); 7.49 (t, 1H); 7.60 (t, 1H); 8.43 (m, 2H); 9.64 (brs, 1H); 12.01 (brs, 1H); Mass Spectrum: (M+H)⁺ 477.

EXAMPLE 53

N²-({4-[(3-chloro-2-fluorophenyl)amino]-7-methoxyquinazolin-6-yl}methyl)-N²-[(1S)-2-methoxy-1-methylethyl]-L-alaninamide (Process (c))

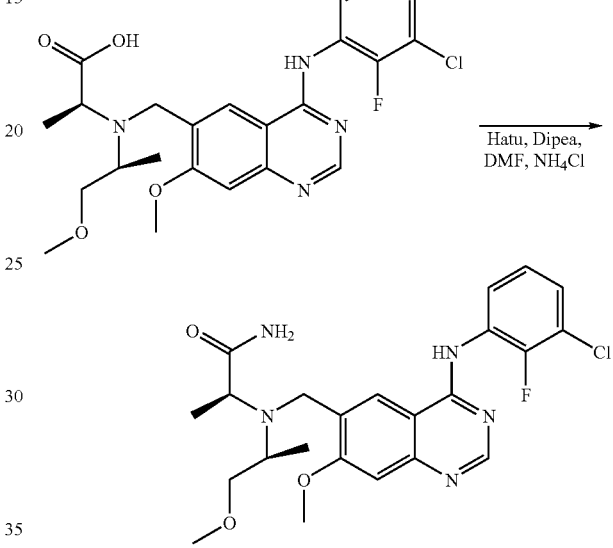

N-({4-[(3-Chloro-2-fluorophenyl)amino]-7-methoxyquinazolin-6-yl}methyl)-N-[(1S)-2-methoxy-1-methylethyl]-L-alanine was coupled with ammonium chloride using a procedure analogous to the equivalent step in Example 16 to give the title product; ¹H NMR Spectrum: (DMSO-$d_6$) 1.09 (d, 3H); 1.23 (d, 3H); 2.99 (m, 1H); 3.21 (s, 3H); 3.25 (dd, 1H); 3.50 (m, 2H); 3.82 (d, 1H); 3.97 (s, 3H); 4.05 (d, 1H); 7.01 (m, 1H); 7.21 (s, 1H); 7.31 (dt, 1H); 7.45 (m, 1H); 7.51 (m, 1H); 7.61 (dt, 1H); 8.38 (s, 1H); 8.44 (s, 1H); 9.64 (s, 1H); Mass Spectrum: (M+H)⁺ 476.

The N-({4-[(3-chloro-2-fluorophenyl)amino]-7-methoxyquinazolin-6-yl}methyl)-N-[(1S)-2-methoxy-1-methylethyl]-L-alanine used as starting material was prepared as follows:

N-(3-Chloro-2-fluorophenyl)-7-methoxy-6-({[(1S)-2-methoxy-1-methylethyl]amino}methyl)quinazolin-4-amine (prepared as described in Example 52) was coupled with ethyl O-trifluoromethanesulfonyl-D-lactate and hydrolysed using analogous methods to those described for the equivalent steps in Example 46 to give N-({4-[(3-chloro-2-fluorophenyl)amino]-7-methoxyquinazolin-6-yl}methyl)-N-[(1S)-2-methoxy-1-methylethyl]-L-alanine; ¹H NMR Spectrum: (DMSO-$d_6$) 1.08 (d, 3H); 1.30 (d, 3H); 3.09 (m, 1H); 3.16 (s, 3H); 3.23 (dd, 1H); 3.39 (dd, 1H); 3.06 (q, 1H); 3.97 (s, 3H); 3.98 (d, 1H); 4.10 (d, 1H); 7.19 (s, 1H); 7.29 (t, 1H); 7.49 (m, 1H); 7.61 (m, 1H); 8.39 (s, 1H); 8.43 (s, 1H); 9.57 (brs, 1H); 12.13 (brs, 1H); Mass Spectrum: (M+H)⁺ 477.

EXAMPLE 54

N²-({4-[(3-chloro-2-fluorophenyl)amino]-7-methoxyquinazolin-6-yl}methyl)-N²-ethyl-L-alaninamide (Process (c))

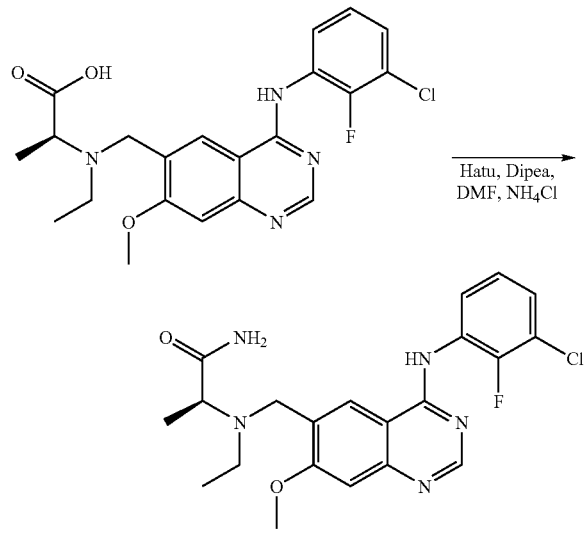

N-({4-[(3-Chloro-2-fluorophenyl)amino]-7-methoxyquinazolin-6-yl}methyl)-N-ethyl-L-alanine was coupled with ammonium chloride using a procedure analogous to the equivalent step in Example 16 to give the title product; ¹H NMR Spectrum: (DMSO-d₆) 1.07 (t, 3H); 1.17 (d, 3H); 2.53 (m, 2H); 3.40 (q, 1H); 3.68 (d, 1H); 3.74 (d, 1H); 3.96 (s, 3H); 7.08 (s, 1H); 7.21 (s, 1H); 7.30 (m, 1H); 7.42 (s, 1H); 7.51 (m, 1H); 7.58 (m, 1H); 8.43 (s, 2H); 9.73 (s, 1H); Mass Spectrum: (M+Na)⁺ 454.

The N-({4-[(3-chloro-2-fluorophenyl)amino]-7-methoxyquinazolin-6-yl}methyl)-N-ethyl-L-alanine used as starting material was prepared as follows:

4-(3-Chloro-2-fluoroanilino)-7-methoxyquinazoline-6-carbaldehyde was coupled with ethylamine using an analogous method to that described for the equivalent step in Example 1 to give N-(3-chloro-2-fluorophenyl)-6-[(ethylamino)methyl]-7-methoxyquinazolin-4-amine; ¹H NMR Spectrum: (DMSO-d₆) 1.09 (t, 3H); 2.63 (q, 2H); 3.83 (s, 2H); 3.97 (s, 3H); 7.20 (s, 1H); 7.27 (t, 1H); 7.50 (m, 2H); 8.33 (s, 1H); 8.43 (s, 1H); 9.77 (s, 1H); Mass Spectrum: (M+H)⁺ 361.

N-(3-Chloro-2-fluorophenyl)-6-[(ethylamino)methyl]-7-methoxyquinazolin-4-amine was coupled with ethyl O-trifluoromethanesulfonyl-D-lactate and hydrolysed using analogous methods to those described for the equivalent steps in Example 46 to give N-({4-[(3-chloro-2-fluorophenyl)amino]-7-methoxyquinazolin-6-yl}methyl)-N-ethyl-L-alanine; ¹H NMR Spectrum: (DMSO-d₆) 1.03 (t, 3H); 1.29 (d, 3H); 2.71 (q, 2H); 3.56 (q, 1H); 3.86 (d, 1H); 3.94 (m, 4H); 7.19 (s, 1H); 7.28 (t, 1H); 7.48 (m, 1H); 7.56 (m, 1H); 8.41 (m, 2H); 9.76 (brs, 1H); Mass Spectrum: (M+H)⁺ 433.

EXAMPLE 55

N²-({4-[(3-chloro-2-fluorophenyl)amino]-7-methoxyquinazolin-6-yl}methyl)-N²-ethyl-D-alaninamide (Process (c))

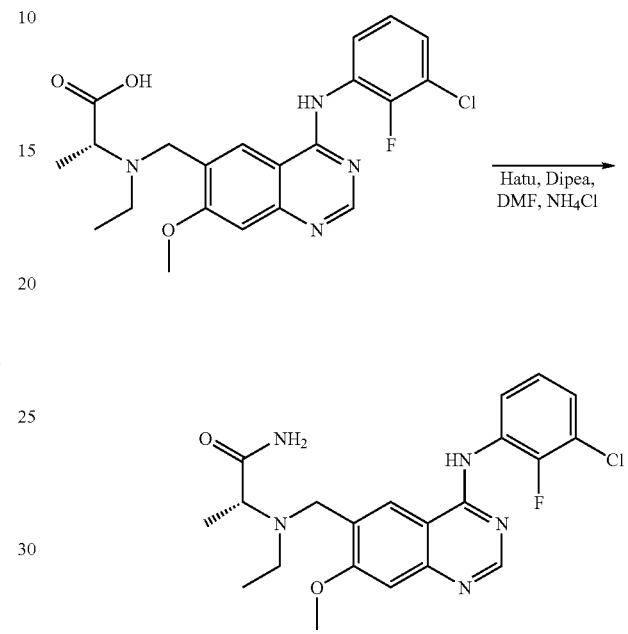

N-({4-[(3-Chloro-2-fluorophenyl)amino]-7-methoxyquinazolin-6-yl}methyl)-N-ethyl-D-alanine (prepared as described in Example 54) was coupled with ammonium chloride using a procedure analogous to the equivalent step in Example 16 to give the title product; ¹H NMR Spectrum: (DMSO-d₆) 1.07 (t, 3H); 1.17 (d, 3H); 2.53 (m, 2H); 3.40 (q, 1H); 3.68 (d, 1H); 3.74 (d, 1H); 3.96 (s, 3H); 7.08 (s, 1H); 7.21 (s, 1H); 7.30 (m, 1H); 7.42 (s, 1H); 7.51 (m, 1H); 7.58 (m, 1H); 8.43 (s, 2H); 9.73 (s, 1H); Mass Spectrum: (M+Na)⁺ 454.

The N-({4-[(3-Chloro-2-fluorophenyl)amino]-7-methoxyquinazolin-6-yl}methyl)-N-ethyl-D-alanine used as starting material was prepared as follows: N-(3-Chloro-2-fluorophenyl)-6-[(ethylamino)methyl]-7-methoxyquinazolin-4-amine (prepared as described in Example 54) was coupled with ethyl O-trifluoromethanesulfonyl-L-lactate and hydrolysed using analogous methods to those described for the equivalent steps in Example 46 to give N-({4-[(3-chloro-2-fluorophenyl)amino]-7-methoxyquinazolin-6-yl}methyl)-N-ethyl-D-alanine; ¹H NMR Spectrum: (DMSO-d₆) 1.03 (t, 3H); 1.29 (d, 3H); 2.71 (q, 2H); 3.56 (q, 1H); 3.86 (d, 1H); 3.94 (m, 4H); 7.19 (s, 1H); 7.28 (t, 1H); 7.48 (m, 1H); 7.56 (m, 1H); 8.41 (m, 2H); 9.76 (brs, 1H); Mass Spectrum: (M+H)⁺ 433.

EXAMPLE 56

N²-({4-[(3-chloro-2-fluorophenyl)amino]-7-methoxyquinazolin-6-yl}methyl)-N²-isopropyl-L-alaninamide (Process (c))

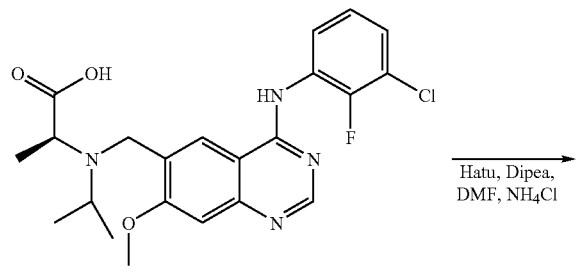

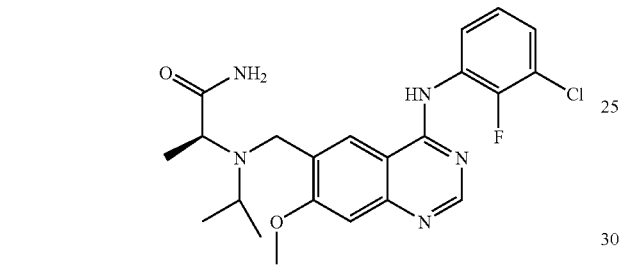

N-({4-[(3-Chloro-2-fluorophenyl)amino]-7-methoxyquinazolin-6-yl}methyl)-N-isopropyl-L-alanine was coupled with ammonium chloride using a procedure analogous to the equivalent step in Example 16 to give the title product; ¹H NMR Spectrum: (DMSO-d₆) 1.08 (t, 6H); 1.20 (d, 3H); 2.97 (m, 1H); 3.41 (q, 1H); 3.78 (d, 1H); 3.87 (d, 1H); 3.97 (s, 3H); 7.04 (s, 1H); 7.21 (s, 1H); 7.31 (t, 1H); 7.50 (m, 2H); 7.58 (m, 1H); 8.41 (s, 1H); 8.43 (s, 1H); 9.70 (s, 1H); Mass Spectrum: (M+H)⁺ 446.

The N-({4-[(3-chloro-2-fluorophenyl)amino]-7-methoxyquinazolin-6-yl}methyl)-N-isopropyl-L-alanine used as starting material was prepared as follows: 4-(3-Chloro-2-fluoroanilino)-7-methoxyquinazoline-6-carbaldehyde was coupled with isopropylamine using an analogous method to that described for the equivalent step in Example 1 to give N-(3-chloro-2-fluorophenyl)-6-[(isopropylamino)methyl]-7-methoxyquinazolin-4-amine; ¹H NMR Spectrum: (DMSO-d₆) 1.07 (d, 6H); 1.90 (brs, 1H); 2.80 (m, 1H); 3.83 (s, 2H); 3.97 (s, 3H); 7.20 (s, 1H); 7.28 (t, 1H); 7.50 (m, 2H); 8.32 (s, 1H); 8.43 (s, 1H); 9.76 (s, 1H); Mass Spectrum: (M+H)⁺ 375.

N-(3-Chloro-2-fluorophenyl)-6-[(isopropylamino)methyl]-7-methoxyquinazolin-4-amine was coupled with ethyl O-trifluoromethanesulfonyl-D-lactate and hydrolysed using analogous methods to those described for the equivalent steps in Example 46 to give N-({4-[(3-chloro-2-fluorophenyl)amino]-7-methoxyquinazolin-6-yl}methyl)-N-isopropyl-L-alanine; ¹H NMR Spectrum: (DMSO-d₆) 1.08 (d, 6H); 1.31 (d, 3H); 3.10 (m, 1H); 3.63 (q, 1H); 3.98 (s, 3H); 4.02 (s, 2H); 7.20 (s, 1H); 7.29 (t, 1H); 7.49 (m, 1H); 7.59 (m, 1H); 8.42 (s, 2H); 9.68 (brs, 1H); Mass Spectrum: (M+H)⁺ 447.

EXAMPLE 57

N²-({4-[(3-chloro-2-fluorophenyl)amino]-7-methoxyquinazolin-6-yl}methyl)-N²-isopropyl-D-alaninamide (Process (c))

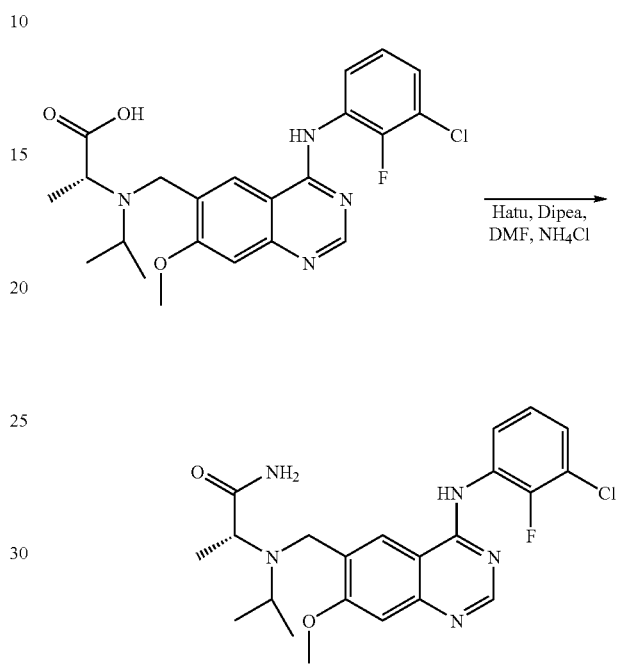

N-({4-[(3-Chloro-2-fluorophenyl)amino]-7-methoxyquinazolin-6-yl}methyl)-N-isopropyl-D-alanine was coupled with ammonium chloride using a procedure analogous to the equivalent step in Example 16 to give the title product; ¹H NMR Spectrum: (DMSO-d₆) 1.08 (t, 6H); 1.20 (d, 3H); 2.97 (m, 1H); 3.41 (q, 1H); 3.78 (d, 1H); 3.87 (d, 1H); 3.97 (s, 3H); 7.04 (s, 1H); 7.21 (s, 1H); 7.31 (t, 1H); 7.50 (m, 2H); 7.58 (m, 1H); 8.41 (s, 1H); 8.43 (s, 1H); 9.70 (s, 1H); Mass Spectrum: (M+H)⁺ 446.

The N-({4-[(3-Chloro-2-fluorophenyl)amino]-7-methoxyquinazolin-6-yl}methyl)-N-isopropyl-D-alanine used as starting material was prepared as follows:

N-(3-Chloro-2-fluorophenyl)-6-[(isopropylamino)methyl]-7-methoxyquinazolin-4-amine (prepared as described in Example 56) was coupled with ethyl O-trifluoromethanesulfonyl-L-lactate and hydrolysed using analogous methods to those described for the equivalent steps in Example 46 to give N-({4-[(3-chloro-2-fluorophenyl)amino]-7-methoxyquinazolin-6-yl}methyl)-N-isopropyl-D-alanine; ¹H NMR Spectrum: (DMSO-d₆) 1.08 (d, 6H); 1.31 (d, 3H); 3.10 (m, 1H); 3.63 (q, 1H); 3.98 (s, 3H); 4.02 (s, 2H); 7.20 (s, 1H); 7.29 (t, 1H); 7.49 (m, 1H); 7.59 (m, 1H); 8.42 (s, 2H); 9.68 (brs, 1H); Mass Spectrum: (M+H)⁺ 447.

EXAMPLE 58

N²-({4-[(3-chloro-2-fluorophenyl)amino]-7-methoxyquinazolin-6-yl}methyl)-3-(dimethylamino)-N²-methyl-L-alaninamide (Process (c))

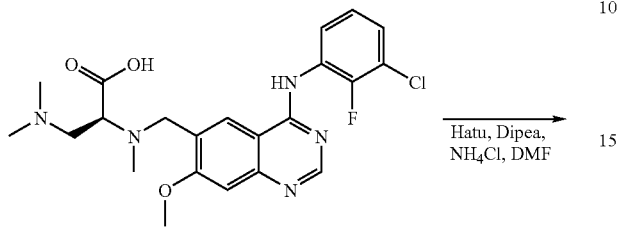

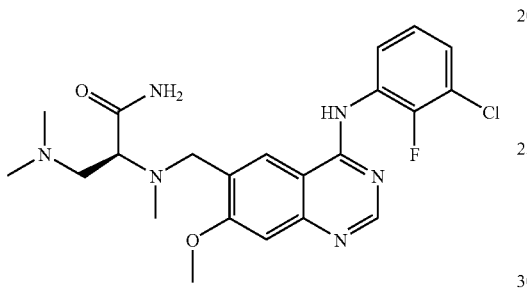

N-({4-[(3-Chloro-2-fluorophenyl)amino]-7-methoxyquinazolin-6-yl}methyl)-3-(dimethylamino)-N-methyl-L-alanine was coupled with ammonium chloride using an analogous to that described for the equivalent step in Example 16 to give the title product; $^1$H NMR Spectrum: (DMSO-d$_6$) 2.21 (s, 6H); 2.30 (s, 3H); 2.76 (m, 2H); 3.36 (t, 1H); 3.82 (m, 2H); 3.95 (s, 3H); 7.01 (s, 1H); 7.21 (s, 1H); 7.29 (t, 1H); 7.51 (m, 3H); 8.33 (s, 1H); 8.43 (s, 1H); 9.77 (s, 1H); Mass Spectrum: (M+H)$^+$ 461.

The N-({4-[(3-Chloro-2-fluorophenyl)amino]-7-methoxyquinazolin-6-yl}methyl)-3-(dimethylamino)-N-methyl-L-alanine used as starting material was prepared as follows:

4-(3-Chloro-2-fluoroanilino)-7-methoxyquinazoline-6-carbaldehyde was coupled with 3-[(tert-butoxycarbonyl)amino]-L-alanine (Tetrahedron Letters (1993), 34(20), 3201-4) using an analogous method to that described for the equivalent step in Example 1 to give 3-[(tert-butoxycarbonyl)amino]-N-({4-[(3-chloro-2-fluorophenyl)amino]-7-methoxyquinazolin-6-yl}methyl)-L-alanine; $^1$H NMR Spectrum: (DMSO-d$_6$) 1.32 (s, 9H); 3.26 (m, 3H); 3.86 (d, 1H); 3.97 (m, 4H); 6.73 (s, 1H); 7.21 (s, 1H); 7.27 (t, 1H); 7.47 (t, 1H); 7.54 (t, 1H); 8.40 (s, 1H); 8.44 (s, 1H); 9.86 (s, 1H); Mass Spectrum: (M+H)$^+$ 520.

3-[(tert-butoxycarbonyl)amino]-N-({4-[(3-chloro-2-fluorophenyl)amino]-7-methoxyquinazolin-6-yl}methyl)-L-alanine was deprotected using an analogous method to that described for the equivalent step in Example 7 to give 3-amino-N-({4-[(3-chloro-2-fluorophenyl)amino]-7-methoxyquinazolin-6-yl}methyl)-L-alanine; $^1$H NMR Spectrum: (DMSO d$_6$+CD$_3$COOD) 2.96 (dd, 1H); 3.04 (dd, 1H); 3.18 (t, 1H); 3.90 (d, 1H); 3.98 (d, 1H); 4.01 (s, 3H); 7.25 (s, 1H); 7.32 (t, 1H); 7.51 (t, 1H); 7.59 (t, 1H); 8.47 (m, 2H); Mass Spectrum: (M+H)$^+$ 420.

3-Amino-N-({4-[(3-chloro-2-fluorophenyl)amino]-7-methoxyquinazolin-6-yl}methyl)-L-alanine was reacted with paraformaldehyde using an analogous method to that described for the equivalent step in Example 11 to give N-({4-[(3-chloro-2-fluorophenyl)amino]-7-methoxyquinazolin-6-yl}methyl)-3-(dimethylamino)-N-methyl-L-alanine; $^1$H NMR Spectrum: (DMSO-d$_6$) 2.40 (s, 3H); 2.43 (s, 6H); 2.74 (dd, 1H); 2.30 (t, 1H); 3.51 (dd, 1H); 3.93 (m, 5H); 7.19 (s, 1H); 7.28 (t, 1H); 7.51 (m, 2H); 8.33 (s, 1H); 8.43 (s, 1H); 9.80 (s, 1H); Mass Spectrum: (M+H)$^+$ 462.

EXAMPLES 59, 60 and 61

(Process (e))

Compounds of the formula:

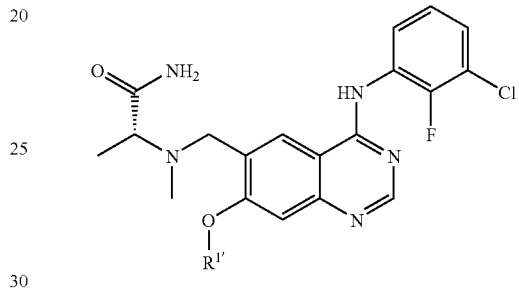

wherein R$^{1'''}$ is as shown in Table 2 below were prepared as follows:

Solid di-tert-butyl azodicarboxylate (DTAD) (0.063 g, 0.273 mmol, 2.2 molar equivalents) was added to a solution of triphenylphosphine (0.073 g, 0.273 mmol, 2.2 molar equivalents) and the alcohol R$^1$OH in THF (0.5 ml) at room temperature and the reaction mixture was left to stand for 30 minutes. The resulting pale yellow solution was added to N²-({4-[(3-chloro-2-fluorophenyl)amino]-7-hydroxyquinazolin-6-yl}methyl)-N²-methyl-D-alaninamide (0.050 g, 0.134 mmol Example 2) in THF (0.5 ml) and the resulting solution was left to stand at room temperature for 16 hours, concentrated and purified by preparative LCMS (standard acidic system) to afford the title compounds as white solids.

TABLE 2

| Example | R$^{1'}$ | Characterising Data |
|---|---|---|
| 59 N²-({4-[(3-chloro-2-fluorophenyl)amino]-7-isopropoxyquinazolin-6-yl}methyl)-N²-methyl-D-alaninamide | —CH(CH$_3$)$_2$ | $^1$H NMR Spectrum: (DMSO-d$_6$)1.25(d, 3H), 1.35(d, 6H), 2.21(s, 3H), 3.40-3.71(m, 3H), 4.89 (m, 1H), 7.15(s, 1H), 7, 20 (s, 1H), 7.27(t, 1H), 7.35 (brs, 1H), 7.50-7.55(m, 2H), 8.42(s, 2H), 9.79(s, 1H); Mass Spectrum: (M+H)$^+$ 446. |
| 60 N²-{[4-[(3-chloro-2-fluorophenyl)amino]-7-(2-methoxyethoxy)quinazolin-6-yl]methyl}-N²-methyl-D-alaninamide | —CH$_2$CH$_2$OCH$_3$ | $^1$H NMR Spectrum: (DMSO-d$_6$)1.26(d, 3H), 2.20(s, 3H), 3.29(s, 3H), 3.62-3.72(m, 3H), 3.76(t, 2H), 4.29(t, 2H), 7.12(s, 1H), 7, 21(s, 1H), 7.31(t, 1H), 7.36(brs, 1H), 7.49-7.56(m, 2H), 8.42(s, 2H), 9.81(s, 1H); Mass Spectrum: (M+H)$^+$ 462. |

TABLE 2-continued

| Example | R[1'] | Characterising Data |
|---|---|---|
| 61 [1]<br>N²-{[4-[(3-chloro-2-fluorophenyl)amino]-7-(2-hydroxyethoxy)quinazolin-6-yl]methyl}-N²-methyl-D-alaninamide | —CH₂CH₂OH | ¹H NMR Spectrum: (DMSO-d₆)1.23(d, 3H), 2.21(s, 3H), 3.65-3.73(m, 3H), 3.80(t, 2H), 4.18(t, 2H), 4.95(t, 1H), 7.10(s, 1H), 7, 20(s, 1H), 7.28(t, 1H), 7.40(brs, 1H), 7.50-7.56(m, 2H), 8.42(s, 2H), 9.80(s, 1H); Mass Spectrum: (M+H)⁺ 448. | footnote to Table 2: [1]: In Example 61, 2-(tetrahydro-2H-pyran-2-yloxy)ethanol was coupled with the to N²-({4-[(3-chloro-2-fluorophenyl)amino]-7-hydroxyquinazolin-6-yl}methyl)-N-methyl-D-alaninamide. The resulting 2-({4-[(3-chloro-2-fluorophenyl)amino]-7-[2-(tetrahydro-2H-pyran-2-yloxy)ethoxy]quinazolin-6-yl}methyl)-N-methyl-D-alaninamide was deprotected by reacting the compound with pyridinium p-toluenesulfonate (100 mg) in MeOH (1 ml) at 60° C. for 1 hour. The product was concentrated and then purified by preparative LCMS (standard acidic system) to give Example 61: N²-({4-[(3-chloro-2-fluorophenyl)amino]-7-(2-hydroxyethoxy)quinazolin-6-yl}methyl)-N²-methyl-D-alaninamide.

The starting material 2-({4-[(3-chloro-2-fluorophenyl)amino]-7-hydroxyquinazolin-6-yl}methyl)-N-methyl-D-alaninamide was prepared as follows: Solid N²-({4-[3-Chloro-2-fluoroanilino]-7-methoxyquinazolin-6-yl}methyl)-N²-methyl-D-alaninamide Example 2 (0.200 g, 0.480 mmol) was added over a period of 1 minute to a stirred solution of anhydrous lithium iodide (0.121 g, 2.40 mmol) in 2,4,6-collidine at 130° C., previously stirred for 30 minutes at 130° C. The reaction mixture was allowed to stir for 3 hours, cooled, concentrated and purified by preparative LCMS (standard acidic system) to afford N²-({4-[(3-chloro-2-fluorophenyl)amino]-7-hydroxyquinazolin-6-yl}methyl)-N'-methyl-D-alaninamide (0.094 g, 48.7%) as a pale orange foam; Mass Spectrum: (M+H)⁺ 404.

EXAMPLE 62

N²-{[4-[(3-chloro-2-fluorophenyl)amino]-7-(piperidin-4-yloxy)quinazolin-6-yl]methyl}-N¹,N¹,N²-trimethylglycinamide (Process (e))

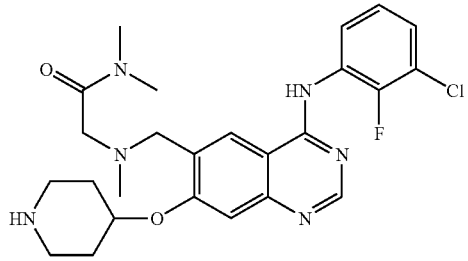

Solid DTAD (0.050 g, 0.22 mmol) was added to a solution of triphenylphosphine (0.057 g, 0.22 mmol) and tert-butyl 4-hydroxypiperidine-1-carboxylate (0.032 g, 0.16 mmol) in tetrahydrofuran (0.5 ml) at room temperature and the reaction mixture was left to stand for 30 minutes. The resulting pale yellow solution was added to N²-({4-[(3-chloro-2-fluorophenyl)amino]-7-hydroxyquinazolin-6-yl}methyl)-N¹,N¹-dimethylglycinamide (0.030 g, 0.072 mmol) in tetrahydrofuran (1 ml) and the resulting orange solution was left to stand at room temperature for 2 hours. The reaction mixture was concentrated and the residue was dissolved in dichloromethane (1 ml). Trifluoroacetic acid (1 ml) was added the resulting orange solution was left to stand for 1 hour, concentrated and purified by preparative LCMS (standard acidic system) to give the title product (0.03 g, 83%) as white foam; Mass Spectrum: (M+H)⁺ 501.

The N²-({4-[(3-chloro-2-fluorophenyl)amino]-7-hydroxyquinazolin-6-yl}methyl)-N¹,N¹-dimethylglycinamide starting material was prepared as follows:

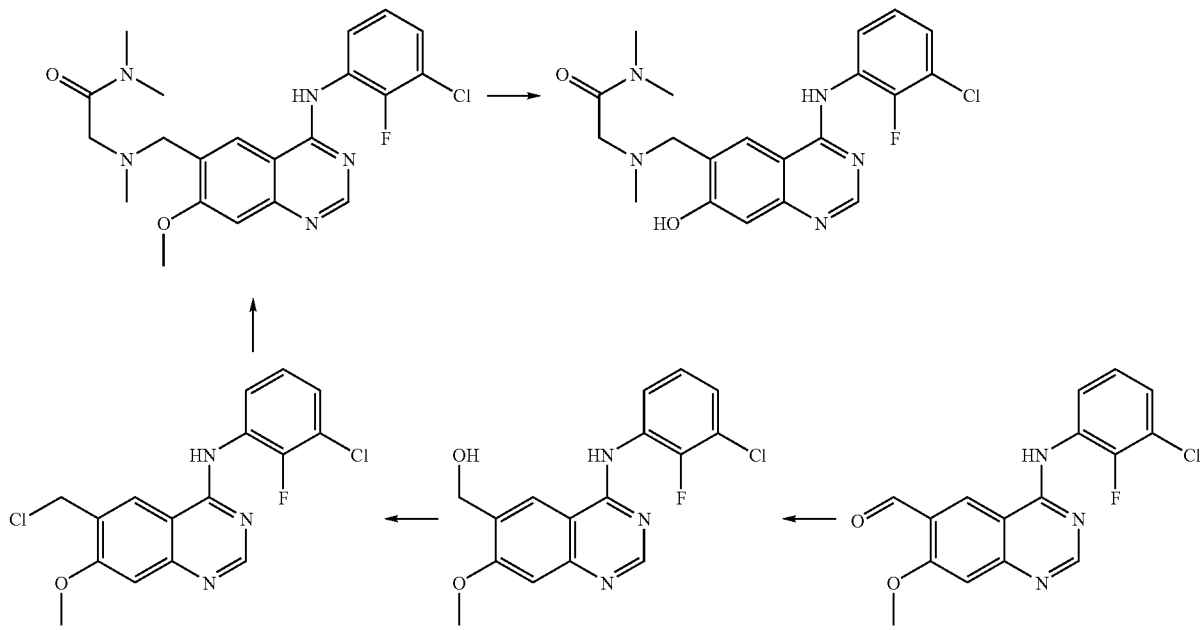

Sodium borohydride (0.046 g, 1.21 mmol) was added to a stirred suspension of 4-[(3-chloro-2-fluorophenyl)amino]-7-methoxyquinazoline-6-carbaldehyde (0.20 g, 0.604 mmol) in methanol (1 ml) at 0° C., over period of 5 minutes. The reaction mixture was allowed to stir at room temperature for 10 minutes and concentrated to dryness. The resulting grey solid was washed with water (2×1 ml) and dried to a constant weight under high vacuum at 40° C. to afford {4-[(3-chloro-2-fluorophenyl)amino]-7-methoxyquinazolin-6-yl}methanol (0.2 g, 100%) as a grey solid; Mass Spectrum: (M+H)+ 334.

{4-[(3-Chloro-2-fluorophenyl)amino]-7-methoxyquinazolin-6-yl}methanol (0.20 g, 0.604 mmol) was added to neat thionyl chloride (1 ml) over a period of 5 minutes. The resulting solution was stirred for 30 minutes, concentrated to dryness and the residue was subjected to an azeotropic distillation with toluene (2×10 ml). The resulting solid was triturated with acetonitrile (5 ml) filtered and dried to a constant weight in a vacuum oven at 40° C. to give the hydrochloride salt of N-(3-chloro-2-fluorophenyl)-6-(chloromethyl)-7-methoxyquinazolin-4-amine (0.21 g, 100%) as a white solid; Mass Spectrum: (M+H)+ 352.

N-(3-chloro-2-fluorophenyl)-6-(chloromethyl)-7-methoxyquinazolin-4-amine (0.21 g, 0.60 mmol) was added to a stirred solution of N$^1$,N$^1$,N$^2$-trimethylglycinamide (Me$_2$N-Gly-Nme) (0.348 g, 1.81 mmol) and DIPEA (0.234 g, 1.81 mmol) in dimethylformamide (1 ml) at 140° C., over a period of 5 minutes. The reaction mixture was stirred for 5 minutes, cooled to room temperature and purified by preparative LCMS (standard acidic system) to give N$^2$-({4-[(3-chloro-2-fluorophenyl)amino]-7-methoxyquinazolin-6-yl}methyl)-N$^1$,N$^1$-dimethylglycinamide (0.193 g, 74.2%) as a white solid. $^1$H NMR Spectrum: (DMSO-d$_6$) 2.27 (s, 3H), 2.80 (s, 3H), 2.98 (s, 3H), 3.71 (s, 2H), 3.94 (s, 3H), 7.19 (s, 1H), 7.27 (t, 1H), 7.47-7.52 (m, 2H), 8.30 (s, 1H), 8.43 (s, 1H), 9.85 (s, 1H); Mass Spectrum: (M+H)+ 432. Solid N$^2$-({4-[(3-chloro-2-fluorophenyl)amino]-7-methoxyquinazolin-6-yl}methyl)-N$^1$,N$^1$-dimethylglycinamide (0.150 g, 0.348 mmol) was added over a period of 1 minute to a stirred solution of anhydrous lithium iodide (0.232 g, 1.74 mmol) in 2,4,6-collidine (0.5 ml) at 130° C., previously stirred for 30 minutes at 130° C. The reaction mixture was allowed to stir for 5 hours, cooled, concentrated and purified by preparative LCMS (standard acidic system) to afford N$^2$-({4-[(3-chloro-2-fluorophenyl)amino]-7-hydroxyquinazolin-6-yl}methyl)-N$^1$,N$^1$-dimethylglycinamide (0.080 g, 55.2%) as an orange foam; Mass Spectrum: (M+H)+ 418.

EXAMPLE 63

N$^2$-{[4-[(3-chloro-2-fluorophenyl)amino]-7-({1-[(2S)-2-hydroxypropanoyl]piperidin-4-yl}oxy)quinazolin-6-yl]methyl}-N$^1$,N$^1$,N$^2$-trimethylglycinamide (Process (e))

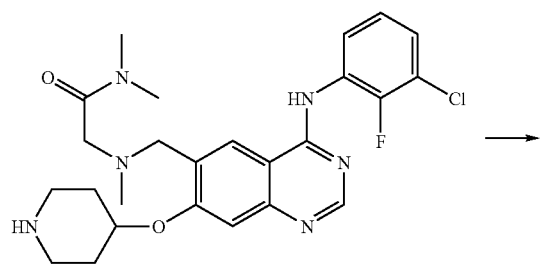

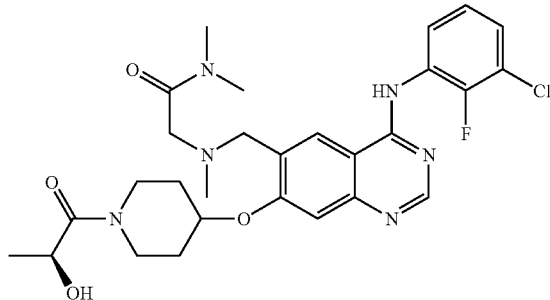

DIPEA (0.048 g, 0.15 mmol) and lactic acid (0.014 g, 0.15 mmol) were added to a stirred solution of N$^2$-{[4-[(3-chloro-2-fluorophenyl)amino]-7-(piperidin-4-yloxy)quinazolin-6-yl]methyl}-N$^1$,N$^1$,N$^2$-trimethylglycinamide (0.05 g, 0.100 mmol Example 62) in dichloromethane at room temperature (0.048 g, 0.15 mmol) was added and the reaction mixture was stirred for 30 minutes, concentrated and purified by preparative LCMS (standard acidic system) to give the title compound (0.0317 g, 55.3%) as a white solid; $^1$H NMR Spectrum: (DMSO-d$_6$) 1.30 (d, 3H), 1.72 (m, 2H), 2.04 (m, 2H), 2.30 (s, 3H), 2.77 (s, 3H), 2.93 (s, 3H), 3.34 (m, 2H), 3.74 (m, 2H), 3.78 (m, 2H), 4.48 (m, 2H), 4.97 (m, 1H), 5.29 (m, 1H), 7.30 (m, 2H), 7.47-7.56 (m, 2H), 8.37 (s, 1H), 8.42 (s, 1H), 9.81 (s, 1H); Mass Spectrum: (M+H)+ 573.

EXAMPLE 64

4-[({4-[(3-chloro-2-fluorophenyl)amino]-7-methoxyquinazolin-6-yl}methyl)(methyl)amino]-1-(cyclopropylmethyl)piperidine-4-carboxamide

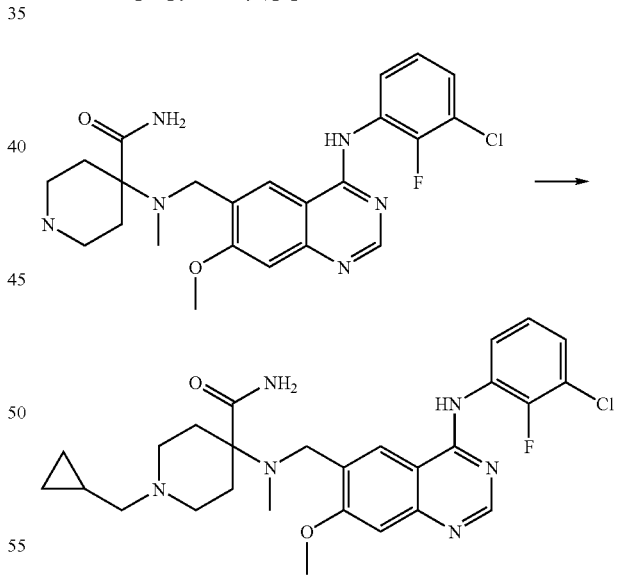

DIPEA (0.068 g, 0.522 mmol) and cyclopropylmethylbromide (0.035 g, 0.260 mmol) were added to a stirred solution of 4-[({4-[(3-chloro-2-fluorophenyl)amino]-7-methoxyquinazolin-6-yl}methyl)(methyl)amino]piperidine-4-carboxamide hydrochloride (0.10 g, 0.172 mmol) in dimethylformamide (1 ml). The reaction mixture was heated at 100° C. for 5 hours, cooled to room temperature and purified by preparative LCMS (standard acidic system) to give the title product (0.0253 g, 27.8%) as a white solid; $^1$H NMR Spectrum: (DMSO-d$_6$) 0.00 (m, 2H), 0.41 (m, 2H), 0.76 (m, 1H), 1.77 (m, 2H), 2.03-2.13 (m, 7H), 2.81 (m, 2H), 3.32 (m, 2H), 3.61 (s, 2H), 3.91 (s, 3H), 7.06 (s, 1H), 7.14 (s, 2H), 7.26 (t, 1H), 7.47-7.53 (m, 2H), 8.32 (s, 1H), 8.38 (s, 1H), 9.70 (s, 1H); Mass Spectrum: (M+H)+ 527.

The starting material 4-[({4-[(3-chloro-2-fluorophenyl)amino]-7-methoxyquinazolin-6-yl}methyl)(methyl)amino]piperidine-4-carboxamide hydrochloride was prepared as follows:

Di-tert-butyl dicarbonate (0.556 g, 2.55 mmol) was added in one portion to a stirred suspension of the 4-(methylamino)piperidine-4-carboxamide (0.40 g, 2.55 mmol) (intermediate in Example 22) and triethylamine (0.284 g, 2.81 mmol) in dichloromethane (5 ml) at −78° C. The resulting suspension was allowed to warm to room temperature. The reaction mixture was diluted with dichloromethane (10 ml), washed with brine, dried over magnesium sulfate, filtered and evaporated. This was triturated with ether, collected by filtration and dried to a constant weight to give tert-butyl 4-(aminocarbonyl)-4-(methylamino)piperidine-1-carboxylate as a white solid, (0.532 g, 81.2%); $^1$H NMR Spectrum: (DMSO-d$_6$) 1.39 (s, 9H), 1.47 (m, 2H), 1.64 (m, 2H), 2.09 (s, 3H), 3.14 (br s, 2H), 3.49 (m, 2H), 7.00 (brs, 1H), 7.26 (t, 1H).

N-(3-chloro-2-fluorophenyl)-6-(chloromethyl)-7-methoxyquinazolin-4-amine hydrochloride (0.30 g, 0.775 mmol) was added over a period of 40 minutes to a stirred solution of tert-butyl 4-(aminocarbonyl)-4-(methylamino)piperidine-1-carboxylate (0.498 g, 1.93 mmol) and DIPEA (0.50 g, 3.89 mmol) in DMF (1 ml) at 120° C. The reaction mixture was stirred for 1 hour, cooled, concentrated and purified by column chromatography on silica eluting with acetonitrile to afford tert-butyl 4-(aminocarbonyl)-4-[({4-[(3-chloro-2-fluorophenyl)amino]-7-methoxyquinazolin-6-yl}methyl)(methyl)amino]piperidine-1-carboxylate (0.35 g, 79%) as a white foam; Mass Spectrum: (M+H)+ 573.

Trifluoroacetic acid (1 ml) was added to a stirred solution of tert-butyl 4-(aminocarbonyl)-4-[({4-[(3-chloro-2-fluorophenyl)amino]-7-methoxyquinazolin-6-yl}methyl)(methyl)amino]piperidine-1-carboxylate (0.35 g, 0.612 mmol) in dichloromethane (1 ml) at room temperature. The resulting solution was stirred for 1 hour, concentrated to dryness and the residue re-dissolved in dichloromethane (1 ml). 4.0 M hydrogen chloride in dioxane (1 ml) was then added to give a white precipitate. This was collected by filtration, washed with diethyl ether (2×10 ml) and dried to a constant weight to give 4-[({4-[(3-chloro-2-fluorophenyl)amino]-7-methoxyquinazolin-6-yl}methyl)(methyl)amino]piperidine-4-carboxamide hydrochloride (0.35 g, 100%), as a white solid; Mass Spectrum: (M+H)+ 473.

EXAMPLE 65

1-acetyl-4-[({4-[(3-chloro-2-fluorophenyl)amino]-7-methoxyquinazolin-6-yl}methyl)(methyl)amino]piperidine-4-carboxamide

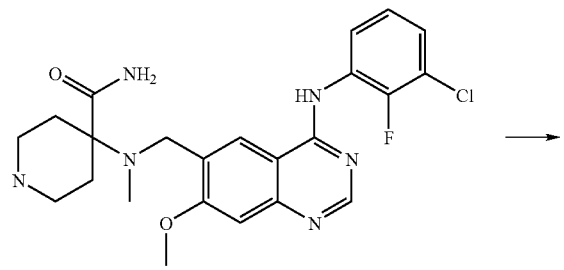

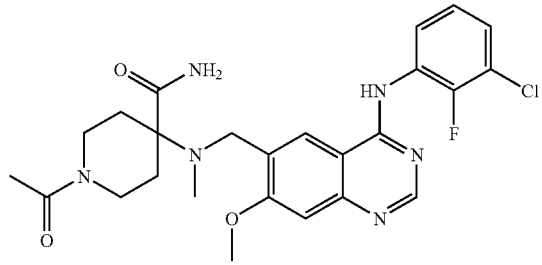

Acetyl chloride (7 μl, 0.094 mmol) was added to a stirred solution of 4-[({4-[(3-chloro-2-fluorophenyl)amino]-7-methoxyquinazolin-6-yl}methyl)(methyl)amino]piperidine-4-carboxamide hydrochloride (0.05 g, 0.085 mmol, prepared as described in Example 64) and triethylamine (53 μl, 0.38 mmol) in dichloromethane (1 ml) at room temperature. The reaction mixture was stirred at room temperature for 1 hour, concentrated and purified by column chromatography on silica eluting with increasingly polar mixtures of dichloromethane/methanol (100/0-90/10) to give the title product (0.039 g, 91%) as a pale yellow solid; $^1$H NMR Spectrum: (DMSO-d$_6$) 1.75-1.98 (m, 2H), 2.05 (m, 5H), 2.19 (s, 3H), 3.32-3.75 (m, 6H), 3.94 (s, 3H), 7.20 (s, 1H), 7.26 (m, 2H), 7.34 (t, 1H), 7.51-7.57 (m, 2H), 8.38 (s, 1H), 8.46 (s, 1H), 9.80 (s, 1H); Mass Spectrum: (M+H)+ 515.

EXAMPLE 66

4-[({4-[(3-chloro-2-fluorophenyl)amino]-7-methoxyquinazolin-6-yl}methyl)(methyl)amino]-1-(methylsulfonyl)piperidine-4-carboxamide

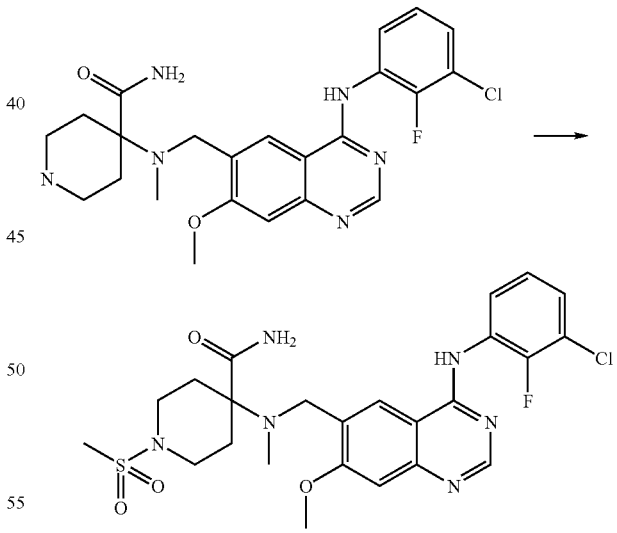

Methanesulfonyl chloride (7.5 μl, 0.094 mmol) was added to a stirred solution of 4-[({4-[(3-chloro-2-fluorophenyl)amino]-7-methoxyquinazolin-6-yl}methyl)(methyl)amino]piperidine-4-carboxamide hydrochloride (0.05 g, 0.085 mmol) and triethylamine (53 μl, 0.38 mmol) in dichloromethane (1 ml) at room temperature. The reaction mixture was stirred at room temperature for 1 hour, concentrated and purified by preparative LCMS (standard basic system) to give the title product (0.0107 g, 23%) as a white solid; $^1$H NMR Spectrum: (DMSO-d$_6$) 1.98 (m, 2H), 2.22 (m, 2H), 2.36 (s, 3H), 2.84 (s, 3H), 2.96 (m, 2H), 3.44 (m, 2H), 3.66 (s, 2H), 3.98 (s, 3H), 7.19 (s, 1H), 7.26-7.30 (m, 3H), 7.52-7.53 (m, 2H), 8.33 (s, 1H), 8.42 (s, 1H), 9.70 (s, 1H); Mass Spectrum: (M+H)+ 551.

EXAMPLE 67

4-[({4-[(3-chloro-2-fluorophenyl)amino]-7-methoxyquinazolin-6-yl}methyl)(methyl)amino]-1-[(2S)-2-hydroxypropanoyl]piperidine-4-carboxamide

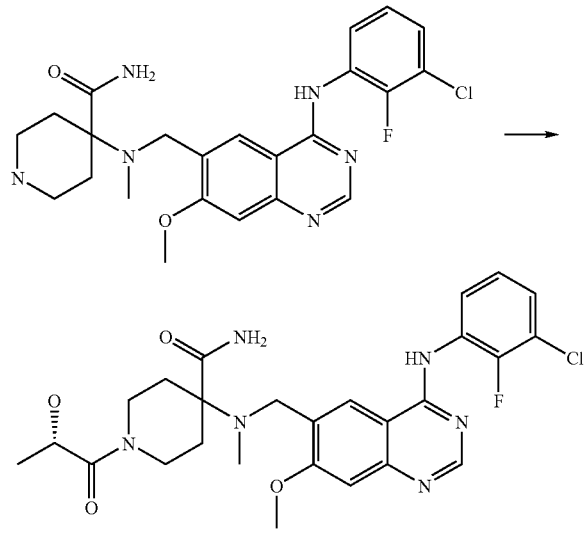

DIPEA (0.120 g, 0.92 mmol) and L-lactic acid (0.083 g, 0.92 mmol) were added to a stirred solution of 4-[({4-[(3-chloro-2-fluorophenyl)amino]-7-methoxyquinazolin-6-yl}methyl)(methyl)amino]piperidine-4-carboxamide hydrochloride (0.10 g, 0.184 mmol) in dimethylformamide at room temperature. O-(1H-Benzotriazol-1-yl)-N,N,N'N'-tetramethyluronium tetrafluoroborate (0.295 g, 0.92 mmol) was added and the reaction mixture was stirred for 30 minutes, concentrated and purified by preparative LCMS (standard acidic system) to give the title product (0.044 g, 43.4%) as a white solid; $^{1}$H NMR Spectrum: (DMSO-d$_{6}$) 1.29 (d, 3H), 1.91 (m, 2H), 2.06 (m, 2H), 2.20 (m, 3H), 3.34 (m, 4H), 3.65 (s, 2H), 3.94 (s, 3H), 4.45 (m, 1H), 4.83 (m, 1H), 7.19 (s, 1H), 7.29 (m, 3H), 7.49-7.57 (m, 2H), 8.34 (s, 1H), 8.42 (s, 1H), 9.73 (s, 1H); Mass Spectrum: (M+H)+ 545.

EXAMPLE 68

3-[({4-[(3-chloro-2-fluorophenyl)amino]-7-methoxyquinazolin-6-yl}methyl)(methyl)amino]-1-methylpiperidine-3-carboxamide (Process (c))

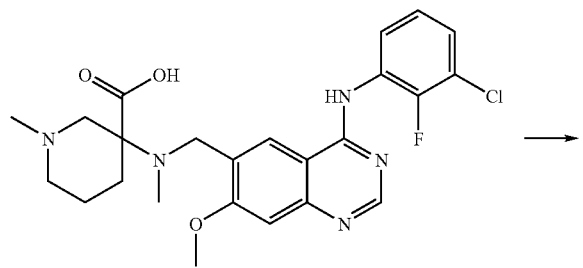

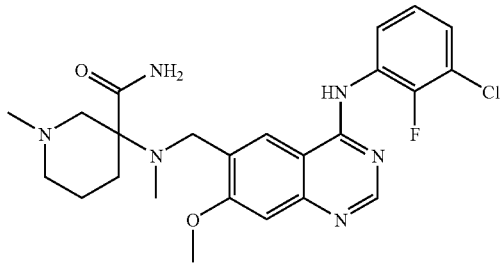

N-methylmorpholine (0.02 g, 0.20 mmol) and O-(1H-Benzotriazol-1-yl)-N,N,N'N'-tetramethyluronium tetrafluoroborate (TBTU) (0.076 g, 0.20 mmol) were added to a stirred solution of 3-[({4-[(3-chloro-2-fluorophenyl)amino]-7-methoxyquinazolin-6-yl}methyl)(methyl)amino]-1-methylpiperidine-3-carboxylic acid (0.020 g, 0.04 mmol) in dichloromethane pre-saturated with anhydrous ammonia (2 ml). The reaction mixture was stirred overnight, concentrated and purified by preparative LCMS (standard basic system) to give the title product as a white solid (0.011 g, 56%); $^{1}$H NMR Spectrum: (DMSO-d$_{6}$) 1.37 (m, 1H), 1.57 (m, 2H), 1.89 (m, 1H), 2.17 (m, 1H), 2.20 (s, 3H), 2.25 (s, 3H), 2.64 (m, 2H), 3.14 (m, 1H), 3.52 (d, 1H), 3.78 (d, 1H), 3.94 (s, 3H), 7.11 (s, 1H), 7.17 (s, 1H), 7.29 (m, 1H), 7.49-7.56 (m, 3H), 8.30 (s, 1H), 8.41 (s, 1H), 9.73 (s, 1H); Mass Spectrum: (M+H)+ 487.

The starting material 3-[({4-[(3-chloro-2-fluorophenyl)amino]-7-methoxyquinazolin-6-yl}methyl)(methyl)amino]-1-methylpiperidine-3-carboxylic acid was prepared as follows:

3-Amino-1-(tert-butoxycarbonyl)piperidine-3-carboxylic acid (Pharmacore, or may be prepared using analogous methodology described for the preparation of 4-Amino-1-(tert-butoxycarbonyl)piperidine-4-carboxylic acid in J. Org. Chem. 1996, 61, 7650-7651, 0.221 g, 0.906 mmol) and molecular sieves 4 Å (ca. 200 mg) were added to a rapidly stirred suspension of 4-[(3-chloro-2-fluorophenyl)amino]-7-methoxyquinazoline-6-carbaldehyde (0.20 g, 0.604 mmol) in a mixture of 5% v/v acetic acid in dichloromethane (2 ml). Sodium triacetoxyborohydride (0.192 g, 0.906 mmol) was added over a period of 3 hours. The reaction mixture was concentrated, dissolved in dichloromethane (1 ml) and treated with trifluoroacetic acid (1 ml). The reaction mixture was stirred for 1 hour at room temperature, concentrated and purified by preparative LCMS (acidic hydrophilic system) to afford the intermediate 3-[({4-[(3-chloro-2-fluorophenyl)amino]-7-methoxyquinazolin-6-yl}methyl)amino]piperidine-3-carboxylic acid as a white foam; Mass Spectrum: (M+H)+ 560. The foam was dissolved in aqueous formaldehyde (1 ml) and acetic acid (0.1 ml) was added followed by sodium cyanoborohydride (100 mg) at 0° C. The reaction mixture was purified directly by preparative LCMS (acidic system) to give 3-[({4-[(3-chloro-2-fluorophenyl)amino]-7-methoxyquinazolin-6-yl}methyl)(methyl)amino]-1-methylpiperidine-3-carboxylic acid (0.03 g, 10.2%) as a white foam; Mass Spectrum: (M+H)+ 488.

EXAMPLE 69

3-[({4-[(3-chloro-2-fluorophenyl)amino]-7-methoxyquinazolin-6-yl}methyl)(methyl)amino]-1-methylpyrrolidine-3-carboxamide (Process (c))

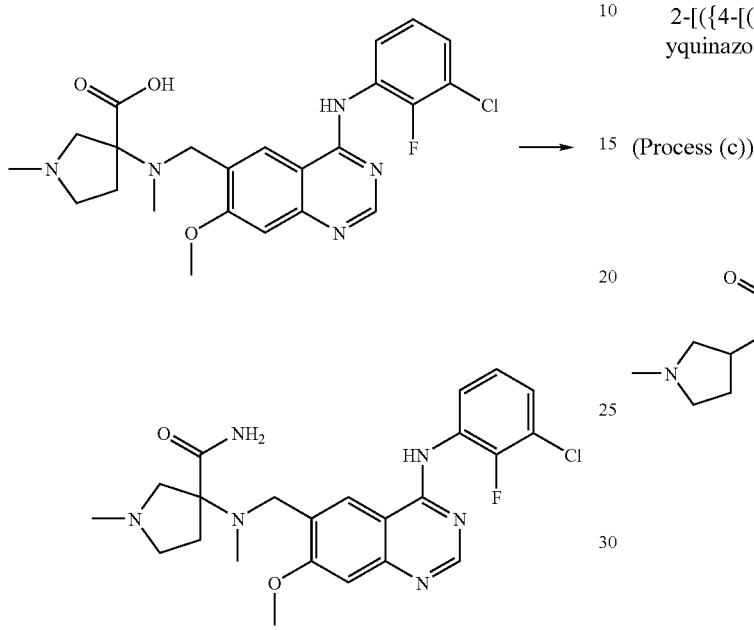

N-methylmorpholine (0.08 g, 0.80 mmol) and O-(1H-Benzotriazol-1-yl)-N,N,N'N'-tetramethyluronium tetrafluoroborate (TBTU) (0.304 g, 0.80 mmol) were added to a stirred solution of 3-[({4-[(3-chloro-2-fluorophenyl)amino]-7-methoxyquinazolin-6-yl}methyl)(methyl)amino]-1-methylpyrrolidine-3-carboxylic acid (0.075 g, 0.16 mmol) in dichloromethane pre-saturated with anhydrous ammonia (2 ml). The reaction mixture was stirred overnight, concentrated and purified by preparative LCMS (standard basic system) to give the title product as a white solid, (0.030 g, 40%); $^1$H NMR Spectrum: (DMSO-$d_6$) 1.94 (m, 1H), 2.12 (s, 3H), 2.18 (m, 4H), 2.31-2.36 (m, 2H), 2.84 (t, 1H), 2.96 (dd, 1H), 3.32 (m, 1H), 3.85 (d, 1H), 3.95 (s, 3H), 7.20 (s, 1H), 7.29 (s, 1H), 7.31 (m, 1H), 7.38 (s, 1H), 7.51-7.58 (m, 2H), 8.42 (s, 1H), 8.43 (s, 1H), 9.77 (s, 1H); Mass Spectrum: (M+H)$^+$ 473.

The starting material 3-[({4-[(3-chloro-2-fluorophenyl)amino]-7-methoxyquinazolin-6-yl}methyl)(methyl)amino]-1-methylpyrrolidine-3-carboxylic acid was prepared as follows:

4-[(3-chloro-2-fluorophenyl)amino]-7-methoxyquinazoline-6-carbaldehyde was coupled with 3-amino-1-(tert-butoxycarbonyl)pyrrolidine-3-carboxylic acid (commercially available or may be prepared made using analogous methodology as that described for the preparation of 4-amino-1-(tert-butoxycarbonyl)piperidine-4-carboxylic acid in J. Org. Chem. 1996, 61, 7650-7651). The resultant product was deprotected and methylated by reaction with aqueous formaldehyde using analogous methods to those described for the equivalent steps in Example 68 to give 3-[({4-[(3-chloro-2-fluorophenyl)amino]-7-methoxyquinazolin-6-yl}methyl)(methyl)amino]-1-methylpyrrolidine-3-carboxylic acid as a pale yellow foam; Mass Spectrum: (M+H)$^+$ 474.

EXAMPLE 70

2-[({4-[(3-chloro-2-fluorophenyl)amino]-7-methoxyquinazolin-6-yl}methyl)(methyl)amino]-2-(1-methylpyrrolidin-3-yl)acetamide (Process (c))

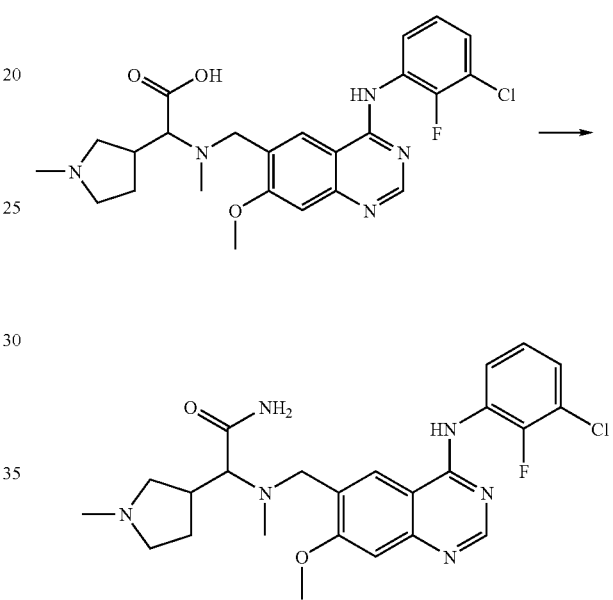

N-methylmorpholine (0.159 g, 1.55 mmol) and O-(1H-Benzotriazol-1-yl)-N,N,N'N'-tetramethyluronium tetrafluoroborate (TBTU) (0.590 g, 1.55 mmol) was added to a stirred solution of [({4-[(3-chloro-2-fluorophenyl)amino]-7-methoxyquinazolin-6-yl}methyl)(methyl)amino](1-methylpyrrolidin-3-yl)acetic acid (0.150 g, 0.31 mmol) in dichloromethane pre-saturated with anhydrous ammonia (2 ml). The reaction mixture was stirred overnight, concentrated and purified by preparative LCMS (standard basic system) to give the title product as a white solid, (0.065 g, 44%); $^1$H NMR Spectrum: (DMSO-$d_6$) 1.34 (m, 0.5H), 1.80 (m, 1H), 1.94 (m, 0.5H), 2.15 (m, 0.5H), 2.22 (m, 5.5H), 2.40 (m, 2H), 2.50-2.67 (m, 3H), 3.03 (dd, 1H), 3.66 (m, 1H), 3.84 (m, 1H), 3.95 (s, 3H), 7.06 (s, 1H), 7.19 (s, 1H), 7.29 (m, 1H), 7.43-7.57 (m, 3H), 8.28 (m, 1H), 8.43 (m, 1H), 9.76 (s, 1H); Mass Spectrum: (M+H)$^+$ 487.

The starting material [({4-[(3-chloro-2-fluorophenyl)amino]-7-methoxyquinazolin-6-yl}methyl)(methyl)amino](1-methylpyrrolidin-3-yl)acetic acid was prepared as follows:

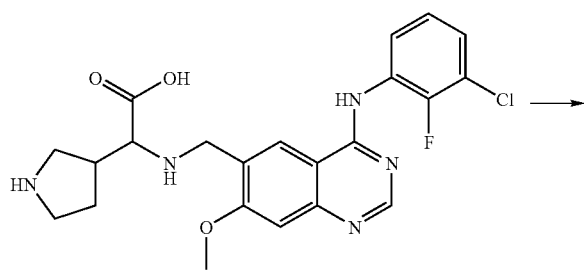
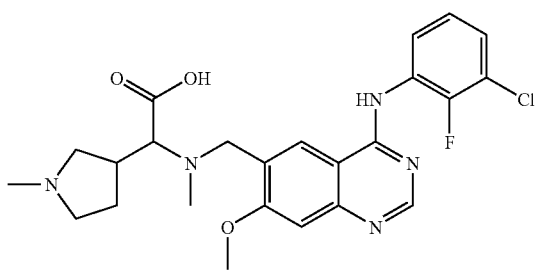

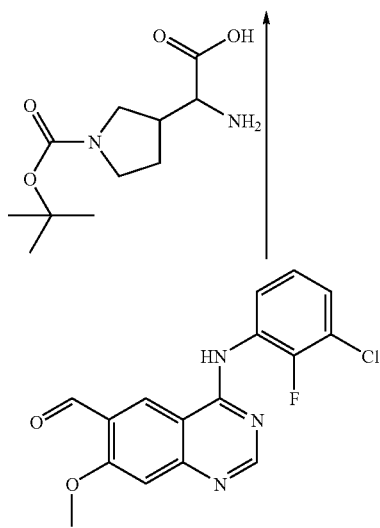

4-[(3-chloro-2-fluorophenyl)amino]-7-methoxyquinazoline-6-carbaldehyde was coupled with amino[1-(tert-butoxycarbonyl)pyrrolidin-3-yl]acetic acid, deprotected and methylated by reaction with aqueous formaldehyde using analogous methods to those described for the equivalent steps in Example 68 to give [({4-[(3-chloro-2-fluorophenyl)amino]-7-methoxyquinazolin-6-yl}methyl)(methyl)amino](1-methylpyrrolidin-3-yl)acetic acid as a pale yellow foam; Mass Spectrum: (M+H)+ 488.

EXAMPLE 71

$N^2$-{[4-[(3-chloro-2-fluorophenyl)amino]-7-(2-methoxyethoxy)quinazolin-6-yl]methyl}-D-alaninamide (Process (a))

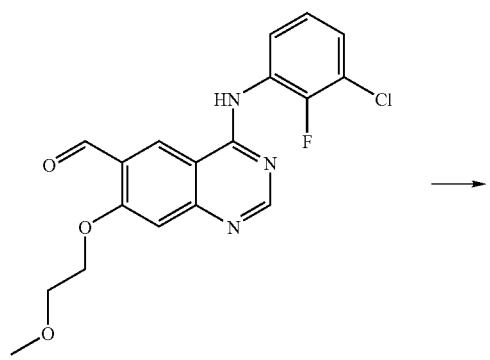

-continued

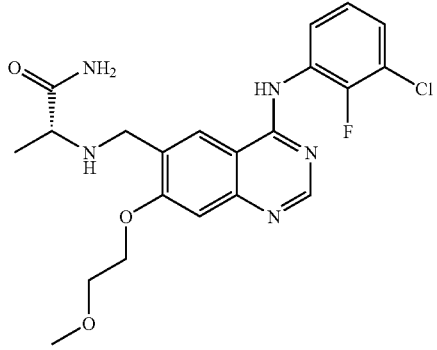

DIPEA (0.032 g, 0.25 mmol) was added to a stirred suspension of 4-[(3-chloro-2-fluorophenyl)amino]-7-(2-methoxyethoxy)quinazoline-6-carbaldehyde (0.10 g, 0.27 mmol) and D-alaninamide hydrochloride (H-D-Ala-NH$_2$.HCl) (0.031 g, 0.25 mmol) in methanol (1 ml). The resulting solution was stirred for 10 minutes and sodium triacetoxy borohydride (0.053 g, 0.25 mmol) was added over a period of 10 minutes. The reaction mixture was stirred for an additional 10 minutes, concentrated and purified by preparative LCMS (standard basic system) to give the title product as a yellow solid, (0.10 g, 84%); $^1$H NMR Spectrum: (DMSO-d$_6$) 1.24 (d, 3H), 3.29 (s, 3H), 3.61-3.74 (m, 3H), 3.74 (t, 2H), 4.29 (t, 2H), 7.11 (s, 1H), 7.24 (s, 1H), 7.30 (t, 1H), 7.36 (brs, 1H), 7.47-7.57 (m, 2H), 8.41 (s, 2H), 9.80 (s, 1H); Mass Spectrum: (M+H)+ 448.

The starting material 4-[(3-chloro-2-fluorophenyl)amino]-7-(2-methoxyethoxy)quinazoline-6-carbaldehyde was prepared as follows:

Solid anhydrous magnesium bromide (3.66 g, 19.9 mmol) was carefully added to a stirred solution of 4-[(3-chloro-2-fluorophenyl)amino]-7-methoxyquinazoline-6-carbaldehyde (2.0 g, 6.04 mmol) in pyridine (30 ml) at room temperature. The resulting suspension was heated at 130° C. for 16 hours, cooled to room temperature and concentrated to dryness to give a yellow solid. This was suspended in water (100 ml), collected by filtration and washed several times with water. The resulting yellow solid was dried to a constant weight in a vacuum oven at 40° C. to give 4-[(3-chloro-2-fluorophenyl)amino]-7-hydroxyquinazoline-6-carbaldehyde, (1.93 g, 100%); Mass Spectrum: (M+H)+ 318.

2-Chloroethyl methyl ether (0.967 g, 6.2 mmol) was added to a stirred suspension of 4-[(3-chloro-2-fluorophenyl)amino]-7-hydroxyquinazoline-6-carbaldehyde (1.0 g, 3.1 mmol) and K$_2$CO$_3$ (1.30 g, 9.45 mmol) in dimethyl formamide (10 ml) at room temperature. The resulting suspension was heated at 90° C. for 8 hours, cooled to room temperature, concentrated and purified by preparative LCMS (standard basic system) to give 4-[(3-chloro-2-fluorophenyl)amino]-7-(2-methoxyethoxy)quinazoline-6-carbaldehyde as a pale yellow solid, (0.150 g, 15%); Mass Spectrum: (M+H)+ 376.

EXAMPLE 72

N$^2$-({4-[(3-chloro-2-fluorophenyl)amino]-7-methoxyquinazolin-6-yl}methyl)-O-isopropyl-L-serinamide (Process (a))

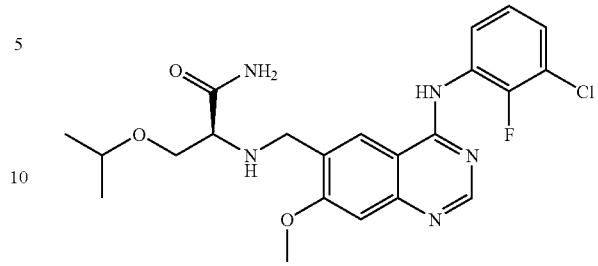

A suspension of the free base of O-isopropyl-L-serinamide {H-Ser(O-iPr)—NH$_2$} (0.132 g, 0.72 mmol) in methanol (1 ml) (liberated with DIPEA from the hydrochloride salt (0.093 g, 0.72 mmol) was added to a stirred suspension of 4-[(3-chloro-2-fluorophenyl)amino]-7-methoxyquinazoline-6-carbaldehyde (0.20 g, 0.60 mmol) and molecular sieves in a mixture of acetic acid in dichloromethane (5 ml, 5% v/v). The resulting orange solution was heated at 60° C. for 10 minutes and concentrated to 2 ml. Sodium triacetoxy borohydride (0.140 g, 0.66 mmol) was added over a period of 1 minute. The reaction mixture was stirred for an additional 10 minutes, concentrated and purified by preparative LCMS (standard acidic system) to give the title product as a white solid, (0.172 g, 62%); $^1$H NMR Spectrum: (DMSO-d$_6$) 1.10 (m, 6H), 3.20 (m, 1H), 3.33 (m, 1H), 3.50 (m, 2H), 3.78-3.88 (dd, 2H), 3.96 (s, 3H), 7.21 (s, 2H), 7.28 (t, 1H), 7.45-7.54 (m, 3H), 8.35 (s, 1H), 8.44 (s, 1H), 9.80 (s, 1H); Mass Spectrum: (M+H)+ 462.

The starting material, O-isopropyl-L-serinamide hydrochloride {H-Ser(O-iPr)—NH$_2$.HCl} was prepared as follows:

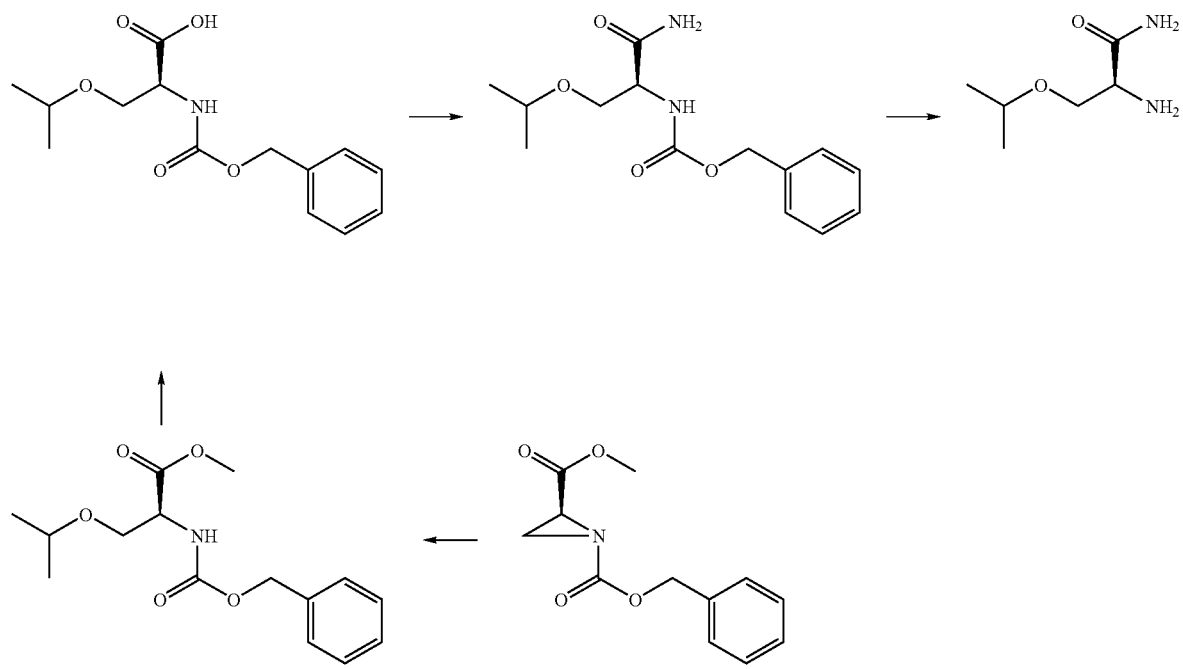

16 syringe drops of boron trifluoride diethyletherate (catalyst) was added to a stirred solution of 1-benzyl 2-methyl (2S)-aziridine-1,2-dicarboxylate (0.50 g, 2.1 mmol) in isopropanol/dichloromethane (30 ml, 1:2) at room temperature. The resulting solution was stirred overnight at room temperature. The reaction mixture was diluted with dichloromethane (20 ml), washed with a saturated aqueous sodium bicarbonate (5 ml), water (5 ml), dried over magnesium sulfate, filtered and concentrated to give methyl N-[(benzyloxy)carbonyl]-O-isopropyl-L-serinate as a clear colourless oil, (0.432 g, 68%); $^1$H NMR Spectrum: (CDCl$_3$) 1.09 (m, 6H), 3.56 (m, 1H), 3.65 (m, 1H), 3.79 (s, 3H), 3.82 (m, 1H), 4.46 (m, 1H), 5.16 (s, 2H), 5.60 (d, 1H), 7.38 (m, 5H).

Lithium hydroxide monohydrate (0.078 g, 1.86 mmol) was added to a stirred solution of methyl N-[(benzyloxy)carbonyl]-O-isopropyl-L-serinate (0.432 g, 1.47 mmol) in a mixture of tetrahydrofuran/water (10 ml, 1:1) at 0° C. The reaction mixture was stirred overnight, acidified with a 10% w/v aqueous solution of potassium hydrogensulfate and extracted with EtOAc (2×30 ml). The organic layers were combined, dried over magnesium sulfate, filtered and concentrated to give N-[(benzyloxy)carbonyl]-O-isopropyl-L-serine as a clear colourless oil, (0.346 g, 84%); $^1$H NMR Spectrum: (CDCl$_3$) 1.14 (m, 6H), 3.64 (m, 2H), 3.95 (m, 1H), 4.49 (m, 1H), 5.14 (s, 2H), 5.62 (d, 1H), 7.36 (m, 5H).

N-[(benzyloxy)carbonyl]-O-isopropyl-L-serine (0.346 g, 1.23 mmol) was dissolved in tetrahydrofuran (5 ml) and the resulting solution was cooled to −10° C. N-methyl morpholine (0.189 g, 1.84 mmol) was added, followed by isobutylchloroformate (0.21 g, 1.48 mmol) over a period of 5 minutes. The reaction mixture was stirred for 10 minutes at −10° C. and aqueous ammonia (approximately 500 μl) was added in one portion and the reaction mixture was allowed to warm to room temperature. The resulting suspension was concentrated and extracted with EtOAc (2×20 ml). The combined extracts were washed with water (5 ml), 10% w/v aqueous solution of potassium hydrogensulfate, saturated aqueous sodium bicarbonate (5 ml) and water (5 ml). The organics were dried over magnesium sulfate filtered and concentrated to give benzyl [(1S)-2-amino-1-(isopropoxymethyl)-2-oxoethyl]carbamate as a white solid, (0.340 g, 100%); $^1$H NMR Spectrum: (CDCl$_3$) 1.15 (m, 6H), 3.66 (m, 1H), 3.86 (m, 2H), 4.28 (m, 1H), 5.13 (s, 2H), 5.43 (br s, 1H), 5.72 (br s, 1H), 6.54 (br s, 1H), 7.35 (m, 5H).

A 10% Pd—C (0.03 g) catalyst was added to a solution of benzyl [(1S)-2-amino-1-(isopropoxymethyl)-2-oxoethyl] carbamate (0.340 g, 1.23 mmol) in ethanol (5 ml). The resulting suspension was exposed to 1 atmosphere of hydrogen for 30 minutes. The catalyst was removed by filtration and the filtrates evaporated to dryness. The resulting oil was dissolved in diethylether (10 ml) and a 4.0M hydrogen chloride in dioxane (1 ml) was added. The resulting precipitate was collected by filtration and dried to a constant weight at 40° C. in a vacuum oven to give O-isopropyl-L-serinamide hydrochloride as a white solid, (0.132 g, 60%); $^1$H NMR Spectrum: (DMSO-d$_6$) 1.17 (m, 6H), 3.60 (m, 1H), 3.68 (m, 2H), 3.86 (m, 1H), 7.43-7.59 (br t, 2H), 7.88 (br s, 1H), 7.98 (br s, 1H).

EXAMPLE 73

N$^2$-({4-[(3-chloro-2-fluorophenyl)amino]-7-methoxyquinazolin-6-yl}methyl)-O-isopropyl-N$^2$-methyl-L-serinamide (Process (b))

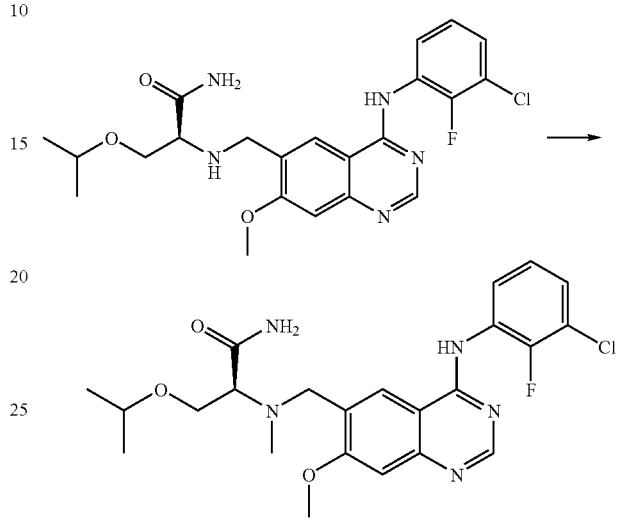

Solid sodium triacetoxy borohydride (0.076 g, 0.36 mmol) followed rapidly by aqueous formaldehyde (1 ml) was added to a stirred solution of N$^2$-({4-[(3-chloro-2-fluorophenyl) amino]-7-methoxyquinazolin-6-yl}methyl)-O-isopropyl-L-serinamide (0.15 g, 0.32 mmol Example 72) in a mixture of acetic acid in dichloromethane (5 ml, 5% v/v) in the presence of molecular sieves 4 Å. After 10 minutes the reaction mixture was concentrated and purified by preparative LCMS (standard acidic system) to afford the title compound as a white solid (0.063 g, 42%); $^1$H NMR Spectrum: (DMSO-d$_6$) 1.19 (m, 6H), 2.30 (s, 3H), 3.39 (m, 2H), 3.59 (m, 1H), 3.71 (m, 1H), 3.82 (m, 2H), 3.95 (s, 3H), 7.20 (s, 2H), 7.28 (t, 1H), 7.48-7.55 (m, 3H), 8.35 (s, 1H), 8.43 (s, 1H), 9.82 (s, 1H); Mass Spectrum: (M+H)$^+$ 476.

EXAMPLE 74

3-[({4-[(3-chloro-2-fluorophenyl)amino]-7-methoxyquinazolin-6-yl}methyl)(methyl)amino]azetidine-3-carboxamide (Process (b))

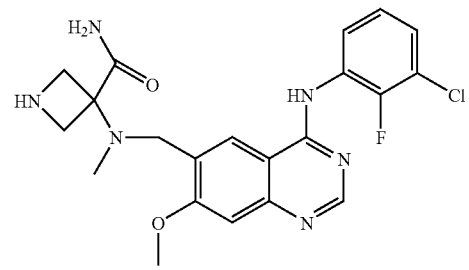

A solution of concentrated hydrochloric acid (5 ml) in 1,4-dioxan (25 ml) was added dropwise to a solution of tert-butyl 3-(aminocarbonyl)-3-[({4-[(3-chloro-2-fluorophenyl)amino]-7-methoxyquinazolin-6-yl}methyl)(methyl)amino]azetidine-1-carboxylate (303 mg, 0.56 mmol) in 1,4-dioxan (6 ml). The reaction mixture was stirred overnight, then concentrated under reduced pressure. The residues were triturated with a mixture of methanol/dichloromethane/diethyl-ether to give the hydrochloride salt of 3-[({4-[(3-chloro-2-fluorophenyl)amino]-7-methoxyquinazolin-6-yl}methyl)(methyl)amino]azetidine-3-carboxamide as a solid (330 mg, 100%); $^1$H NMR Spectrum: (DMSO-$d_6$) 2.19 (s, 3H), 3.73 (s, 2H), 3.95 (brd, 2H), 4.04 (s, 3H), 4.13 (brd, 2H), 7.38 (m, 2H), 7.56 (t, 1H), 7.61 (s, 1H), 7.66 (s, 1H), 7.75 (brs, 1H), 8.92 (s, 1H), 8.92 (brs, 1H), 9.30 (s, 1H), 9.80 (brs, 1H); Mass Spectrum: (M+H)$^+$ 445.

The preparation of the starting material tert-butyl 3-(aminocarbonyl)-3-[({4-[(3-chloro-2-fluorophenyl)amino]-7-methoxyquinazolin-6-yl}methyl)(methyl)amino]azetidine-1-carboxylate was as follows:

N,N-diisopropylethylamine (0.22 ml, 1.24 mmol) was added to a solution of N-(3-chloro-2-fluorophenyl)-6-(chloromethyl)-7-methoxyquinazolin-4-amine (160 mg, 0.41 mmol prepared as described in Example 62) in dimethylformamide (1 ml). After 5 minutes of stirring, the reaction mixture became homogeneous and tert-butyl 3-(aminocarbonyl)-3-(methylamino)azetidine-1-carboxylate (98 mg, 0.43 mmol) was added. After 30 minutes of stirring at 80° C., the reaction mixture was cooled down to room temperature, water was added and the aqueous layer was extracted with ethyl acetate (×2). The combined organics were dried over magnesium sulfate, filtered and concentrated under reduced pressure. The residues were purified by column chromatography on silica eluting with increasingly polar mixtures of methanol/dichloromethane (0/100-5/95) to give tert-butyl 3-(aminocarbonyl)-3-[({4-[(3-chloro-2-fluorophenyl)amino]-7-methoxyquinazolin-6-yl}methyl)(methyl)amino]azetidine-1-carboxylate as a yellow solid, (100 mg, 44%); $^1$H NMR Spectrum: (CDCl$_3$) 1.46 (s, 9H), 2.39 (s, 3H), 3.82 (s, 2H), 3.99 (s, 3H), 4.17 (d, 2H), 4.25 (brd, 2H), 5.47 (brs, 1H), 6.79 (brs, 1H), 7.17 (m, 2H), 7.29 (s, 1H), 7.66 (brs, 1H), 7.83 (s, 1H), 8.49 (brs, 1H), 8.75 (s, 1H); Mass Spectrum: (M+H)$^+$ 545.

The 3-(aminocarbonyl)-3-(methylamino)azetidine-1-carboxylate starting material were prepared as follows:

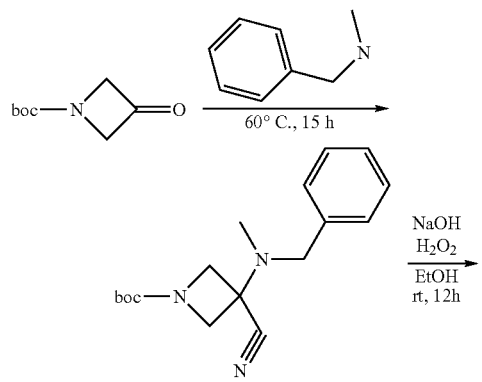

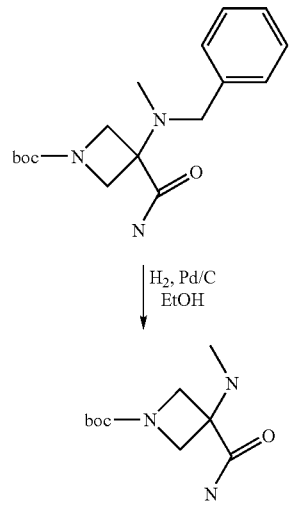

Methylbenzylamine (1.42 ml, 11 mmol) and acetic acid (0.63 ml, 11 mmol) in 2 ml of water were added to a solution of tert-butyl 3-oxoazetidine-1-carboxylate (1.5 g, 8.77 mmol) in diethylether (1.5 ml). After five minutes, a solution of sodium cyanide (451 mg, 9.21 mmol) in 1 ml of water was added, and the mixture was heated at 60° C. for 15 hours. After cooling the reaction mixture was extracted with ethyl acetate (×2), washed with brine, dried over magnesium sulfate, filtered and concentrated under reduced pressure. The resulting residues were purified by column chromatography on silica eluting with ethyl acetate in petroleum ether (5/95) to give tert-butyl 3-[benzyl(methyl)amino]-3-cyanoazetidine-1-carboxylate as a pale yellow oil, (2.52 g, 96%); $^1$H NMR Spectrum: (CDCl$_3$) 1.46 (s, 9H), 2.18 (s, 3H), 3.42 (s, 2H), 4.00 (d, 2H), 4.17 (d, 2H), 7.26-7.35 (m, 5H).

A 1M solution of sodium hydroxide (12.5 ml, 12.5 mmol) at 0° C. was added dropwise to a solution of 3-[benzyl(methyl)amino]-3-cyanoazetidine-1-carboxylate (800 mg, 2.66 mmol) in ethanol (25 ml). Hydrogen peroxide 30% wt (1 ml) was then added and the reaction mixture was allowed to stir at room temperature overnight. After removal of solvent under reduced pressure, the remaining aqueous layer was extracted with ethyl acetate (×2) and the combined organic layers washed with water, dried over magnesium sulfate, filtered and concentrated under reduced pressure to afford tert-butyl 3-(aminocarbonyl)-3-[benzyl(methyl)amino]azetidine-1-carboxylate (702 mg, 87%) as a white solid, used without any further purification in the next step; $^1$H NMR Spectrum: (CDCl$_3$) 1.45 (s, 9H), 2.27 (s, 3H), 3.61 (s, 2H), 4.07 (d, 2H), 4.22 (brd, 2H), 5.51 (brs, 1H), 6.70 (brs, 1H), 7.26-7.36 (m, 5H); Mass Spectrum: (M+H)$^+$ 320.

10% wt Palladium on charcoal (160 mg) in ethyl acetate (2 ml) was added to a solution of 3-[benzyl(methyl)amino]-3-(aminocarbonyl)azetidine-1-carboxylate (500 mg, 1.57 mmol) in ethanol (45 ml). After addition of a few drops of saturated hydrogen chloride in dichloromethane, the reaction mixture was stirred at room temperature under 2 bars of hydrogen for 3 hours. Filtration of the catalyst and concentration under reduced pressure afforded tert-butyl 3-(aminocarbonyl)-3-(methylamino)azetidine-1-carboxylate (335 mg, 93%) as a white solid; ¹H NMR Spectrum: (CDCl₃) 1.44 (s, 9H), 2.35 (s, 3H), 3.71 (d, 2H), 4.29 (brd, 2H), 5.51 (brs, 1H), 6.95 (brs, 1H).

EXAMPLE 75

3-[({4-[(3-chloro-2-fluorophenyl)amino]-7-methoxyquinazolin-6-yl}methyl)(ethyl)amino]azetidine-3-carboxamide (Process (b))

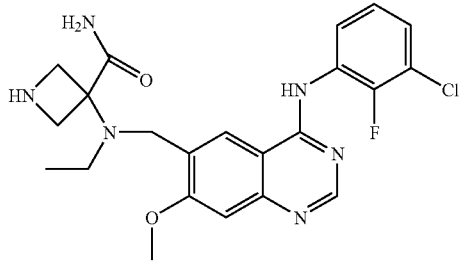

N-(3-Chloro-2-fluorophenyl)-6-(chloromethyl)-7-methoxyquinazolin-4-amine (360 mg, 0.93 mmol, prepared as described in Example 62) was added portionwise over 2 hours to a solution of tert-butyl 3-(aminocarbonyl)-3-(ethylamino)azetidine-1-carboxylate (294 mg, 1.21 mmol) and diisopropylethylamine (0.5 ml, 2.79 mmol) in DMF (1 ml) at 120° C. The resulting product was purified on preparative HPLC (standard basic conditions) to give tert-butyl 3-(aminocarbonyl)-3-[({4-[(3-chloro-2-fluorophenyl)amino]-7-methoxyquinazolin-6-yl}methyl)(ethyl)amino]azetidine-1-carboxylate as a solid (100 mg, 19%); Mass Spectrum: (M+H)⁺ 559. This was dissolved in 1,4-dioxan (3 ml) and a solution of concentrated hydrochloric acid (5 ml) in 1,4-dioxan (25 ml) was added dropwise. The reaction mixture was stirred overnight and concentrated under reduced pressure. The residues were triturated with a mixture of methanol/dichloromethane/diethylether to give a hydrochloride salt of 3-[({4-[(3-chloro-2-fluorophenyl)amino]-7-methoxyquinazolin-6-yl}methyl)(ethyl)amino]azetidine-3-carboxamide as a solid (89 mg, 100%); ¹H NMR Spectrum: (CDCl₃) 1.16 (t, 3H), 2.59 (q, 2H), 3.41 (d, 2H), 3.76 (d, 2H), 3.89 (s, 2H), 3.98 (s, 3H), 5.47 (brs, 1H), 7.15 (m, 2H), 7.24 (s, 1H), 7.77 (s, 1H), 7.90 (s, 1H), 8.44 (m, 1H), 8.72 (s, 1H); Mass Spectrum: (M+H)⁺ 459.

The tert-butyl 3-[benzyl(ethyl)amino]-3-cyanoazetidine-1-carboxylate starting material was prepared analogously as for the equivalent steps in Example 74 but using ethylbenzylamine in place of methylbenzylamine; ¹H NMR Spectrum: (CDCl₃) 1.13 (t, 3H), 1.44 (s, 9H), 2.54 (m, 2H), 3.71 (d, 2H), 4.29 (brd, 2H), 5.48 (brs, 1H), 6.96 (brs, 1H).

EXAMPLE 76

3-[({4-[(3-chloro-2-fluorophenyl)amino]-7-methoxyquinazolin-6-yl}methyl)(methyl)amino]-1-methylazetidine-3-carboxamide (Process (d))

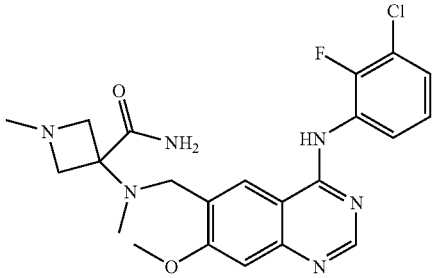

The hydrochloride salt of 3-[({4-[(3-chloro-2-fluorophenyl)amino]-7-methoxyquinazolin-6-yl}methyl)(methyl)amino]azetidine-3-carboxamide Example 74 (100 mg, 0.19 mmol) and formaldehyde (51 μl of a 37% wt aqueous solution, 0.63 mmol) were stirred at room temperature in 5% acetic acid in 1,2-dichloroethane (2 ml) in the presence of 3 A molecular sieves. Sodium triacetoxyborohydride (89 mg, 0.42 mmol) was added portionwise over 0.5 hours. After the final addition the reaction mixture was concentrated under reduced pressure. The resulting product was purified on preparative HPLC (standard basic conditions) to give the title product (50 mg, 53%) as a white powder; ¹H NMR Spectrum: (CDCl₃) 2.41 (s, 3H), 2.45 (s, 3H), 3.35 (brs, 2H), 3.65 (d, 2H), 3.96-4.01 (m, 5H), 5.33 (brs, 1H), 7.15 (m, 2H), 7.25 (s, 1H), 7.47 (brs, 1H), 7.77 (brs, 1H), 7.98 (s, 1H), 8.55 (brs, 1H), 8.74 (s, 1H); Mass Spectrum: (M+H)⁺ 459.

EXAMPLE 77

3-[({4-[(3-chloro-2-fluorophenyl)amino]-7-methoxyquinazolin-6-yl}methyl)(ethyl)amino]-1-methylazetidine-3-carboxamide (Process (d))

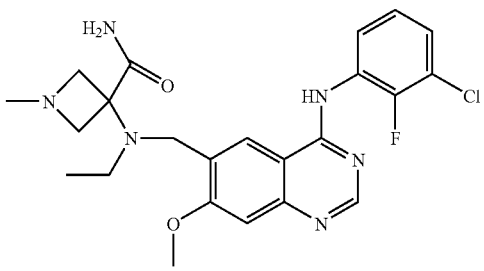

3-[({4-[(3-chloro-2-fluorophenyl)amino]-7-methoxyquinazolin-6-yl}methyl)(ethyl)amino]azetidine-3-carboxamide hydrochloride salt (Example 75) was coupled with aqueous formaldehyde using the same method as for the equivalent step in Example 76 to give 3-[({4-[(3-chloro-2-fluorophenyl)amino]-7-methoxyquinazolin-6-yl}methyl)(ethyl)amino]-1-methylazetidine-3-carboxamide (55%) as a white powder; ¹H NMR Spectrum: (CDCl₃) 1.03 (t, 3H), 2.45

(s, 3H), 2.83 (q, 2H), 3.37 (brs, 2H), 3.65 (m, 2H), 3.97 (s, 3H), 4.05 (s, 2H), 5.41 (brs, 1H), 7.16 (m, 2H), 7.22 (s, 1H), 7.47 (brs, 1H), 7.95 (brs, 1H), 8.28 (s, 1H), 8.59 (m, 1H), 8.76 (s, 1H); Mass Spectrum: (M+H)+ 473.

EXAMPLE 78

3-[({4-[(3-chloro-2-fluorophenyl)amino]-7-methoxyquinazolin-6-yl}methyl)(methyl)amino]-1-isopropylazetidine-3-carboxamide (Process (d))

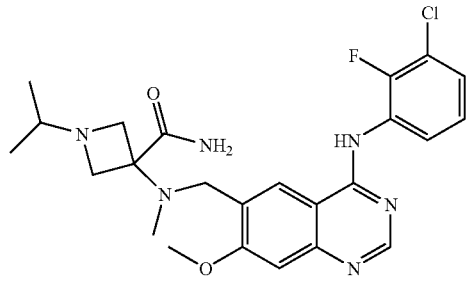

3-[({4-[(3-chloro-2-fluorophenyl)amino]-7-methoxyquinazolin-6-yl}methyl)(methyl)amino]azetidine-3-carboxamide hydrochloride salt Example 74 was coupled with acetone using the same method as for the equivalent step in Example 76 to give the title product (50 mg, 50%) as a white powder; ¹H NMR Spectrum: (CDCl₃) 0.95 (d, 6H), 2.42 (s, 3H), 2.49 (brs, 1H), 3.24 (brs, 2H), 3.63 (d, 2H), 3.97 (m, 5H), 5.32 (brs, 1H), 7.14 (m, 2H), 7.24 (s, 1H), 7.65 (brs, 1H), 7.75 (brs, 1H), 7.99 (s, 1H), 8.54 (brs, 1H), 8.73 (s, 1H); Mass Spectrum: (M+H)+ 487.

EXAMPLE 79

3-[({4-[(3-chloro-2-fluorophenyl)amino]-7-methoxyquinazolin-6-yl}methyl)(ethyl)amino]-1-[3-(dimethylamino)-1-methyl-3-oxopropyl]azetidine-3-carboxamide (Process (d))

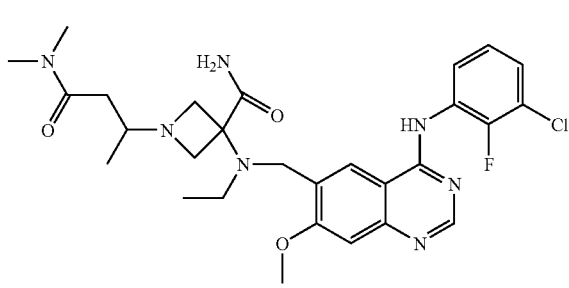

3-[({4-[(3-chloro-2-fluorophenyl)amino]-7-methoxyquinazolin-6-yl}methyl)(ethyl)amino]azetidine-3-carboxamide hydrochloride salt Example 75 was coupled with N,N-dimethylacetoacetamide using the same methodology as for the equivalent step in Example 76 to give the title product (58 mg, 50%) as a white powder; ¹H NMR Spectrum: (CDCl₃) 1.05 (d, 3H), 2.22 (m, 1H), 2.41 (s, 3H), 2.45 (m, 1H), 2.92 (s, 3H), 2.98 (m, 1H), 3.03 (s, 3H), 3.31 (m, 2H), 3.61 (m, 2H), 3.96 (s, 2H), 3.98 (s, 3H), 5.33 (brs, 1H), 7.17 (m, 2H), 7.24 (s, 1H), 7.51 (brs, 1H), 7.87 (brs, 1H), 7.99 (s, 1H), 8.44 (m, 1H), 8.72 (s, 1H); Mass Spectrum: (M+H)+ 558.

EXAMPLE 80

3-[({4-[(3-chloro-2-fluorophenyl)amino]-7-methoxyquinazolin-6-yl}methyl)(methyl)amino]-1-(2-hydroxyethyl)azetidine-3-carboxamide

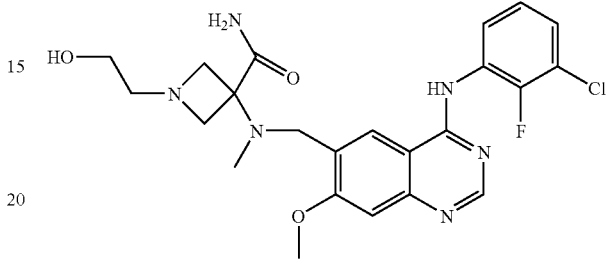

A solution of the hydrochloride salt of 3-[({4-[(3-chloro-2-fluorophenyl)amino]-7-methoxyquinazolin-6-yl}methyl)(methyl)amino]azetidine-3-carboxamide (100 mg, 0.19 mmol Example 74), diisopropylethylamine (100 μl, 0.58 mmol), 2-chloroethanol (60 μl, 0.58 mmol) and potassium iodide (32 mg, 0.19 mmol) in acetonitrile (1.5 ml) was heated in a microwave at 160° C. for 20 minutes. Purification of the resulting product on preparative HPLC (standard basic condition) gave the title product (10 mg, 11%) as a white solid; ¹H NMR Spectrum: (CDCl₃) 2.40 (s, 3H), 2.75 (t, 2H), 3.47 (s, 2H), 3.61 (t, 2H), 3.70 (s, 2H), 3.93 (s, 3H), 3.93 (s, 2H), 5.41 (brs, 1H), 6.79 (brs, 1H), 7.18 (m, 2H), 7.21 (s, 1H), 7.75 (brs, 1H), 7.86 (s, 1H), 8.52 (brs, 1H), 8.74 (s, 1H); Mass Spectrum: (M+H)+ 489.

EXAMPLE 81

3-[({4-[(3-chloro-2-fluorophenyl)amino]-7-methoxyquinazolin-6-yl}methyl)(methyl)amino]-1-(2-methoxyethyl)azetidine-3-carboxamide

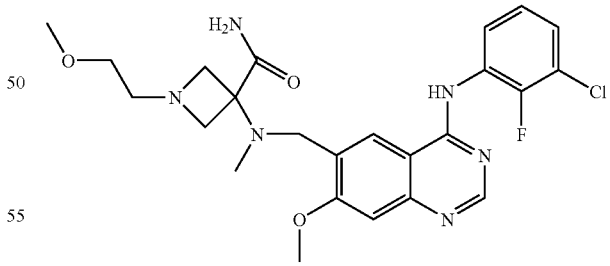

A solution of the hydrochloride salt of 3-[({4-[(3-chloro-2-fluorophenyl)amino]-7-methoxyquinazolin-6-yl}methyl)(methyl)amino]azetidine-3-carboxamide (55 mg, 0.11 mmol Example 74), diisopropylethylamine (84 μl, 0.48 mmol), 2-chloroethyl methyl ether (29 μl, 0.32 mmol) and potassium iodide (18 mg, 0.11 mmol) in acetonitrile (0.5 ml) was heated in a microwave at 145° C. for 30 minutes. Purification of the crude product on preparative HPLC (standard basic condition) gave the title product (20 mg, 36%) as a white solid; ¹H NMR Spectrum: (CDCl₃) 2.41 (s, 3H), 2.76 (t, 2H), 3.34 (s, 3H), 3.36 (d, 2H), 3.44 (t, 2H), 3.66 (d, 2H), 3.96 (s, 3H), 4.00 (s, 2H), 5.38 (brs, 1H), 7.16 (m, 2H), 7.24 (s, 1H), 7.21 (s, 1H), 7.42 (brs, 1H), 7.87 (brs, 1H), 8.01 (s, 1H), 8.75 (m, 1H); Mass Spectrum: (M+H)⁺ 503.

EXAMPLE 82

1-acetyl-3-[({4-[(3-chloro-2-fluorophenyl)amino]-7-methoxyquinazolin-6-yl}methyl)(methyl)amino]azetidine-3-carboxamide

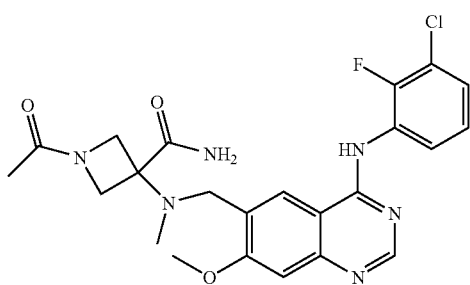

Diisopropylethylamine (0.11 ml, 0.63 mmol) and then HATU (95 mg, 0.25 mmol) were added to a solution of acetic acid (18 µl, 0.31 mmol) in dichloromethane (1 ml). After 10 minutes, the hydrochloride salt of 3-[({4-[(3-chloro-2-fluorophenyl)amino]-7-methoxyquinazolin-6-yl}methyl)(methyl)amino]azetidine-3-carboxamide (100 mg, 0.21 mmol Example 74) was added and the mixture stirred overnight at room temperature. After removal of the solvent, the resulting product was dissolved in dimethylformamide and purified on preparative HPLC (standard basic conditions) to give the title product as a powder (52 mg, 51%); ¹H NMR Spectrum: (CDCl₃) 1.92 (d, 3H), 2.38 (s, 3H), 3.70 (d, 1H), 3.83 (d, 1H), 3.98 (s, 3H), 4.18-4.27 (m, 3H), 4.55 (d, 1H), 5.80 (brs, 1H), 6.94 (brs, 1H), 7.15 (m, 2H), 7.29 (s, 1H), 7.96 (brs, 2H), 8.34 (brs, 1H), 8.72 (s, 1H); Mass Spectrum: (M+H)⁺ 487.

EXAMPLE 83

1-[({4-[(3-chloro-2-fluorophenyl)amino]-7-methoxyquinazolin-6-yl}methyl)(ethyl)amino]cyclopropanecarboxamide (Process (c))

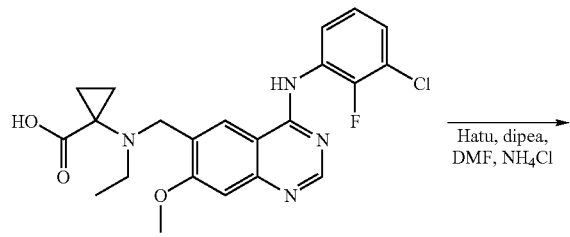

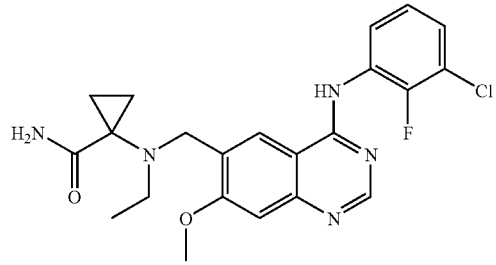

1-[({4-[(3-chloro-2-fluorophenyl)amino]-7-methoxyquinazolin-6-yl}methyl)(ethyl)amino]cyclopropanecarboxylic acid was coupled with ammonium chloride using an analogous method to that described for the equivalent step in Example 16 to give the title product; ¹H NMR Spectrum: (DMSO d₆) 0.98 (t, 3H), 1.07 (m, 4H); 2.45-2.60 (m, 2H+DMSO), 3.76 (s, 2H), 3.95 (s, 3H), 7.08 (bs, 1H); 7.20 (s, 1H); 7.28 (dd, 1H), 7.42-7.60 (m, 3H), 8.29 (s, 1H), 8.42 (s, 1H); 9.71 (s, 1H); Mass Spectrum: (M+H)⁺ 444.

The 1-[({4-[(3-chloro-2-fluorophenyl)amino]-7-methoxyquinazolin-6-yl}methyl)(ethyl)amino]cyclopropanecarboxylic acid used as starting material was prepared as follows:

1-[({4-[(3-Chloro-2-fluorophenyl)amino]-7-methoxyquinazolin-6-yl}methyl)amino]cyclopropanecarboxylic acid (prepared as described in Example 27) was reacted with acetaldehyde using an analogous method to that described for the equivalent step in Example 24 to give 1-[({4-[(3-chloro-2-fluorophenyl)amino]-7-methoxyquinazolin-6-yl}methyl)(ethyl)amino]cyclopropanecarboxylic acid; ¹H NMR Spectrum: (DMSO d₆) 0.90 (t, 3H); 0.95-1.30 (m, 4H); 2.90 (m, 2H); 3.91 (s, 3H); 4.08 (s, 2H); 7.12 (s, 1H); 7.28 (dd, 1H); 7.40-7.60 (m, 2H); 8.20 (s, 1H); 8.40 (s, 1H); 9.65 (bs, 1H), 12.18 (bs, 1H); Mass Spectrum: (M+H)⁺ 445.

EXAMPLE 84

1-[({4-[(3-chloro-2-fluorophenyl)amino]-7-methoxyquinazolin-6-yl}methyl)(ethyl)amino]-N-methylcyclopropanecarboxamide (Process (c))

1-[({4-[(3-chloro-2-fluorophenyl)amino]-7-methoxyquinazolin-6-yl}methyl)(ethyl)amino]cyclopropanecarboxylic acid (Example 83) was coupled with methylamine hydrochloride using an analogous method to that described for the equivalent step in Example 20 to give the title product; ¹H NMR Spectrum: (DMSO d₆) 0.90-1.15 (m, 7H); 2.40-2.60 (m, 2H+DMSO); 2.62 (d, 3H); 3.70 (s, 2H), 3.99 (s, 3H); 7.22

(s, 1H); 7.29 (dd, 1H); 7.40-7.60 (m, 2H); 7.92 (m, 1H); 8.30 (s, 1H); 8.42 (s, 1H); 9.68 (s, 1H). Mass Spectrum: (M+H)+ 458.

EXAMPLE 85

(3S)-3-[({4-[(3-Chloro-2-fluorophenyl)amino]-7-methoxyquinazolin-6-yl}methyl)amino]piperidin-2-one (Process (a))

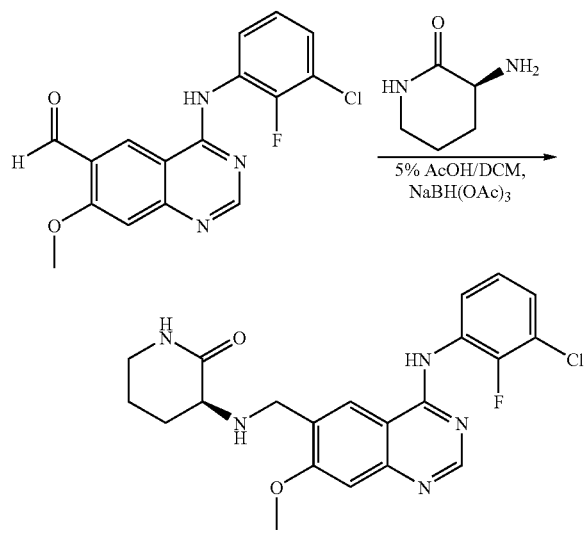

4-(3-Chloro-2-fluoroanilino)-7-methoxyquinazoline-6-carbaldehyde was coupled with (3S)-3-aminopiperidin-2-one (prepared from L-ornithine according to the method in Synthesis 1978, 614) using an analogous method to that described for the equivalent step in Example 1 to give the title product; ¹H NMR Spectrum: (DMSO d₆) 1.54 (m, 1H); 1.68 (m, 1H); 1.84 (m, 1H); 2.16 (m, 1H); 2.73 (brs, 1H); 3.05 (dd, 1H); 3.13 (m, 2H); 3.84 (d, 1H); 3.93 (d, 1H); 3.98 (s, 3H); 7.21 (s, 1H); 7.28 (t, 1H); 7.48 (t, 1H); 7.53 (m, 2H); 8.35 (s, 1H); 8.44 (s, 1H); 9.80 (s, 1H). Mass Spectrum: (M+H)+ 430.

EXAMPLE 86

(3S)-3-[({4-[(3-chloro-2-fluorophenyl)amino]-7-methoxyquinazolin-6-yl}methyl)(methyl)amino]piperidin-2-one (Process (d))

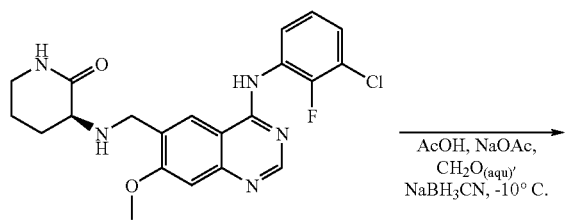

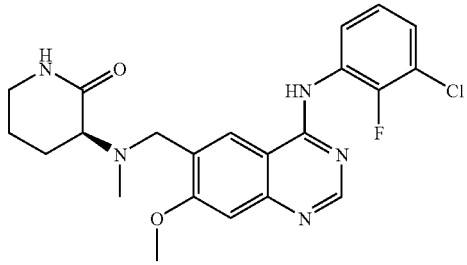

(3S)-3-[({4-[(3-Chloro-2-fluorophenyl)amino]-7-methoxyquinazolin-6-yl}methyl)amino]piperidin-2-one (165 mg, 0.38 mmol, Example 85) was dissolved in 37% aqueous formaldehyde (2 ml) and acetic acid (0.22 ml, 3.84 mmol) and sodium acetate (315 mg, 3.84 mmol) added. The mixture was cooled to −10° C. and sodium cyanoborohydride (24 mg, 0.38 mmol) added. The mixture was stirred for 15 minutes and then purified by reverse phase HPLC to give the title product (114 mg, 67%) as a white solid; ¹H NMR Spectrum: (DMSO d₆) 1.77 (m, 3H); 2.02 (m, 1H); 2.40 (s, 3H); 3.09 (m, 2H); 3.29 (dd, 1H); 3.95 (s, 5H); 7.18 (s, 1H); 7.28 (t, 1H); 7.40 (brs, 1H); 7.48 (t, 1H); 7.55 (m, 1H); 8.35 (s, 1H); 8.42 (s, 1H); 9.76 (s, 1H). Mass Spectrum: (M+H)+ 444.

EXAMPLE 87

(3R)-3-[({4-[(3-chloro-2-fluorophenyl)amino]-7-methoxyquinazolin-6-yl}methyl)amino]piperidin-2-one (Process (a))

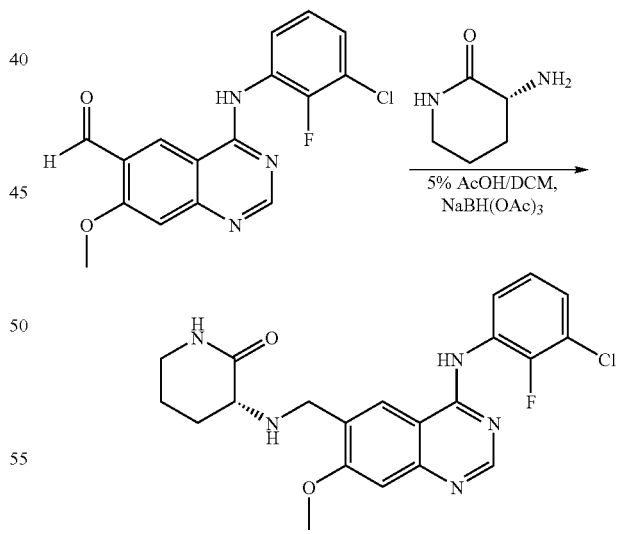

4-(3-Chloro-2-fluoroanilino)-7-methoxyquinazoline-6-carbaldehyde was coupled with (3R)-3-aminopiperidin-2-one (prepared from R-ornithine according to the method in Synthesis 1978, 614) using an analogous method to that described for the equivalent step in Example 1 to give the title product; ¹H NMR Spectrum (DMSO d₆) 1.54 (m, 1H); 1.68 (m, 1H); 1.84 (m, 1H); 2.16 (m, 1H); 2.73 (brs, 1H); 3.05 (dd, 1H); 3.13 (m, 2H); 3.84 (d, 1H); 3.93 (d, 1H); 3.98 (s, 3H);

7.21 (s, 1H); 7.28 (t, 1H); 7.48 (t, 1H); 7.53 (m, 2H); 8.35 (s, 1H); 8.44 (s, 1H); 9.80 (s, 1H); Mass Spectrum: (M+H)+ 430.

EXAMPLE 88

(3R)-3-[({4-[(3-chloro-2-fluorophenyl)amino]-7-methoxyquinazolin-6-yl}methyl)(methyl)amino]piperidin-2-one (Process (d))

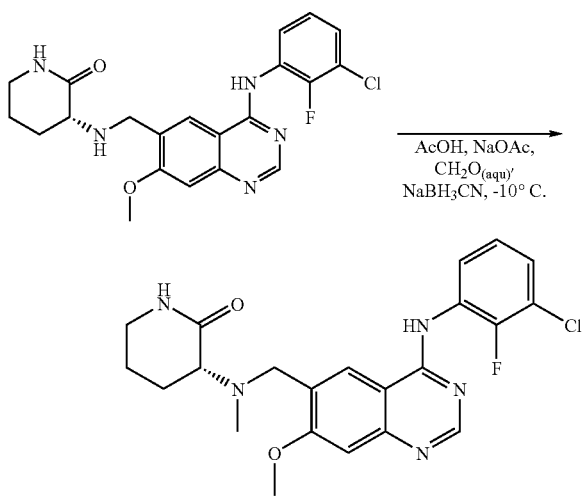

(3R)-3-[({4-[(3-chloro-2-fluorophenyl)amino]-7-methoxyquinazolin-6-yl}methyl)amino]piperidin-2-one (Example 87) was reacted with 37% aqueous formaldehyde using an analogous method to that described for the equivalent step in Example 86 to give the title product; 1H NMR Spectrum: (DMSO d6) 1.77 (m, 3H); 2.02 (m, 1H); 2.40 (s, 3H); 3.09 (m, 2H); 3.29 (dd, 1H); 3.95 (s, 5H); 7.18 (s, 1H); 7.28 (t, 1H); 7.40 (brs, 1H); 7.48 (t, 1H); 7.55 (m, 1H); 8.35 (s, 1H); 8.42 (s, 1H); 9.76 (s, 1H). Mass Spectrum: (M+H)+ 444.

EXAMPLES 89 and 89.1

(R or S)-3-[({4-[(3-chloro-2-fluorophenyl)amino]-7-methoxyquinazolin-6-yl}methyl)(methyl)amino]-N-methyl-1-(methylsulfonyl)piperidine-3-carboxamide (Isomer 1)

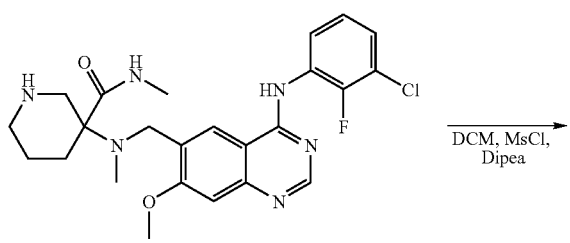

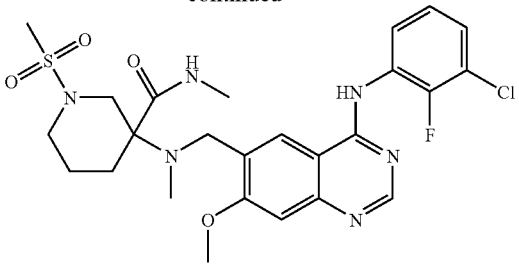

3-[({4-[(3-Chloro-2-fluorophenyl)amino]-7-methoxyquinazolin-6-yl}methyl)(methyl)amino]-N-methylpiperidine-3-carboxamide (Example 89.1, Isomer 1) (100 mg, 0.21 mmol) was dissolved in dichloromethane (2.5 ml) and diisopropylethylamine (54 µl, 0.31 mmol) added. Methanesulfonyl chloride (19 µl, 0.25 mmol) was added and the mixture stirred for 1 hour, absorbed onto an Isolute SCX column, washed with methanol and eluted with ammonia in methanol. The appropriate fractions were concentrated and the residues purified by column chromatography on silica, eluting with methanol/dichloromethane (2/98) to give the title product (Isomer 1) (70 mg, 60%) as a white solid; 1H NMR Spectrum: (DMSO d6) 1.67 (m, 1H); 1.92 (m, 2H); 2.07 (m, 1H); 2.21 (s, 3H); 2.66 (d, 3H); 2.88 (s, 3H); 3.03 (m, 1H); 3.21 (m, 1H); 3.34 (d, 1H); 3.52 (d, 1H); 3.62 (d, 1H); 3.79 (d, 1H); 3.96 (s, 3H); 7.20 (s, 1H); 7.30 (dt, 1H); 7.50 (m, 1H); 7.62 (m, 2H); 8.32 (s, 1H); 8.44 (s, 1H); 9.57 (s, 1H). Mass Spectrum: (M+H)+ 565.5

The compound of Example 89.1 (Isomer 1) was prepared as follows:

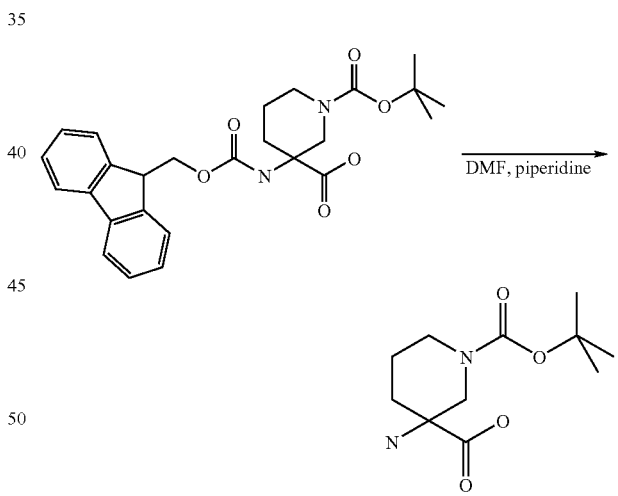

1-(tert-butoxycarbonyl)-3-{[(9H-fluoren-9-ylmethoxy)carbonyl]amino}piperidine-3-carboxylic acid was resolved by chiral HPLC resolution {Merck 50 mm 16 µm Kromasil Chirose 2 No. CT9014, tert-butylmethylether/iso-propanol (90/10). The first eluted enantiomer (800 mg, 1.71 mmol) 1-(tert-butoxycarbonyl)-3-{[(9H-fluoren-9-ylmethoxy)carbonyl]amino}piperidine-3-carboxylic acid (Isomer 1) was dissolved in N,N-dimethylformamide (10 ml) and piperidine (0.85 ml, 8.55 mmol) added. The mixture was stirred at room temperature over night. The resulting white precipitate was filtered off. The filtrates were concentrated and the residues purified by column chromatography on silica eluting with saturated ammonia in methanol/dichloromethane (25/75).

The fractions containing the desired product were combined with the filtered solids and evaporated to give 3-amino-1-(tert-butoxycarbonyl)piperidine-3-carboxylic acid (Isomer 1) (339 mg, 81%); $^1$H NMR Spectrum: (D$_2$O) 1.44 (s, 9H); 1.63 (m, 1H); 1.79 (d, 1H); 1.97 (d, 1H); 2.10 (m, 1H); 2.88 (t, 1H); 3.33 (d, 1H); 4.09 (m, 2H).

4-(3-Chloro-2-fluoroanilino)-7-methoxyquinazoline-6-carbaldehyde was coupled with 3-amino-1-(tert-butoxycarbonyl)piperidine-3-carboxylic acid (Isomer 1) using an analogous method to that described for the equivalent step in Example 1 to give 1-(tert-butoxycarbonyl)-3-[({4-[(3-chloro-2-fluorophenyl)amino]-7-methoxyquinazolin-6-yl}methyl)amino]piperidine-3-carboxylic acid (Isomer 1); $^1$H NMR Spectrum: (DMSO d$_6$+d4 AcOH) 1.27 (s, 9H); 1.46 (m, 1H); 1.92 (m, 3H); 3.08 (m, 1H); 3.52 (m, 2H); 3.72 (m, 2H); 3.86 (d, 1H); 3.96 (s, 3H); 7.19 (s, 1H); 7.28 (dt, 1H); 7.48 (t, 1H); 7.56 (m, 1H); 8.31 (s, 1H); 8.43 (s, 1H). Mass Spectrum: (M+H)$^+$ 560.5.

1-(tert-Butoxycarbonyl)-3-[({4-[(3-chloro-2-fluorophenyl)amino]-7-methoxyquinazolin-6-yl}methyl)amino]piperidine-3-carboxylic acid (Isomer 1) (400 mg, 0.71 mmol) was dissolved in 5% acetic acid in dichloromethane (25 ml) and 37% aqueous formaldehyde (5 ml) added. The mixture was stirred rapidly and sodium triacetoxyborohydride (151 mg, 0.71 mmol) added. Over a period of 5 hours a further 3 equivalents of sodium triacetoxyborohydride were added. The mixture was neutralized with saturated aqueous sodium hydrogen carbonate, the layers separated and the organic phased dried (MgSO$_4$) and concentrated under reduced pressure. Column chromatography on silica, eluting with 10% ammonia in methanol/dichloromethane gave 1-(tert-butoxycarbonyl)-3-[({4-[(3-chloro-2-fluorophenyl)amino]-7-methoxyquinazolin-6-yl}methyl)(methyl)amino]piperidine-3-carboxylic acid (Isomer 1) (364 mg, 85%) as a white solid; $^1$H NMR Spectrum: (DMSO d$_6$ 100° C.) 1.27 (s, 9H); 1.47 (m, 1H); 1.86 (m, 1H); 2.01 (m, 2H); 2.30 (s, 3H); 3.30 (m, 1H); 3.44 (m, 1H); 3.63 (d, 1H); 3.74 (d, 1H); 3.81 (d, 1H); 3.88 (d, 1H); 3.96 (s, 3H); 7.19 (s, 1H); 7.25 (t, 1H); 7.40 (t, 1H); 7.65 (m, 1H); 8.22 (s, 1H); 8.41 (s, 1H); Mass Spectrum: (M+H)$^+$ 574.5.

1-(tert-Butoxycarbonyl)-3-[({4-[(3-chloro-2-fluorophenyl)amino]-7-methoxyquinazolin-6-yl}methyl)(methyl)amino]piperidine-3-carboxylic acid (Isomer 1) was deprotected using an analogous method to that described for the equivalent step in Example 7 to give 3-[({4-[(3-chloro-2-fluorophenyl)amino]-7-methoxyquinazolin-6-yl}methyl)(methyl)amino]piperidine-3-carboxylic acid (Isomer 1); $^1$H NMR Spectrum: (DMSO d$_6$+d4 AcOH) 1.63 (m, 1H); 1.81 (m, 2H); 2.03 (m, 1H); 2.37 (s, 3H); 2.94 (m, 1H); 3.08 (m, 2H); 3.38 (d, 1H); 3.58 (d, 1H); 3.86 (d, 1H); 3.69 (s, 3H); 7.20 (s, 1H); 7.28 (dt, 1H); 7.48 (m, 1H); 7.56 (t, 1H); 8.35 (s, 1H); 8.43 (s, 1H). Mass Spectrum: (M+H)$^+$ 474.4.

3-[({4-[(3-Chloro-2-fluorophenyl)amino]-7-methoxyquinazolin-6-yl}methyl)(methyl)amino]piperidine-3-carboxylic acid (Isomer 1) was coupled with methylamine hydrochloride using an analogous method to that described for the equivalent step in Example 20 to give 3-[({4-[(3-chloro-2-fluorophenyl)amino]-7-methoxyquinazolin-6-yl}methyl)(methyl)amino]-N-methylpiperidine-3-carboxamide (Example 89.1 Isomer 1); $^1$H NMR Spectrum: (DMSO d$_6$) 1.43 (m, 1H); 1.66 (m, 1H); 1.84 (m, 1H); 2.11 (m, 1H); 2.29 (s, 3H); 2.58 (m, 1H); 2.73 (d, 3H); 2.84 (m, 2H); 3.28 (d, 1H); 3.69 (d, 1H); 3.78 (d, 1H); 4.00 (s, 3H); 7.24 (s, 1H); 7.35 (t, 1H); 7.56 (t, 1H); 7.64 (t, 1H); 7.79 (m, 1H); 8.37 (s, 1H); 8.48 (s, 1H); 9.75 (s, 1H); Mass Spectrum: (M+H)$^+$ 487.3.

EXAMPLES 90 and 90.1

(S or R)-3-[({4-[(3-chloro-2-fluorophenyl)amino]-7-methoxyquinazolin-6-yl}methyl)(methyl)amino]-N-methyl-1-(methylsulfonyl)piperidine-3-carboxamide (Isomer 2)

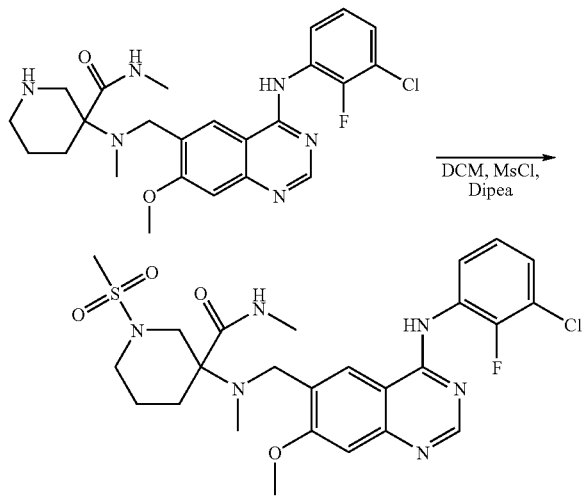

3-[({4-[(3-Chloro-2-fluorophenyl)amino]-7-methoxyquinazolin-6-yl}methyl)(methyl)amino]-N-methylpiperidine-3-carboxamide (Example 90.1, Isomer 2) was coupled with methanesulfonyl chloride using an analogous method to that described for the equivalent step in Example 89 to give (S or R)-3-[({4-[(3-chloro-2-fluorophenyl)amino]-7-methoxyquinazolin-6-yl}methyl)(methyl)amino]-N-methyl-1-(methylsulfonyl)piperidine-3-carboxamide (Example 90, Isomer 2); $^1$H NMR Spectrum: (DMSO d$_6$) 1.67 (m, 1H); 1.92 (m, 2H); 2.07 (m, 1H); 2.21 (s, 3H); 2.66 (d, 3H); 2.88 (s, 3H); 3.03 (m, 1H); 3.21 (m, 1H); 3.34 (d, 1H); 3.52 (d, 1H); 3.62 (d, 1H); 3.79 (d, 1H); 3.96 (s, 3H); 7.20 (s, 1H); 7.30 (dt, 1H); 7.50 (m, 1H); 7.62 (m, 2H); 8.32 (s, 1H); 8.44 (s, 1H); 9.57 (s, 1H); Mass Spectrum: (M+H)$^+$ 565.

The 3-[({4-[(3-Chloro-2-fluorophenyl)amino]-7-methoxyquinazolin-6-yl}methyl)(methyl)amino]-N-methylpiperidine-3-carboxamide (Example 90.1, Isomer 2) was prepared as follows:

1-(tert-butoxycarbonyl)-3-{[(9H-fluoren-9-ylmethoxy)carbonyl]amino}piperidine-3-carboxylic acid was resolved by chiral HPLC resolution {Merck 50 mm 16 μm Kromasil Chirose 2 No. CT9014, tert-butylmethylether/iso-propanol (90/10). The second eluted enantiomer (800 mg, 1.71 mmol) 1-(tert-butoxycarbonyl)-3-{[(9H-fluoren-9-ylmethoxy)carbonyl]amino}piperidine-3-carboxylic acid (Isomer 2) was deprotected using an analogous procedure to that described for the equivalent step in Example 89 to give 3-amino-1-(tert-butoxycarbonyl)piperidine-3-carboxylic acid (Isomer 2); $^1$H NMR Spectrum: (D$_2$O) 1.44 (s, 9H); 1.63 (m, 1H); 1.79 (d, 1H); 1.97 (d, 1H); 2.10 (m, 1H); 2.88 (t, 1H); 3.33 (d, 1H); 4.09 (m, 2H).

4-(3-Chloro-2-fluoroanilino)-7-methoxyquinazoline-6-carbaldehyde was coupled with 3-amino-1-(tert-butoxycarbonyl)piperidine-3-carboxylic acid (Isomer 2) then treated using analogous methods to those described for the equivalent steps in Example 89 to give 3-[({4-[(3-Chloro-2-fluorophenyl)amino]-7-methoxyquinazolin-6-yl}methyl)(methyl)amino]-N-methylpiperidine-3-carboxamide (Example 90.1, Isomer 2); $^1$H NMR Spectrum: (DMSO $d_6$) 1.43 (m, 1H); 1.66 (m, 1H); 1.84 (m, 1H); 2.11 (m, 1H); 2.29 (s, 3H); 2.58 (m, 1H); 2.73 (d, 3H); 2.84 (m, 2H); 3.28 (d, 1H); 3.69 (d, 1H); 3.78 (d, 1H); 4.00 (s, 3H); 7.24 (s, 1H); 7.35 (t, 1H); 7.56 (t, 1H); 7.64 (t, 1H); 7.79 (m, 1H); 8.37 (s, 1H); 8.48 (s, 1H); 9.75 (s, 1H); Mass Spectrum: (M+H)$^+$ 487.

EXAMPLE 91

$N^2$-(1-{4-[(3-chloro-2-fluorophenyl)amino]-7-methoxyquinazolin-6-yl}ethyl)-$N^2$-methylglycinamide (Process (b))

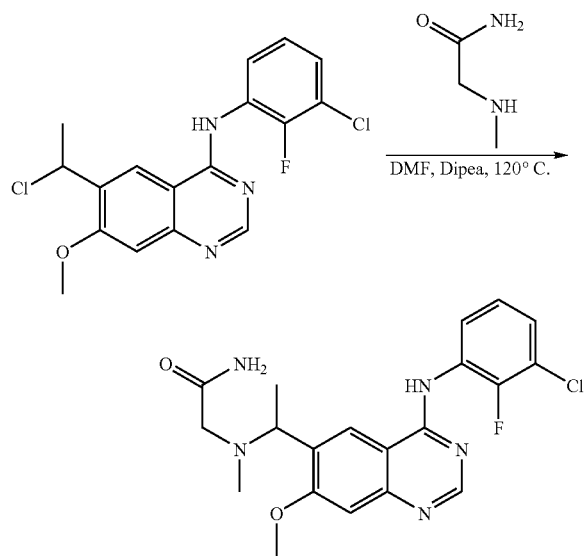

6-(1-Chloroethyl)-N-(3-chloro-2-fluorophenyl)-7-methoxyquinazolin-4-amine hydrochloride was coupled with N-methylglycinamide using an analogous method to that described for the equivalent step in Example 62 to give the title product; $^1$H NMR Spectrum: (DMSO $d_6$) 1.38 (d, 3H); 2.23 (s, 3H); 2.82 (d, 1H); 2.97 (d, 1H); 3.97 (s, 3H); 4.24 (q, 1H); 7.16 (s, 1H); 7.22 (s, 1H); 7.30 (m, 2H); 7.51 (m, 1H); 7.56 (m, 1H); 8.43 (s, 1H); 8.47 (s, 1H); 9.80 (s, 1H); Mass Spectrum: (M+H)$^+$ 418.

The starting material 6-(1-chloroethyl)-N-(3-chloro-2-fluorophenyl)-7-methoxyquinazolin-4-amine hydrochloride was prepared as follows:

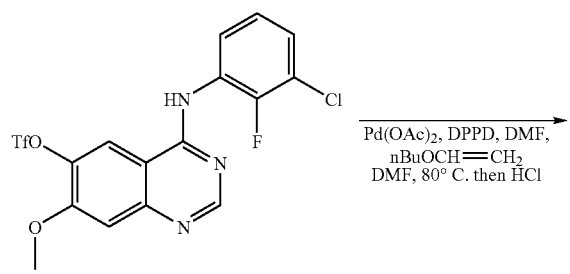

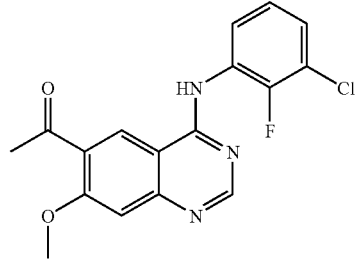

4-[(3-Chloro-2-fluorophenyl)amino]-7-methoxyquinazolin-6-yl trifluoromethanesulfonate, (described in Example 1 preparation of starting materials), (3 g, 6.64 mmol) was dissolved in dimethylformamide (21 ml) and n-butyl vinyl ether (4.3 ml, 33.2 mmol), triethylamine (2.3 ml, 16.6 mmol), 1,3-bis(diphenylphosphino)propane (438 mg, 1.06 mmol) and palladium acetate (223 mg, 1 mmol) added. The mixture was heated at 80° C. for 2 hours, allowed to cool and stirred at room temperature over night. 2M aqueous hydrochloric acid (24 ml) was added and the mixture stirred for 0.5 hours. The mixture was basified with saturated aqueous sodium hydrogen carbonate and extracted with ethyl acetate. The organic extracts were washed with brine, dried over magnesium sulfate and concentrated under reduced pressure. The resulting solid was suspended in methanol and filtered to give 1-{4-[(3-chloro-2-fluorophenyl)amino]-7-methoxyquinazolin-6-yl}ethanone (1.7 g, 74%) as a pale yellow solid; $^1$H NMR (spectrum): (DMSO $d_6$) 2.62 (s, 3H); 4.02 (s, 3H); 7.27 (m, 2H); 7.49 (t, 2H); 8.48 (s, 1H); 8.72 (s, 1H); 10.19 (s, 1H). Mass Spectrum: (M+H)$^+$ 346.

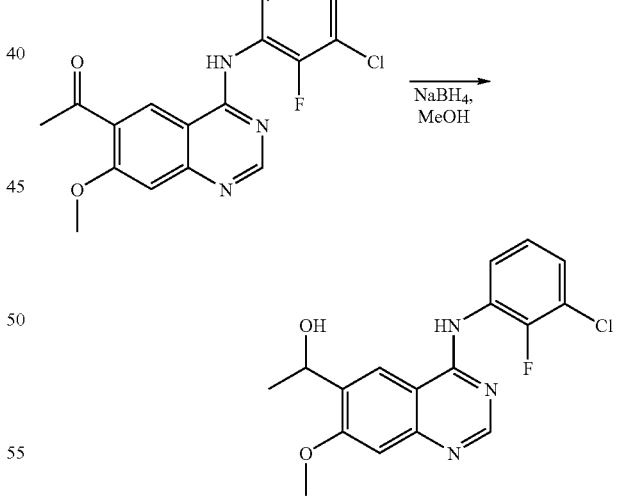

1-{4-[(3-Chloro-2-fluorophenyl)amino]-7-methoxyquinazolin-6-yl}ethanone was reduced with sodium borohydride using an analogous procedure to that described for the equivalent step in Example 62 to give 1-{4-[(3-chloro-2-fluorophenyl)amino]-7-methoxyquinazolin-6-yl}ethanol; $^1$H NMR Spectrum: (DMSO $d_6$) 1.38 (d, 3H); 3.95 (s, 3H); 5.12 (m, 1H); 5.28 (d, 1H); 7.16 (s, 1H); 7.24 (t, 1H); 7.45 (m, 2H); 8.39 (s, 1H); 8.48 (s, 1H); 9.93 (s, 1H). Mass Spectrum: (M+H)$^+$ 348.

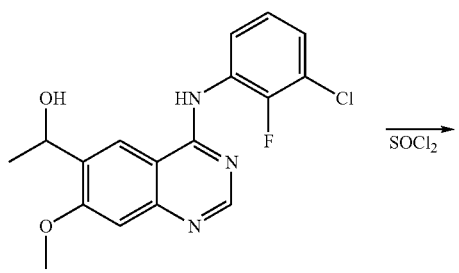

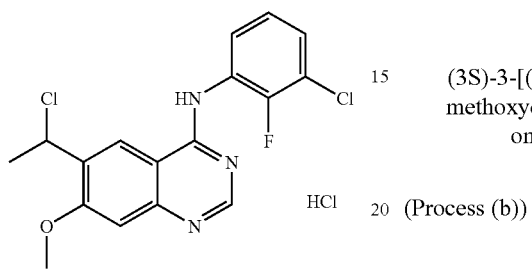

1-{4-[(3-Chloro-2-fluorophenyl)amino]-7-methoxyquinazolin-6-yl}ethanol was reacted with thionyl chloride using an analogous procedure to that described for the equivalent step in Example 62 to give 6-(1-chloroethyl)-N-(3-chloro-2-fluorophenyl)-7-methoxyquinazolin-4-amine hydrochloride; $^1$H NMR Spectrum: (DMSO d$_6$) 1.97 (d, 3H); 4.07 (s, 3H); 5.66 (q, 1H); 7.37 (m, 2H); 7.56 (m, 1H); 7.65 (m, 1H); 8.87 (s, 1H); 9.04 (s, 1H).

EXAMPLE 92

N$^2$-(1-{4-[(3-chloro-2-fluorophenyl)amino]-7-methoxyquinazolin-6-yl}ethyl)-N$^2$-methyl-D-alaninamide (Process (b))

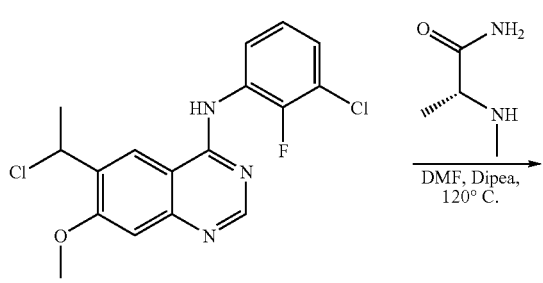

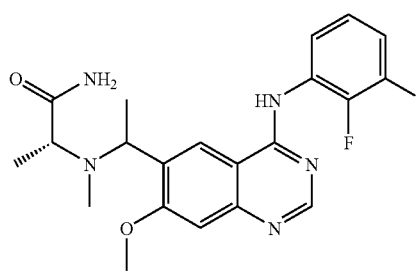

6-(1-Chloroethyl)-N-(3-chloro-2-fluorophenyl)-7-methoxyquinazolin-4-amine hydrochloride (described in Example 91) was coupled with N$^2$-methyl-D-alaninamide using an analogous method to that described for the equivalent step in Example 62 to give N$^2$-(1-{4-[(3-chloro-2-fluorophenyl)amino]-7-methoxyquinazolin-6-yl}ethyl)-N$^2$-methyl-D-alaninamide as a 1:1 mixture of diastereoisomers; $^1$H NMR Spectrum: (DMSO d$_6$) 1.03 and 1.08 (both d, 1.5H); 1.38 (d, 3H); 2.06 and 2.22 (both s, 1.5H); 3.13 and 3.51 (both q, 0.5H); 3.97 (s, 3H); 4.31 (m, 1H); 7.07 (s, 1H); 7.22 (m, 1H); 7.23 (m, 1.5H); 7.44 (s, 0.5H); 7.53 (m, 2H); 8.44 (m, 1.5H); 8.60 (s, 0.5H); 9.77 and 9.80 (both s, 0.5H). Mass Spectrum: (M+H)$^+$ 432.

EXAMPLE 93

(3S)-3-[(1-{4-[(3-chloro-2-fluorophenyl)amino]-7-methoxyquinazolin-6-yl}ethyl)amino]pyrrolidin-2-one (1:1 mixture of diastereoisomers)

(Process (b))

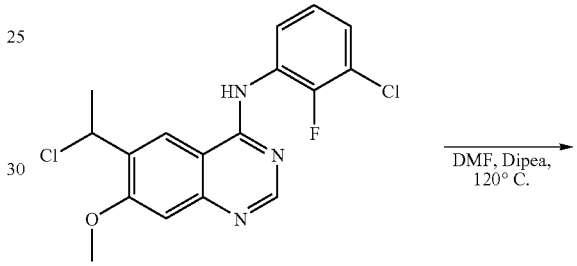

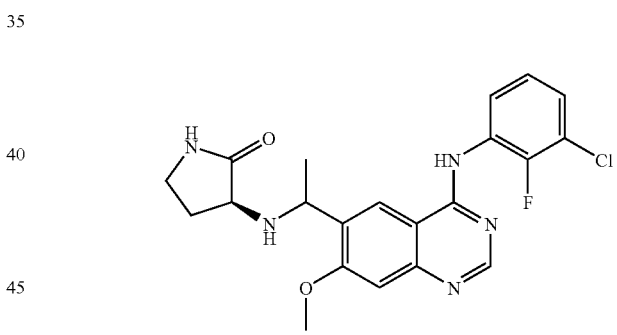

6-(1-Chloroethyl)-N-(3-chloro-2-fluorophenyl)-7-methoxyquinazolin-4-amine hydrochloride (Described in Example 91) was coupled with (3S)-3-aminopyrrolidin-2-one (prepared from (2S)-2,4-diaminobutanoic acid according to the method in Synthesis 1978, 614) using an analogous method to that described for the equivalent step in Example 62 to give (3S)-3-[(1-{4-[(3-chloro-2-fluorophenyl)amino]-7-methoxyquinazolin-6-yl}ethyl)amino]pyrrolidin-2-one as a 1:1 mixture of diastereoisomers; $^1$H NMR Spectrum: (DMSO d$_6$) 1.42 and 1.46 (both d, 1.5H); 1.71 and 1.81 (both m, 0.5H); 2.09 and 2.31 (both m, 0.5H); 3.00 (t, 0.5H); 3.11 (m, 1.5H); 3.23 (t, 1H); 4.03 (s, 3H); 4.27 and 4.52 (both m, 0.5H); 7.25 and 7.27 (both s, 0.5H); 7.34 (m, 1H); 7.53 (m, 1H); 7.61 (m, 1H); 7.74 and 7.77 (both s, 0.5H); 8.49 (m, 2H); 9.79 and 9.88 (both s, 0.5H); Mass Spectrum: (M+H)$^+$ 430.

EXAMPLE 94

(3S)-3-[(1-{4-[(3-chloro-2-fluorophenyl)amino]-7-methoxyquinazolin-6-yl}ethyl)(methyl)amino]pyrrolidin-2-one (as a 1:1 mixture of diastereoisomers)

(Process (a))

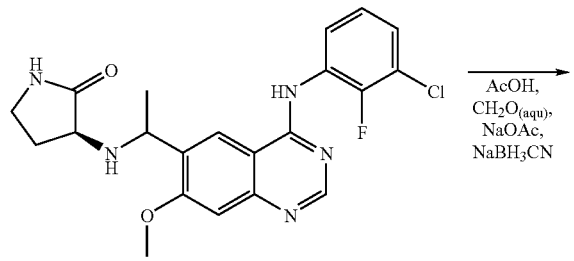

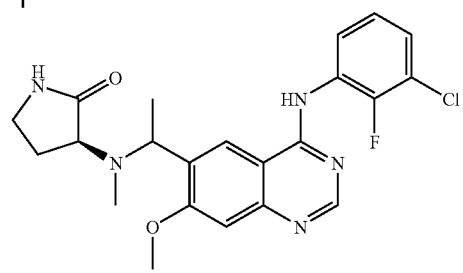

(3S)-3-[(1-{4-[(3-Chloro-2-fluorophenyl)amino]-7-methoxyquinazolin-6-yl}ethyl)amino]pyrrolidin-2-one (1:1 mixture of diastereoisomers Example 93) was reacted with 37% aqueous formaldehyde using an analogous method to that described for the equivalent step in Example 85 to give the title product; $^1$H NMR Spectrum: (DMSO $d_6$) 1.41 (m, 3H); 1.97 (m, 2H); 2.18 and 2.21 (both s, 1.5H); 3.10 (m, 2H); 3.57 (q, 1H); 3.97 (s, 3H); 4.43 and 4.56 (both q, 0.5H); 7.20 (s, 1H); 7.28 (t, 1H); 7.48 (t, 1H); 7.54 (m, 1H); 7.61 (s, 1H); 8.42 (s, 1H); 8.48 (m, 1H); 9.84 (s, 1H). Mass Spectrum: (M+H)$^+$ 444.

EXAMPLE 95

N$^2$-({4-[(3-chloro-2-fluorophenyl)amino]-7-methoxyquinazolin-6-yl}methyl)-N$^1$,2-dimethylalaninamide (Process (b))

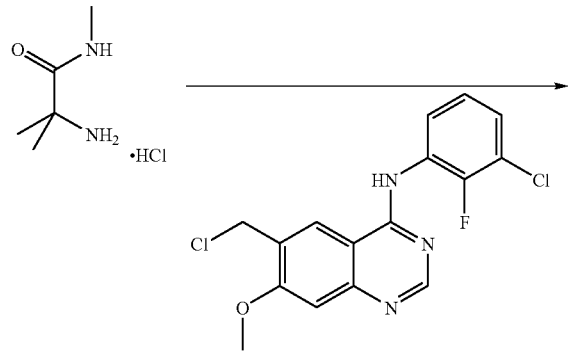

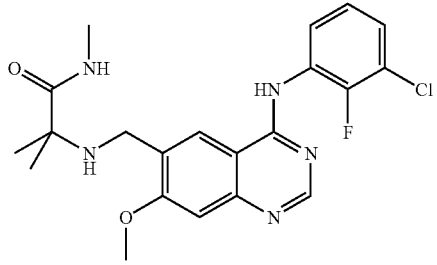

N-(3-Chloro-2-fluorophenyl)-6-(chloromethyl)-7-methoxyquinazolin-4-amine was coupled with N$^1$,2-dimethylalaninamide using an analogous method to that described for the equivalent step in Example 62 to give the title product (0.12 g, 49.1%); Mass Spectrum: (M+H)$^+$ 432.

EXAMPLE 96

N$^2$-({4-[(3-chloro-2-fluorophenyl)amino]-7-methoxyquinazolin-6-yl}methyl)-N$^1$,N$^2$,2-trimethylalaninamide (Process (d))

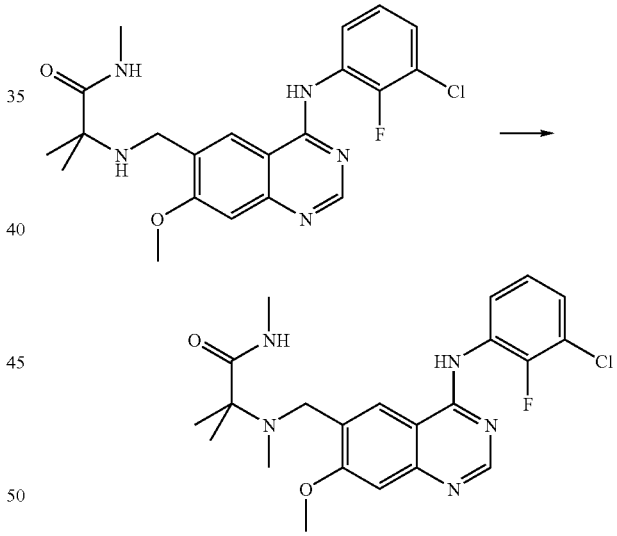

Solid sodium triacetoxy borohydride (0.2 g, 0.94 mmol) was added to a stirred solution of N$^2$-({4-[(3-chloro-2-fluorophenyl)amino]-7-methoxyquinazolin-6-yl}methyl)-N$^1$,2-dimethylalaninamide (0.12 g, 0.28 mmol Example 95) in a mixture of acetic acid/dichloromethane (10 ml, 5% v/v) and in the presence of type 4 Å molecular sieves, followed rapidly by aqueous formaldehyde (1 ml). After 10 minutes the reaction mixture was concentrated and purified by preparative LCMS (standard basic system) to give the title product as a white solid, (0.085 g, 69%); $^1$H NMR Spectrum: (DMSO $d_6$) 1.24 (s, 6H), 2.18 (s, 3H), 2.65 (d, 3H), 3.52 (s, 2H), 3.96 (s, 3H), 7.20 (s, 1H), 7.29 (t, 1H), 7.52-7.62 (m, 2H), 7.79 (m, 1H), 8.44 (m, 2H), 9.78 (s, 1H); Mass Spectrum: (M+H)$^+$ 446.

EXAMPLE 97

N²-({4-[(3-chloro-2-fluorophenyl)amino]-7-methoxyquinazolin-6-yl}methyl)-2-methylalaninamide

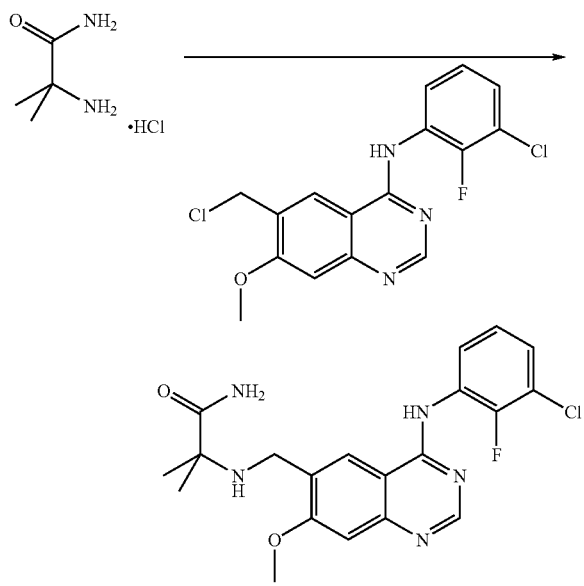

N-(3-Chloro-2-fluorophenyl)-6-(chloromethyl)-7-methoxyquinazolin-4-amine (0.2 g, 0.568 mmol) was coupled with 2-methylalaninamide hydrochloride using an analogous method to that described for the equivalent step in Example 62 to give the title product (0.12 g, 49.1%); Mass Spectrum: (M+H)⁺ 418.

EXAMPLE 98

N²-({4-[(3-chloro-2-fluorophenyl)amino]-7-methoxyquinazolin-6-yl}methyl)-N²,2-dimethylalaninamide

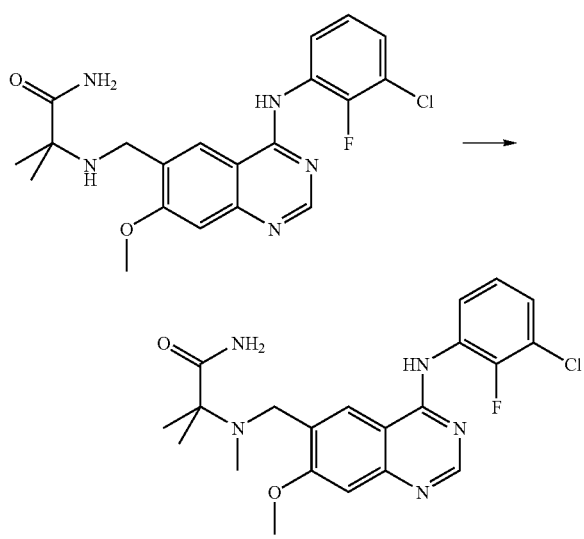

N²-({4-[(3-chloro-2-fluorophenyl)amino]-7-methoxyquinazolin-6-yl}methyl)-2-methylalaninamide (Example 97) was coupled with aqueous formaldehyde using an analogous method to that described for the equivalent step in Example 96 to give the title product as a white solid, (0.078 g, 76%); ¹H NMR Spectrum: (DMSO-d₆) 1.24 (s, 3H), 2.14 (s, 3H), 3.55 (s, 2H), 3.95 (s, 3H), 7.11 (m, 1H), 7.21 (s, 1H), 7.30 (t, 1H), 7.37 (m, 1H), 7.52-7.58 (m, 2H), 8.44 (m, 2H), 9.76 (s, 1H); Mass Spectrum: (M+H)⁺ 432.

The starting materials N¹,2-dimethylalaninamide and 2-methylalaninamide used in Examples 95 and 97 were prepared from 2-aminoisobutyric acid (ex. Aldrich) following the procedure below:

Di-tert-butlydicarbonate (6.98 g, 32.0 mmol) was added to a stirred solution of the 2-aminoisobutyric acid (3 g, 29.13 mmol) in methanol/triethylmine (10/90) (100 ml). The reaction mixture was heated at 60° C./30 minutes, cooled to room temperature and concentrated to dryness. The residue was taken up in dichloromethane (100 ml), washed with 10% aqueous potassium hydrogensulfate, water, dried over magnesium sulfate, filtered and evaporated to dryness to give N-(tert-butoxycarbonyl)-2-methylalanine (2.87 g, 49%) as a white solid; ¹H NMR Spectrum: (CDCl₃) 1.45 (s, 6H), 1.53 (s, 9H), 5.2 (br s, 1H).

N-(tert-butoxycarbonyl)-2-methylalanine (2.87 g, 14.13 mmol) was dissolved in THF (20 ml) and cooled to −10° C. (acetone/ice). N-methylmorpholine (2.14 g, 21.2 mmol) was added followed by iso-butylchloroformate (2.12 g, 15.5 mmol, 1.1 equivalents) over a period of 3 minutes. The reaction mixture was allowed to stir for 10 minutes, split in two equal halves (approximately 12 ml each). One sample was treated with methylamine in THF (5 ml of 2.0M solution) and the resulting mixture was evaporated to dryness. The residues were re-dissolved in dichloromethane (30 ml), washed with water, saturated aqueous sodium hydrogen carbonate, water, dried over magnesium sulfate and evaporated to dryness to give N²-(tert-butoxycarbonyl)-N¹,2-dimethylalaninamide (0.67 g, 42.6%), which was used without further purification, ¹H NMR Spectrum: (DMSO-d₆) 1.29 (s, 6H), 1.37 (s, 9H), 2.50 (s, 3H), 6.57 (br s, 1H), 6.93 (br s, 1H)

The second aliquot was treated with aqueous ammonia (2 ml) using a method analogous to that described above to give N²-(tert-butoxycarbonyl)-2-methylalaninamide, (0.83 g, 57.6%); ¹H NMR Spectrum: (DMSO-d₆) 1.24 (s, 6H), 1.37 (s, 9H), 6.46 (br s, 1H), 6.68 (br s, 1H), 7.02 (br s, 1H), N²-(tert-butoxycarbonyl)-N¹,2-dimethylalaninamide was deprotected using a method analogous to that used for the equivalent step in Example 7 to give N¹,2-dimethylalaninamide hydrochloride as a crystalline white solid which was used without further purification.

N²-(tert-butoxycarbonyl)-2-methylalaninamide was deprotected using a method analogous to that described above to give 2-methylalaninamide hydrochloride.

EXAMPLE 99

3-[({4-[(3-chloro-2-fluorophenyl)amino]-7-methoxyquinazolin-6-yl}methyl)(methyl)amino]-N-methylazetidine-3-carboxamide hydrochloride

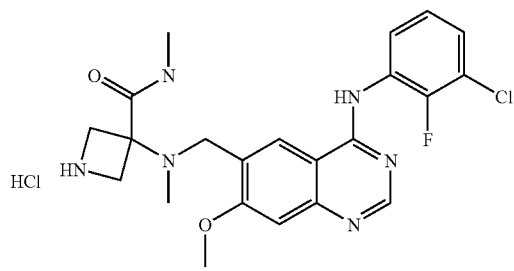

A solution of HCl/1,4-dioxan (1/5) (2 ml) was added dropwise to a solution of tert-butyl 3-[({4-[(3-chloro-2-fluorophenyl)amino]-7-methoxyquinazolin-6-yl}methyl)(methyl)amino]-3-[(methylamino)carbonyl]azetidine-1-carboxylate (310 mg, 0.56 mmol) in 1,4-dioxan (6 ml). The reaction mixture was stirred overnight, then concentrated under reduced pressure. Three triturations in methanol/dichloromethane/diethyl ether afforded the isolation of a hydrochloride salt of 3-[({4-[(3-chloro-2-fluorophenyl)amino]-7-methoxyquinazolin-6-yl}methyl)(methyl)amino]-N-methylazetidine-3-carboxamide as a solid (336 mg, 100%).
$^1$H NMR Spectrum: (DMSO $d_6$) 2.16 (s, 3H), 2.71 (d, 3H), 3.70 (s, 2H), 3.97 (m, 2H), 4.03 (s, 3H), 4.13 (m, 2H), 7.37 (m, 2H), 7.55 (t, 1H), 7.66 (t, 1H), 8.31 (brs, 1H), 8.90 (brs, 2H), 9.27 (s, 1H), 9.75 (brs, 1H); Mass Spectrum: (M+H)$^+$ 459.

The tert-butyl 3-[({4-[(3-chloro-2-fluorophenyl)amino]-7-methoxyquinazolin-6-yl}methyl)(methyl)amino]-3-[(methylamino)carbonyl]azetidine-1-carboxylate starting material was prepared as follows:

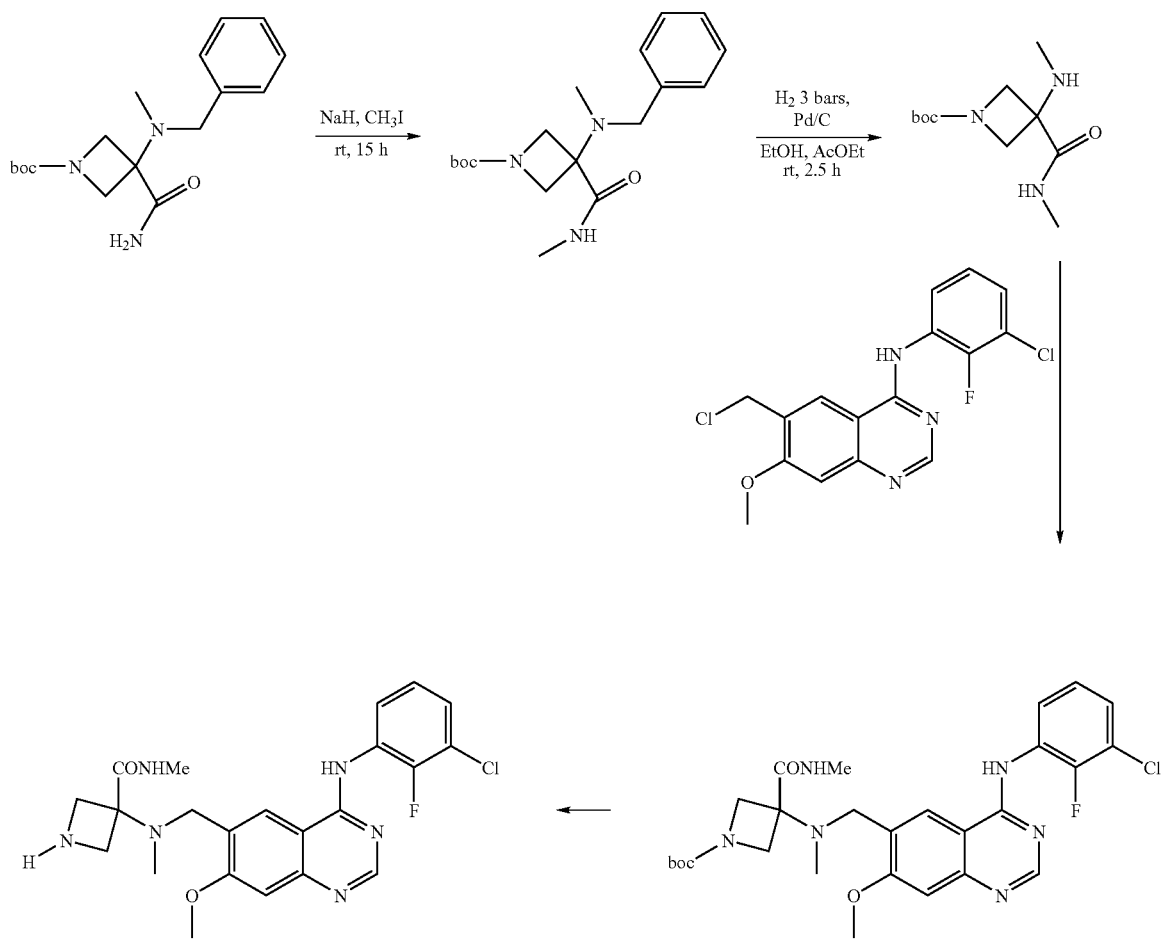

Sodium hydride (60% dispersion in mineral oil) (351 mg, 8.78 mmol) was added to a solution of tert-butyl 3-(aminocarbonyl)-3-[benzyl(methyl)amino]azetidine-1-carboxylate (described in Example 74) (1.4 g, 4.39 mmol) in dimethylformamide (14 ml) at 0° C.). After 1 hour at room temperature the reaction mixture was cooled to 0° C. and methyl iodide (0.44 ml, 7.02 mmol) added dropwise. The reaction mixture was allowed to stir at room temperature overnight, evaporated and the residues purified by preparative HPLC (standard basic conditions) to give tert-butyl 3-[benzyl(methyl)amino]-3-[(methylamino)carbonyl]azetidine-1-carboxylate as a solid, (460 mg, 31%). $^1$H NMR Spectrum: (CDCl$_3$) 1.45 (s, 9H), 2.23 (s, 3H), 2.87 (d, 3H), 3.56 (s, 2H), 4.05 (d, 2H), 4.20 (brs, 2H), 6.80 (brs, 1H), 7.28 (m, 3H), 7.35 (m, 2H); Mass Spectrum: (M+H)$^+$ 334.

10% wt Palladium on charcoal (160 mg) in ethyl acetate (2 ml) was added to a solution of tert-butyl 3-[benzyl(methyl)amino]-3-[(methylamino)carbonyl]azetidine-1-carboxylate (580 mg, 1.74 mmol) in ethanol (45 ml). After the addition of a few drops of saturated hydrogen chloride in dichloromethane, the reaction mixture was stirred at room temperature under 3 bars of hydrogen for 3 hours. Filtration of the catalyst and concentration under reduced pressure gave tert-butyl 3-(methylamino)-3-[(methylamino)carbonyl]azetidine-1-carboxylate (395 mg, 93%) as a white solid, which was used without further purification in the next step. $^1$H NMR Spectrum: (CDCl$_3$) 1.43 (s, 9H), 2.30 (s, 3H), 2.84 (s, 3H), 3.68 (d, 2H), 4.27 (brs, 2H), 7.05 (brs, 1H).

Diisopropylethylamine (0.55 ml, 3.10 mmol) was added to a solution of tert-butyl 3-(methylamino)-3-[(methylamino)carbonyl]azetidine-1-carboxylate (301 mg, 1.24 mmol) in DMF (0.5 ml). After 5 minutes of stirring, the reaction mixture became homogeneous and was warmed up to 85° C. N-(3-chloro-2-fluorophenyl)-6-(chloromethyl)-7-methoxyquinazolin-4-amine (400 mg, 1.03 mmol) was added portionwise over 2 hours. The reaction mixture was cooled to room temperature, diluted with DMF (2 ml) and purified by preparative HPLC (standard basic condition) to afford tert-butyl 3-[({4-[(3-chloro-2-fluorophenyl)amino]-7-methoxyquinazolin-6-yl}methyl)(methyl)amino]-3-[(methylamino)carbonyl]azetidine-1-carboxylate (235 mg, 41%) as a white solid. $^1$H NMR Spectrum: (CDCl$_3$) 1.45 (s, 9H), 2.34 (s, 3H), 2.90 (d, 3H), 3.78 (brs, 2H), 4.01 (s, 3H), 4.10 (d, 2H), 4.25 (brs, 2H), 6.84 (brs, 1H), 7.17 (m, 2H), 7.29 (s, 1H), 7.60 (brs, 1H), 7.78 (brs, 1H), 8.53 (brs, 1H), 8.75 (s, 1H); Mass Spectrum: (M+H)$^+$ 559.

EXAMPLE 100

3-[({4-[(3-chloro-2-fluorophenyl)amino]-7-methoxyquinazolin-6-yl}methyl)(methyl)amino]-1-isopropyl-N-methylazetidine-3-carboxamide (Process (d))

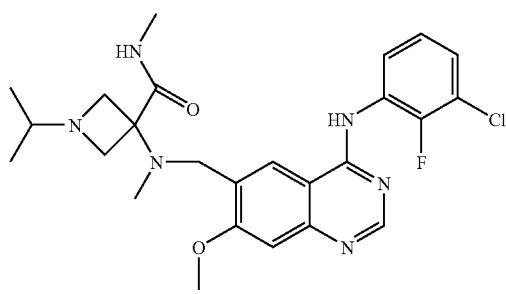

The hydrochloride salt of 3-[({4-[(3-chloro-2-fluorophenyl)amino]-7-methoxyquinazolin-6-yl}methyl)(methyl)amino]-N-methylazetidine-3-carboxamide (110 mg, 0.22 mmol Example 99), acetone (23 μl, 0.31 mmol) and diisopropylethylamine (78 μl, 0.45 mmol) were stirred at room temperature in 5% acetic acid in 1,2-dichloroethane (2 ml) with 3 Å molecular sieves, and sodium triacetoxyborohydride (95 mg, 0.45 mmol) was added portionwise over 0.5 hours. After 2 hours, the reaction mixture was concentrated under reduced pressure. The resulting product was purified on preparative HPLC (standard basic conditions) to give the title product (52 mg, 47%) as a white powder; $^1$H NMR Spectrum: (CDCl$_3$) 0.98 (d, 6H), 2.41 (s, 3H), 2.49 (m, 1H), 2.90 (s, 3H), 3.25 (brs, 2H), 3.57 (m, 2H), 3.96 (s, 2H), 3.97 (s, 3H), 7.16 (m, 2H), 7.24 (s, 1H), 7.57 (brs, 1H), 7.78 (brs, 1H), 8.00 (brs, 1H), 8.54 (brs, 1H), 8.73 (s, 1H); Mass Spectrum: (M+H)$^+$ 501.

EXAMPLE 101

3-[({4-[(3-chloro-2-fluorophenyl)amino]-7-methoxyquinazolin-6-yl}methyl)(methyl)amino]-N,1-dimethylazetidine-3-carboxamide (Process (d))

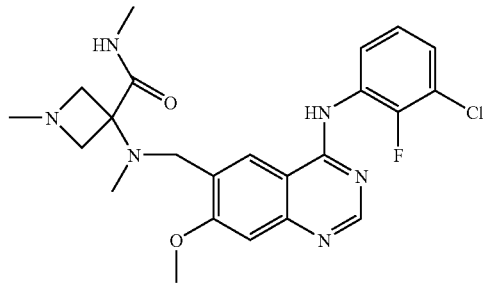

The hydrochloride salt of 3-[({4-[(3-chloro-2-fluorophenyl)amino]-7-methoxyquinazolin-6-yl}methyl)(methyl)amino]-N-methylazetidine-3-carboxamide (110 mg, 0.22 mmol Example 99), formaldehyde (54 μl of a 37% wt aqueous solution, 0.67 mmol) and diisopropylethylamine (78 μl, 0.45 mmol) were stirred at room temperature in 5% acetic acid in 1,2-dichloroethane (2 ml) with 3 Å molecular sieves. Sodium triacetoxyborohydride (95 mg, 0.45 mmol) was added portionwise over 0.5 hours. After 2 hours, the reaction mixture was concentrated under reduced pressure and the residues purified preparative HPLC (standard basic conditions) to give the title product (68 mg, 65%) as a white powder. $^1$H NMR Spectrum: (CDCl$_3$) 2.40 (s, 3H), 2.45 (m, 3H), 2.89 (s, 3H), 3.39 (brs, 2H), 3.60 (d, 2H), 3.95 (s, 2H), 3.98 (s, 3H), 7.17 (m, 2H), 7.25 (s, 1H), 7.44 (brs, 1H), 7.84 (brs, 1H), 8.00 (s, 1H), 8.51 (brs, 1H), 8.74 (s, 1H); Mass Spectrum: (M+H)$^+$ 473.

EXAMPLE 102

3-[({4-[(3-chloro-2-fluorophenyl)amino]-7-methoxyquinazolin-6-yl}methyl)(methyl)amino]-1-(methylsulfonyl)azetidine-3-carboxamide

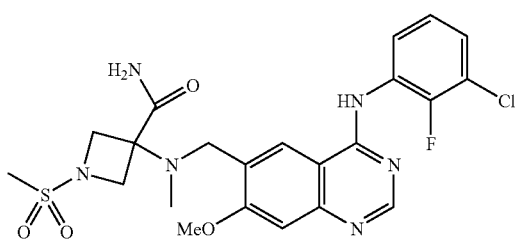

Diisopropylethylamine (72 μl, 0.41 mmol) then sulfonyl chloride (11 μl, 0.14 mmol) were added to a solution of the hydrochloride salt of 3-[({4-[(3-chloro-2-fluorophenyl)amino]-7-methoxyquinazolin-6-yl}methyl)(methyl)amino] azetidine-3-carboxamide (Example 74) (60 mg, 0.12 mmol) in $CH_2Cl_2$ (1 ml) at 0° C. After 1 hour, the reaction mixture was diluted in 50 ml $CH_2Cl_2$ and washed with water. The organic layer was dried on $MgSO_4$, then concentrated under reduced pressure. The crude product was purified on preparative HPLC (standard basic condition) to give the title product (20 mg, 33%) as a white powder; $^1$H NMR Spectrum: ($CDCl_3$) 2.17 (s, 3H), 3.05 (s, 3H), 3.61 (s, 2H), 3.97 (s, 3H), 4.03 (d, 2H), 4.11 (s, 2H), 7.21 (s, 1H), 7.30 (m, 1H), 7.48 (m, 2H), 7.60 (brs, 2H), 8.38 (s, 1H), 8.44 (s, 1H), 9.75 (s, 1H); Mass Spectrum: $(M+H)^+$ 523.

The invention claimed is:
1. A quinazoline compound of the formula I:

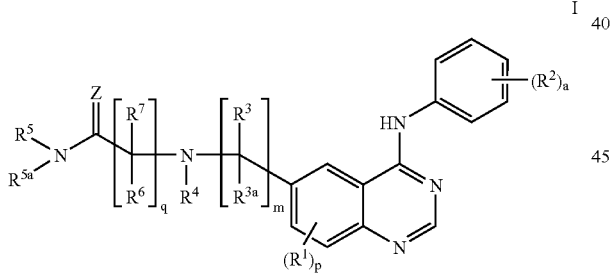

wherein:
p is 1 or 2;
each $R^1$, which may be the same or different, is selected from hydrogen, hydroxy, (1-6C)alkoxy, (2-6C)alkenyloxy, (2-6C)alkynyloxy, or from a group of the formula:

$Q^1—X^1—$ wherein $X^1$ is a direct bond or is O, and $Q^1$ is (3-7C)cycloalkyl, (3-7C)cycloalkyl-(1-6C)alkyl, (3-7C)cycloalkenyl, (3-7C)cycloalkenyl-(1-6C)alkyl, heterocyclyl or heterocyclyl-(1-6C)alkyl, and wherein any $CH_2$ or $CH_3$ group within a $R^1$ substituent, other than a $CH_2$ group within a heterocyclyl ring, optionally bears on each said $CH_2$ or $CH_3$ group one or more halogeno or (1-6C)alkyl substituents or a substituent selected from hydroxy, amino, cyano, carbamoyl, (1-6C)alkoxy, (1-6C)alkylamino, di-[(1-6C)alkyl]amino, N-(1-6C)alkylcarbamoyl and N,N-di-[(1-6C)alkyl]carbamoyl;

and wherein any heterocyclyl group within a substituent on $R^1$ optionally bears one or more $R^{11}$ substituents, which may be the same or different;

a is 1, 2, 3, 4 or 5;

each $R^2$, which may be the same or different, is selected from halogeno, cyano, nitro, hydroxy, amino, carboxy, carbamoyl, sulfamoyl, trifluoromethyl, trifluoromethoxy, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino and a group of the formula:

$—X^4—R^{12}$ wherein $X^4$ is a direct bond or is selected from O and $N(R^{13})$, wherein $R^{13}$ is hydrogen or (1-6C)alkyl, and $R^{12}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or (1-6C)alkoxycarbonylamino-(1-6C)alkyl;

m is 1 or 2;

each of $R^3$ and $R^{3a}$, which may be the same or different, is selected from hydrogen and (1-6C)alkyl, or $R^3$ and $R^{3a}$ together with the carbon atom to which they are attached form a (3-7C)cycloalkyl ring, and wherein any $R^3$ or $R^{3a}$ optionally bears on carbon one or more $R^{14}$ substituents, which may be the same or different;

$R^4$ is selected from is selected from hydrogen, (1-6C)alkyl, (2-6C)alkenyl, (2-6C)alkynyl, carbamoyl, N-(1-6C)alkylcarbamoyl, N,N-di-[(1-6C)alkyl]carbamoyl, (2-6C)alkanoyl, (1-6C)alkoxycarbonyl and (1-6C)alkylsulfonyl, and wherein a $R^4$ substituent optionally bears on carbon one or more $R^{15}$ substituents, which may be the same or different;

$R^5$ and $R^{5a}$, which may be the same or different, is selected from hydrogen, (1-4C)alkyl, (2-4C)alkenyl, (2-4C)alkynyl, (3-7C)cycloalkyl, (3-7C)cycloalkyl-(1-4C)alkyl, (3-7C)cycloalkenyl, (3-7C)cycloalkenyl-(1-4C)alkyl, heterocyclyl and heterocyclyl-(1-4C)alkyl, and wherein and wherein any $CH_2$ or $CH_3$, other than a $CH_2$ group within a heterocyclyl ring, within a $R^5$ or $R^{5a}$ substituent optionally bears on each said $CH_2$ or $CH_3$ one or more $R^{16}$ substituents, which may be the same or different, and wherein any heterocyclyl group within a substituent on $R^5$ or $R^{5a}$ optionally bears one or more substituents, which may be the same or different, selected from halogeno, (1-4C)alkyl, (2-4C)alkanoyl, hydroxy-(2-4C)alkanoyl, (1-4C)alkoxy-(2-4C)alkanoyl and (1-4C)alkylsulfonyl, and wherein any heterocyclyl group within a $R^5$ or $R^{5a}$ substituent optionally bears 1 or 2 oxo or thioxo substituents, or $R^5$ and $R^{5a}$ together with the nitrogen atom to which they are attached form a heterocyclyl group, which group optionally bears one or more substituents, which may be the same or different, selected from halogeno, (1-4C)alkyl, (2-4C)alkanoyl, hydroxy-(2-4C)alkanoyl, (1-4C)alkoxy-(2-4C)alkanoyl and (1-4C)alkylsulfonyl, and wherein any heterocyclyl group formed by $R^5$ and $R^{5a}$ together with the nitrogen atom to which they are attached, optionally bears 1 or 2 oxo or thioxo substituents;

Z is O or S;

q is 1 or 2;

each $R^6$, which may be the same or different, is selected from hydrogen, (1-6C)alkyl, (2-6C)alkenyl, and (2-6C)alkynyl, and wherein $R^6$ optionally bears on carbon one or more $R^{17}$ substituents, which may be the same or different;

each $R^7$, which may be the same or different, is selected from hydrogen, (1-6C)alkyl, (2-6C)alkenyl, (2-6C)alkynyl, aryl, aryl-(1-6C)alkyl, (3-7C)cycloalkyl, (3-7C)cycloalkyl-(1-6C)alkyl, (3-7C)cycloalkenyl, (3-7C)cycloalkenyl-(1-6C)alkyl, heteroaryl, heteroaryl-(1-6C)alkyl, heterocyclyl and heterocyclyl-(1-6C)alkyl, provided that when $R^7$ is heterocyclyl or heteroaryl and q is 1, $R^7$ is linked to the carbon carrying $R^6$ and the $R^{5a}R^5NC(Z)$ group by a ring carbon, and wherein an $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, and wherein any aryl, heteroaryl or heterocyclyl group within a substituent on $R^7$ optionally bears one or more $R^{21}$ substituents, which may be the same or different;

or $R^6$ and $R^7$ together with the carbon atom to which they are attached form a (3-7C)cycloalkyl, (3-7C)cycloalkenyl or heterocyclyl group, which group optionally bears one or more $R^{22}$ substituents, which may be the same or different;

or $R^7$ and the group $R^{5a}R^5NC(Z)$ together with the carbon atom to which they are attached form a heterocyclyl group, which group optionally bears one or more $R^{23}$ substituents, which may be the same or different;

wherein the term heterocyclyl as used herein denotes a saturated or partially saturated 4-, 5- or 6-membered monocyclic ring with 1 or 2 ring heteroatoms selected from nitrogen, sulfur or oxygen, which may, unless otherwise specified, be carbon or nitrogen linked;

wherein the term heteroaryl as used herein denotes an aromatic 5- or 6-membered monocyclic ring with 1, 2 or 3 ring heteroatoms selected from nitrogen, sulfur and oxygen, which may, unless otherwise specified, be carbon or nitrogen linked;

each $R^{11}$, $R^{21}$, $R^{22}$ and $R^{23}$, which may be the same or different, is selected from hydroxy, carboxy, (1-6C)alkyl, (2-8C)alkenyl, (2-8C)alkynyl, (1-6C)alkylsulfinyl, (1-6C)alkylsulfonyl, (2-6C)alkanoyl, a group of the formula:

$$-X^7-R^{25}$$

wherein $X^7$ is a direct bond or C(O), and $R^{25}$ is hydroxy-(1-6C)alkyl, carboxy-(1-6C)alkyl, (1-6C)alkoxy-(1-6C)alkyl, carbamoyl-(1-6C)alkyl, N-(1-6C)alkylcarbamoyl-(1-6C)alkyl or N,N-di-[(1-6C)alkyl]carbamoyl-(1-6C)alkyl, and from a group of the formula:

$$-X^8-Q^6$$

wherein $X^8$ is a direct bond, and $Q^6$ is (3-7C)cycloalkyl-(1-6C)alkyl, and wherein $R^{11}$, $R^{21}$, $R^{22}$ and $R^{23}$ optionally bears on carbon one or more $R^{29}$ substituents, which may be the same or different;

each of $R^{14}$, $R^{15}$, $R^{16}$ and $R^{17}$, which may be the same or different, is selected from halogeno, hydroxy, cyano, (1-6C)alkoxy and $NR^{27}R^{28}$, wherein $R^{27}$ and $R^{28}$, which may be the same or different, are selected from hydrogen, formyl, (1-4C)alkyl, (2-4C)alkenyl, (2-4C)alkynyl and (2-4C)alkanoyl, and wherein any of $R^{14}$, $R^{15}$, $R^{16}$ and $R^{17}$ optionally bears on carbon one or more $R^{30}$ substituents, which may be the same or different;

$R^{29}$, $R^{30}$ and $R^{36}$, which may be the same or different, are selected from hydroxy, methoxy and ethoxy;

or a pharmaceutically acceptable salt thereof.

2. The quinazoline compound of the formula I according to claim 1 or a pharmaceutically acceptable salt thereof wherein:

q is 1;

$R^{5a}$ is hydrogen; and $R^5$ is selected from hydrogen, (1-4C)alkyl, (2-4C)alkenyl, and (2-4C)alkynyl, and wherein $R^5$ optionally bears on carbon one or more $R^{16}$ substituents, which may be the same or different, wherein $R^{16}$ is as defined in claim 1.

3. The quinazoline compound of the formula I according to claim 1 or a pharmaceutically acceptable salt thereof wherein Z is O.

4. The quinazoline compound of the formula I according to claim 1 or a pharmaceutically acceptable salt thereof wherein $R^4$ is (1-4C)alkyl and wherein $R^4$ optionally bears on carbon one or more $R^{15}$ substituents, which may be the same or different, wherein $R^{15}$ is selected from halogeno, hydroxy, cyano, (1-3C)alkoxy.

5. The quinazoline compound of the formula I according to claim 1, or a pharmaceutically acceptable salt thereof wherein m is 1; $R^{3a}$ is hydrogen and $R^3$ is hydrogen or (1-4C)alkyl.

6. The quinazoline compound of the formula I according to claim 1, or a pharmaceutically acceptable salt thereof wherein m is 1;

q is 1;

Z is O;

$R^{5a}$ is hydrogen; and $R^5$ is selected from hydrogen, (1-4C)alkyl, (2-4C)alkenyl, and (2-4C)alkynyl, and wherein $R^5$ optionally bears on carbon one or more substituents, which may be the same or different, selected from hydroxy and (1-3C)alkoxy.

7. The quinazoline compound of the formula I according to claim 1, or a pharmaceutically acceptable salt thereof wherein one of $R^6$ and $R^7$ is not hydrogen.

8. The quinazoline compound of the formula I according to claim 1, or a pharmaceutically acceptable salt thereof wherein $R^7$ is selected from (1-6C)alkyl, (2-6C)alkenyl, (2-6C)alkynyl, (3-7C)cycloalkyl, (3-7C)cycloalkyl-(1-6C)alkyl, (3-7C)cycloalkenyl, (3-7C)cycloalkenyl-(1-6C)alkyl, heterocyclyl and heterocyclyl-(1-6C)alkyl, provided that when $R^7$ is heterocyclyl and q is 1, $R^7$ is linked to the carbon carrying $R^6$ and the $R^{5a}R^5NC(Z)$ group by a ring carbon, and wherein any $CH_2$ or $CH_3$, other than a $CH_2$ group within a heterocyclyl ring, within a $R^7$ substituent optionally bears on each said $CH_2$ or $CH_3$ group one or more halogeno or (1-6C)alkyl substituents or a substituent selected from hydroxy, cyano, amino, (1-6C)alkoxy, (1-6C)alkylthio, (1-6C)alkylsulfinyl, (1-6C)alkylsulfonyl, (1-6C)alkylamino and di-[(1-6C)alkyl]amino, and wherein any heterocyclyl group within a substituent on $R^7$ optionally bears one or more $R^{21}$ substituents, which may be the same or different, as defined in claim 1, or $R^6$ and $R^7$ together with the carbon atom to which they are attached form a (3-7C)cycloalkyl, (3-7C)cycloalkenyl or heterocyclyl group, which group optionally bears one or more $R^{22}$ substituents, which may be the same or different, as defined in claim 1, or $R^7$ and the group $R^{5a}R^5NC(Z)$ together with the carbon atom to which they are attached form a heterocyclyl group, which group optionally bears one or more $R^{23}$ substituents, which may be the same or different, as defined in claim 1.

9. The quinazoline compound of the formula I according to claim 1, or a pharmaceutically acceptable salt thereof wherein $R^7$ is selected from methyl, ethyl, isopropyl, hydroxymethyl, methoxymethyl, isopropyloxymethyl, 2-hydroxyethyl, 2-methoxyethyl, aminomethyl, 2-aminoethyl, methylaminomethyl, 2-(methylamino)ethyl, dimethylaminomethyl, 2-(dimethylamino)ethyl, pyrrolidin-3-yl and 1-methylpyrrolidin-3-yl, or $R^6$ and $R^7$ together with the carbon atom to which they are attached form a cyclopropyl, cyclobutyl, cyclopentyl, cyclohexyl, cyclopent-3-en-1-yl, azetidin-3-yl, piperidin-3-yl, piperidin-4-yl, tetrahydropyran-3-yl or tetrahydropyran-4-yl group, which group optionally bears 1 or 2 substituents, which may be the same or different, selected from (1-4C)alkyl, hydroxy-(1-4C)alkyl, (1-3C)alkoxy-(1-4C)alkyl, (2-4C)alkanoyl, hydroxy-(2-4C)alkanoyl, (1-3C)alkoxy-(2-4C)alkanoyl, (1-4C)alkylsulfonyl, carbamoyl-(1-4C)alkyl, N-(1-4C)alkylcarbamoyl-(1-4C)alkyl and N,N-di-[(1-4C)alkyl]carbamoyl-(1-4C)alkyl, or $R^7$ and the group $R^{5a}R^5NC(Z)$ together with the carbon atom to which they are attached form a heterocyclyl group selected from a group of the formula:

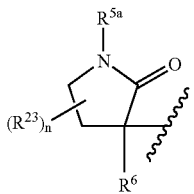 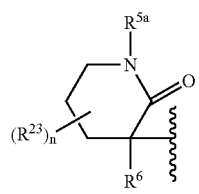

wherein $R^6$ is hydrogen, and $R^{5a}$ is selected from hydrogen, methyl and ethyl;

n is 0, 1 or 2; and each $R^{23}$, which may be the same or different, is methyl.

10. The quinazoline compound of the formula I according to claim 1, or a pharmaceutically acceptable salt thereof wherein $R^6$ is hydrogen.

11. The quinazoline compound of the formula I according to claim 1, or a pharmaceutically acceptable salt thereof wherein a is 1, 2 or 3 and each $R^2$, which may be the same or different, is selected from halogeno and (2-4C)alkynyl.

12. The quinazoline compound of the formula I according to claim 1, or a pharmaceutically acceptable salt thereof wherein p is 1, $R^1$ is located at the 7-position and $R^1$ is selected from (1-3C)alkoxy, hydroxy-(2-3C)alkoxy and (1-3C)alkoxy-(2-3C)alkoxy.

13. The quinazoline compound of the formula I according to claim 1, or a pharmaceutically acceptable salt thereof wherein the anilino group at the 4-position on the quinazoline ring in formula (I) is selected from 3-chloro-2-fluoroanilino, 3-chloro-4-fluoroanilino, 3-bromo-2-fluoroanilino, 3-chloro-2,4-difluoroanilino, 3-chloro-2,6-difluoroanilino and 3-chloro-5-fluoroanilino.

14. The quinazoline compound of the formula I according to claim 1 of the formula Ic:

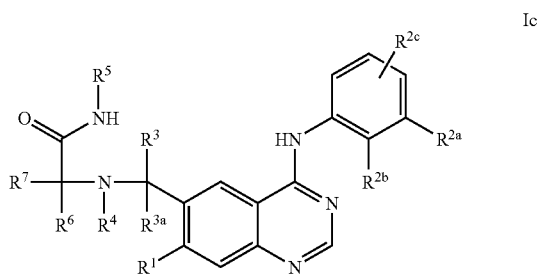

wherein:
$R^1$ is selected from (1-3C)alkoxy, hydroxy-(2-3C)alkoxy and (1-3C)alkoxy-(2-3C)alkoxy;

$R^{2a}$ is selected from fluoro, chloro and bromo;

one of $R^{2b}$ and $R^{2c}$ is selected from fluoro, chloro and bromo, and the other of $R^{2b}$ and $R^{2c}$ is hydrogen;

$R^{3a}$ is hydrogen;

$R^3$ is selected from hydrogen and (1-3C)alkyl;

$R^4$ is (1-3C)alkyl;

$R^5$ is selected from hydrogen and (1-3C)alkyl;

$R^6$ is selected from hydrogen and (1-3C)alkyl;

$R^7$ is selected from methyl, ethyl, isopropyl, hydroxymethyl, methoxymethyl, isopropyloxymethyl, 2-hydroxyethyl, 2-methoxyethyl, aminomethyl, 2-aminoethyl, methylaminomethyl, 2-(methylamino)ethyl, dimethylaminomethyl, 2-(dimethylamino)ethyl, pyrrolidin-3-yl and 1-methylpyrrolidin-3-yl, or $R^6$ and $R^7$ together with the carbon atom to which they are attached form a cyclopropyl, cyclobutyl, cyclopentyl, cyclohexyl, cyclopent-3-en-1-yl, azetidin-3-yl, piperidin-3-yl, piperidin-4-yl, tetrahydropyran-3-yl or tetrahydropyran-4-yl group, which group optionally bears 1 or 2 substituents, which may be the same or different, selected from (1-4C)alkyl, hydroxy-(1-4C)alkyl, (1-3C)alkoxy-(1-4C)alkyl, (2-4C)alkanoyl, hydroxy-(2-4C)alkanoyl, (1-3C)alkoxy-(2-4C)alkanoyl, (1-4C)alkylsulfonyl, carbamoyl-(1-4C)alkyl, N-(1-4C)alkylcarbamoyl-(1-4C)alkyl and N,N-di-[(1-4C)alkyl]carbamoyl-(1-4C)alkyl, or $R^7$ and the group $R^5NHC(O)$ together with the carbon atom to which they are attached form a heterocyclyl group selected from a group of the formula:

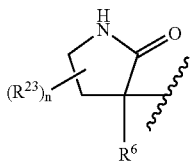 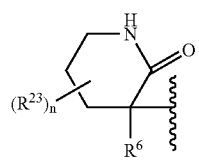

wherein $R^6$ is hydrogen; n is 0, 1 or 2 and each $R^{23}$, which may be the same or different, is methyl;

or a pharmaceutically acceptable salt thereof.

15. The quinazoline compound of the formula I according to claim 1 selected from:

$N^2$-({4-[(3-chloro-2-fluorophenyl)amino]-7-methoxyquinazolin-6-yl}methyl)-$N^2$-methylglycinamide;

$N^2$-({4-[(3-chloro-2-fluorophenyl)amino]-7-methoxyquinazolin-6-yl}methyl)-$N^2$-methyl-D-alaninamide;

$N^2$-({4-[(3-chloro-2-fluorophenyl)amino]-7-methoxyquinazolin-6-yl}methyl)-$N^2$-methyl-L-alaninamide;

$N^2$-({4-[(3-chloro-2-fluorophenyl)amino]-7-methoxyquinazolin-6-yl}methyl)-$N^2$-methyl-L-serinamide;

$N^2$-({4-[(3-chloro-2-fluorophenyl)amino]-7-methoxyquinazolin-6-yl}methyl)-D-alaninamide;

$N^2$-({4-[(3-chloro-2-fluorophenyl)amino]-7-methoxyquinazolin-6-yl}methyl)glycinamide;

$N^2$-({4-[(3-chloro-2-fluorophenyl)amino]-7-methoxyquinazolin-6-yl}methyl)-$N^2$,O-dimethyl-L-serinamide;

$N^2$-({4-[(3-chloro-2-fluorophenyl)amino]-7-methoxyquinazolin-6-yl}methyl)-$N^2$,O-dimethyl-D-serinamide;

$N^2$-({4-[(3-chloro-2-fluorophenyl)amino]-7-methoxyquinazolin-6-yl}methyl)-$N^2$,O-dimethyl-L-homoserinamide;

$N^2$-({4-[(3-chloro-4-fluorophenyl)amino]-7-methoxyquinazolin-6-yl}methyl)-$N^2$,O-dimethyl-L-serinamide;

$N^2$-({4-[(3-chloro-4-fluorophenyl)amino]-7-methoxyquinazolin-6-yl}methyl)-$N^2$-methyl-D-alaninamide;

3-[({4-[(3-chloro-2-fluorophenyl)amino]-7-methoxyquinazolin-6-yl}methyl)(methyl)amino]-1-isopropylazetidine-3-carboxamide;

3-[({4-[(3-chloro-2-fluorophenyl)amino]-7-methoxyquinazolin-6-yl}methyl)(methyl)amino]-1-methylazetidine-3-carboxamide;

1-[({4-[(3-chloro-2-fluorophenyl)amino]-7-methoxyquinazolin-6-yl}methyl)(methyl)amino]cyclopropanecarboxamide;

3-[({4-[(3-chloro-2-fluorophenyl)amino]-7-methoxyquinazolin-6-yl}methyl)(methyl)amino]-1-methylpiperidine-3-carboxamide;

1-[({4-[(3-chloro-2-fluorophenyl)amino]-7-methoxyquinazolin-6-yl}methyl)(methyl)amino]cyclopent-3-ene-1-carboxamide;

4-[({4-[(3-chloro-2-fluorophenyl)amino]-7-methoxyquinazolin-6-yl}methyl)(methyl)amino]-N,1-dimethylpiperidine-4-carboxamide;

4-[({4-[(3-chloro-2-fluorophenyl)amino]-7-methoxyquinazolin-6-yl}methyl)(methyl)amino]-1-methylpiperidine-4-carboxamide;

$N^2$-{[4-[(3-chloro-2-fluorophenyl)amino]-7-(2-methoxyethoxy)quinazolin-6-yl]methyl}-$N^2$-methyl-D-alaninamide;

3-[({4-[(3-chloro-2-fluorophenyl)amino]-7-methoxyquinazolin-6-yl}methyl)(methyl)amino]-1-(2-methoxyethyl)azetidine-3-carboxamide;

$N^2$-({4-[(3-chloro-2-fluorophenyl)amino]-7-methoxyquinazolin-6-yl}methyl)-$N^2$-ethyl-D-alaninamide;

2-[({4-[(3-chloro-2-fluorophenyl)amino]-7-methoxyquinazolin-6-yl}methyl)(methyl)amino]-2-(1-methylpyrrolidin-3-yl)acetamide;

$N^2$-({4-[(3-chloro-2-fluorophenyl)amino]-7-methoxyquinazolin-6-yl}methyl)-$N^1$,$N^2$-dimethyl-D-alaninamide;

1-[({4-[(3-chloro-2-fluorophenyl)amino]-7-methoxyquinazolin-6-yl}methyl)(ethyl)amino]cyclopropanecarboxamide; and $N^2$-(1-{4-[(3-chloro-2-fluorophenyl)amino]-7-methoxyquinazolin-6-yl}ethyl)-$N^2$-methyl-D-alaninamide;

or a pharmaceutically acceptable salt thereof.

16. A pharmaceutical composition which comprises a quinazoline compound of the formula I, or a pharmaceutically-acceptable salt thereof, as defined in claim 1 or claim 2 in association with a pharmaceutically-acceptable diluent or carrier.

* * * * *